US008372973B2

(12) United States Patent
Coats et al.

(10) Patent No.: US 8,372,973 B2
(45) Date of Patent: *Feb. 12, 2013

(54) PROKINETICIN 1 RECEPTOR ANTAGONISTS

(75) Inventors: Steven J. Coats, McDonough, GA (US); Alexey B. Dyatkin, Maple Glen, PA (US); Wei He, Audubon, PA (US); Joseph Lisko, Glenmoore, PA (US); Tamara Miskowski, Chalfont, PA (US); Janet L. Ralbovsky, Yorktown Heights, NY (US); Mark Schulz, Skippack, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 56 days.

This patent is subject to a terminal disclaimer.

(21) Appl. No.: 12/970,461

(22) Filed: Dec. 16, 2010

(65) Prior Publication Data

US 2012/0028997 A1 Feb. 2, 2012

Related U.S. Application Data

(62) Division of application No. 11/647,091, filed on Dec. 28, 2006, now Pat. No. 7,902,358.

(60) Provisional application No. 60/754,939, filed on Dec. 29, 2005.

(51) Int. Cl.
| C07D 403/06 | (2006.01) |
| C07D 403/12 | (2006.01) |
| C07D 403/14 | (2006.01) |
| C07D 401/06 | (2006.01) |
| C07D 401/12 | (2006.01) |
| C07D 401/14 | (2006.01) |
| A61K 31/506 | (2006.01) |
| A61P 1/00 | (2006.01) |
| A61P 1/06 | (2006.01) |
| A61P 1/12 | (2006.01) |

(52) U.S. Cl. .................. 544/309; 544/310; 544/311
(58) Field of Classification Search ................ 544/309, 544/310, 311; 514/269, 274
See application file for complete search history.

(56) References Cited

U.S. PATENT DOCUMENTS

| 6,485,938 | B1 | 11/2002 | Sheppard et al. | |
| 7,902,358 | B2 * | 3/2011 | Coats et al. | 544/223 |
| 7,968,710 | B2 * | 6/2011 | Coats et al. | 544/223 |
| 2004/0156842 | A1 | 8/2004 | Thompson et al. | |

FOREIGN PATENT DOCUMENTS

| WO | WO 02/36625 A2 | 5/2002 |
| WO | WO 2004/014868 | 2/2004 |
| WO | WO 2004/087054 | 10/2004 |
| WO | WO 2006/104713 | 10/2006 |
| WO | WO 2006/104715 | 10/2006 |

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
Zhou et al., Molecular Interventions, vol. 6(6), 330-338, 2006.*
Akehurst et al., "Treatment of irritable bowel syndrome: a review of randomised controlled trials.", Gut 2001, pp. 272-282, vol. 48.
Bullock et al., "Identification of Two Prokineticin cDNAs: Recombinant Proteins Potently Contract Gastrointestinal Smooth Muscle", Mol. Pharmacol, 2004, pp. 582-588, vol. 65(3).
Goi et al., "Angiogenesis and Tumor Proliferation/Metastasis of Human Colorectal Cancer Cell Line SW620 Transfected with Endocrine Glands-Derived-Vascular Endothelial Growth Factor, As a New Angiogenic Factor.", Cancer Res. 2004, pp. 1906-1910, vol. 64.
Jackson et al., "Treatment of Functional Gastrointestinal Disorders with Antidepressant Medications: A Meta-Analysis.", Am. J. Med. 2000, pp. 65-72, vol. 108.
Jailwala et al., "Pharmacologic Treatment of the Irritable Bowel Syndrome: A Systematic Review of Randomized, Controlled TrialsIntern.", Med. 2000, pp. 136-147, vol. 133.
Lecouter et al., "Identifcation of an angiogenic mitogen selective for endocrine gland endothelium.", Nature 2001, pp. 877-884, vol. 412.
Lecouter et al., "The endocrine-gland-derived VEGF homologue Bv8 promotes angiogenesis in the testis: Localization of Bv8 receptors to endothelial cells.", Proc. Natl. Acad. Sci, Mar. 4, 2003, pp. 2685-2690, vol. 100(5).
Lecouter, et al., "The Role of EG-VEGF in the Regulation of Angiogenesis in Endocrine Glands.", Cold Spring Harb Symp Quant Biol., 2002, pp. 217-221, vol. 67.
Li et al., "Structural Determinants Required for the Bioactivities of Prokineticins and Identification of Prokineticin Receptor Antagonists.", Mol. Pharmacol. 2001, pp. 692-698, vol. 59.
Masuda et al., "Isolation and identification of EG-VEGF/prokineticins as cognate ligands for two orphan G-protein-coupled receptors.", Biophys Res. Commun. 2002, pp. 396-402, vol. 293(1).
Mollay et al., "Bv8, a small protein from frog skin and its homologue from snake venom induce hyperalgesia in rats.", Eur. J. Pharmacol, 1999, pp. 189-196, vol. 374.

(Continued)

Primary Examiner — Venkataraman Balasubramanian
(74) Attorney, Agent, or Firm — Timothy E. Tracy

(57) ABSTRACT

The present invention relates to certain novel compounds of Formula (I):

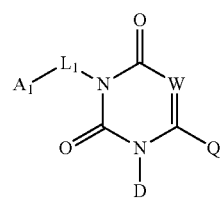

Formula (I)

and methods for preparing these compounds, compositions, intermediates and derivatives thereof and for the treatment of prokineticin 1 or prokinetin 1 receptor mediated disorders.

30 Claims, 5 Drawing Sheets

OTHER PUBLICATIONS

Negri et al., "Bv8, the amphibian homologue of the mammalian prokineticins, modulates ingestive behaviour in rats.", Brit. J. Pharmacol, 2004, pp. 181-191, vol. 142.

Negri et al., "Nociceptive sensitization by the secretory protein Bv8.", Brit. J. Pharmacol 2002 pp. 1147-1154, vol. 137(8).

Poynard et al., "Meta-analysis of smooth muscle relaxants in the treatment of irritable bowel syndrome.", Aliment Pharmacol. Ther. 2001, pp. 355-361, vol. 15.

Rome II Diagnostic criteria for the Functional Gastrointestinal Disorders, Second Edition, Senior Editor Douglas A. Drossman, M.D., Management Services, McLean, VA (2000)).

Saito et al., "The Epidemiology of Irritable Bowel Syndrome in North America: A Systematic Review.". Am. J. Gastroenterol, 2002, pp. 1910-1915, vol. 97.

Thompson et al., "Functional Bowel Disorders in Apparently Healthy People.", Gastroenerology, 1980, pp. 283-288, vol. 79.

Berge et al., "Pharmaceutical Salts.", J. Pharm. Sci., 1977, pp. 1-19, vol. 66(1).

Gould P.L., "Salt Selection for Basic Drugs.", International J. Pharm., 1986, pp. 201-217, vol. 33.

* cited by examiner

Figure 1. Matrix Assisted Laser Desorption (MALDI) mass spectrum of protein mixture.
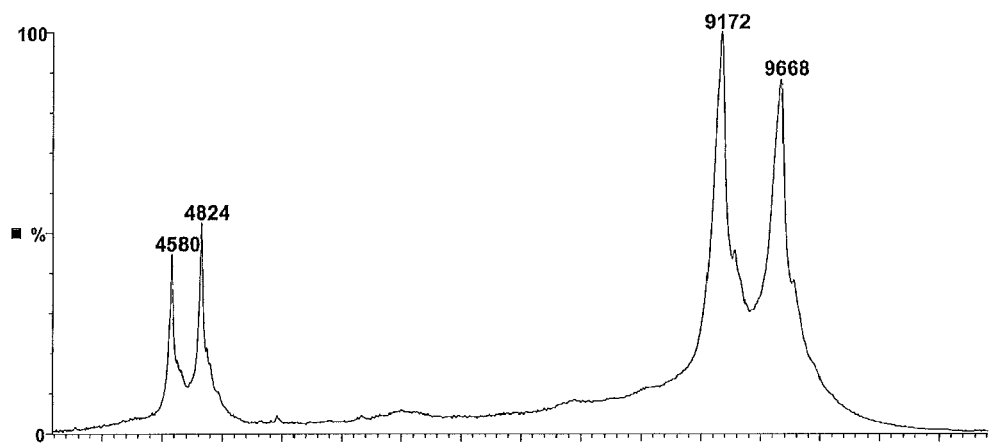

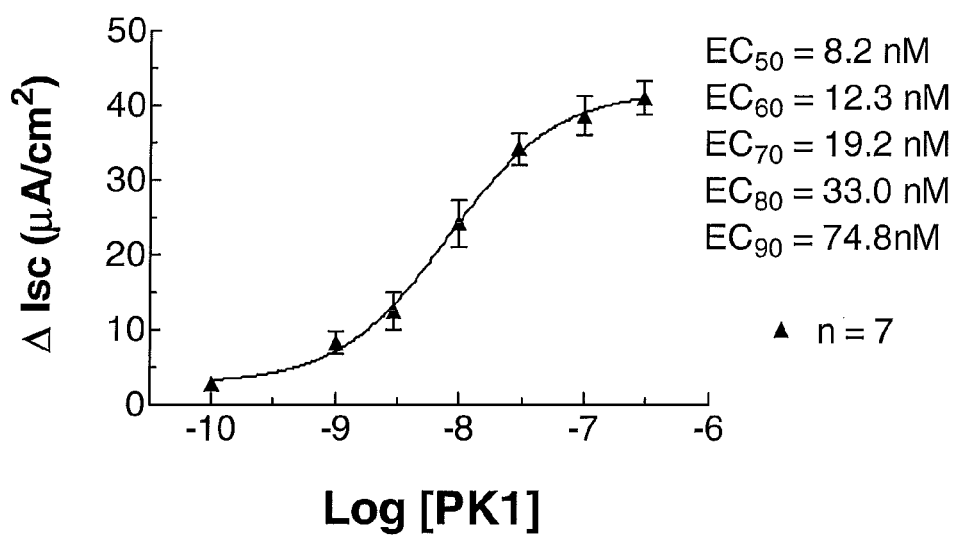
Figure 2. *Effect of Prokineticin 1 Peptide on Gut Mucosal Ion Transport ex vivo.*

Figure 3. The PK1 evoked increase in Isc was suppressed by the aminopyridine, Cpd 3, a small molecule antagonist at the PK1 receptor.
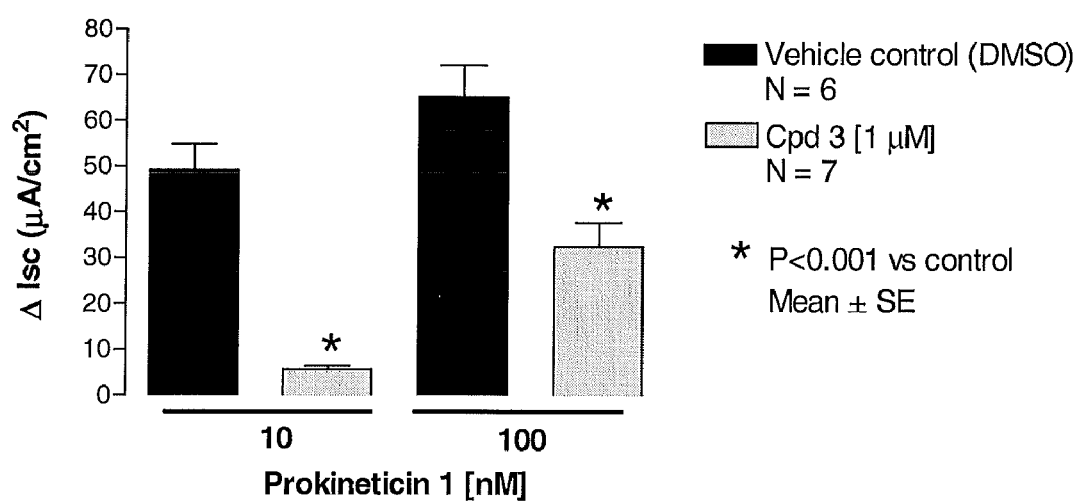

Fig. 4. Increased Isc evoked in Response to the cholinergic agonist Carbachol
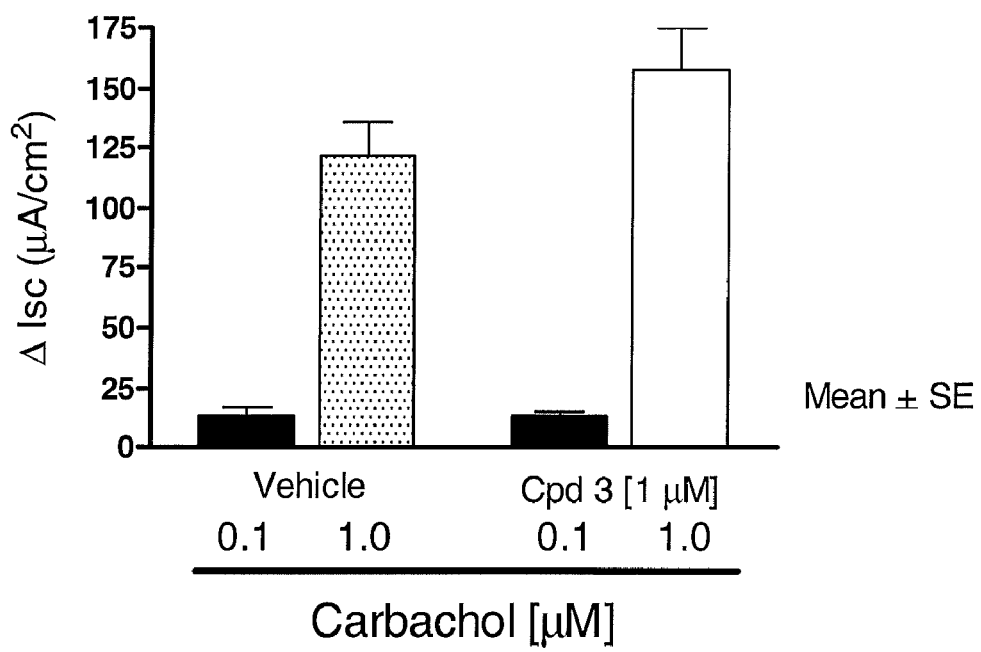

Figure 5. Vibrio cholera toxin induced increase in baseline Isc of muscle-stripped rat ileum mucosa
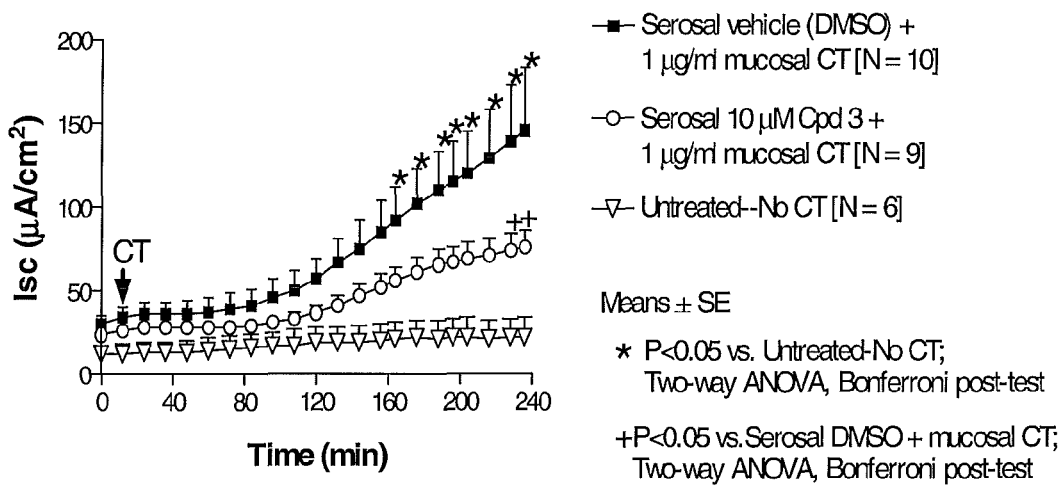

PROKINETICIN 1 RECEPTOR ANTAGONISTS

CROSS REFERENCE TO RELATED APPLICATIONS

This application is a Divisional of U.S. Ser. No. 11/647,091, currently, filed Dec. 28, 2006 now U.S. Pat. No. 7,902,358 and in turn claims priority to U.S. Provisional Patent Application No. 60/754,939, filed Dec. 29, 2005, now abandoned, which are hereby incorporated by reference in their entirety.

STATEMENT REGARDING FEDERALLY SPONSORED RESEARCH OR DEVELOPMENT

The research and development of the invention described herein was not federally sponsored.

BACKGROUND OF THE INVENTION

Digestion involves the breakdown of food materials into molecules that can be delivered to and utilized by individual cells of the body. These molecules may serve as energy sources; they may provide essential chemical elements, such as calcium, nitrogen or iron; or they may be complete molecules, e.g., certain amino acids, fatty acids and vitamins, that the cells need but cannot synthesize themselves. Digestion which incorporates the processes of breakdown and assimilation of food materials as well as the elimination of undigestable waste material takes place in a long convoluted tube that extends from the mouth to the anus, known as the gastrointestinal (GI) tract. The GI tract begins with the oral cavity, the mouth, and continues to include the, pharynx, esophagus, stomach, small intestine, large intestine and anus. The GI tract, from beginning to end, has four tissue layers: (1) the mucosa, which is the innermost layer, is made up of columnar epithelial cells that are in direct contact with ingested materials and facilitate fluid and electrolyte transport and digestion and absorption of nutrients, an underlying basement membrane consisting of connective tissue and a thin layer of smooth muscle; (2) the submucosa, which is the second innermost layer, is made up of connective tissue containing small clusters of nerve cells and nerve fibers, and blood and lymph vessels; (3) the muscularis externa, which is the third innermost layer, is made up of two separate layers of smooth muscle tissue oriented in opposing directions and containing a vast network of nerve cell clusters and nerve fibers sandwiched in-between these layers; and (4) the serosa, which is the outermost layer consisting of a coating of connective tissue that is in contact with the environment of the peritoneal cavity of the abdomen.

Along most of the GI tract, the muscularis externa is made up of two opposing layers of smooth muscle, the inner layer, in which the cellular orientation is perpendicular to the long axis of the gut, and the outer layer, in which cellular orientation is parallel to the long axis of the gut. Coordinated contractions of these muscle layers produce ring-like constrictions that mix food, as well as wave-like motions, known as peristalsis, that move food along the GI tract. At several points, the circular layer of muscle thickens into heavy bands forming valve-like constrictions called sphincters, which by relaxing and contracting, act to regulate the passage of food from one area of the GI tract to another.

Breakdown and assimilation of nutrients from food materials is accomplished chiefly by the highly coordinated activities of the stomach and small intestine. The stomach is influenced by both the nervous and endocrine systems. Anticipation of food and the presence of food in the mouth stimulate churning movements of the stomach and the production of gastric juices. When food reaches the stomach, its presence causes the release of the hormone gastrin from gastric endocrine cells into the bloodstream. Gastrin acts on the cells of the stomach to increase their secretion of gastric juices.

Food is converted in the stomach to a semiliquid mass as a result of gastric juices, including pepsin, hydrochloric acid and the churning motions. The food is then emptied into the small intestine, where the breakdown of food is completed. The resulting nutrient molecules are then absorbed into the circulatory system, from which they are delivered to the individual cells. The small intestine contains a variety of digestive secretions, some produced by the intestinal cells and some by the pancreas and liver. Other epithelial cells, the goblet cells of the mucosa, secrete mucus. The digestive activities of the small intestine are coordinated and regulated by hormones. In addition to hormonal influences, the intestinal tract is also regulated by the autonomic and enteric nervous systems, which are involved in regulating the secretion of digestive enzymes, and coordinating the activities of contraction and epithelial secretion. Thus, a complex interplay of stimuli and checks and balances serves to activate digestive enzymes, adjust the chemical environment and regulate the movement of ingested materials in the intestines.

The large intestine is involved in the absorption of water, sodium and other electrolytes. Some of its epithelial cells secrete mucus, which lubricates undigested food residue. Large amounts of water enter the stomach and small intestine by osmosis from body fluids or as secretions of the glands lining the digestive tract. When the absorption process is interfered with and/or secretions from the mucosal glands becomes enhanced, as in diarrhea, severe dehydration can result.

Functional bowel disorders involve abnormal motility and secretion within organs of the GI tract, and are characterized by abdominal discomfort/pain. The Criteria for these disorders are summarized by gastroenterologists in the 'Rome II criteria' (See, for example, Rome II Diagnostic criteria for the Functional Gastrointestinal Disorders, Second Edition, Senior Editor Douglas A. Drossman, M.D., Management Services, McLean, Va. (2000)). Based on these criteria the disorders are common and include, but are not limited to, functional dyspepsia, irritable bowel syndrome (IBS), gastroesophageal reflux disease (GERD), non-erosive reflux disease (NERD), and chronic constipation (including colonic inertia, idiopathic pseudoobstruction). GERD is extremely prevalent, is usually associated with non-cardiac chest pain and may be treated with acid-suppressing agents and prokinetic agents. IBS is characterized by the presence of reoccurring constipation and/or diarrhea, which can be associated with gaseous distention/bloating and abdominal discomfort/pain (Thompson, W. G. and Heaton, K. W. *Gastroenterology* 1980, 79, 283-288). The onset of the pain of IBS is associated with a change in the frequency and/or form of stool and can be relieved by defecation. IBS is an extremely prevalent condition that occurs to varying severity in 10-15% of the population (Saito, Y. A.; Schoenfeld, P.; and Locke, G. R. *Am. J. Gastroenterol.* 2002, 97, 1910-1915). The pain may be treated with smooth muscle relaxants and antidepressants (Jackson, J. L.; O'Malley, P. G.; Tomkins, G.; Balden, E.; Santoro, J.; and Kroenke, K.; *Am. J. Med.* 2000, 108, 65-72; Jailwala, J.; Imperiale, T. F.; and Kroenke, K.; *Ann. Intern. Med.* 2000, 133:136-147; Akehurst, R. and Kaltenthaler, E. *Gut* 2001, 48, 272-282; Poynard, T.; Regimbeau, C.; and Benhamou, Y.; *Aliment Pharmacol. Ther.* 2001, 15, 355-361). Severe diarrhea predominant IBS is treated by alosetron, whereas constipation predominant IBS is treated by tegaserod. Functional dyspepsia is a disorder of the upper GI tract with symptoms exacerbated by a meal and associated with early satiety, nausea and vomiting. Although its etiology is unknown, prokinetic agents may relieve the symptoms of IBS. In some patients there is overlap in symptoms between GERD/NERD, functional dyspepsia and IBS. Treatments for functional bowel disorders, such as IBS, have low efficacy and are associated with adverse effects. For example, alosetron is approved by the FDA on a risk management program because it is associated with an increase in ischemic colitis. No treatments effectively alleviate pain in functional bowel disorders.

In addition to functional disorders, inflammatory bowel diseases (IBD) are common and include ulcerative colitis (UC) and Crohn's disease (CD). Although there may be a genetic component to CD, the etiology of both UC and CD is unknown. UC is a diffuse mucosal disease of the colon, characterized by inflammation and ulceration, which is associated with diarrhea and abdominal cramping. The mucosal inflammation progresses from the rectal area to eventually extend through the large bowel. CD is a transmural inflammation that most frequently involves the distal small bowel and colon. The inflammation can result in ulcers of varying involvement and in severe cases can result in transmural scarring and chronic inflammation. Both infectious and dysregulated immune functions may contribute to disease onset. Therapies for IBD include corticosteroids, immunosuppressives (azathioprine, mercaptopurine, and methotrexate) and aminosalicylates (5-ASA). These therapies involve suppression of the immune system by mimicking corticosteroids, or have unknown mechanisms of action. Oral corticosteroid use is associated with serious adverse effects, whereas immunosuppressives and aminosalicylates are only moderately effective. Infliximab (a chimeric monoclonal anti-tumor necrosis factor antibody) is effective in CD, however, its use is associated with the presence of antibodies, which reduce its efficacy. There are currently no treatments that target the motility and secretory abnormalities or painful sensation that are associated with gut inflammation.

The cysteine rich proteins known as Prokineticin 1 (PK1) and Prokineticin 2 (PK2), as well as variants, fragments and molecules having PK activity, have been identified. PK1 and PK2 have been shown to contract gastrointestinal smooth muscle (Li, M.; Bullock, C. M.; Knauer, D. J.; Ehlert, F. J.; and Zhou, Q. Y., *Mol. Pharmacol.* 2001, 59, 692-698), and suppress feeding (Negri, L.; Lattanzi, R.; Giannini, E.; De Felice, M.; Colucci, A. and Melchiorri, P. *Brit. J. Pharmacol.* 2004, 142, 181-191). PK1 and PK2 act on both PK1 and PK2 receptors, and limited structural changes of C-terminal cysteine-rich regions of these related PKs are tolerated. For example, chimeric PKs, where the cysteine-rich domains of PK1 and PK2 were exchanged between the two and a splice variant of PK2 that included a 21 residue insertion in its C-terminal domain retained activity (Bullock, C M; Li J. D.; Zhou, Q. Y.; *Mol. Pharmacol.* 2004, 65(3), 582-8). A PK variant binds to receptors of primary sensory neurons, and results in an intense sensitization of peripheral nociceptors to thermal and mechanical stimuli (Mollay, C.; Weschelberger, C.; Mignogna, G.; Negri, L.; Melchiorri, P.; Barra, D.; Kreil, G.; *Eur. J. Pharmacol.* 1999, 374, 189-196; Negri, L.; Lattanzi, R.; Giannini, E.; Metere, A.; Colucci, M.; Barra, D.; Kreil, G.; Melchiorri, P.; *Brit. J. Pharmacol.* 2002, 137(8), 1147-54).

PK1 (also known as EG-VEGF) induces proliferation, migration and fenestration in capillary endothelial cells derived from endocrine glands. The expression of PK mRNA has been observed in steroidogenic glands, ovary, testis, adrenal and placenta. (LeCouter, J.; Kowalski, J.; Foster, J.; Hass, P., Zhang, Z.; Dillard-Telm, L., Frantz, G., Rangell, L.; DeGuzman, L.; Keller, G. A.; Peale, F.; Gurney, A.; Hillan, K. J.; Ferrara, N. *Nature* 2001, 412 (6850), 877-84). In 2002 the identification of the PK1 receptor provided a novel molecular basis for the regulation of angiogenesis in endocrine glands (Masuda, Y.; Takatsu, Y.; Terao, Y.; Kumano, S.; Ishibashi, Y.; Suenaga, M.; Abe, M.; Fukusumi, S.; Watanabe, T.; Shintani, Y.; Yamada, T.; Hinuma, S.; Inatomi, N.; Ohtaki, T.; Onda, H.; Fujino, M.; *Biochem. Biophys. Res. Commun.* 2002, 293(1), 396-402; LeCouter, J.; Lin, R.; Ferrara, N.; *Cold Spring Harb Symp Quant Biol.* 2002, 67, 217-21). For example, adenoviral delivery of PK1 to the mouse testis results in a potent angiogenic response (LeCouter, J.; Lin, R.; Tejada, M.; Frantz, G.; Peale, F.; Hillan, K. J.; Ferrara, N. *Proc. Natl. Acad. Sci. USA.* 2003, 100, 2685-90). Recently, it was shown that PK1 mRNA is not normally expressed in colorectal normal mucosa but is detected in colorectal cancer cells (Goi, T.; Fujioka, M.; Satoh, Y.; Tabata, S.; Koneri, K.; Nagano, H.; Hirono, Y.; Katayama, K.; Hirose, K. and Yamaguchi., *Cancer Res.* 2004, 64, 1906-1910).

Thus, PK1 receptor modulators, and in particular PK1 receptor antagonists, may be useful in the treatment and prevention of various mammalian disease states, for example, visceral pain that is associated with IBS and IBD. Additionally, PK1 receptor modulators, and in particular PK1 receptor antagonists, may be useful for the treatment of GERD or other forms of secretory diarrhea. Additionally, PK1 receptor modulators, and in particular PK1 receptor antagonists, may be useful in treating cancer-specific angiogenesis factor in the large intestine and reproductive organs.

WO200236625 discloses PK1 and PK2 polynucleotides and polypeptides and uses thereof.

U.S. 20040156842 and corresponding U.S. Pat. No. 6,485, 938 disclose the use of peptide antagonists of PK1 and PK2 to treat inflammation in the intestine. The references disclose that the antagonists include antibodies that specifically bind with PK1 and PK2 and receptors that bind to amino acid sequences disclosed therein.

WO2004087054 discloses methods of modulating gastric acid or pepsinogen secretion by administering a prokineticin receptor antagonist to alter one or more indicia of gastric acid secretion. The reference discloses that the prokineticin receptor antagonist is a modified version of a prokineticin from any species that contains an amino acid sequence at least 80% identical to an amino acid sequence disclosed therein.

It is an object of the present invention to provide compounds that are prokineticin 1 receptor antagonists. It is also an object of the invention to provide a method of treating or ameliorating a condition mediated by prokineticin 1 receptor. And, it is an object of the invention to provide a useful pharmaceutical composition comprising a compound of the present invention useful as a prokineticin 1 receptor antagonist.

The present invention is also directed to methods for producing the instant compounds and pharmaceutical compositions and medicaments thereof.

The present invention is further directed to methods for treating or ameliorating a Prokineticin 1-mediated disorder. In particular, the method of the present invention is directed to treating or ameliorating a Prokineticin-mediated disorder such as, but not limited to, visceral pain that is associated with IBS and IBD, GERD and other forms of secretory diarrhea, and cancer-specific angiogenesis factor in the large intestine and reproductive organs.

SUMMARY OF THE INVENTION

The present invention is directed to a compound of Formula (I):

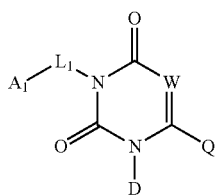

Formula (I)

wherein:
$A_1$ is $CF_3$, $C_{1-4}$alkoxy, aryl, aryloxy, benzofused heterocyclyl, or heteroaryl; wherein aryl, aryloxy, and heteroaryl are optionally substituted with pyrazol-1-yl or [1,2,3]thiadiazol-4-yl; or aryl, aryloxy, the benzo portion of benzofused heterocyclyl, and heteroaryl are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl; provided that $A_1$ is other than 3,5-di-t-butyl-phenyl;
$L_1$ is —$(CH_2)_r$—, —$CH_2C_{2-4}$alkenyl-, or —$CH_2CH_2X(CH_2)_s$—, wherein $L_1$ is optionally substituted with one to two substituents independently selected from the group consisting of $C_{1-6}$alkyl, $C_{2-6}$alkenyl, $C_{2-6}$alkynyl, and halogen; and, r is an integer of 1 to 5; such that r is greater than or equal to 4 when $A_1$ is $C_{1-4}$alkoxy;
s is an integer of 1 to 3;
X is O or S;
D is -P-$A_2$;
wherein P is —$(CH_2)_{1-2}$— or —$CH_2CH=CH$— when $A_2$ is phenyl, benzofused heterocyclyl, heteroaryl, or $C_{3-8}$cycloalkyl; alternatively, P is —$(CH_2)_{3-6}$—, when $A_2$ is hydrogen, $C_{1-4}$alkoxy, or $C_{1-4}$alkoxycarbonyl; and wherein P is optionally substituted with one to two substituents independently selected from the group consisting of $C_{1-6}$alkyl, $C_{2-6}$alkenyl, $C_{2-6}$alkynyl, and halogen;
$A_2$ is hydrogen, $C_{1-4}$alkoxy, $C_{1-4}$alkoxycarbonyl, phenyl, benzofused heterocyclyl, heteroaryl, tetrahydro-pyranyl, piperidinyl, or $C_{3-8}$cycloalkyl; wherein phenyl, heteroaryl, the benzo portion of benzofused heterocyclyl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, N-isoindole-1,3-dione, $C_{1-6}$alkylthio, $C_{1-6}$alkylsulfonyl, $C_{1-6}$alkoxycarbonyl, amino, $C_{1-6}$alkylamino, di($C_{1-6}$alkyl)amino, cyano, hydroxy, nitro, $C_{1-6}$alkylaminocarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; such that no more than two substituents on $A_2$ are aryl($C_{1-6}$)alkoxy, phenyl, N-isoindole-1,3-dione, or a non fused $C_{3-6}$cycloalkyloxy; provided that $A_2$ is other than 3,5-di-t-butyl-phenyl;
W is N or $C(R_W)$; wherein $R_W$ is H or $C_{1-2}$alkyl;
Q is selected from the group consisting of (a) to (g), wherein
(a) is —$NH(CH_2)_2$—$Ar_1$ wherein $Ar_1$ is pyridinyl optionally substituted with one to three $C_{1-4}$alkyl substituents or a substituent selected from the group consisting of $C_{1-4}$alkoxy and amino;
provided that when $Ar_1$ is unsubstituted pyridin-3-yl or unsubstituted pyridin-4-yl, and $A_2$ is 4-methoxy-phenyl, $A_1$ is other than unsubstituted phenyl or 3,4-dichloro-phenyl;
(b)—$NHCH(R_z)$—$Ar_2$ wherein $R_z$ is H or $C_{1-3}$alkyl; $Ar_2$ is pyridinyl, pyrimidinyl, pyrazinyl,

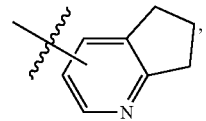

1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein $Ar_2$ is optionally substituted with one to three substituents independently selected from the group consisting of $C_{1-4}$alkyl, trifluoromethyl, hydroxyl-$C_{1-4}$alkyl, amino($C_{1-4}$alkyl, ($C_{1-4}$alkyl)amino-($C_{1-4}$)alkyl, di($C_{1-4}$alkyl)amino-($C_{1-4}$)alkyl, $C_{1-4}$alkoxy, $C_{3-8}$ cycloalkylamino, amino, ($C_{1-6}$alkyl)amino, and di($C_{1-6}$alkyl)amino; or $Ar_2$ is optionally substituted with one amino group and three substituents independently selected from the group consisting of $C_{1-4}$alkyl and $C_{1-4}$alkoxy;
wherein the $C_{1-6}$alkyl group of ($C_{1-6}$alkyl)amino and di($C_{1-6}$alkyl)amino is optionally substituted with amino, ($C_{1-4}$alkyl)amino, di($C_{1-4}$alkyl)amino, $C_{3-8}$cycloalkylamino, $C_{1-4}$alkoxy, $C_{1-4}$alkylthio, hydroxy, a 5 to 6 membered heteroaryl, or a 5 to 6 membered heterocyclyl; wherein a nitrogen atom of the 5 to 6 membered heterocyclyl is optionally substituted with a $C_{1-4}$alkyl substituent;
and wherein pyridin-2-yl and pyridin-3-yl are optionally further substituted with N-pyrrolidinyl, N-piperazinyl, N-piperidinyl, N-morpholinyl, N-thiomorpholinyl, —$CH_2$—O—$CH_2$—PH, and phenyl; wherein the phenyl substituent of pyridin-2-yl and pyridin-3-yl is optionally substituted with one to three substituents independently selected from the group consisting of $C_{1-4}$alkyl, $C_{1-4}$alkoxy, and halogen;
provided that when Q is —$NHCH_2$(2-amino-pyridin-3-yl), and $A_1$ is pyridin-4-yl, 4-$C_{1-6}$alkyl-phenyl, 3,4-dichloro-phenyl, or 4-methanesulfonyl-phenyl, $A_2$ is other than 4-methoxy-phenyl;
provided that when Q is —$NHCH_2$(2-amino-pyridin-3-yl), $L_1$ is —$(CH_2)_2$— or —$(CH_2)_5$—, and $A_1$ is methoxy, $A_2$ is other than 4-difluoromethoxy-phenyl or 4-methoxy-phenyl;
provided that when Q is —$NHCH_2$(2-amino-pyridin-3-yl), and $A_1$ is benzotriazol-1-yl, $A_2$ is other than 4-difluoromethoxy-phenyl;
provided that when Q is —$NHCH_2$(2-amino-pyridin-3-yl), $L_1$ is —$(CH_2)_3$—, and $A_1$ is pyrrol-1-yl, $A_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, -P-A$_2$ is other than —(CH$_2$)$_5$-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(c) is —CH$_2$NHCH$_2$—Ar$_3$, wherein W is N or CH, and Ar$_3$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8] naphthyridinyl is at the 6 or 7 position, and that the point of attachment to quinolinyl is at the 2, 3, or 4-position; wherein Ar$_3$ is optionally substituted with one to three substituents independently selected from the group consisting of C$_{1-4}$alkyl, amino(C$_{1-4}$)alkyl, (C$_{1-4}$alkyl)amino-(C$_{1-4}$)alkyl, di(C$_{1-4}$alkyl)amino-(C$_{1-4}$)alkyl, C$_{1-4}$alkoxy, amino, (C$_{1-6}$alkyl)amino, and di(C$_{1-6}$alkyl)amino;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

(d) is —(CH$_2$)$_2$—Ar$_4$, wherein Ar$_4$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; wherein Ar$_4$ is optionally substituted with one to three substituents independently selected from the group consisting of C$_{1-4}$alkyl, amino(C$_{1-4}$)alkyl, (C$_{1-4}$alkyl)amino-(C$_{1-4}$)alkyl, di(C$_{1-4}$alkyl)amino-(C$_{1-4}$)alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

(e) is —CH═CH—Ar$_5$; wherein Ar$_5$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; wherein Ar$_5$ is optionally substituted with one to three substituents independently selected from the group consisting of C$_{1-4}$alkyl, amino(C$_{1-4}$)alkyl, (C$_{1-4}$alkyl)amino-(C$_{1-4}$)alkyl, di(C$_{1-4}$alkyl)amino-(C$_{1-4}$)alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

(f) is —O—CH(R$_1$)—Ar$_6$ when W is CH; or, (f) is —S—CH(R$_1$)—Ar$_6$ and W is N or CH; wherein R$_1$ is hydrogen or C$_{1-4}$alkyl, and Ar$_6$ is pyridinyl, pyrimidinyl, 1,2,3,4-tetrahydro-[1,8]naphthyridinyl, imidazo[1,2-a] pyridinyl, or quinolinyl such that the point of attachment to 1,2,3,4-tetrahydro-[1,8]naphthyridinyl is at the 6 or 7 position, and the point of attachment to quinolinyl is at the 2, 3, or 4-position;

wherein Ar$_6$ is optionally substituted with one to three substituents independently selected from the group consisting of C$_{1-4}$alkyl, amino(C$_{1-4}$)alkyl, (C$_{1-4}$alkyl)amino-(C$_{1-4}$)alkyl, di(C$_{1-4}$alkyl)amino-(C$_{1-4}$)alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

provided that when Q is —O—CH(R$_1$)—Ar$_6$, A$_1$ and A$_2$ are 4-methoxy-phenyl, and R$_1$ is hydrogen, Ar$_6$ is other than unsubstituted pyridin-2-yl or 2-amino-pyridin-4-yl;

and (g) is —X$_1$—(CH(R$_x$))$_2$—Ar$_7$ when W is CH; wherein X$_1$ is O or S, R$_x$ is H or C$_{1-4}$-alkyl, and Ar$_7$ is pyridinyl, pyrimidinyl, 1,2,3,4-tetrahydro-[1,8]naphthyridinyl, imidazo[1,2-a]pyridinyl, or quinolinyl such that the point of attachment to 1,2,3,4-tetrahydro-[1,8]naphthyridinyl is at the 6 or 7 position, and the point of attachment to quinolinyl is at the 2, 3, or 4-position;

wherein Ar$_7$ is optionally substituted with one to three substituents independently selected from the group consisting of C$_{1-4}$alkyl, amino(C$_{1-4}$)alkyl, (C$_{1-4}$alkyl)amino-(C$_{1-4}$)alkyl, di(C$_{1-4}$alkyl)amino-(C$_{1-4}$)alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

provided that when Q is —O(CH$_2$)$_2$—Ar$_7$ and A$_1$ and A$_2$ are 4-methoxy-phenyl, Ar$_7$ is other than unsubstituted pyridin-2-yl or unsubstituted pyridin-3-yl;

wherein a nitrogen atom of Ar$_1$, Ar$_2$, Ar$_3$, Ar$_4$, Ar$_5$, Ar$_6$, and Ar$_7$ is optionally substituted with oxo;

and enantiomers, diastereomers, tautomers, solvates, and pharmaceutically acceptable salts thereof.

BRIEF DESCRIPTION OF THE DRAWINGS

FIG. 1 shows a MALDI-TOF ANALYSIS of a Prokineticin-1 ligand preparation mixture. The mixture includes a four C-terminal residue truncated product (MW=9172), and a full-length prokineticin-1 ligand (MW=9668).

FIG. 2 shows a cumulative concentration-response curve evoked in the short-circuit current (Isc) response to PK1 peptide in PK1 exposed rat ileal tissues mounted in Ussing-type ion flux chambers.

FIG. 3 is a graphical representation that shows that Compound 3 of the present invention suppresses the PK1-evoked stimulation of gut secretion in rat ileum, without inhibiting the stimulatory action of an unrelated secretagogue.

FIG. 4 is a graphical representation that shows that Compound 3 of the present invention suppresses the Cholera toxin-evoked stimulation of gut secretion in rat ileum, without inhibiting the stimulatory action of an unrelated secretagogue.

FIG. 5 shows that Compound 3 of the present invention suppresses *Vibrio cholera* toxin induced increased in baseline Isc of muscle-stripped rat ileum mucosa.

DETAILED DESCRIPTION OF THE INVENTION

As used herein, the following terms are intended to have the following meanings:

With reference to substituents, the term "independently" means that when more than one of such substituent is possible, such substituents may be the same or different from each other. Therefore, designated numbers of carbon atoms (e.g. C$_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom with a group such as hydroxyl and alkoxy. In substituent groups with multiple alkyl groups such as (C$_{1-6}$alkyl)$_2$-amino- the C$_{1-6}$alkyl groups of the dialkylamino may be the same or different.

"Halogenated alkyl" refers to a saturated branched or straight chain alkyl radical derived by removal of 1 hydrogen atom from the parent alkyl; the parent alkyl chain contains from 1 to 8 carbon atoms with 1 or more hydrogen atoms substituted with halogen atoms up to and including substitution of all hydrogen atoms with halogen. Preferred halogenated alkyl groups include trifluoromethyl substituted alkyls and perfluorinated alkyls; more preferred fluorinated alkyls include trifluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, monocyclic or polycyclic hydrocarbon rings of from 3 to 20 carbon atom members (preferably from 3 to 14 carbon atom members). Examples of such rings include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), a 5 or 6 membered heteroaryl ring (containing one of O, S or N and, optionally, one additional nitrogen) to form a heteroaryl fused cycloalkyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. The term heterocyclyl includes a heterocyclyl ring fused to a benzene ring (benzo fused heterocyclyl) such as

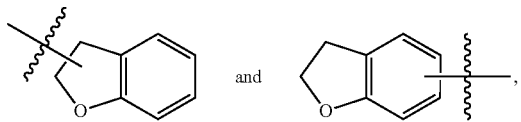

a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For such compounds in which the heterocyclyl ring is fused to a moiety as described above, the point of attachment is through the heterocycyl ring portion of the compound. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzo fused heteroaryl) such as

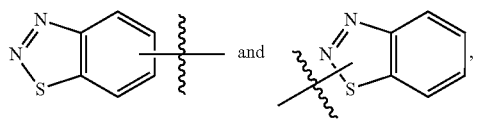

a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). For such compounds in which the heteroaryl ring is fused to a moiety as described above, the point of attachment is through the heteroaryl ring portion of the compound. Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "oxo" whether used alone or as part of a substituent group refers to an O= to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

As used herein, positions on a tetrahydro[1,8]naphthyridinyl substituent will be referred to using the following numbering system:

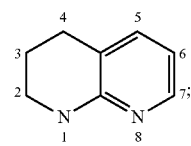

however, one of ordinary skill in the art will recognize that the numbering of the tetrahydro[1,8]naphthyridinyl ring system in a compound described herein, such as those shown in a specific example, may differ from that shown above.

Throughout this disclosure, the terminal portion of the designated side chain is described first, followed by the adjacent functionality toward the point of attachment. Thus, for example, a "phenyl$C_{1-6}$alkylaminocarbonyl$C_{1-6}$alkyl" substituent refers to a group of the formula

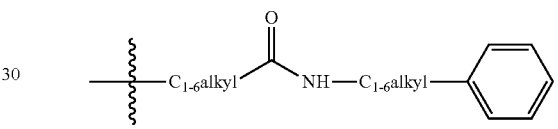

Embodiments of the present invention include compounds of Formula (I) wherein:
(i) $A_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of $C_{1-4}$alkyl, $C_{1-4}$alkoxy, nitro, fluoro, chloro, iodo, halogenated $C_{1-4}$alkyl, halogenated $C_{1-4}$alkoxy, and $C_{1-4}$alkylthio; provided that $A_1$ is other than 3,5-di-t-butyl-phenyl;
(ii) $A_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of $C_{1-3}$alkyl, methoxy, fluoro, chloro, trifluoromethyl, trifluoromethoxy, and methylthio;
(iii) $A_1$ is substituted phenyl, heteroaryl, or a benzofused heterocyclyl selected from the group consisting of benzo[1,3]dioxalyl and 2,3-dihydro-benzofuranyl; wherein substituted phenyl and heteroaryl are optionally substituted with one to three substituents independently selected from the group consisting of $C_{1-3}$alkyl, methoxy, fluoro and methylthio;
(iv) $A_1$ is substituted phenyl, benzotriazolyl, benzofuranyl, benzo[1,3]dioxalyl, or 2,3-dihydro-benzofuranyl; wherein phenyl is substituted with, and benzotriazolyl and benzofuranyl are optionally substituted with, one to three substituents independently selected from the group consisting of $C_{1-4}$alkyl, $C_{1-4}$alkoxy, nitro, fluoro, chloro, iodo, halogenated $C_{1-4}$alkyl, halogenated $C_{1-4}$alkoxy, and $C_{1-4}$alkylthio; provided that $A_1$ is other than 3,5-di-t-butyl-phenyl;

(v) $A_1$ is substituted phenyl, benzotriazolyl, benzofuranyl, benzo[1,3]dioxalyl, or 2,3-dihydro-benzofuranyl; wherein phenyl is substituted at the 4-position with methoxy, fluoro, or methylthio; and wherein $A_1$ other than substituted phenyl is optionally substituted with one to two substituents independently selected from the group consisting of methyl, methoxy, fluoro and methylthio;

(vi) $L_1$ is —$(CH_2)_r$—, wherein $L_1$ is optionally substituted with one to two substituents independently selected from the group consisting of $C_{1-4}$alkyl and $C_{2-4}$alkenyl, and r is 1 or 2;

(vii) $L_1$ is —$CH_2$—;

(viii) P is —$(CH_2)_{1-2}$— when $A_2$ is phenyl, benzofused heterocyclyl, heteroaryl, or $C_{3-8}$cycloalkyl; alternatively, P is —$(CH_2)_{4-6}$—, when $A_2$ is hydrogen, $C_{1-4}$alkoxy, or $C_{1-4}$alkoxycarbonyl;

(ix) P is —$CH_2$— when $A_2$ is phenyl, benzofused heterocyclyl, heteroaryl, or $C_{3-8}$cycloalkyl; alternatively, P is —$(CH_2)_{4-6}$—, when $A_2$ is hydrogen, $C_{1-4}$alkoxy, or $C_{1-4}$alkoxycarbonyl;

(x) $A_2$ is hydrogen, $C_{1-4}$alkoxy, $C_{1-4}$alkoxycarbonyl, phenyl, benzofused heterocyclyl, heteroaryl other than pyridin-4-yl, or $C_{3-8}$cycloalkyl; wherein phenyl, heteroaryl and $C_{3-8}$cycloalkyl are optionally substituted with one to two substituents independently selected from the group consisting of $C_{1-6}$alkyl, $C_{1-6}$alkoxy, fluoro, chloro, halogenated $C_{1-6}$alkoxy, phenyl, N-isoindole-1,3-dione, $C_{1-6}$alkylthio, $C_{1-6}$alkylsulfonyl, $C_{1-6}$alkoxycarbonyl, nitro, hydroxy, and $C_{1-6}$alkylcarbonylamino; such that no more than one substituent on $A_2$ is phenyl or N-isoindole-1,3-dione; and provided that $A_2$ is other than 3,5-di-t-butyl-phenyl;

(xi) $A_2$ is $C_{1-4}$alkoxy, phenyl, benzofused heterocyclyl, or a heteroaryl other than pyridin-4-yl; wherein phenyl and heteroaryl are optionally substituted with one to two substituents independently selected from the group consisting of $C_{1-4}$alkyl, $C_{1-4}$alkoxy, fluoro, chloro, halogenated $C_{1-4}$alkoxy, N-isoindole-1,3-dione, $C_{1-4}$alkylthio, $C_{1-4}$alkylsulfonyl, $C_{1-4}$alkoxycarbonyl, nitro, hydroxy, and $C_{1-4}$alkylcarbonylamino; such that no more than one substituent on $A_2$ is N-isoindole-1,3-dione; and provided that $A_2$ is other than 3,5-di-t-butyl-phenyl;

(xii) $A_2$ is $C_{1-4}$alkoxy, phenyl, benzofused heterocyclyl, or a heteroaryl other than pyridin-4-yl; wherein phenyl and heteroaryl are optionally substituted with one to two substituents independently selected from the group consisting of $C_{1-4}$alkoxy, fluoro, halogenated $C_{1-4}$alkoxy, $C_{1-4}$alkylthio, $C_{1-4}$alkylsulfonyl, $C_{1-4}$alkoxycarbonyl, nitro, and hydroxy;

(xiii) $A_2$ is $C_{1-4}$alkoxy, phenyl, 2,3-dihydro-benzofuranyl, indolyl, benzofuranyl, pyridin-3-yl, or benzothiophenyl; wherein $A_2$ other than $C_{1-4}$alkoxy is optionally substituted with one to two substituents independently selected from the group consisting of $C_{1-4}$alkoxy, fluoro, fluorinated $C_{1-4}$alkoxy, $C_{1-4}$alkylthio, $C_{1-4}$alkylsulfonyl, $C_{1-4}$alkoxycarbonyl, nitro, and hydroxy;

(xiv) W is N or CH;

(xv) W is N;

(xvi) Q is selected from the group consisting of (a)-(g) wherein:
  (a) is —$NH(CH_2)_2$—$Ar_1$ wherein $Ar_1$ is pyridinyl substituted with one to three $C_{1-4}$alkyl substituents or a substituent selected from the group consisting of $C_{1-4}$alkoxy and amino;
  (b) is —$NHCH_2$—$Ar_2$ wherein $Ar_2$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein $Ar_2$ is optionally substituted with one to three substituents independently selected from the group consisting of $C_{1-4}$alkyl, trifluoromethyl, $C_{1-4}$alkoxy, amino, ($C_{1-6}$alkyl)amino, and di($C_{1-6}$alkyl)amino;

wherein the $C_{1-6}$alkyl group of ($C_{1-6}$alkyl)amino and di($C_{1-6}$alkyl)amino is optionally substituted with ($C_{1-4}$alkyl)amino, di($C_{1-4}$alkyl)amino, $C_{1-4}$alkoxy, $C_{1-4}$alkylthio, hydroxy, a 5 to 6 membered heteroaryl, or a 5 to 6 membered heterocyclyl; wherein a nitrogen atom of the 5 to 6 membered heterocyclyl is optionally substituted with a $C_{1-4}$alkyl substituent;

and wherein pyridin-2-yl and pyridin-3-yl are optionally further substituted with N-pyrrolidinyl, N-piperazinyl, N-piperidinyl, N-morpholinyl, N-thiomorpholinyl, and phenyl; wherein the phenyl substituent of pyridin-2-yl and pyridin-3-yl is optionally substituted with one to three substituents independently selected from the group consisting of $C_{1-4}$alkyl, $C_{1-4}$alkoxy, and halogen;

provided that when Q is —$NHCH_2$(2-amino-pyridin-3-yl), and $A_1$ is pyridin-4-yl, 4-$C_{1-6}$alkyl-phenyl, 3,4-dichloro-phenyl, or 4-methanesulfonyl-phenyl, $A_2$ is other than 4-methoxy-phenyl;

provided that when Q is —$NHCH_2$(2-amino-pyridin-3-yl), $L_1$ is —$(CH_2)_2$— or —$(CH_2)_5$—, and $A_1$ is methoxy, $A_2$ is other than 4-difluoromethoxy-phenyl or 4-methoxy-phenyl;

provided that when Q is —$NHCH_2$(2-amino-pyridin-3-yl), and $A_1$ is benzotriazol-1-yl, $A_2$ is other than 4-difluoromethoxy-phenyl;

provided that when Q is —$NHCH_2$(2-amino-pyridin-3-yl), $L_1$ is —$(CH_2)_3$—, and $A_1$ is pyrrol-1-yl, $A_2$ is other than 4-methoxy-phenyl;

provided that when Q is —$NHCH_2$(2-amino-pyridin-3-yl), $L_1$ is —$(CH_2)_2$—, and $A_1$ is 4-nitro-phenyl or ethoxy, $A_2$ is other than 4-methoxy-phenyl;

provided that when Q is —$NHCH_2$(2-amino-pyridin-3-yl), and $A_1$ is 4-fluoro-phenyl, $A_2$ is other than 4-fluoro-phenyl;

provided that when Q is —$NHCH_2$(6-amino-pyridin-2-yl), and $A_1$ is 4-fluoro-phenyl, $A_2$ is other than 4-trifluoromethoxy-phenyl;

provided that when Q is —$NHCH_2$(6-methyl-pyridin-2-yl), and $A_1$ is 4-methoxy-phenyl, $A_2$ is other than 4-methoxy-phenyl;

provided that when Q is —$NHCH_2$(imidazo[1,2-a]pyridinyl), and $A_1$ is 4-fluoro-phenyl, $A_2$ is other than 4-methoxy-phenyl;

provided that when Q is —$NHCH_2$(pyridin-4-yl), and $A_1$ is unsubstituted phenyl or 3,4-dichloro-phenyl, $A_2$ is other than 4-methoxy-phenyl;

provided that when Q is —$NHCH_2$(4,6-dimethyl-pyridin-3-yl), and $A_1$ is 4-methoxy-phenyl, -P-$A_2$ is other than —$(CH_2)_5$-methoxy;

provided that when Q is —$NHCH_2$(4,6-dimethyl-pyridin-3-yl), $L_1$ is —$(CH_2)_2$—, and $A_1$ is pyrazol-1-yl, $A_2$ is other than 4-difluoromethoxy-phenyl;

provided that when Q is —$NHCH_2$(4,6-dimethyl-pyridin-3-yl) and $A_1$ is 4-methoxy-phenyl, $A_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(c) is —CH$_2$NHCH$_2$—Ar$_3$, wherein W is N or CH, and Ar$_3$ is pyridinyl optionally substituted with amino;

(d) is —(CH$_2$)$_2$—Ar$_4$, wherein Ar$_4$ is pyridinyl, or pyrimidinyl; wherein Ar$_4$ is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

(e) is —CH=CH-pyridinyl;

(f) is —O—CH(R$_1$)—Ar$_6$ when W is CH; or, (f) is —S—CH(R$_1$)—Ar$_6$ and W is N or CH; wherein R$_1$ is hydrogen or C$_{1-4}$alkyl, and Ar$_6$ is pyridinyl or pyrimidinyl; wherein Ar$_6$ is optionally substituted with one to three substituents independently selected from the group consisting of C$_{1-4}$alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

provided that when Q is —O—CH(R$_1$)—Ar$_6$, A$_1$ and A$_2$ are 4-methoxy-phenyl, and R$_1$ is hydrogen, Ar$_6$ is other than unsubstituted pyridin-2-yl or 2-amino-pyridin-4-yl; and (g) is —X$_1$—(CH(R$_x$))$_2$—Ar$_7$ and W is CH; wherein X$_1$ is O, R$_x$ is H, and Ar$_7$ is pyridinyl or pyrimidinyl; wherein Ar$_7$ is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

provided that when Q is —O(CH$_2$)$_2$—Ar$_7$ and A$_1$ and A$_2$ are 4-methoxy-phenyl, Ar$_7$ is other than unsubstituted pyridin-2-yl or unsubstituted pyridin-3-yl;

wherein a nitrogen atom of Ar$_1$, Ar$_2$, Ar$_3$, Ar$_4$, Ar$_6$, and Ar$_7$ is optionally substituted with oxo;

(xvii) Q is selected from the group consisting of (b) and (d) wherein:

(b) is —NHCH$_2$—Ar$_2$ wherein Ar$_2$ is pyridinyl, pyrimidinyl, or quinolinyl; such that the point of attachment to quinolinyl is at the 2, 3, or 4-position; and wherein Ar$_2$ is optionally substituted with one to three substituents independently selected from the group consisting of C$_{1-4}$alkyl, trifluoromethyl, C$_{1-4}$alkoxy, amino, (C$_{1-4}$alkyl)amino, and di(C$_{1-4}$alkyl)amino;

wherein the C$_{1-4}$alkyl group of (C$_{1-4}$alkyl)amino and di(C$_{1-4}$alkyl)amino is optionally substituted with (C$_{1-4}$alkyl)amino, di(C$_{1-4}$alkyl)amino, C$_{1-4}$alkoxy, C$_{1-4}$alkylthio, hydroxy, a 5 to 6 membered heteroaryl, or a 5 to 6 membered heterocyclyl;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-6}$alkyl-phenyl, 3,4-dichloro-phenyl, or 4-methanesulfonyl-phenyl, A$_2$ is other than 4-methoxy-phenyl;

provided that when Q is —NHCH$_2$(2-amino-pyridin-3-yl), L$_1$ is —(CH$_2$)$_2$— or —(CH$_2$)$_5$—, and A$_1$ is methoxy, A$_2$ is other than 4-difluoromethoxy-phenyl or 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, -P-A$_2$ is other than —(CH$_2$)$_5$-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(d) is —(CH$_2$)$_2$—Ar$_4$ and W is CH; wherein Ar$_4$ is pyridinyl is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

wherein a nitrogen atom of Ar$_2$ and Ar$_4$ is optionally substituted with oxo;

(xviii) Q is selected from the group consisting of (b) and (d) wherein:

(b) is —NHCH$_2$—Ar$_2$ wherein Ar$_2$ is pyridin-2-yl, pyridin-3-yl, or pyrimidinyl; wherein Ar$_2$ is optionally substituted with one to three substituents independently selected from the group consisting of $C_{1-4}$alkyl, trifluoromethyl, $C_{1-4}$alkoxy, amino, and $(C_{1-4}$alkyl)amino;
wherein the $C_{1-4}$alkyl group of $(C_{1-4}$alkyl)amino is optionally substituted with di($C_{1-4}$alkyl)amino, $C_{1-4}$alkoxy, or hydroxy;
and wherein pyridin-2-yl and pyridin-3-yl are optionally further substituted with N-morpholinyl;
provided that when Q is —NHCH$_2$(2-amino-pyridin-3-yl), and A$_1$ is pyridin-4-yl, 4-$C_{1-6}$alkyl-phenyl, 3,4-dichloro-phenyl, or 4-methanesulfonyl-phenyl, A$_2$ is other than 4-methoxy-phenyl;
provided that when Q is —NHCH$_2$(2-amino-pyridin-3-yl), L$_1$ is —(CH$_2$)$_2$— or —(CH$_2$)$_5$—, and A$_1$ is methoxy, A$_2$ is 4-difluoromethoxy-phenyl or 4-methoxy-phenyl;
provided that when Q is —NHCH$_2$(2-amino-pyridin-3-yl), and A$_1$ is benzotriazol-1-yl, A$_2$ is other than 4-difluoromethoxy-phenyl;
provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;
provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;
provided that when Q is —NHCH$_2$(2-amino-pyridin-3-yl), and A$_1$ is 4-fluoro-phenyl, A$_2$ is other than 4-fluoro-phenyl;
provided that when Q is —NHCH$_2$(6-amino-pyridin-2-yl), and A$_1$ is 4-fluoro-phenyl, A$_2$ is other than 4-trifluoromethoxy-phenyl;
provided that when Q is —NHCH$_2$(6-methyl-pyridin-2-yl), and A$_1$ is 4-methoxy-phenyl, A$_2$ is other than 4-methoxy-phenyl;
provided that when Q is —NHCH$_2$(imidazo[1,2-a]pyridinyl), and A$_1$ is 4-fluoro-phenyl, A$_2$ is other than 4-methoxy-phenyl;
provided that when Q is —NHCH$_2$(pyridin-4-yl), and A$_1$ is unsubstituted phenyl or 3,4-dichloro-phenyl, A$_2$ is other than 4-methoxy-phenyl;
provided that when Q is —NHCH$_2$(4,6-dimethyl-pyridin-3-yl), and A$_1$ is 4-methoxy-phenyl, -P-A$_2$ is other than —(CH$_2$)$_5$-methoxy;
provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;
provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;
provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;
and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;
(d) is —(CH$_2$)$_2$—Ar$_4$ and W is CH; wherein Ar$_4$ is pyridinyl is optionally substituted with amino;
wherein a nitrogen atom of Ar$_2$ and Ar$_4$ is optionally substituted with oxo;
(xviv) Q is —NHCH$_2$—Ar$_2$ wherein Ar$_2$ is unsubstituted pyridin-2-yl, 4,6-dimethyl-pyridin-3-yl, 2-amino-pyridin-3-yl, or 2-((C$_{1-4}$alkyl)amino)-pyridin-3-yl;
wherein the C$_{1-4}$alkyl group of (C$_{1-4}$alkyl)amino is optionally substituted with di(C$_{1-4}$alkyl)amino, C$_{1-4}$alkoxy, or hydroxy;
and wherein 2-amino-pyridin-3-yl is optionally further substituted with 4,6-dimethyl or 4-methoxy;
provided that when Q is —NHCH$_2$(2-amino-pyridin-3-yl), and A$_1$ is pyridin-4-yl, 4-t-butyl-phenyl, 3,4-dichloro-phenyl, or 4-methanesulfonyl-phenyl, A$_2$ is other than 4-methoxy-phenyl;
provided that when Q is —NHCH$_2$(2-amino-pyridin-3-yl), L$_1$ is —(CH$_2$)$_2$— or —(CH$_2$)$_5$—, and A$_1$ is methoxy, A$_2$ is other than 4-difluoromethoxy-phenyl or 4-methoxy-phenyl;
provided that when Q is —NHCH$_2$(2-amino-pyridin-3-yl), and A$_1$ is benzotriazol-1-yl, A$_2$ is other than 4-difluoromethoxy-phenyl;
provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;
provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;
provided that when Q is —NHCH$_2$(2-amino-pyridin-3-yl), and A$_1$ is 4-fluoro-phenyl, A$_2$ is other than 4-fluoro-phenyl;
provided that when Q is —NHCH$_2$(6-amino-pyridin-2-yl), and A$_1$ is 4-fluoro-phenyl, A$_2$ is other than 4-trifluoromethoxy-phenyl;
provided that when Q is —NHCH$_2$(6-methyl-pyridin-2-yl), and A$_1$ is 4-methoxy-phenyl, A$_2$ is other than 4-methoxy-phenyl;
provided that when Q is —NHCH$_2$(imidazo[1,2-a]pyridinyl), and A$_1$ is 4-fluoro-phenyl, A$_2$ is other than 4-methoxy-phenyl;
provided that when Q is —NHCH$_2$(pyridin-4-yl), and A$_1$ is unsubstituted phenyl or 3,4-dichloro-phenyl, A$_2$ is other than 4-methoxy-phenyl;
provided that when Q is —NHCH$_2$(4,6-dimethyl-pyridin-3-yl), and A$_1$ is 4-methoxy-phenyl, -P-A$_2$ is other than —(CH$_2$)$_5$-methoxy;
provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;
provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;
provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;
and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

wherein a nitrogen atom of $Ar_2$ and $Ar_4$ is optionally substituted with oxo;
and combinations of (i) through (xviv) above.

One aspect of the present invention is directed to compositions comprising a compound of Formula (I)

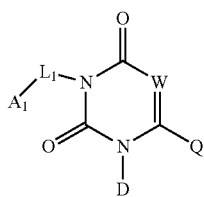

Formula (I)

wherein:
$A_1$ is $CF_3$, aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of $C_{1-4}$alkyl, $C_{1-4}$alkoxy, nitro, fluoro, chloro, iodo, halogenated $C_{1-4}$alkyl, halogenated $C_{1-4}$alkoxy, and $C_{1-4}$alkylthio; provided that $A_1$ is other than 3,5-di-t-butyl-phenyl;
$L_1$ is —$(CH_2)_r$—, wherein $L_1$ is optionally substituted with one to two substituents independently selected from the group consisting of $C_{1-4}$alkyl and $C_{2-4}$alkenyl and r is 1 or 2;
D is -P-$A_2$;
wherein P is —$(CH_2)_{1-2}$— when $A_2$ is phenyl, benzofused heterocyclyl, heteroaryl, or $C_{3-8}$cycloalkyl; alternatively, P is —$(CH_2)_{4-6}$—, when $A_2$ is hydrogen, $C_{1-4}$alkoxy, or $C_{1-4}$alkoxycarbonyl;
$A_2$ is hydrogen, $C_{1-4}$alkoxy, $C_{1-4}$alkoxycarbonyl, phenyl, benzofused heterocyclyl, heteroaryl other than pyridin-4-yl, tetrahydro-pyranyl, piperidinyl, or $C_{3-8}$cycloalkyl; wherein phenyl, heteroaryl and $C_{3-8}$cycloalkyl are optionally substituted with one to two substituents independently selected from the group consisting of $C_{1-6}$alkyl, $C_{1-6}$alkoxy, fluoro, chloro, halogenated $C_{1-6}$alkoxy, phenyl, N-isoindole-1,3-dione, $C_{1-6}$alkylthio, $C_{1-6}$alkylsulfonyl, $C_{1-6}$alkoxycarbonyl, nitro, hydroxy, and $C_{1-6}$alkylcarbonylamino; provided that no more than one substituent on $A_2$ is phenyl or N-isoindole-1,3-dione; and provided that $A_2$ is other than 3,5-di-t-butyl-phenyl;
W is CH or N;
Q is selected from the group consisting of (a)-(g) wherein:
(a) —NH$(CH_2)_2$—$Ar_1$ wherein $Ar_1$ is pyridinyl substituted with one to three $C_{1-4}$alkyl substituents or a substituent selected from the group consisting of $C_{1-4}$alkoxy and amino;
(b) is —NHCH$(R_z)$—$Ar_2$ wherein $R_z$ is H or $C_{1-3}$alkyl; $Ar_2$ is pyridinyl, pyrimidinyl, pyrazinyl,

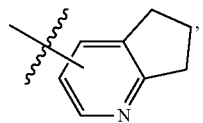

1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein $Ar_2$ is optionally substituted with one to three substituents independently selected from the group consisting of $C_{1-4}$alkyl, trifluoromethyl, hydroxyl-$C_{1-4}$alkyl, amino$(C_{1-4})$alkyl, $(C_{1-4}$alkyl)amino-$(C_{1-4})$alkyl, di$(C_{1-4}$alkyl)amino-$(C_{1-4})$alkyl, $C_{1-4}$alkoxy, $C_{3-8}$ cycloalkylamino, amino, $(C_{1-6}$alkyl)amino, and di$(C_{1-6}$alkyl)amino; or $Ar_2$ is optionally substituted with one amino group and three substituents independently selected from the group consisting of $C_{1-4}$alkyl and $C_{1-4}$alkoxy;
wherein the $C_{1-6}$alkyl group of $(C_{1-6}$alkyl)amino and di$(C_{1-6}$alkyl)amino is optionally substituted with $(C_{1-4}$alkyl)amino, di$(C_{1-4}$alkyl)amino, $C_{1-4}$alkoxy, $C_{1-4}$alkylthio, hydroxy, a 5 to 6 membered heteroaryl, or a 5 to 6 membered heterocyclyl; wherein a nitrogen atom of the 5 to 6 membered heterocyclyl is optionally substituted with a $C_{1-4}$alkyl substituent;
and wherein pyridin-2-yl and pyridin-3-yl are optionally further substituted with N-pyrrolidinyl, N-piperazinyl, N-piperidinyl, N-morpholinyl, N-thiomorpholinyl, —$CH_2$—O—$CH_2$—PH, and phenyl; wherein the phenyl substituent of pyridin-2-yl and pyridin-3-yl is optionally substituted with one to three substituents independently selected from the group consisting of $C_{1-4}$alkyl, $C_{1-4}$alkoxy, and halogen;
provided that when Q is —NHCH$_2$(2-amino-pyridin-3-yl), and $A_1$ is pyridin-4-yl, 4-$C_{1-4}$alkyl-phenyl, or 3,4-dichloro-phenyl, $A_2$ is other than 4-methoxy-phenyl;
provided that when Q is —NHCH$_2$(2-amino-pyridin-3-yl), and $A_1$ is benzotriazol-1-yl, $A_2$ is other than 4-difluoromethoxy-phenyl;
provided that when Q is —NHCH$_2$(2-amino-pyridin-3-yl), $L_1$ is —$(CH_2)_2$—, and $A_1$ is 4-nitro-phenyl, $A_2$ is other than 4-methoxy-phenyl;
provided that when Q is —NHCH$_2$(2-amino-pyridin-3-yl), and $A_1$ is 4-fluoro-phenyl, $A_2$ is other than 4-fluoro-phenyl;
provided that when Q is —NHCH$_2$(6-amino-pyridin-2-yl), and $A_1$ is 4-fluoro-phenyl, $A_2$ is other than 4-trifluoromethoxy-phenyl;
provided that when Q is —NHCH$_2$(6-methyl-pyridin-2-yl), and $A_1$ is 4-methoxy-phenyl, $A_2$ is other than 4-methoxy-phenyl;
provided that when Q is —NHCH$_2$(imidazo[1,2-a]pyridinyl), and $A_1$ is 4-fluoro-phenyl, $A_2$ is other than 4-methoxy-phenyl;
provided that when Q is —NHCH$_2$(pyridin-4-yl), and $A_1$ is unsubstituted phenyl or 3,4-dichloro-phenyl, $A_2$ is other than 4-methoxy-phenyl;
provided that when Q is —NHCH$_2$(4,6-dimethyl-pyridin-3-yl), and $A_1$ is 4-methoxy-phenyl, -P-$A_2$ is other than —$(CH_2)_5$-methoxy;
provided that when Q is —NHCH$_2$(4,6-dimethyl-pyridin-3-yl), $L_1$ is —$(CH_2)_2$—, and $A_1$ is pyrazol-1-yl, $A_2$ is other than 4-difluoromethoxy-phenyl;
provided that when Q is —NHCH$_2$(4,6-dimethyl-pyridin-3-yl) and $A_1$ is 4-methoxy-phenyl, $A_2$ is other than 2-ethyl-phenyl, 4-ethyl-phenyl, 3-methoxy-phenyl, and 3-nitro-phenyl;
provided that when Q is —NHCH$_2$(4,6-dimethyl-pyridin-3-yl) and $A_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluorophenyl, 2,6-difluoro-4-methoxy-phenyl, or 4-trifluoromethoxy-phenyl, $A_2$ is other than 4-difluoromethoxy-phenyl;

and, provided that when Q is —NHCH$_2$(4,6-dimethyl-pyridin-3-yl) and $A_1$ is 3-nitro-4-methoxy-phenyl, 2,6-difluoro-4-methoxy-phenyl, or 3,4-dichloro-phenyl, $A_2$ is other than 4-methoxy-phenyl;

(c) is —CH$_2$NHCH$_2$—Ar$_3$, wherein W is N or CH, and Ar$_a$ is pyridinyl optionally substituted with amino;

(d) is —(CH$_2$)$_2$—Ar$_4$, wherein Ar$_4$ is pyridinyl, or pyrimidinyl; wherein Ar$_4$ is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

(e) is —CH=CH-pyridinyl;

(f) is —O—CH(R$_1$)—Ar$_6$ when W is CH; or, (f) is —S—CH(R$_1$)—Ar$_6$ and W is N or CH; wherein R$_1$ is hydrogen or C$_{1-4}$alkyl, and Ar$_6$ is pyridinyl or pyrimidinyl; wherein Ar$_6$ is optionally substituted with one to three substituents independently selected from the group consisting of C$_{1-4}$alkyl, C$_{1-4}$alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

provided that when Q is —O—CH(R$_1$)—Ar$_6$, $A_1$ and $A_2$ are 4-methoxy-phenyl, and R$_1$ is hydrogen, Ar$_6$ is other than unsubstituted pyridin-2-yl or 2-amino-pyridin-4-yl;

and (g) is —X$_1$—(CH(R$_x$))$_2$—Ar$_7$ and W is CH; wherein X$_1$ is O, R$_x$ is H, and Ar$_7$ is pyridinyl or pyrimidinyl; wherein Ar$_7$ is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

provided that when Q is —O(CH$_2$)$_2$—Ar$_7$ and $A_1$ and $A_2$ are 4-methoxy-phenyl, Ar$_7$ is other than unsubstituted pyridin-2-yl or unsubstituted pyridin-3-yl;

wherein a nitrogen atom of Ar$_1$, Ar$_2$, Ar$_3$, Ar$_4$, Ar$_6$, and Ar$_7$ is optionally substituted with oxo;

and enantiomers, diastereomers, tautomers, solvates, and pharmaceutically acceptable salts thereof.

Another aspect of the present invention is directed to compositions comprising a compound of Formula (I)

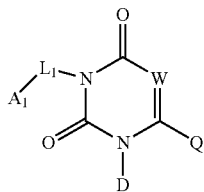

Formula (I)

wherein:

A$_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of C$_{1-3}$alkyl, methoxy, fluoro, chloro, trifluoromethyl, trifluoromethoxy, and methylthio;

L$_1$ is —CH$_2$—;

D is -P-A$_2$;

wherein P is —CH$_2$— when A$_2$ is phenyl, benzofused heterocyclyl, or heteroaryl; alternatively, P is —(CH$_2$)$_{4-6}$—, when A$_2$ is C$_{1-4}$alkoxy;

A$_2$ is C$_{1-4}$alkoxy, phenyl, benzofused heterocyclyl, or a heteroaryl other than pyridin-4-yl; wherein phenyl and heteroaryl are optionally substituted with one to two substituents independently selected from the group consisting of C$_{1-4}$alkyl, C$_{1-4}$alkoxy, fluoro, chloro, halogenated C$_{1-4}$alkoxy, N-isoindole-1,3-dione, C$_{1-4}$alkylthio, C$_{1-4}$alkylsulfonyl, C$_{1-4}$alkoxycarbonyl, nitro, hydroxy, and C$_{1-4}$alkylcarbonylamino; provided that no more than one substituent on A$_2$ is N-isoindole-1,3-dione; and provided that A$_2$ is other than 3,5-di-t-butyl-phenyl;

W is N or CH;

Q is selected from the group consisting of (b) and (d) wherein:

(b) is —NHCH$_2$—Ar$_2$ wherein Ar$_2$ is pyridinyl, pyrimidinyl, or quinolinyl; such that the point of attachment to quinolinyl is at the 2, 3, or 4-position; and wherein Ar$_2$ is optionally substituted with one to three substituents independently selected from the group consisting of C$_{1-4}$alkyl, trifluoromethyl, C$_{1-4}$alkoxy, amino, (C$_{1-4}$alkyl)amino, and di(C$_{1-4}$alkyl)amino;

wherein the C$_{1-4}$alkyl group of (C$_{1-4}$alkyl)amino and di(C$_{1-4}$alkyl)amino is optionally substituted with (C$_{1-4}$alkyl)amino, di(C$_{1-4}$alkyl)amino, C$_{1-4}$alkoxy, C$_{1-4}$alkylthio, hydroxy, a 5 to 6 membered heteroaryl, or a 5 to 6 membered heterocyclyl;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-3}$alkyl-phenyl, or 3,4-dichloro-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, -P-A$_2$ is other than —(CH$_2$)$_5$-methoxy;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, and 3-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-trifluoromethyl-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(d) is —(CH$_2$)$_2$—Ar$_4$ and W is CH; wherein Ar$_4$ is pyridinyl is optionally substituted with one to two substituents independently selected from the group consisting of C$_{1-4}$alkyl, C$_{1-4}$alkoxy, amino, (C$_{1-6}$alkyl)amino, and di(C$_{1-6}$alkyl)amino;

wherein a nitrogen atom of Ar$_2$ and Ar$_4$ is optionally substituted with oxo;

and enantiomers, diastereomers, tautomers, solvates, and pharmaceutically acceptable salts thereof.

A further aspect of the present invention is directed to compositions comprising a compound of Formula (I) wherein:

A$_1$ is substituted phenyl, heteroaryl, or a benzofused heterocyclyl selected from the group consisting of benzo[1,3]dioxalyl and 2,3-dihydro-benzofuranyl; wherein substituted phenyl is substituted with, and heteroaryl is optionally substituted with, one to three substituents independently selected from the group consisting of C$_{1-3}$alkyl, methoxy, fluoro and methylthio;

L$_1$ is —CH$_2$—;

D is -P-A$_2$; wherein P is —CH$_2$— when A$_2$ is phenyl, benzofused heterocyclyl or heteroaryl; alternatively, P is —(CH$_2$)$_{4-6}$—, when A$_2$ is C$_{1-4}$alkoxy;

A$_2$ is C$_{1-4}$alkoxy, phenyl, benzofused heterocyclyl, or a heteroaryl other than pyridin-4-yl; wherein phenyl and heteroaryl are optionally substituted with one to two substituents independently selected from the group consisting of C$_{1-4}$alkoxy, fluoro, halogenated C$_{1-4}$alkoxy, C$_{1-4}$alkylthio, C$_{1-4}$alkylsulfonyl, C$_{1-4}$alkoxycarbonyl, nitro, and hydroxy;

W is N or CH;

Q is selected from the group consisting of (b) and (d) wherein:

(b) is —NHCH$_2$—Ar$_2$ wherein Ar$_2$ is pyridin-2-yl, pyridin-3-yl, or pyrimidinyl; wherein Ar$_2$ is optionally substituted with one to three substituents independently selected from the group consisting of C$_{1-4}$alkyl, trifluoromethyl, C$_{1-4}$alkoxy, amino, and (C$_{1-4}$alkyl)amino;

wherein the C$_{1-4}$alkyl group of (C$_{1-4}$alkyl)amino is optionally substituted with di(C$_{1-4}$alkyl)amino, C$_{1-4}$alkoxy, or hydroxy;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-3}$alkyl-phenyl or 3,4-dichloro-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, -P-A$_2$ is other than —(CH$_2$)$_5$-methoxy;

provided that when Q is —NHCH$_2$(4,6-dimethyl-pyridin-3-yl) and A$_1$ is 4-methoxy-phenyl, provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2,4-difluoro-phenyl, 2,6-difluoro-phenyl, 2,6-dichloro-phenyl, 2-chloro-4-fluoro-phenyl, or 2,6-difluoro-4-methoxy-phenyl, A$_2$ is other than 4-difluoromethoxy-phenyl;

and, provided that when Q is —NHCH$_2$(4,6-dimethyl-pyridin-3-yl) and A$_1$ is 2,6-difluoro-4-methoxy-phenyl or 3,4-dichloro-phenyl-A$_2$ is other than 4-methoxy-phenyl;

(d) is —(CH$_2$)$_2$—Ar$_4$ and W is CH; wherein Ar$_4$ is pyridinyl is optionally substituted with amino;

wherein a nitrogen atom of Ar$_2$ and Ar$_4$ is optionally substituted with oxo;

and enantiomers, diastereomers, tautomers, solvates, and pharmaceutically acceptable salts thereof.

Embodiments of the present invention are even further directed to compositions comprising a compound of Formula (I) wherein:

A$_1$ is substituted phenyl, benzotriazolyl, benzofuranyl, benzo[1,3]dioxalyl or 2,3-dihydro-benzofuranyl; wherein phenyl is substituted at the 4-position with methoxy, fluoro, or methylthio; and wherein A$_1$ other than substituted phenyl is optionally substituted with one to two substituents independently selected from the group consisting of methyl, methoxy, fluoro and methylthio;

L$_1$ is —CH$_2$—;

D is -P-A$_2$;

wherein P is —CH$_2$— when A$_2$ is phenyl, 2,3-dihydro-benzofuranyl, indolyl, benzofuranyl, pyridin-3-yl, or benzothiophenyl; alternatively, P is —(CH$_2$)$_{4-6}$—, when A$_2$ is C$_{1-4}$alkoxy;

A$_2$ is C$_{1-4}$alkoxy, phenyl, 2,3-dihydro-benzofuranyl, indolyl, benzofuranyl, pyridin-3-yl, or benzothiophenyl; wherein A$_2$ other than C$_{1-4}$alkoxy is optionally substituted with one to two substituents independently selected from the group consisting of C$_{1-4}$alkoxy, fluoro, fluorinated C$_{1-4}$alkoxy, C$_{1-4}$alkylthio, C$_{1-4}$alkylsulfonyl, C$_{1-4}$alkoxycarbonyl, nitro, and hydroxy;

W is N or CH;

Q is —NHCH$_2$—Ar$_2$ wherein Ar$_2$ is unsubstituted pyridin-2-yl, 4,6-dimethyl-pyridin-3-yl, 2-amino-pyridin-3-yl, or 2-((C$_{1-4}$alkyl)amino)-pyridin-3-yl;

wherein the C$_{1-4}$alkyl group of (C$_{1-4}$alkyl)amino is optionally substituted with di(C$_{1-4}$alkyl)amino, C$_{1-4}$alkoxy, or hydroxy;

and wherein 2-amino-pyridin-3-yl is optionally further substituted with 4,6-dimethyl or 4-methoxy;

provided that when Q is —NHCH$_2$(2-amino-pyridin-3-yl), and A$_1$ is pyridin-4-yl or 4-methyl-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH₂(6-methyl-pyridin-2-yl), and A₁ is 4-methoxy-phenyl, A₂ is other than 4-methoxy-phenyl;

provided that when Q is —NHCH₂(imidazo[1,2-a]pyridinyl), and A₁ is 4-fluoro-phenyl, A₂ is other than 4-methoxy-phenyl;

provided that when Q is —NHCH₂(4,6-dimethyl-pyridin-3-yl), and A₁ is 4-methoxy-phenyl, -P-A₂ is other than —(CH₂)₅-methoxy;

provided that when Q is —NHCH₂(4,6-dimethyl-pyridin-3-yl) and A₁ is 4-methoxy-phenyl, A₂ is other than 3-methoxy-phenyl or 3-nitro-phenyl;

and provided that when Q is —NHCH₂(4,6-dimethyl-pyridin-3-yl) and A₁ is benzotriazol-1-yl, A₂ is other than 4-difluoromethoxy-phenyl;

wherein a nitrogen atom of Ar₂ and Ar₄ is optionally substituted with oxo;

and enantiomers, diastereomers, tautomers, solvates, and pharmaceutically acceptable salts thereof.

Embodiments of the present invention are even further directed to compositions comprising a compound of Formula (I) wherein:

A₁ is substituted phenyl, benzotriazolyl, benzofuranyl, benzo[1,3]dioxalyl or 2,3-dihydro-benzofuranyl; wherein phenyl is substituted at the 4-position with methoxy, fluoro, or methylthio; and wherein A₁ other than substituted phenyl is optionally substituted with one to two substituents independently selected from the group consisting of methyl, methoxy, fluoro and methylthio;

L₁ is —CH₂—;

D is -P-A₂;

wherein P is —CH₂— when A₂ is phenyl, 2,3-dihydro-benzofuranyl, indolyl, benzofuranyl, pyridin-3-yl, or benzothiophenyl; alternatively, P is —(CH₂)₄₋₆—, when A₂ is $C_{1-4}$alkoxy;

A₂ is $C_{1-4}$alkoxy, phenyl, 2,3-dihydro-benzofuranyl, indolyl, benzofuranyl, pyridin-3-yl, or benzothiophenyl; wherein A₂ other than $C_{1-4}$alkoxy is optionally substituted with one to two substituents independently selected from the group consisting of $C_{1-4}$alkoxy, fluoro, fluorinated $C_{1-4}$alkoxy, $C_{1-4}$alkylthio, $C_{1-4}$alkylsulfonyl, $C_{1-4}$alkoxycarbonyl, nitro, and hydroxy;

W is N;

Q is —NHCH₂—Ar₂ wherein Ar₂ is unsubstituted pyridin-2-yl, 4,6-dimethyl-pyridin-3-yl, 2-amino-pyridin-3-yl, or 2-(($C_{1-4}$alkyl)amino)-pyridin-3-yl;

wherein the $C_{1-4}$alkyl group of ($C_{1-4}$alkyl)amino is optionally substituted with di($C_{1-4}$alkyl)amino, $C_{1-4}$alkoxy, or hydroxy;

and wherein 2-amino-pyridin-3-yl is optionally further substituted with 4,6-dimethyl or 4-methoxy;

provided that when Q is —NHCH₂(2-amino-pyridin-3-yl), and A₁ is pyridin-4-yl or 4-methyl-phenyl, A₂ is other than 4-methoxy-phenyl;

provided that when Q is —NHCH₂(2-amino-pyridin-3-yl), and A₁ is benzotriazol-1-yl, A₂ is other than 4-difluoromethoxy-phenyl;

provided that when Q is —NHCH₂(2-amino-pyridin-3-yl), and A₁ is 4-fluoro-phenyl, A₂ is other than 4-fluoro-phenyl;

provided that when Q is —NHCH₂(6-amino-pyridin-2-yl), and A₁ is 4-fluoro-phenyl, A₂ is other than 4-trifluoromethoxy-phenyl;

provided that when Q is —NHCH₂(6-methyl-pyridin-2-yl), and A₁ is 4-methoxy-phenyl, A₂ is other than 4-methoxy-phenyl;

provided that when Q is —NHCH₂(imidazo[1,2-a]pyridinyl), and A₁ is 4-fluoro-phenyl, A₂ is other than 4-methoxy-phenyl;

provided that when Q is —NHCH₂(4,6-dimethyl-pyridin-3-yl), and A₁ is 4-methoxy-phenyl, -P-A₂ is other than —(CH₂)₅-methoxy;

provided that when Q is —NHCH₂(4,6-dimethyl-pyridin-3-yl) and A₁ is 4-methoxy-phenyl, A₂ is other than 3-methoxy-phenyl or 3-nitro-phenyl;

and provided that when Q is —NHCH₂(4,6-dimethyl-pyridin-3-yl) and A₁ is benzotriazol-1-yl, A₂ is other than 4-difluoromethoxy-phenyl;

wherein a nitrogen atom of Ar₂ and Ar₄ is optionally substituted with oxo;

and enantiomers, diastereomers, tautomers, solvates, and pharmaceutically acceptable salts thereof.

A further embodiment of the present invention is directed to a pharmaceutical composition comprising Formula (I)

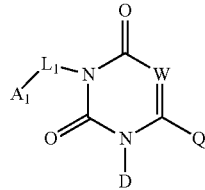

Formula (I)

selected from the group consisting of a compound of Formula (I) wherein A₁ is 4-methoxy-phenyl, L₁ is CH₂, D is 4-methoxy-phenylmethyl, W is N, and Q is

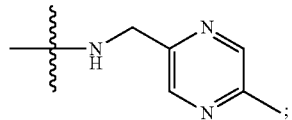 [SMILES: *NCc1cnc(C)cn1]

a compound of Formula (I) wherein A₁ is 4-methoxy-phenyl, L₁ is CH₂, D is 4-methoxy-phenylmethyl, W is N, and Q is

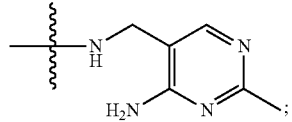

a compound of Formula (I) wherein A₁ is 4-chloro-phenyl, L₁ is CH₂, D is —(CH₂)₅OCH₃, W is N, and Q is

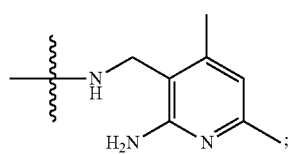 [SMILES: *NCc1c(C)cc(C)nc1N]

a compound of Formula (I) wherein A₁ is 3,4-dichloro-phenyl, L₁ is CH₂, D is 4-methoxy-phenylmethyl, W is N, and Q is 2-(pyridin-2-yl)ethyl-amino;

a compound of Formula (I) wherein A₁ is 3,4-dichloro-phenyl, L₁ is CH₂, D is 4-methoxy-phenylmethyl, W is N, and Q is pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-chloro-phenyl, $L_1$ is $CH_2$, D is 4-methoxy-phenylmethyl, W is N, and Q is 5-amino-pyridin-2-ylmethyl-amino;

a compound of Formula (I) wherein $A_1$ is 4-chloro-phenyl, $L_1$ is $CH_2$, D is 4-methoxy-phenylmethyl, W is N, and Q is 6-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 4-amino-pyrimidin-5-ylmethyl-amino;

a compound of Formula (I) wherein $A_1$ is 4-methoxy-phenyl, $L_1$ is $CH_2$, D is 4-methoxy-phenylmethyl, W is CH, and Q is 2-amino-pyridin-3-ylmethyl-aminomethyl;

a compound of Formula (I) wherein $A_1$ is 4-fluoro-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-amino-quinolin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-(2-amino-pyridin-3-yl)-ethylamino;

a compound of Formula (I) wherein $A_1$ is 4-fluoro-phenyl, $L_1$ is $CH_2$, D is 4-methoxy-phenylmethyl, W is N, and Q is 2-N-pyrrolidinyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-N-piperazinyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-N-piperidinyl-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-methylamino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-n-propylamino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-n-butylamino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-N-morpholino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-N-thiomorpholino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-ethylamino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-N-morpholino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 1,2,3,4-tetrahydro-[1,8]naphthyridin-7-ylmethyl-amino;

a compound of Formula (I) wherein $A_1$ is 4-methoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzofuran-2-yl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methylthio-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 6-(4-fluoro-phenyl)-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-amino-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-(2-dimethylamino-ethylamino)-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-(2-methoxy-ethylamino)-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-(2-hydroxy-ethylamino)-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-(2-amino-ethylamino)-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 2-cyclohexylamino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is N-oxo-2-amino-pyridin-3-ylmethyl-amino;

a compound of Formula (I) wherein $A_1$ is 4-methoxy-phenyl, $L_1$ is $CH_2$, D is 4-hydroxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-n-propylamino-pyridin-3-ylmethyl-amino;

a compound of Formula (I) wherein $A_1$ is 4-methoxy-phenyl, $L_1$ is $CH_2$, D is 4-difluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxycarbonyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methylcarbonylamino-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-trifluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is pyridin-2-ylmethyl-amino;

a compound of Formula (I) wherein $A_1$ is 4-methoxy-phenyl, $L_1$ is $CH_2$, D is 4-methoxy-phenylmethyl, W is N, and Q is pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is pyridin-4-ylmethyl-amino;

a compound of Formula (I) wherein $A_1$ is 3-methoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-cyano-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-trifluoromethoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-ethoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-nitro-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is CH(allyl), D is 4-methoxy-phenylmethyl, W is N, and Q is 2-amino-pyridin-3-ylmethyl-amino;

a compound of Formula (I) wherein $A_1$ is 4-trifluoromethyl-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(2-methoxy-ethylamino)-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(2-dimethylamino-ethylamino)-pyridin-3-ylmethyl-amino;

a compound of Formula (I) wherein $A_1$ is 4-methoxy-phenyl, $L_1$ is $CH_2$, D is 4-aminocarbonyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is N-oxo-pyridin-3-ylmethyl-amino;

a compound of Formula (I) wherein $A_1$ is 4-hydroxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 3-fluoro-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxycarbonyl-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-amino-5-phenyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-amino-4-methoxy-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 6-methyl-pyridin-3-ylmethyl-amino;

a compound of Formula (I) wherein $A_1$ is 4-fluoro-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 4-methyl-pyridin-2-ylmethyl-amino;

a compound of Formula (I) wherein $A_1$ is 4-methoxy-phenyl, $L_1$ is $CH_2$, D is 4-ethyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 6-trifluoromethyl-pyridin-2-ylmethyl-amino;

a compound of Formula (I) wherein $A_1$ is 4-methoxy-phenyl, $L_1$ is $CH_2$, D is 4-methoxy-phenylmethyl, W is N, and Q is 3-methyl-pyridin-2-ylmethyl-amino;

a compound of Formula (I) wherein $A_1$ is 4-methoxy-phenyl, $L_1$ is $CH_2$, D is 4-methoxy-phenylmethyl, W is N, and Q is 2-(2-methylthio-ethylamino)-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(3-methyl-butylamino)-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(tetrahydro-furan-2-ylmethyl)-amino)-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(furan-2-ylmethyl-amino)-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(N-ethyl-pyrrolidin-2-ylmethyl-amino)-pyridin-3-ylmethyl-amino;

a compound of Formula (I) wherein $A_1$ is phenyl, $L_1$ is $CH_2CH_2$, D is 4-methoxy-phenylmethyl, W is N, and Q is 2-(2-methoxy-ethylamino)-pyridin-3-ylmethyl-amino;

a compound of Formula (I) wherein $A_1$ is phenoxy, $L_1$ is $CH_2CH_2$, D is 4-methoxy-phenylmethyl, W is N, and Q is 2-(2-methoxy-ethylamino)-pyridin-3-ylmethyl-amino;

a compound of Formula (I) wherein $A_1$ is 2,3-dihydro-benzo[1,4]dioxin-2-yl, $L_1$ is $CH_2$, D is 4-methoxy-phenylmethyl, W is N, and Q is 2-(2-methoxy-ethylamino)-pyridin-3-ylmethyl-amino;

a compound of Formula (I) wherein $A_1$ is 4-nitro-phenyl, $L_1$ is $CH_2CH_2$, D is 4-methoxy-phenylmethyl, W is N, and Q is 2-(2-methoxy-ethylamino)-pyridin-3-ylmethyl-amino;

a compound of Formula (I) wherein $A_1$ is 4-methoxy-phenyl, $L_1$ is $CH_2$, D is 4-methylthio-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is pyridin-4-ylmethyl, W is N, and Q is 2-amino-pyridin-3-ylmethyl-amino;

a compound of Formula (I) wherein $A_1$ is 4-methoxy-phenyl, $L_1$ is $CH_2$, D is benzofuran-2-ylmethyl, W is N, and Q is 2-amino-pyridin-3-ylmethyl-amino;

a compound of Formula (I) wherein $A_1$ is 4-methoxy-phenyl, $L_1$ is $CH_2$, D is 5-methoxy-n-pentyl, W is N, and Q is 2-amino-pyridin-3-ylmethyl-amino;

a compound of Formula (I) wherein $A_1$ is 4-methoxy-phenyl, $L_1$ is $CH_2$, D is n-hexyl, W is N, and Q is 2-amino-pyridin-3-ylmethyl-amino;

a compound of Formula (I) wherein $A_1$ is 4-methoxy-phenyl, $L_1$ is $CH_2$, D is 3-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-cyano-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-nitro-phenylmethyl, W is N, and Q is 2-amino-pyridin-3-ylmethyl-amino;

a compound of Formula (I) wherein $A_1$ is 4-difluoromethoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-difluoromethoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-difluoromethoxy-phenyl, $L_1$ is $CH_2$, D is 4-difluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-ethyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-trifluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-cyano-phenylmethyl, W is N, and Q is 2-amino-pyridin-3-ylmethyl-amino;

a compound of Formula (I) wherein $A_1$ is 4-iodo-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-pyrazol-1-yl-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-fluoro-phenyl, $L_1$ is $CH_2$, D is 4-trifluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-methoxycarbonyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-(4-methoxy-phenyl)-ethyl, W is N, and Q is 2-amino-pyridin-3-ylmethyl-amino;

a compound of Formula (I) wherein $A_1$ is 4-methoxy-phenyl, $L_1$ is $CH_2$, D is 6-methoxy-pyridin-3-ylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-amino-4,6-dimethyl-pyridin-3-ylmethyl-amino;

a compound of Formula (I) wherein $A_1$ is 4-methoxy-phenyl, $L_1$ is $CH_2$, D is 3-trifluoromethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-trifluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methylthio-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is pyridin-4-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is benzofuran-2-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is n-hexyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 6-methoxy-pyridin-3-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 2-trifluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 2-methoxy-phenylmethyl, W is N, and Q is 4,6-dimethyl-pyridin-3-ylmethyl-amino;

a compound of Formula (I) wherein $A_1$ is 4-ethoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-nitro-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is CH(allyl), D is 4-methoxy-phenylmethyl, W is N, and Q is 4,6-dimethyl-pyridin-3-ylmethyl-amino;

a compound of Formula (I) wherein $A_1$ is 4-trifluoromethyl-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 3-methoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 3-fluoro-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is pyridin-4-ylmethyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-methoxycarbonyl-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 6-amino-pyridin-2-ylmethyl-amino;

a compound of Formula (I) wherein $A_1$ is 4-methoxy-phenyl, $L_1$ is $CH_2$, D is 4-fluoro-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-chloro-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is N-oxo-4,6-dimethyl-pyridin-3-ylmethyl-amino;

a compound of Formula (I) wherein $A_1$ is indol-3-yl, $L_1$ is $CH_2CH_2$, D is 4-methoxy-phenylmethyl, W is N, and Q is 2-amino-pyridin-3-ylmethyl-amino;

a compound of Formula (I) wherein $A_1$ is 2,3-dihydro-benzo[1,4]dioxin-2-yl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is pyridin-3-ylmethoxy;

a compound of Formula (I) wherein $A_1$ is 4-methoxy-phenyl, $L_1$ is $CH_2$, D is 4-methoxy-phenylmethyl, W is N, and Q is 6-trifluoromethyl-pyridin-3-ylmethyl-amino;

a compound of Formula (I) wherein $A_1$ is 2,3-dihydro-benzofuran-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 3-nitro-4-methoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2,3-dihydro-benzofuran-5-ylmethyl, W is N, and Q is 2-amino-pyridin-3-ylmethyl-amino;

a compound of Formula (I) wherein $A_1$ is 4-methoxy-phenyl, $L_1$ is $CH_2$, D is benzofuran-5-ylmethyl, W is N, and Q is 2-amino-pyridin-3-ylmethyl-amino;

a compound of Formula (I) wherein $A_1$ is 4-methoxy-phenyl, $L_1$ is $CH_2$, D is indol-5-ylmethyl, W is N, and Q is 2-amino-pyridin-3-ylmethyl-amino;

a compound of Formula (I) wherein $A_1$ is 4-methoxy-phenyl, $L_1$ is $CH_2$, D is 2,3-dihydro-benzofuran-5-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is benzofuran-5-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is indol-5-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methanesulfonyl-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methanesulfonyl-phenylmethyl, W is N, and Q is 4,6-dimethyl-pyridin-3-ylmethyl-amino;

a compound of Formula (I) wherein $A_1$ is benzofuran-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzofuran-5-yl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-t-butoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-nitro-4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 3-nitro-4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is indol-4-ylmethyl, W is N, and Q is 2-amino-pyridin-3-ylmethyl-amino;

a compound of Formula (I) wherein $A_1$ is 4-methoxy-phenyl, $L_1$ is $CH_2$, D is indol-4-ylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is benzothiophen-5-ylmethyl, W is N, and Q is 2-amino-pyridin-3-ylmethyl-amino;

a compound of Formula (I) wherein $A_1$ is 4-fluoro-phenoxy, $L_1$ is $CH_2CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is benzothiophen-5-ylmethyl, W is N, and Q is 4,6-dimethyl-pyridin-3-ylmethyl-amino;

a compound of Formula (I) wherein $A_1$ is 2-methoxy-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 2-methoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzothiophen-5-yl, $L_1$ is $CH_2$, D is 4-methoxy-phenylmethyl, W is N, and Q is 2-amino-pyridin-3-ylmethyl-amino;

a compound of Formula (I) wherein $A_1$ is benzothiophen-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 6-n-propylamino-pyridin-2-ylmethyl-amino;

a compound of Formula (I) wherein $A_1$ is 4-methoxy-phenyl, $L_1$ is $CH_2$, D is 4-methoxy-phenylmethyl, W is CH, and Q is 6-amino-pyridin-2-ylmethyl-amino;

a compound of Formula (I) wherein $A_1$ is 4-methoxy-phenyl, $L_1$ is $CH_2$, D is 4-methoxy-cyclohexylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-cyclohexylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 3,4-dichloro-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-(isoindol-1,3-dione-2-yl)-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 3-methoxycarbonyl-n-propyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-pyridin-2-yl-ethylamino;

a compound of Formula (I) wherein $A_1$ is 4-methoxy-phenyl, $L_1$ is $CH_2$, D is indol-4-ylmethyl, W is N, and Q is 2-amino-4,6-dimethyl-pyridin-3-ylmethyl-amino;

a compound of Formula (I) wherein $A_1$ is 4-fluoro-phenyl, $L_1$ is $CH_2$, D is 4-difluoromethoxy-phenylmethyl, W is N, and Q is 6-amino-pyridin-2-ylmethyl-amino;

a compound of Formula (I) wherein $A_1$ is 4-methoxy-phenyl, $L_1$ is $CH_2$, D is 2,3-dihydro-benzofuran-5-ylmethyl, W is N, and Q is 2-amino-4,6-dimethyl-pyridin-3-ylmethyl-amino;

a compound of Formula (I) wherein $A_1$ is 4-pyrazol-1-yl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-iodo-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-fluoro-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methyl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-trifluoromethyl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-difluoromethoxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-cyano-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methoxycarbonyl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is phenoxy, $L_1$ is $CH_2CH_2$, D is 4-difluoromethoxy-phenylmethyl, W is N, and Q is 4,6-dimethyl-pyridin-3-ylmethyl-amino;

a compound of Formula (I) wherein $A_1$ is 4-fluoro-phenoxy, $L_1$ is $CH_2CH_2$, D is 4-difluoromethoxy-phenylmethyl, W is N, and Q is 4,6-dimethyl-pyridin-3-ylmethyl-amino;

a compound of Formula (I) wherein $A_1$ is 4-[1,2,3]thiadiazol-4-yl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-pyridin-3-yl-ethyl;

a compound of Formula (I) wherein $A_1$ is 4-methoxy-phenyl, $L_1$ is $CH_2$, D is indol-6-ylmethyl, W is N, and Q is 2-amino-pyridin-3-ylmethyl-amino;

a compound of Formula (I) wherein $A_1$ is 4-methoxy-phenyl, $L_1$ is $CH_2$, D is indol-7-ylmethyl, W is N, and Q is 2-amino-pyridin-3-ylmethyl-amino;

a compound of Formula (I) wherein $A_1$ is 4-methoxy-phenyl, $L_1$ is $CH_2$, D is indol-7-ylmethyl, W is N, and Q is 4,6-dimethyl-pyridin-3-ylmethyl-amino;

a compound of Formula (I) wherein $A_1$ is 4-methylthio-phenyl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is benzothiophen-5-yl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is benzofuran-5-yl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is 2,3-dihydro-benzofuran-5-yl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is 4-methylthio-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is benzofuran-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 2,3-dihydro-benzofuran-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 2-cyano-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-hydroxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methylcarbonyloxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenyl, W is CH, and Q is 2-pyridin-4-yl-ethyl;

a compound of Formula (I) wherein $A_1$ is 4-methoxy-phenyl, $L_1$ is $CH_2$, D is 4-methoxy-phenyl, W is CH, and Q is cis-2-pyridin-4-yl-vinyl;

a compound of Formula (I) wherein $A_1$ is 2,3-dihydro-benzofuran-5-yl, $L_1$ is $CH_2$, D is 2,3-dihydro-benzofuran-5-ylmethyl, W is N, and Q is 2-amino-4,6-dimethyl-pyridin-3-ylmethyl-amino;

a compound of Formula (I) wherein $A_1$ is benzofuran-5-yl, $L_1$ is $CH_2$, D is 2,3-dihydro-benzofuran-5-ylmethyl, W is N, and Q is 2-amino-4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-pyridin-2-yl-ethyl;

a compound of Formula (I) wherein $A_1$ is 4-methoxy-phenyl, $L_1$ is $CH_2$, D is 4-methoxy-phenylmethyl, W is N, and Q is imidazo[1,2-a]pyridin-8-ylmethyl-amino;

a compound of Formula (I) wherein $A_1$ is 4-methoxy-phenyl, $L_1$ is $CH_2$, D is 4-methoxy-phenylmethyl, W is CH, and Q is 2-(2-aminocarbonyl-pyridin-3-yl)-ethyl;

a compound of Formula (I) wherein $A_1$ is 4-methoxy-phenyl, $L_1$ is $CH_2$, D is 4-methoxy-phenylmethyl, W is CH, and Q is 2-amino-pyridin-3-ylmethoxy;

a compound of Formula (I) wherein $A_1$ is 4-hydroxymethyl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 1-methyl-1H-benzotriazol-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 2-methoxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-aminocarbonyl-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 2,6-difluoro-4-methoxy-phenyl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is benzo[1,2,3]thiadiazol-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is methoxy, $L_1$ is $(CH_2)_5$, D is 4-methoxy-phenylmethyl, W is N, and Q is 4,6-dimethyl-pyridin-3-ylmethyl-amino;

a compound of Formula (I) wherein $A_1$ is methoxy, $L_1$ is $(CH_2)_5$, D is 4-difluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-(2-amino-pyridin-3-yl)-ethyl;

a compound of Formula (I) wherein $A_1$ is 4-methoxy-phenyl, $L_1$ is $CH_2$, D is 2,4-dimethoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 4-methyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-amino-4,6-dimethyl-pyridin-3-ylmethoxy;

a compound of Formula (I) wherein $A_1$ is 4-methoxy-phenyl, $L_1$ is $CH_2$, D is 3-fluoro-4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 3-fluoro-4-methoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 2-fluoro-4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 2-fluoro-4-methoxy-phenylmethyl, W is N, and Q is 4,6-dimethyl-pyridin-3-ylmethyl-amino;

a compound of Formula (I) wherein $A_1$ is benzo(1,3)dioxal-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzo(1,3)dioxal-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 2,3-dihydro-benzo[1,4]dioxin-6-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 2,3-dihydro-benzo[1,4]dioxin-6-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is pyridin-3-ylmethylthio;

a compound of Formula (I) wherein $A_1$ is 4-methoxy-phenyl, $L_1$ is $CH_2$, D is 2-methyl-2,3-dihydro-benzofuran-5-ylmethyl, W is N, and Q is 2-amino-4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is N, and Q is 2-(N-piperidinyl)-4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-(4-amino-pyridin-3-yl)-ethyl;

a compound of Formula (I) wherein $A_1$ is 4-methoxy-phenyl, $L_1$ is $CH_2$, D is 4-methoxy-phenylmethyl, W is N, and Q is 2-(pyridin-4-yl)-ethylamino;

a compound of Formula (I) wherein $A_1$ is 1-methyl-1H-benzotriazol-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzo[1,2,3]thiadiazol-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is 3-fluoro-4-methoxy-phenyl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is benzo(1,3)dioxal-5-yl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is benzo(1,3)dioxal-5-yl, $L_1$ is $CH_2$, D is 4-methoxy-phenylmethyl, W is N, and Q is 2-amino-4,6-dimethyl-pyridin-3-ylmethyl-amino;

a compound of Formula (I) wherein $A_1$ is 1-methyl-1H-benzotriazol-5-yl, $L_1$ is $CH_2$, D is 4-difluoromethoxy-phenylmethyl, W is N, and Q is 2-amino-4,6-dimethyl-pyridin-3-ylmethyl-amino;

a compound of Formula (I) wherein $A_1$ is 1-methyl-1H-benzotriazol-5-yl, $L_1$ is $CH_2$, D is 4-methoxy-phenylmethyl, W is N, and Q is 2-amino-4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-(6-amino-pyridin-2-yl)ethyl;

a compound of Formula (I) wherein $A_1$ is 4-methoxy-phenyl, $L_1$ is $CH_2$, D is 5-methoxy-n-pentyl, W is N, and Q is 2-amino-4,6-dimethyl-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 1-(2-amino-pyridin-4-yl)-ethoxy;

a compound of Formula (I) wherein $A_1$ is 2,3-dihydro-benzofuran-5-yl, $L_1$ is $CH_2$, D is 2,3-dihydro-benzofuran-5-ylmethyl, W is N, and Q is N-oxo-2-amino-4,6-dimethyl-pyridin-3-ylmethyl-amino;

a compound of Formula (I) wherein $A_1$ is indol-5-yl, $L_1$ is $CH_2$, D is 4-difluoromethoxy-phenylmethyl, W is N, and Q is 4,6-dimethyl-pyridin-3-ylmethyl-amino;

a compound of Formula (I) wherein $A_1$ is indol-5-yl, $L_1$ is $CH_2$, D is 4-difluoromethoxy-phenylmethyl, W is N, and Q is 2-amino-pyridin-3-ylmethyl-amino;

a compound of Formula (I) wherein $A_1$ is indol-5-yl, $L_1$ is $CH_2$, D is 4-methoxy-phenylmethyl, W is N, and Q is 4,6-dimethyl-pyridin-3-ylmethyl-amino;

a compound of Formula (I) wherein $A_1$ is indol-5-yl, $L_1$ is $CH_2$, D is 4-methoxy-phenylmethyl, W is N, and Q is 2-amino-pyridin-3-ylmethyl-amino;

a compound of Formula (I) wherein $A_1$ is 4-chloro-phenyl, $L_1$ is $CH_2$, D is 4-methoxy-phenylmethyl, W is N, and Q is 2-amino-pyridin-3-ylmethyl-amino;

a compound of Formula (I) wherein $A_1$ is 4-methoxy-phenyl, $L_1$ is $CH_2$, D is 4-methoxy-phenylmethyl, W is CH, and Q is 2-amino-pyrimidin-4-ylmethoxy;

a compound of Formula (I) wherein $A_1$ is 2,3-dihydro-benzofuran-5-yl, $L_1$ is $CH_2$, D is 4-difluoromethoxy-phenylmethyl, W is N, and Q is N-oxo-2-amino-4,6-dimethyl-pyridin-3-ylmethyl-amino;

and combinations thereof.

Additional embodiments of the present invention include those compounds wherein the substituents are selected from one or more of the variables defined herein (i.e. $A_1$, $L_1$, s, X, P, $A_2$, W, and Q) are independently selected to be any individual substituent or any subset of substituents selected from the complete list as defined herein.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient, or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

The instant pharmaceutical composition will generally contain a per dosage unit (e.g., tablet, capsule, powder, injection, teaspoonful and the like) from about 0.001 to about 50 mg/kg. In one embodiment, the instant pharmaceutical composition contains a per dosage unit of from about 0.01 to about 20 mg/kg of compound, and preferably from about 0.05 to about 10 mg/kg. Methods are known in the art for determining therapeutically effective doses for the instant pharmaceutical composition. The therapeutically effective amount for administering the pharmaceutical composition to a human, for example, can be determined mathematically from the results of animal studies.

A therapeutically effective amount for use of the instant compounds or a pharmaceutical composition thereof comprises a dose range from about 0.1 mg to about 3000 mg, in particular from about 1 mg to about 1000 mg or, more particularly from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as prokineticin receptor antagonists is required for a subject in need thereof.

The invention also provides a pharmaceutical or veterinary pack or kit comprising one or more containers filled with one or more of the ingredients of the pharmaceutical and veterinary compositions of the invention.

As antagonists of a Prokineticin 1 receptor, the compounds of Formula (I) are useful in methods for treating or preventing a disease or condition in a mammal which disease or condition is affected by the antagonistic activity of one or more Prokineticin 1 receptors. Such methods comprise administering to a mammal in need of such treatment or prevention a therapeutically effective amount of a compound, salt or solvate of Formula (I). The compounds of Formula (I) are useful in methods for preventing or treating gastrointestinal (GI) diseases, cancers of the GI tract and reproductive organs, and pain. Examples of GI diseases to be within the scope of the present invention include, but are not limited to: irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens. Examples of cancers within the scope of the present invention include, but are not limited to, testicular cancer, ovarian cancer, Leydig cell carcinoma, and cancers of the small or large bowel. An example of pain to be covered within the scope of the present invention, is, but not restricted to, visceral hyperalgesia often associated with IBS and IBD.

While the present invention comprises compositions comprising one or more of the compounds of Formula (I) the present invention also comprises compositions comprising intermediates used in the manufacture of compounds of Formula (I).

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada.

Abbreviations used in the instant specification, particularly the Schemes and Examples, are as follows:
AIBN=2,2'-azobisisobutyronitrile
Boc=tert-butoxycarbonyl
BuLi=n-butyllithium
Cpd or Cmpd=compound
d=day/days
DCM=dichloromethane
DIAD=diisopropyl azodicarboxylate
DIPEA or DIEA=diisopropylethylamine
DMEM=Dulbecco's Modified Eagle Medium
DMF=N,N-dimethylformamide
DMSO=dimethylsulfoxide
EDCl=1-(3-Dimethylaminopropyl)-3-ethylcarbodiimide hydrochloride
EtOAc=ethyl acetate
EtOH=ethanol
h=hour/hours
HBTU O-Benzotriazol-1-yl-N,N,N',N'-tetramethyluronium hexafluorophosphate
LDA=lithium diisopropylamide
M=molar
MeCN=acetonitrile
MeOH=methanol
min=minutes
NaOMe=sodium methoxide
NBS=N-bromosuccinimide
PyBOP=benzotriazole-1-yl-oxy-tris-pyrrolidino-phosphonium hexafluorophosphate
rt/RT=room temperature
TBAF=tetra-n-butylammonium fluoride
TEBA=benzyltriethylammonium chloride
THF=tetrahydrofuran
TFA=trifluoroacetic acid
UHP=urea-hydrogen peroxide addition complex
μw=microwave General Schemes Representative compounds of the present invention can be synthesized in accordance with the general synthetic methods described below and are illustrated in the schemes that follow. The starting materials and reagents used in the schemes that follow are understood to be either commercially available or prepared by methods known to those skilled in the art. Since the schemes are an illustration, the invention should not be construed as being limited by the chemical reactions and conditions expressed.

Scheme A describes the preparation of certain compounds of the present invention wherein Q of Formula (I) is (a) or (b) and W is N. More specifically, Q is —NH(CH$_2$)$_2$Ar$_1$ or —NHCH(R$_z$)—Ar$_2$. In Scheme A, n is 1 or 2 and Ar$_m$ is A$_1$ or Ar$_2$, such that when n is 2, Ar$_m$ is Ar$_1$, and when n is 1 and R$_z$ is H or C$_{1-3}$alkyl, Ar$_m$ is Ar$_2$.

Scheme A

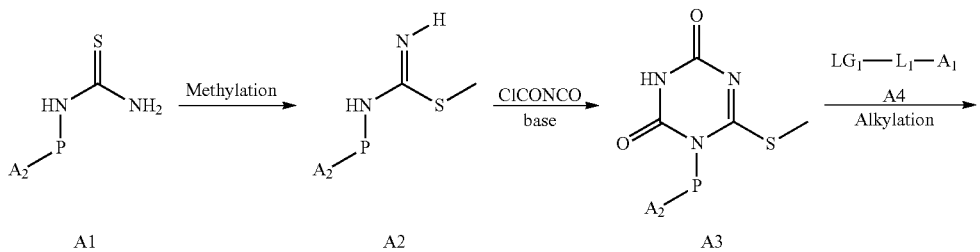

-continued

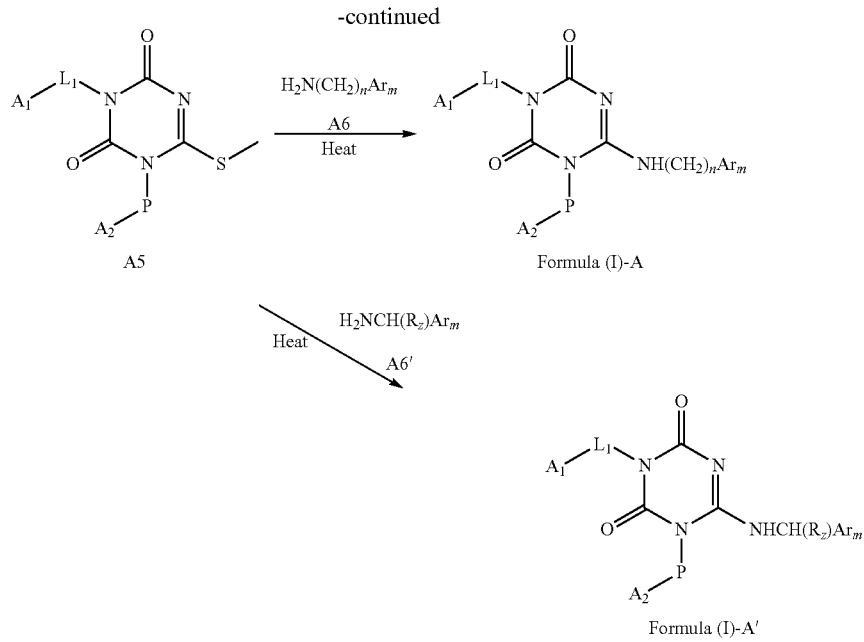

A compound of formula A1 is either commercially available or may be prepared by known methods described in the scientific literature. A compound of formula A1 may be methylated with a methylating agent such as methyl iodide in a polar solvent such as methanol to give a compound of formula A2. A compound of formula A2 may be condensed with an appropriately substituted isocyanate such as N-chlorocarbonyl isocyanate in the presence of excess of a tertiary amine such as diisopropylethylamine to give a triazine of formula A3. A compound of formula A3 may be alkylated with a compound of formula A4, which is either commercially available or may be prepared by known methods described in the scientific literature, wherein $LG_1$ is a leaving group, using conventional chemistry known to one versed in the art. For instance, when $LG_1$ is a hydroxy group, compound A4 may be coupled with a compound of formula A3 in the presence of a coupling agent such as DIAD in a non-alcoholic polar solvent such as THF or methylene chloride. Alternatively, $LG_1$ may be a halide, tosylate, or the like such that $LG_1$ is displaced by the amino portion of a compound of A3 to give a compound of formula A5. The Q-portion of a compound of Formula (I)-A may be installed by treating a compound of formula A5 with a compound of formula A6 or A6' to afford a compound of Formula (I)-A or (I)-A', respectively.

Scheme A-1 describes the synthesis of intermediates of formula A6.

Scheme A-1

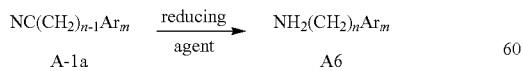

A compound of formula A-1a is either commercially available or may be prepared by known methods described in the scientific literature. A compound of formula A-1a may be reduced under various reaction conditions, such as Raney Nickel with hydrazine or under a pressurized atmosphere of hydrogen gas in the presence of an organometallic catalyst such as Pd/C, to afford a compound of formula A6.

Scheme B illustrates the general synthesis of compounds of the present invention wherein Q of Formula (I) is (d) or (e) and W is N. More specifically, Q is —$(CH_2)_2Ar_4$ or —CH=CH—$Ar_5$. In Scheme B, $Ar_y$ is $Ar_4$ or $Ar_y$.

Scheme B

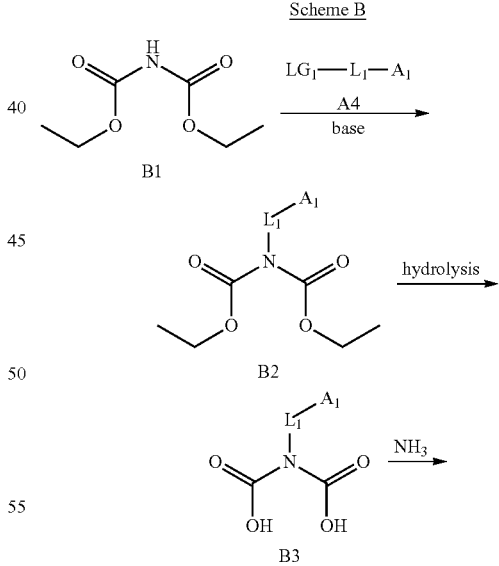

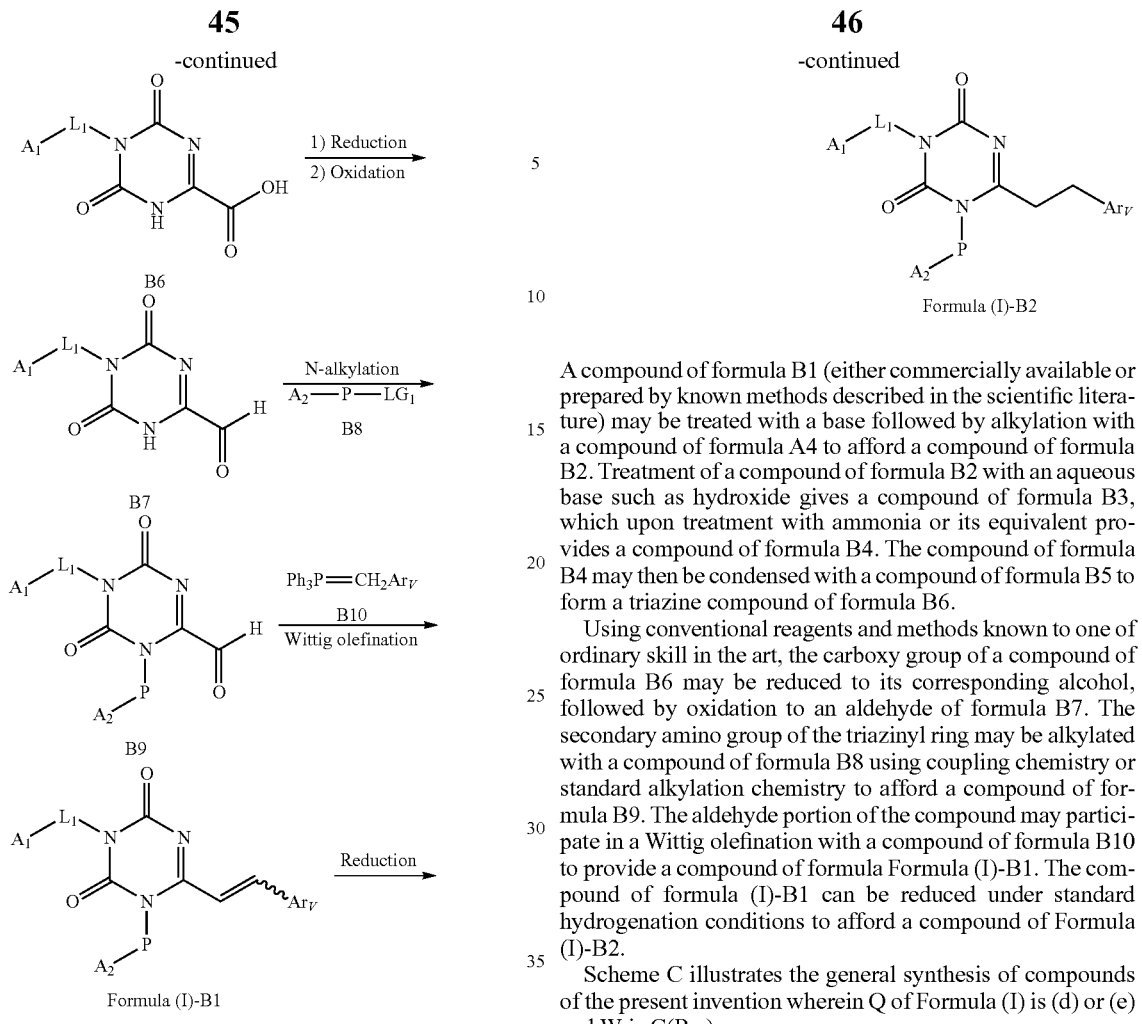

A compound of formula B1 (either commercially available or prepared by known methods described in the scientific literature) may be treated with a base followed by alkylation with a compound of formula A4 to afford a compound of formula B2. Treatment of a compound of formula B2 with an aqueous base such as hydroxide gives a compound of formula B3, which upon treatment with ammonia or its equivalent provides a compound of formula B4. The compound of formula B4 may then be condensed with a compound of formula B5 to form a triazine compound of formula B6.

Using conventional reagents and methods known to one of ordinary skill in the art, the carboxy group of a compound of formula B6 may be reduced to its corresponding alcohol, followed by oxidation to an aldehyde of formula B7. The secondary amino group of the triazinyl ring may be alkylated with a compound of formula B8 using coupling chemistry or standard alkylation chemistry to afford a compound of formula B9. The aldehyde portion of the compound may participate in a Wittig olefination with a compound of formula B10 to provide a compound of formula Formula (I)-B1. The compound of formula (I)-B1 can be reduced under standard hydrogenation conditions to afford a compound of Formula (I)-B2.

Scheme C illustrates the general synthesis of compounds of the present invention wherein Q of Formula (I) is (d) or (e) and W is C($R_W$).

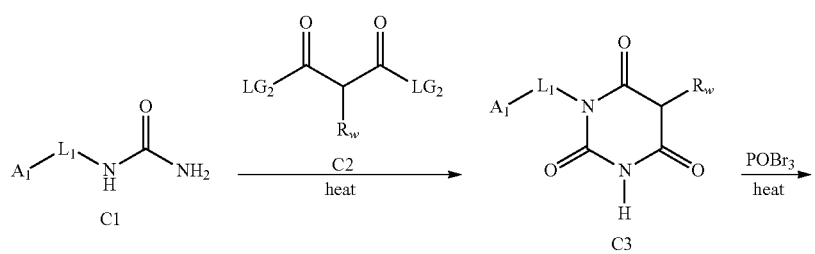

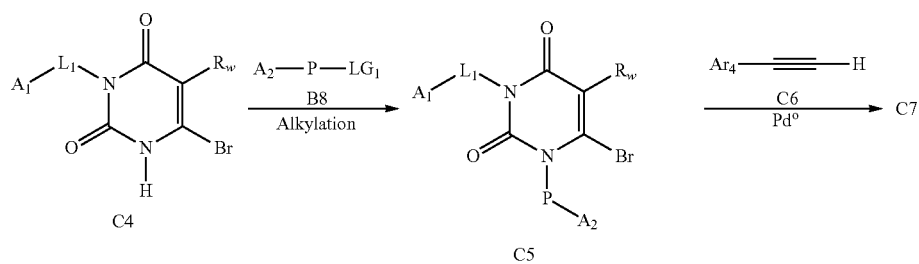

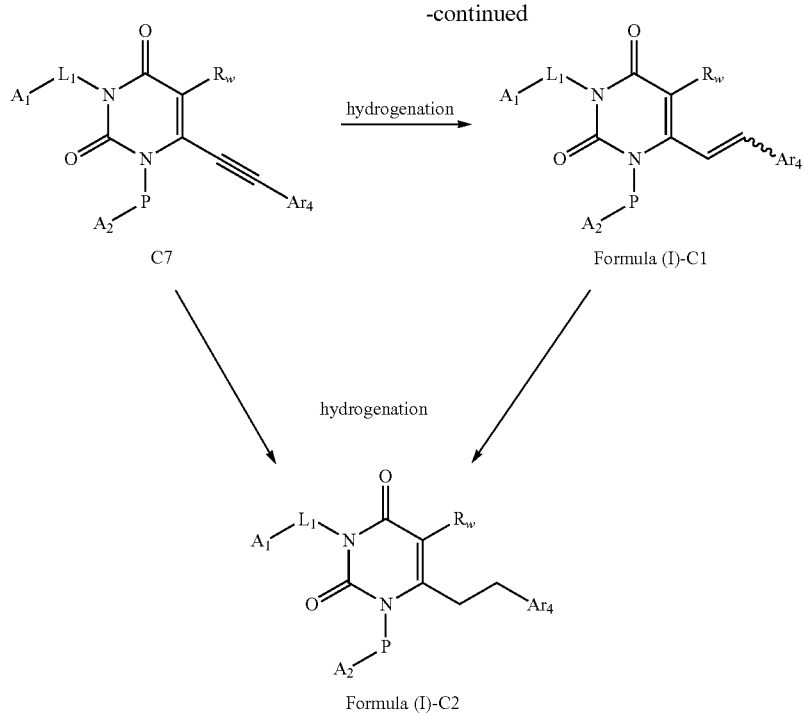

A compound of formula C1 (either commercially available or prepared by known methods described in the scientific literature) may be condensed with a compound of formula C2 with heating, wherein $LG_2$ is $C_{1-4}$alkoxy, choro, or the like, to form a compound of formula C3. Compound C3 can be reacted with phosphorus oxybromide with heating to provide a bromo-uracil of formula C4. A compound of formula C4 may be alkylated with a compound of formula B8 to provide a compound of formula C5. A compound of formula C5 may be coupled with a compound of formula C6 in the presence of an organometallic reagent such as tetrakis(triphenylphosphine)-palladium to yield a compound of formula C7. Hydrogenation of a compound of formula C7 provides a compound of Formula (I)-C1 which may be further reduced by prolonged exposure to hydrogenation conditions to yield a compound of Formula (I)-C2. Alternatively, a compound of formula C7 may be converted directly to a compound of formula (I)-C2 using conventional hydrogenation reagents and methods. One of ordinary skill in the art will recognize that the duration of exposure of a compound to hydrogenation conditions is one way of controlling the degree of reduction of an alkyne to an alkene or alkane.

Scheme D illustrates the general synthesis of compounds of the present invention wherein Q of Formula (I) is (a) or (b) and W is $C(R_W)$. Scheme D also illustrates the general synthesis of compounds of the present invention wherein Q if Formula (I) is (g) and W is $C(R_W)$.

Scheme D

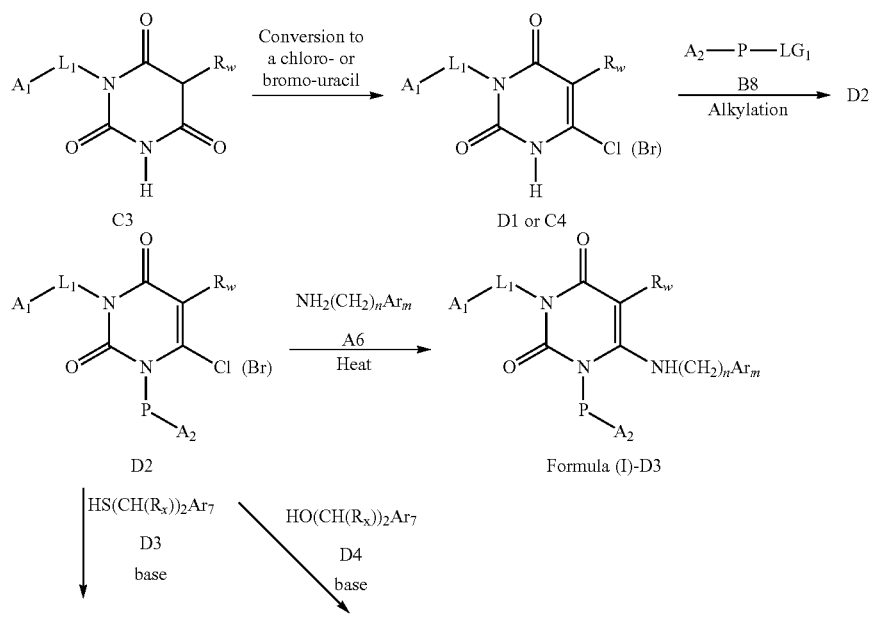

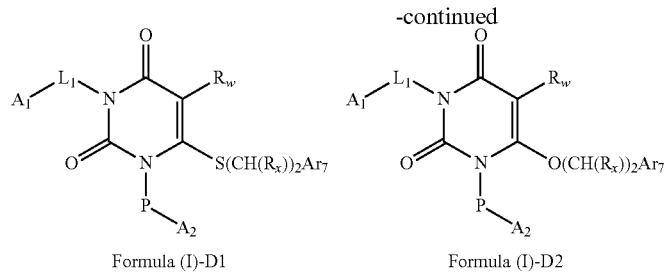

Formula (I)-D1    Formula (I)-D2

A compound of formula C3 may be treated with phosphorus oxychloride, PCl$_5$, or the like, with heating to afford a compound of formula D1; alternatively, the bromo analog (Formula C4) may be used in this synthetic sequence. A compound of formula B8 may be used to install -P-A$_2$ via conventional alkylation procedures as described herein. A compound of formula D2 may be elaborated via a nucleophilic displacement of the chloride (or bromide) with an amine of formula A6 (wherein Ar$_m$ is defined as Ar$_1$ or Ar$_2$) to afford a compound of Formula (I)-D3. A compound of formula D2 may be elaborated via a nucleophilic displacement of the chloride (or bromide) under basic conditions with alcohol D4 to provide a compound of Formula (I)-D2 (when X$_1$=O). A compound of formula D2 may also be elaborated via a nucleophilic displacement of the chloride (or bromide) under basic conditions with a compound of formula D3 to provide a compound of Formula (I)-D1 (when X$_1$=S).

Scheme E depicts the general synthesis of compounds of the present invention wherein Q of Formula (I) is —S—CH(R$_1$)Ar$_6$ of (f) or Q is —S(CH(R$_x$))$_2$—Ar$_7$ of (g), and W is N.

Scheme E

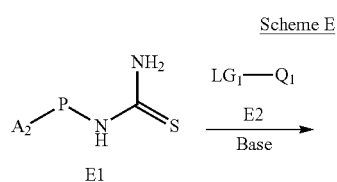

E1

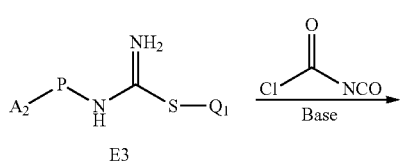

E3

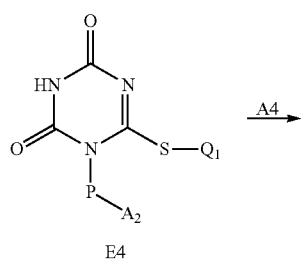

E4

-continued

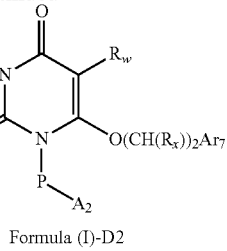

Formula (I)-E

Q$_1$ = —CH(R$_1$)Ar$_6$ or —(CH(R$_x$))$_2$Ar$_7$

A compound of formula E1 (either commercially available or prepared by known methods described in the scientific literature) may be alkylated under basic conditions with a compound of formula E2 (wherein Q$_1$ is —CH(R$_1$)Ar$_6$ or —(CH(R$_x$))$_2$Ar$_7$) to provide a compound of formula E3. A compound of formula E3 may be condensed with an appropriately substituted isocyanate such as N-chlorocarbonyl isocyanate in the presence of excess tertiary amine such as diisopropylethylamine to give a triazine of formula E4. A compound of formula E4 may be alkylated with a compound of formula A4 to provide a compound of Formula (I)-E.

Scheme F illustrates the general synthesis of compounds of the present invention wherein Q of Formula (I) is (c) and W is CH.

Scheme F

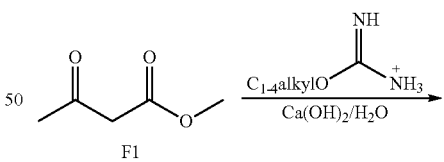

F1

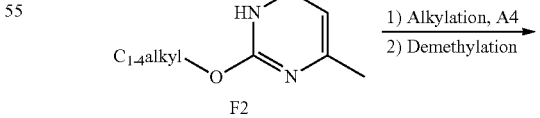

F2

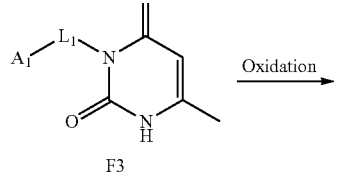

F3

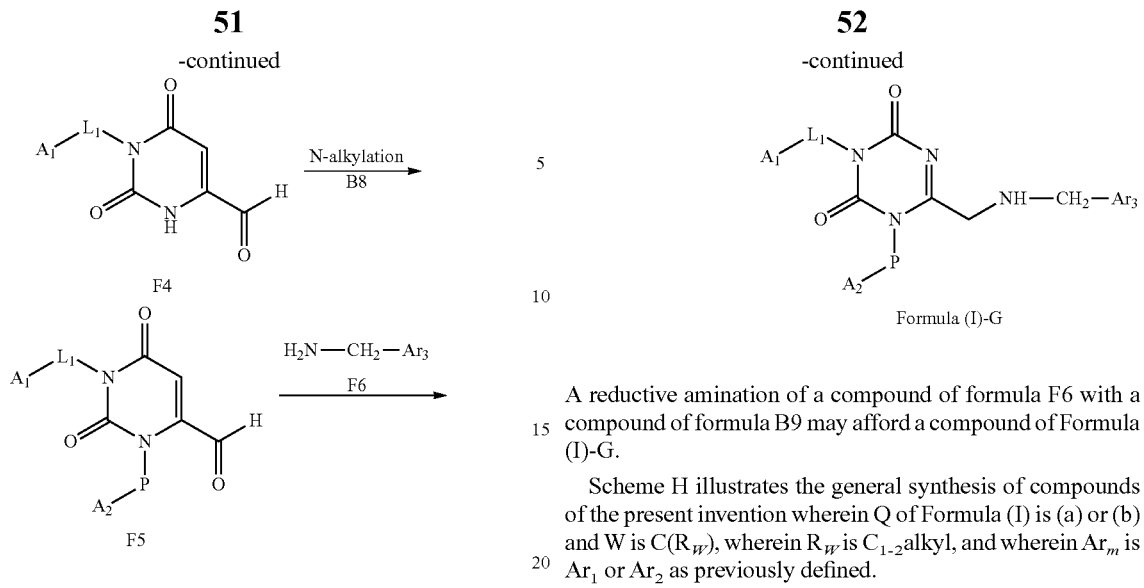

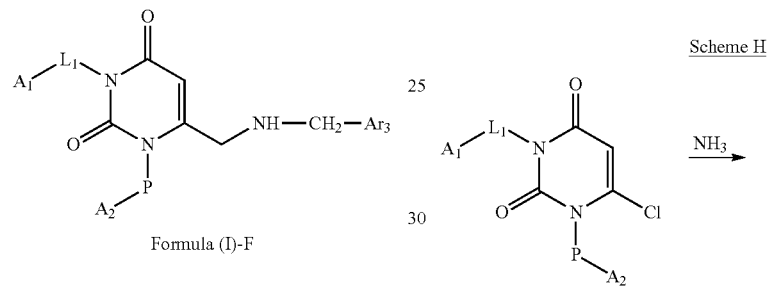

A compound of formula F1 (either commercially available or prepared by known methods described in the scientific literature) may be condensed with an O-alkylated isourea to afford a cyclic compound of formula F2. The amino functionality of a compound of formula F2 may be deprotonated selectively with a base such as lithium hydride and subsequently treated with a compound of formula A4. The O-demethylation of the alkylated compounds formula F2 affords compounds of formula F3. Using conventional oxidation chemistry, the methyl substituent of a compound of formula F3 may be converted to its corresponding aldehyde, affording a compound of formula F4. The secondary amino group may be substituted with -P-$A_2$ of Formula (I) using coupling chemistry or standard alkylation with a compound of formula B8 to afford a compound of formula F5. A reductive amination with a compound of formula F6 may afford a compound of Formula (I)-F.

Scheme G illustrates the general synthesis of compounds of the present invention wherein Q of Formula (I) is (c) and W is N.

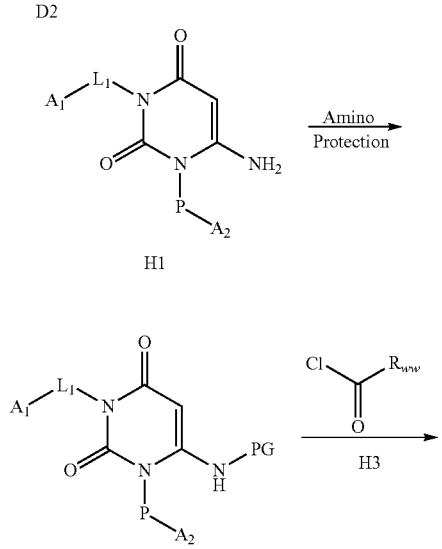

A reductive amination of a compound of formula F6 with a compound of formula B9 may afford a compound of Formula (I)-G.

Scheme H illustrates the general synthesis of compounds of the present invention wherein Q of Formula (I) is (a) or (b) and W is C($R_W$), wherein $R_W$ is $C_{1-2}$alkyl, and wherein $Ar_m$ is $Ar_1$ or $Ar_2$ as previously defined.

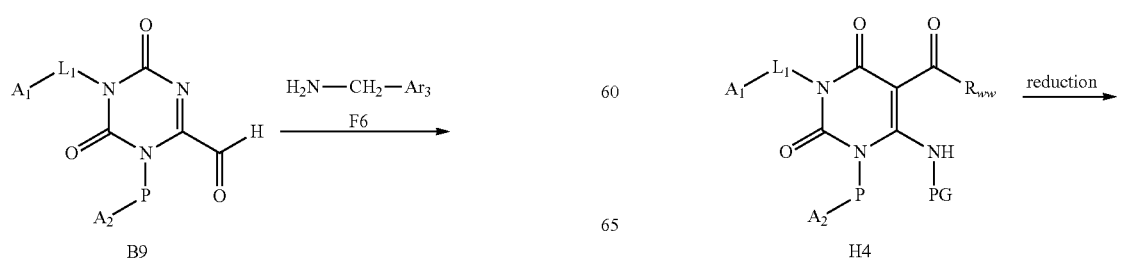

-continued

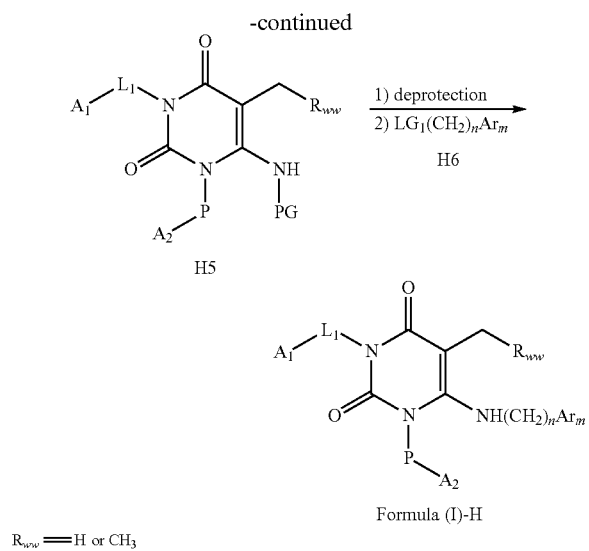

Formula (I)-H $R_{ww} = H$ or $CH_3$

Compound D2 may be reacted with an ammonium salt or an ammonium equivalent to provide a compound of formula H1. The amino functionality of a compound of formula H1 may be protected with an appropriate amino protecting group to provide a compound of formula H2. Acylation of a compound of formula H2 with a compound of formula H3 (wherein $R_{ww}$ may be H or methyl) may give a compound of formula H4. Reduction of the carbonyl group of a compound of formula H4 using standard procedures may provide a compound of formula H5. Removal of the amino protecting group (PG), followed by alkylation of the amino group with a compound of formula H6 provides a compound of Formula (I)-H.

In preparing compounds of Formula (I) wherein $A_2$ is piperidinyl, a standard protecting group such as N-boc can be used to protect the —NH— in the piperidinyl ring in the synthetic steps shown above. A standard deprotection step can be used after the last step in each scheme to provide compounds of Formula (I) wherein $A_2$ is piperidinyl.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker-Biospin Inc. DRX 500 (500 MHz) or DPX 300 (300 MHz) spectrometer. The values are expressed in parts per million downfield from TMS. The mass spectra (MS) were determined on a Micromass Platform LC spectrometer, an Agilent LC spectrometer or a Micromass LCT spectrometer using electrospray techniques. Microwave accelerated reactions were performed using a CEM Discover microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

2-amino-3-methylaminopyridine (Cpd 1a)

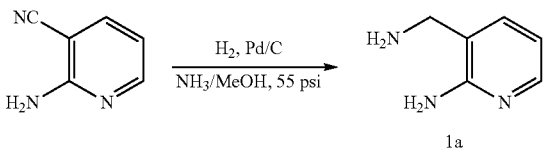 [SMILES: N#Cc1cccnc1N ; NCc1cccnc1N]

2-Amino-3-methylaminopyridine (Cpd 1a). 2-amino-3-cyanopyridine (3.0 g, 25.2 mmol) was dissolved in 2N $NH_3$ in methanol (50 mL) and the solution was added to a Parr reaction vessel containing 10% Palladium on charcoal (500 mg) under argon. The reaction was run on a Parr hydrogenation apparatus at 55 psi until the uptake of hydrogen had ceased (~12 hours). Upon completion, the catalyst was removed via filtration through pad of diatomaceous earth. The pad was rinsed with methanol (3×50 mL) and the filtrate was reduced in vacuo to provide Compound 1a as a yellow solid. The crude mixture was used in further synthesis without additional purification.

Example 2

3-Aminomethyl-4,6-dimethylpyridine (Cpd 2a)

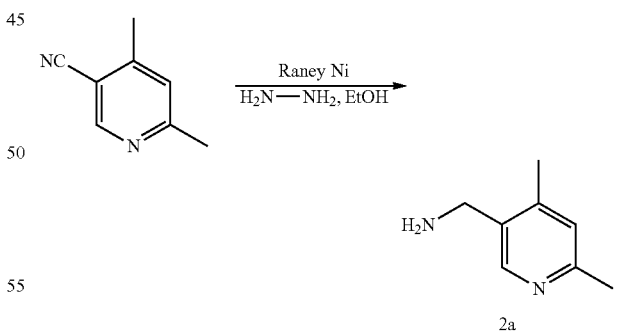

4,6-Dimethylnicotinonitrile (1.0 g, 7.6 mmol) was dissolved in ethanol (35 mL) and the mixture was treated with Raney nickel (5 mL, slurry in water) and hydrazine hydrate (3.8 mL, 75.6 mmol). The solution was stirred overnight at room temperature. Compound 2a was obtained by filtering the reaction mixture through a pad of diatomaceous earth, which was rinsed with methanol (3×50 mL). The filtrate was dried over $Na_2SO_4$, filtered and concentrated under reduced pressure to afford Compound 2a. The compound was used without additional purification. M+ (ES+)=137.1 $^1$H NMR (DMSO, $d_6$) δ2.35 (s, 3H), 2.42 (s, 3H), 4.01 (s, 2H), 7.13 (s, 1H), 8.42 (s, 1H).

Example 3

3-Aminomethyl-4,6-dimethylpyridine (Cpd 2a)

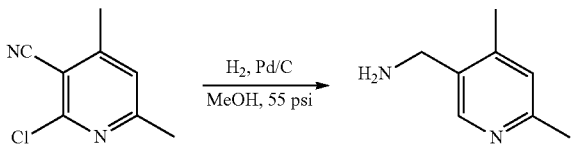

An alternative route for the preparation of compound 2a is described herein. 2-chloro-4,6-dimethylnicotinonitrile (5.0 g, 30 mmol) was dissolved in methanol (50 mL) and the solution was carefully added to a Parr reaction vessel containing 10% Pd on charcoal (500 mg) under argon. The reaction was run on Parr hydrogenation apparatus at 55 psi until uptake of hydrogen had ceased (~12 h). Upon completion, the catalyst was removed via filtration through a pad of diatomaceous earth. The pad was rinsed with methanol (3×50 mL) and the filtrate was reduced in vacuo to provide Compound 2a. The crude mixture was used in further synthesis without additional purification. MS m/z (ES)=137.1 (M+H); $^1$H NMR (DMSO, $d_6$) δ2.35 (s, 3H), 2.42 (s, 3H), 4.01 (s, 2H), 7.13 (s, 1H), 8.42 (s, 1H).

Example 4

2-amino-3-aminomethyl-4,6-dimethylpyridine (Cpd 4a)

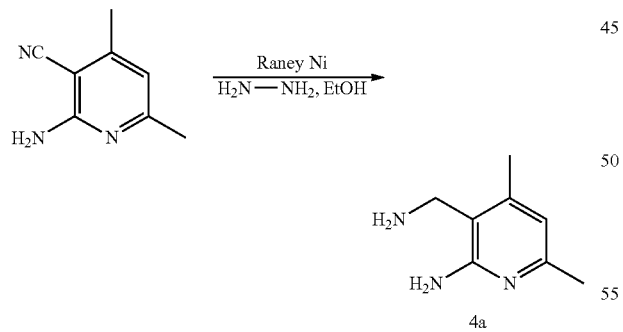

2-Amino-3-aminomethyl-4,6-dimethylpyridine (Cpd 4a). 2-amino-3-cyano-4,6-dimethylpyridine (1.0 g, 6.8 mmol) was dissolved in ethanol (35 mL) and the mixture was treated with Raney nickel (3 mL, slurry in water) and hydrazine hydrate (3.4 mL, 67.9 mmol). The solution was stirred overnight at room temperature. Compound 4a was obtained by filtering the reaction mixture through a pad of diatomaceous earth, which was rinsed with methanol (3×50 mL). The filtrate was dried over $Na_2SO_4$, filtered and concentrated under reduced pressure to afford Compound 4a. The compound was used without additional purification.

Example 5

6-[(4,6-Dimethyl-pyridin-3-ylmethyl)-amino]-1,3-bis-(4-methoxy-benzyl)-1H-[1,3,5]triazine-2,4-dione (Cpd 22)

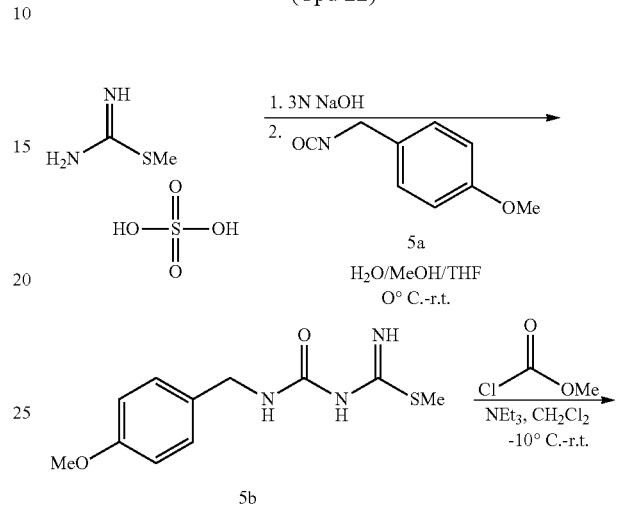

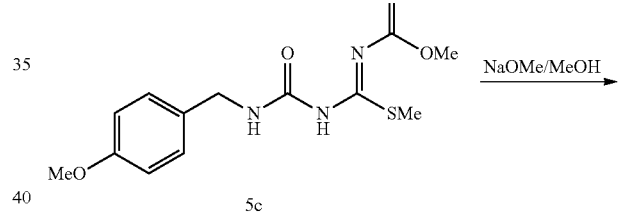

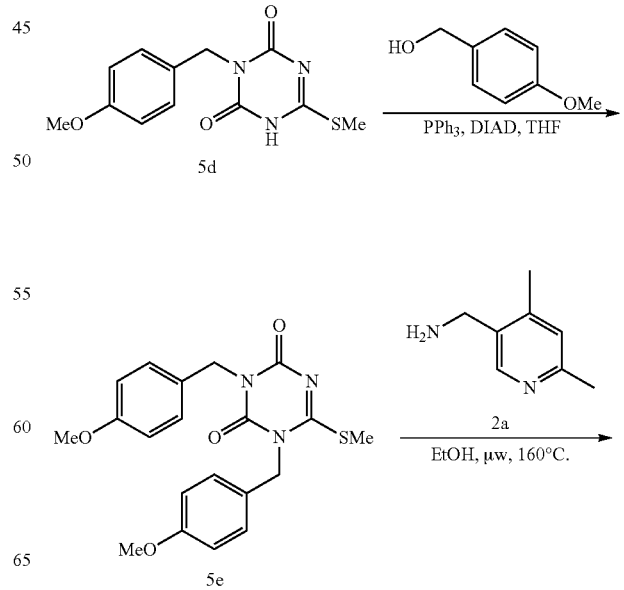

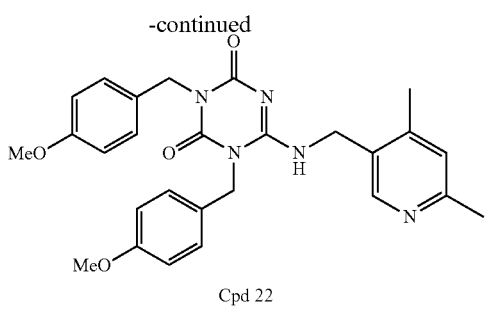

Cpd 22

A. ((4-Methoxybenzyl)amino)carbonyl)carbamimidothioic acid methyl ester (Cpd 5b). S-methylisothiouronium sulfate (15.35 g, 55.2 mmol) was dissolved in 8:2:1 MeOH/H$_2$O/THF (150 mL) and the mixture was treated with 3 N NaOH (18.4 mL, 55.2 mmol). The solution was then cooled to 0° C. and 4-methoxybenzyl isocyanate (Cpd 5a, 9.0 g, 55.2 mmol) was added dropwise over 30 min. The reaction was stirred overnight and gradually warmed to room temperature. The mixture was then washed with saturated aqueous NH$_4$Cl (100 mL) and extracted with dichloromethane (3×75 mL). The combined organic phases were dried over Na$_2$SO$_4$, filtered and concentrated under reduced pressure. The resultant residue was purified by normal phase column chromatography (silica gel, 20% EtOAc—100% EtOAc in heptane), to give Compound 5b.

C. 5-(Methylthio)-3,7-dioxo-1-(4-methoxybenzyl)-2-oxa-4,6,8-triazanon-4-en-9-oic acid methyl ester (Cpd 5c). A solution of Compound 5b (7.9 g, 31.2 mmol) in dichloromethane (150 mL) was treated with triethylamine (5.22 mL, 37.4 mmol) and the mixture was cooled to –10° C. Methyl chloroformate (4.79 mL, 62.4 mmol) was added dropwise over 15 min and the reaction was stirred for 4 h while gradually warming to room temperature. The solution was then washed with saturated aqueous NH$_4$Cl (100 mL) and extracted with dichloromethane (3×75 mL). The combined organic phases were dried over Na$_2$SO$_4$, filtered and concentrated. The resultant residue was purified by normal phase column chromatography (silica gel, 5% MeOH/95% CH$_2$Cl$_2$) to afford Compound 5c.

D. 3-(4-Methoxybenzyl)-6-methylsulfanyl-1H-[1,3,5]triazine-2,4-dione (Cpd 5d). Compound 5c (8.1 g, 26.0 mmol) was dissolved in MeOH (150 mL) and the solution was treated with NaOMe in MeOH (4.6 M, 10.1 mL, 31.2 mmol) and the reaction was allowed to stir at room temperature for 1 h. A white precipitate formed upon addition of the NaOMe. The reaction mixture was diluted with 1N HCl (50 mL) and the resultant precipitate was collected by vacuum filtration. The solid was dried under reduced pressure at 160° C. over xylenes to afford Compound 5d as its HCl salt.

E. 3-(4-Methoxybenzyl)-1-(4-methoxybenzyl)-6-methylsulfanyl-1H-[1,3,5]triazine-2,4 dione (Cpd 5e). Compound 5d (4.0 g, 12.7 mmol) was dissolved in THF and was treated with 4-methoxybenzyl alcohol (1.75 g, 12.7 mmol), triphenylphosphine (6.7 g, 25.4 mmol), and diisopropyl azodicarboxylate (2.57 g, 12.7 mmol). The reaction was allowed to stir overnight at room temperature. The solution was partitioned between water (100 mL) and ethyl acetate (3×75 mL). The combined organic layers were dried over anhydrous sodium sulfate, filtered and concentrated under reduced pressure. The crude mixture was purified by normal phase column chromatography (silica gel, 20% ethyl acetate-100% ethyl acetate in heptane) to afford Compound 5e.

F. 6-[(4,6-Dimethyl-pyridin-3-ylmethyl)-amino]-1,3-bis-(4-methoxy-benzyl)-1H-[1,3,5]triazine-2,4-dione (Cpd 22). Compound 5e (100 mg, 0.25 mmol) and Compound 2a (140 mg, 1.0 mmol) were suspended in EtOH (2 mL) and the reaction was irradiated at 160° C. for a total of 60 min in a microwave instrument. The reaction mixture was then reduced under nitrogen and the residue was purified and isolated by reverse phase HPLC to afford Compound 61. MS m/z (ES)=488.3 (M+H); $^1$H NMR (DMSO, d$_6$) δ 2.39 (s, 3H), 2.62 (s, 3H), 3.71 (s, 3H), 3.74 (s, 3H), 4.53 (m, 2H), 4.82 (s, 2H), 5.08 (s, 2H), 6.88 (m, 4H), 7.22 (m, 4H), 7.67 (s, 1H), 8.47 (s, 1H).

Other compounds of the present invention may be prepared by those skilled in the art by varying the starting materials, reagent(s) and conditions used. Using the general procedure of Example 5, the following compounds were prepared:

| Cpd | MS obs | MS calc |
|---|---|---|
| 1 | 513.7 | 513.4 |
| 2 | 499.6 | 499.4 |
| 4 | 478.8 | 479.9 |
| 5 | 478.8 | 479.9 |
| 6 | 475.8 | 476.5 |
| 8 | 463.1 | 463.5 |
| 9 | 525.2 | 525.6 |
| 10 | 476.9 | 477.5 |
| 12 | 544.2 | 544.6 |
| 13 | 543.2 | 543.6 |
| 20 | 545.1 | 545.6 |
| 25 | 554.3 | 554.6 |
| 35 | 511.2 | 511.5 |
| 36 | 503.2 | 503.5 |
| 37 | 502.2 | 502.5 |
| 38 | 529.2 | 529.5 |
| 39 | 460.2 | 460.5 |
| 40 | 460.2 | 460.5 |
| 41 | 460.2 | 460.5 |
| 52 | 488.2 | 488.5 |
| 57 | 551.2 | 551.6 |
| 58 | 505.2 | 505.5 |
| 59 | 474.2 | 474.5 |
| 60 | 476.2 | 476.5 |
| 62 | 474.2 | 474.5 |
| 63 | 473.2 | 473.5 |
| 64 | 528.2 | 528.5 |
| 65 | 474.0 | 474.5 |
| 75 | 491.2 | 491.6 |
| 76 | 446.2 | 446.5 |
| 77 | 485.2 | 485.5 |
| 78 | 455.2 | 455.5 |
| 79 | 439.2 | 439.5 |
| 80 | 475.2 | 475.5 |
| 81 | 470.1 | 470.5 |
| 82 | 490.1 | 490.5 |
| 86 | 473.2 | 473.5 |
| 87 | 529.2 | 529.5 |
| 88 | 470.1 | 470.5 |
| 91 | 517.1 | 517.5 |
| 92 | 475.2 | 475.5 |
| 93 | 503.2 | 503.5 |
| 94 | 489.1 | 489.5 |
| 95 | 476.1 | 476.5 |
| 96 | 524.2 | 524.5 |
| 98 | 529.2 | 529.5 |
| 99 | 542.3 | 542.5 |
| 100 | 504.1 | 504.6 |
| 101 | 459.1 | 459.5 |
| 102 | 498.1 | 498.6 |
| 103 | 452.2 | 452.6 |
| 104 | 489.1 | 489.5 |
| 105 | 542.3 | 542.5 |
| 106 | 488.2 | 488.6 |
| 116 | 476.2 | 476.5 |
| 117 | 492.1 | 493.0 |
| 122 | 527.8 | 528.5 |

| Cpd | MS obs | MS calc |
|---|---|---|
| 125 | 487.2 | 487.5 |
| 126 | 485.2 | 485.5 |
| 127 | 484.2 | 484.5 |
| 128 | 500.2 | 500.6 |
| 129 | 498.1 | 498.6 |
| 130 | 497.2 | 497.6 |
| 131 | 523.2 | 523.6 |
| 132 | 536.2 | 536.6 |
| 135 | 517.2 | 517.6 |
| 136 | 533.3 | 533.6 |
| 137 | 520.2 | 520.5 |
| 138 | 484.2 | 484.5 |
| 139 | 497.2 | 497.6 |
| 140 | 501.1 | 501.6 |
| 142 | 514.2 | 514.6 |
| 149 | 481.2 | 481.6 |
| 150 | 494.2 | 494.6 |
| 152 | 603.3 | 603.7 |
| 153 | 468.1 | 468.5 |
| 154 | 474.2 | 474.5 |
| 155 | 512.2 | 512.6 |
| 170 | 484.2 | 484.5 |
| 171 | 484.2 | 484.5 |
| 172 | 497.2 | 497.6 |
| 200 | 505.5 | 505.5 |
| 201 | 474.3 | 474.5 |
| 203 | 493.1 | 493.5 |
| 204 | 506.2 | 506.6 |
| 205 | 493.3 | 493.5 |
| 206 | 506.3 | 506.6 |
| 224 | 483.3 | 483.6 |
| 231 | 479.0 | 478.9 |
| 234 | 473.9 | 473.53 |
| 235 | 527.8 | 527.50 |
| 236 | 527.8 | 527.50 |
| 237 | 528.2 | 527.50 |
| 238 | 443.2 | 466.54 |
| 239 | 469.2 | 468.56 |
| 241 | 519.03 | 518.57 |
| 246 | 590.8 | 590.68 |
| 247 | 475.2 | 474.52 |
| 248 | 489.9 | 489.54 |
| 250 | 608.27 | 608.70 |
| 253 | 487.27 | 487.00 |
| 254 | 453.3 | 452.56 |
| 255 | 521.26 | 521.45 |
| 256 | 459.1 | 458.95 |
| 257 | 491.09 | 490.51 |
| 258 | 508.22 | 507.51 |
| 259 | 532.2 | 531.61 |
| 260 | 533.3 | 532.60 |
| 263 | 516.9 | 516.60 |
| 264 | 528.9 | 528.61 |
| 265 | 559.3 | 558.68 |
| 266 | 464.15 | 463.46 |
| 267 | 473.9 | 473.53 |
| 271 | 453.16 | 452.51 |
| 272 | 465.3 | 464.57 |

Additional $^1$H NMR Data for Compounds of Example 5

6-[(2-Amino-pyridin-3-ylmethyl)-amino]-3-(4-methoxy-benzyl)-1-(5-methoxy-pentyl)-1H-[1,3,5]triazine-2,4-dione (Cpd 78). $^1$H NMR (DMSO, d$_6$) δ 1.30 (m, 2H), 1.53 (m, 4H), 3.20 (s, 3H), 3.28 (t, 2H, J=6.25 Hz), 3.71 (s, 3H), 3.79 (m, 2H), 4.38 (d, 2H, J=3.88 Hz), 4.80 (s, 2H), 6.86 (m, 3H), 7.23 (d, 2H, J=8.68 Hz), 7.92 (d, 1H, J=5.31 Hz), 8.18 (m, 1H).

6-[(2-Amino-4,6-dimethyl-pyridin-3-ylmethyl)-amino]-1-(1H-indol-4-ylmethyl)-3-(4-methoxy-benzyl)-1H-[1,3,5]triazine-2,4-dione (Cpd 155). $^1$H NMR (DMSO, d$_6$) δ 2.33 (s, 3H), 2.35 (s, 3H), 3.71 (s, 3H), 4.35 (m, 2H), 4.84 (s, 2H), 5.32 (s, 2H), 6.43 (s, 1H), 6.60 (m, 2H), 6.83 (d, 2H, J=8.67 Hz), 7.01 (t, 1H, J=8.15 Hz), 7.24 (d, 2H, J=8.66 Hz), 7.34 (m, 2H), 7.98 (s, 1H), 11.25 (s, 1H).

6-[(2-Amino-4,6-dimethyl-pyridin-3-ylmethyl)-amino]-3-(4-methoxy-benzyl)-1-(5-methoxy-pentyl)-1H-[1,3,5]triazine-2,4-dione (Cpd 224). $^1$H NMR (DMSO, d$_6$) δ 1.25 (m, 2H), 1.47 (m, 4H), 2.37 (s, 3H), 2.49 (s, 3H), 3.19 (s, 3H), 3.25 (t, 2H, J=6.31 Hz), 3.72 (s, 3H), 3.79 (t, 2H, J=6.97 Hz), 4.37 (d, 2H, J=4.30 Hz), 4.80 (s, 2H), 6.69 (s, 1H), 6.86 (d, 2H, J=8.73 Hz), 7.23 (d, 2H, J=8.68 Hz), 7.60 (s, 1H), 7.80 (m, 1H).

Example 6

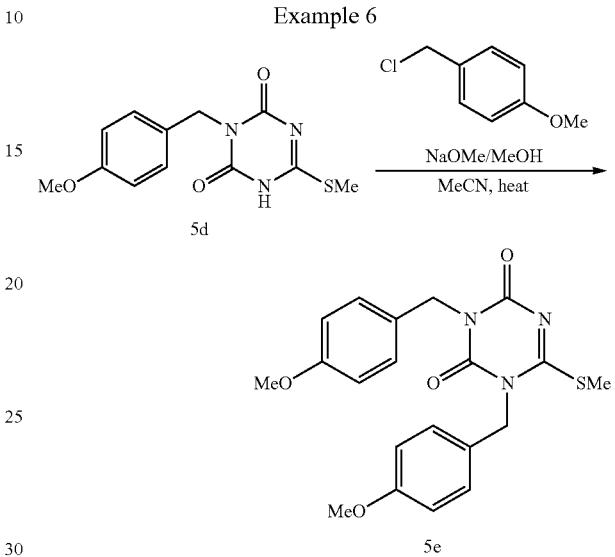

Example 6 describes an alternative route for the preparation of 3-(4-methoxybenzyl)-1-(4-methoxybenzyl)-6-methylsulfanyl-1H-[1,3,5]triazine-2,4 dione, Cpd 5e. Compound 5d (2.0 g, 7.2 mmol) was dissolved in acetonitrile (100 mL) and the reaction mixture was treated with diisopropylethylamine (2.5 mL, 14.3 mmol) and 4-methoxybenzyl chloride (1.35 g, 8.6 mmol). The reaction mixture was then heated to 90° C. and was allowed to stir overnight. Upon cooling, the mixture was partitioned between saturated aqueous NH$_4$Cl (100 mL) and ethyl acetate (3×75 mL). Combined organic extracts were dried over Na$_2$SO$_4$, filtered and reduced. Purification by normal phase column chromatography (silica gel, 20% ethyl acetate-100% ethyl acetate in heptane) afforded Compound 5e as a white solid.

Example 7

6-[(2-Amino-4,6-dimethyl-pyridin-3-ylmethyl)-amino]-1,3-bis-(4-methoxy-benzyl)-1H-[1,3,5]triazine-2,4-dione (Cpd 97)

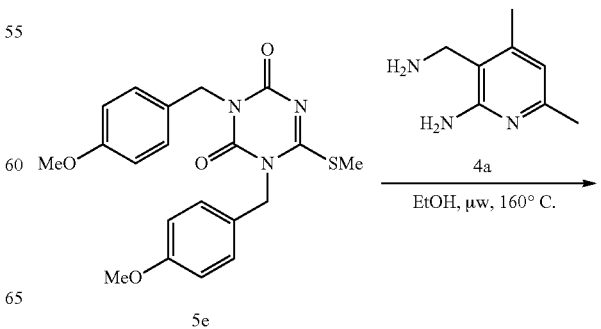

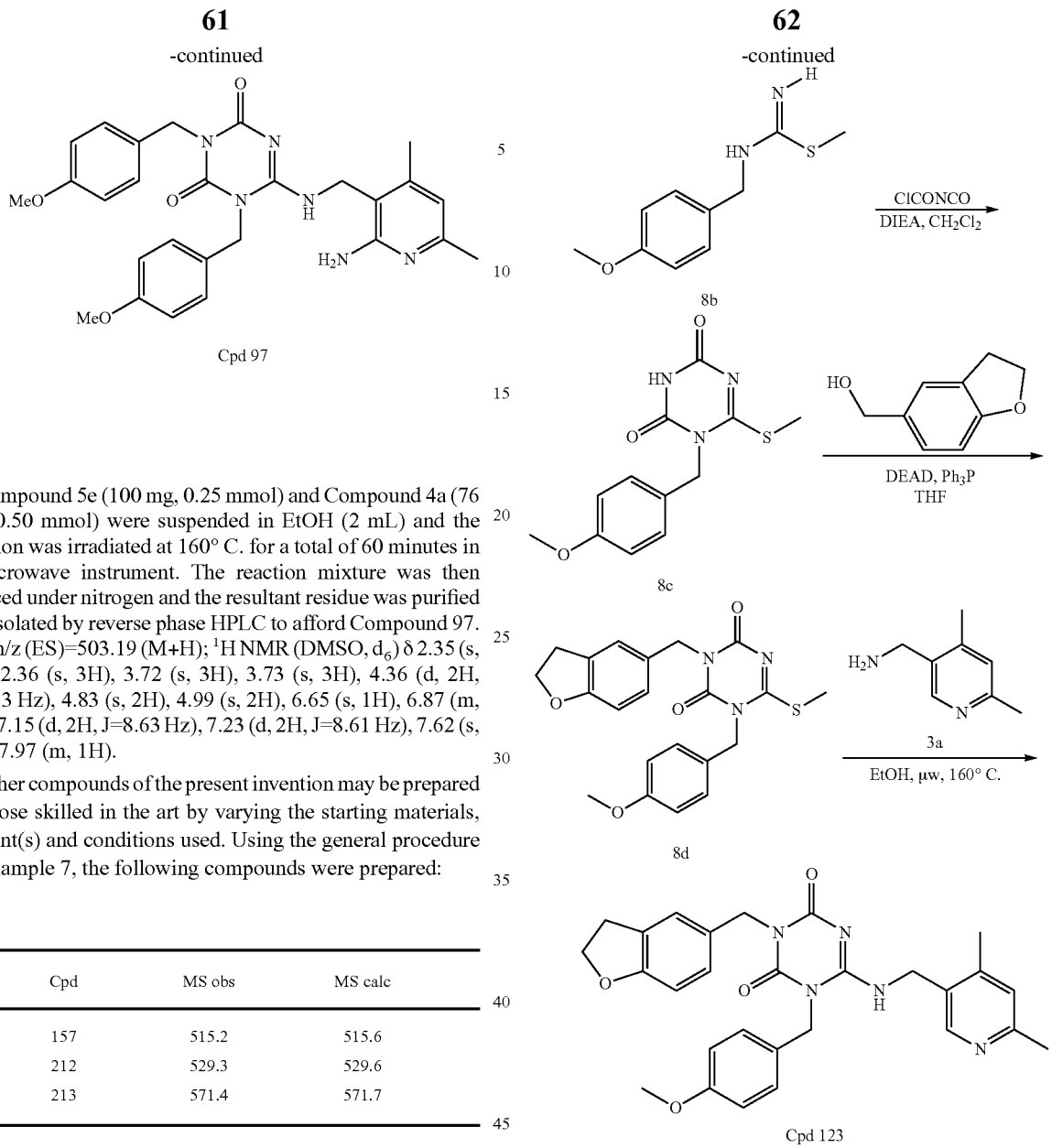

Compound 5e (100 mg, 0.25 mmol) and Compound 4a (76 mg, 0.50 mmol) were suspended in EtOH (2 mL) and the reaction was irradiated at 160° C. for a total of 60 minutes in a microwave instrument. The reaction mixture was then reduced under nitrogen and the resultant residue was purified and isolated by reverse phase HPLC to afford Compound 97. MS m/z (ES)=503.19 (M+H); $^1$H NMR (DMSO, $d_6$) δ 2.35 (s, 3H), 2.36 (s, 3H), 3.72 (s, 3H), 3.73 (s, 3H), 4.36 (d, 2H, J=3.33 Hz), 4.83 (s, 2H), 4.99 (s, 2H), 6.65 (s, 1H), 6.87 (m, 4H), 7.15 (d, 2H, J=8.63 Hz), 7.23 (d, 2H, J=8.61 Hz), 7.62 (s, 2H), 7.97 (m, 1H).

Other compounds of the present invention may be prepared by those skilled in the art by varying the starting materials, reagent(s) and conditions used. Using the general procedure of Example 7, the following compounds were prepared:

| Cpd | MS obs | MS calc |
| --- | --- | --- |
| 157 | 515.2 | 515.6 |
| 212 | 529.3 | 529.6 |
| 213 | 571.4 | 571.7 |

Example 8

3-(2,3-Dihydro-benzofuran-5-ylmethyl)-6-[(4,6-dimethyl-pyridin-3-ylmethyl)-amino]-1-(4-methoxy-benzyl)-1H-[1,3,5]triazine-2,4-dione (Cpd 123)

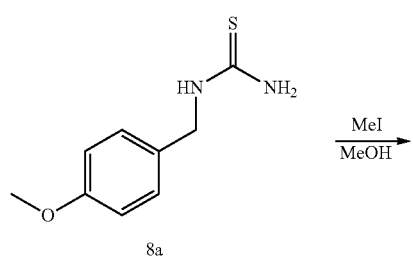

A. 1-(4-Methoxy-benzyl)-6-methylsulfanyl-1H-[1,3,5]triazine-2,4-dione (Cpd 6b). To (4-methoxy-benzyl) thiourea (Cpd 8a, 2.00 g, 10.1 mmol) in MeOH (40 mL) was added methyl iodide (0.64 mL, 10.1 mmol). The reaction was stirred at room temperature for 24 h. The reaction mixture was concentrated to yield crude compound 8b that was used in the next step without further purification.

B. 1-(4-Methoxy-benzyl)-6-methylsulfanyl-1H-[1,3,5]triazine-2,4-dione (Cpd 6c). To Compound 8b (3.6 g, 17.1 mmol) in methylene chloride (40 mL) was added excess diisopropylethylamine (6.61 g, 51.3 mmol). The reaction mixture was cooled to 0° C. A portion of N-chlorocarbonyl isocyanate (1.78 g, 17.1 mmol) was added dropwise. The reaction mixture was allowed to slowly warm to room temperature. After 24 h, water was added and the reaction mixture was extracted with ethyl acetate. The phases were separated, and the organic layer was dried over sodium sulfate, filtered, and concentrated. Methanol was added to the crude product, and the solid was collected by vacuum filtration to give Compound 8c. $^1$H NMR (DMSO-$d_6$) δ 2.45 (3H, s), 3.73 (3H, s), 4.98 (2H, s), 6.89-6.92 (2H, d, J=8.5 Hz), 7.22-7.25 (2H, d, J=8.5 Hz), 11.58 (1H, s).

C. 3-(2,3-Dihydro-benzofuran-5-ylmethyl)-1-(4-methoxy-benzyl)-6-methylsulfanyl-1H-[1,3,5]triazine-2,4-dione (Cpd 8d). To Cpd 8c (0.3 g, 1.07 mmol) in tetrahydrofuran was added 2,3-dihydro-1-benzofuran-5-ylmethanol (0.16 g, 1.07 mmol), triphenylphosphine (0.57 g, 2.15 mmol) and diethyl azodicarboxylate (0.22 g, 1.29 mmol). The reaction was stirred at room temperature for 24 h. The reaction mixture was taken up in ethyl acetate, washed with water, and the phases were separated. The organic layer was dried over sodium sulfate, filtered, and concentrated. The resulting material was purified by normal phase chromatography using an ISCO automated system to give Cpd 8d.

D. 3-(2,3-Dihydro-benzofuran-5-ylmethyl)-6-[(4,6-dimethyl-pyridin-3-ylmethyl)-amino]-1-(4-methoxy-benzyl)-1H-[1,3,5]triazine-2,4-dione (Cpd 8e). Compound 8d (100 mg, 0.24 mmol) and compound 3a (33 mg, 0.25 mmol) were suspended in EtOH (2 mL) and the reaction was irradiated at 160° C. for 60 minutes in a microwave instrument. The reaction mixture was then reduced under nitrogen and the product was purified and isolated by reverse phase HPLC to afford Compound 123. MS m/z (ES)=500.0 (M+H); $^1$H NMR (DMSO, $d_6$) δ 2.49 (3H, s), 2.60 (3H, s), 3.08-3.19 (2H, t, J=8.64 Hz), 3.73 (3H, s), 4.45-4.53 (4H, m), 4.80 (2H, s), 5.05 (2H, s), 6.65-6.68 (1H, d, J=8.18 Hz), 6.87-6.91 (1H, d, J=8.7 Hz), 7.03-7.06 (1H, m), 7.15-7.18 (2H, m), 7.66 (1H, s), 8.30-8.35 (1H, br s), 8.45 (1H, s).

Other compounds of the present invention may be prepared by those skilled in the art by varying the starting materials, reagent(s) and conditions used. Using the general procedure of Example 8, the following compounds were prepared:

| Cpd | MS obs | MS calc |
| --- | --- | --- |
| 45 | 529.1 | 529.5 |
| 46 | 489.3 | 489.5 |
| 47 | 490.2 | 490.5 |
| 48 | 515.2 | 515.6 |
| 49 | 513.2 | 513.5 |
| 55 | 463.2 | 463.5 |
| 56 | 503.3 | 503.5 |
| 107 | 501.9 | 502.6 |
| 108 | 503.0 | 503.5 |
| 109 | 527.8 | 528.6 |
| 110 | 525.9 | 526.5 |
| 111 | 488.0 | 488.6 |
| 112 | 475.9 | 476.5 |
| 113 | 458.9 | 459.5 |
| 114 | 515.8 | 516.6 |
| 124 | 519.9 | 520.5 |
| 133 | 497.9 | 498.6 |
| 134 | 484.9 | 485.5 |
| 143 | 474.9 | 475.5 |
| 144 | 487.9 | 488.6 |
| 145 | 500.9 | 501.6 |
| 146 | 513.9 | 514.6 |

Example 9

6-[(2-Amino-pyridin-3-ylmethyl)-amino]-3-(4-hydroxy-benzyl)-1-(4-methoxy-benzyl)-1H-[1,3,5]triazine-2,4-dione (Cpd 54)

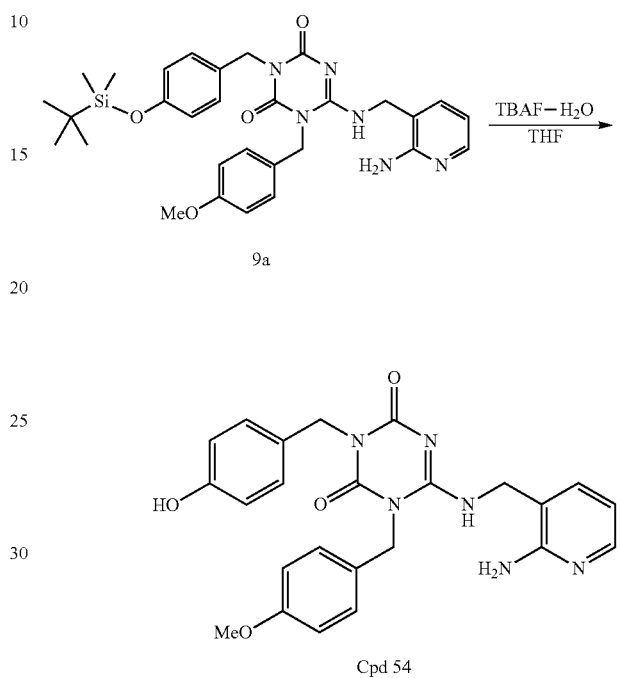

A. 6-[(2-Amino-pyridin-3-ylmethyl)-amino]-3-[4-(tert-butyl-dimethyl-silanyloxy)-benzyl]-1-(4-methoxy-benzyl)-1H-[1,3,5]triazine-2,4-dione (Cpd 9a) (150 mg, 0.26 mmol) was prepared according to the methods described in Example 8, and substituting [4-(tert-butyl-dimethyl-silanyloxy)-phenyl]-methanol for 2,3-dihydro-1-benzofuran-5-ylmethanol in Step C.

B. 6-[(2-Amino-pyridin-3-ylmethyl)-amino]-3-(4-hydroxy-benzyl)-1-(4-methoxy-benzyl)-1H-[1,3,5]triazine-2,4-dione (Cpd 54). Compound 7a was suspended in THF (3 mL) and the reaction mixture was treated with tetrabutylammonium fluoride monohydrate (82 mg, 0.31 mmol). The solution was stirred at room temperature overnight. The mixture was then concentrated under nitrogen and the residue was purified by reverse phase HPLC to give the title compound 54. MS m/z (ES)=461.1 (M+H).

Other compounds of the present invention may be prepared by those skilled in the art by varying the starting materials, reagent(s) and conditions used. Using the general procedure of Example 9, the following compounds were prepared:

| Cpd | MS obs | MS calc |
| --- | --- | --- |
| 181 | 510.2 | 510.5 |

Example 10

6-[(6-Amino-pyridin-2-ylmethyl)-amino]-1,3-bis-(4-methoxy-benzyl)-1H-[1,3,5]triazine-2,4-dione (Cpd 115)

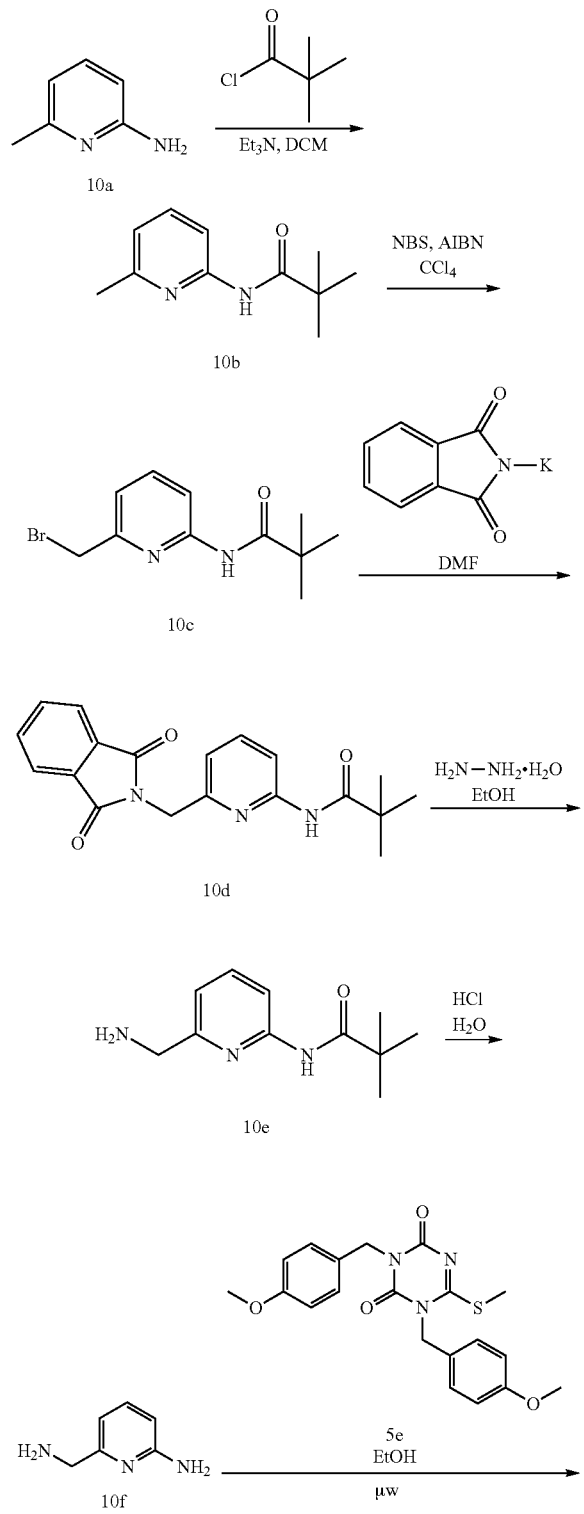

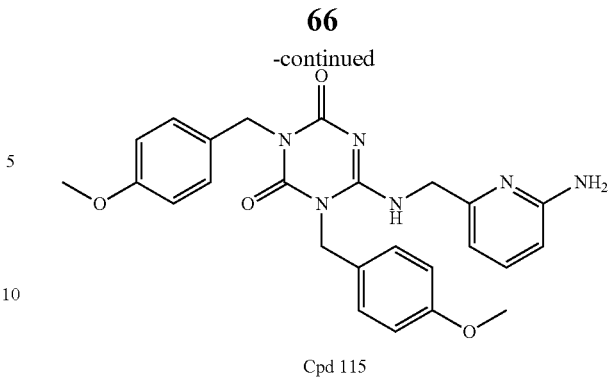

Cpd 115

A. 2,2-Dimethyl-N-(6-methyl-pyridin-2-yl)-propionamide (Cpd 10b) To a mixture of 2-amino-6-methylpyridine 10a (500 mg, 4.6 mmol), and triethylamine (778 µL, 5.98 mmol) in dichloromethane (50 mL) was added pivaloyal chloride (628 µL, 5.1 mmol). The mixture was allowed to stir at room temperature for three hours. The mixture was washed with saturated sodium bicarbonate followed by brine. The organic extract was dried over magnesium sulfate and concentrated to give Compound 10b (876 mg) as a crude oil, which solidified upon standing.

B. N-(6-Bromomethyl-pyridin-2-yl)-2,2-dimethyl-propionamide (Cpd 10c) A mixture of compound 10b, (776 mg, 4.03 mmole), N-bromosuccinimide (NBS) (431 mg, 2.4 mmol), and 2,2'-azobisisobutyronitrile (66 mg, 0.4 mmol) in carbon tetrachloride (100 mL) was heated to 90° C. for 2.5 hours. LC analysis indicated a mixture of the desired product, undesired di-bromonated material and starting material. The mixture was cooled to room temperature, washed with saturated sodium bicarbonate and brine. The organic extract was dried over magnesium sulfate and concentrated to yellow oil. The oil was purified by normal phase chromatography, eluting with 10-30% ethyl acetate in heptane to yield compound 10c. MS m/z (ES)=193.2 (M+H).

C. N-[6-(1,3-Dioxo-1,3-dihydro-isoindol-2-ylmethyl)-pyridin-2-yl]-2,2-dimethyl-propionamide (Cpd 10d) A mixture of compound 10c (335 mg, 1.24 mmol) and potassium phthalamide (230 mg, 1.24 mmol) in DMF (3 mL) was heated to 160° C. in an oil bath for 4 hours. The mixture was cooled to room temperature and allowed to stir overnight. The mixture was diluted with water (100 mL) and extracted 2× with ethyl acetate. The combined organic extracts were washed with water, dried over magnesium sulfate and concentrated to a yellow oil-solid. This material was purified by normal phase chromatography, eluting with 30-50% ethyl acetate in heptane to give compound 10d. MS m/z (ES)=338.1 (M+H).

D. N-(6-Aminomethyl-pyridin-2-yl)-2,2-dimethyl-propionamide (Cpd 10e). A mixture of compound 10d (200 mg, 0.59 mmol), and hydrazine monohydrate (29 µL, 0.59 mmol) in ethanol (10 mL) was heated to 90° C. for six hours then cooled to rt and allowed to stir overnight. LC analysis indicated the reaction was incomplete so an additional 54 of hydrazine monohydrate was added and the mixture was heated to 90° C. for 22 h. The mixture was concentrated, and the resultant residue was taken up in ethyl acetate, giving a white precipitate. The precipitate was removed by filtration, and the filtrate was concentrated and then purified by reverse phase liquid chromatography to afford Compound 10e. MS m/z (ES)=208.1 (M+H). $^1$H NMR (MeOD, $d_4$). δ 1.25 (s, 9H), 4.12 (s, 3H), 7.18 (d, 1H, J=7.7 Hz), 7.84 (t, 1H, J=8.0, 7.8 Hz), 8.01-8.04 (d, 1H, J=8.0 Hz).

E. 6-Aminomethyl-pyridin-2-ylamine (Cpd 10f). To a solution of compound 10e (100 mg, 0.48 mmol) in water (10 mL) was added concentrated HCl (500 μL, 12M). The mixture was heated to reflux for 30 minutes. After cooling to rt, the solution was allowed to stir overnight. Nitrogen gas was bubbled through the solution for one hour. The solution was then lyophilized to obtain compound 10f. MS m/z (ES)=124.1 (M+H).

F. 6-[(6-Amino-pyridin-2-ylmethyl)-amino]-1,3-bis-(4-methoxy-benzyl)-1H-[1,3,5]triazine-2,4-dione (Cpd 115). A mixture of compound 5e (168 mg, 0.42 mmol), compound 10f (95 mg, 0.42 mmol), diisopropylethylamine (187 μL, 1.7 mmol) and ethanol (3 mL) was irradiated at 140° C. for 20 minutes in a microwave instrument. Subsequently, the mixture was irradiated at 160° C. for 20 minutes in a microwave instrument. The resulting mixture was purified by reverse phase HPLC to give compound 115 as its TFA salt. MS m/z (ES)=474.9 (M+H). $^1$H NMR (DMSO, d$_6$). 53.65 (s, 3H), 3.74 (s, 3H), 4.44 (s, 2H), 4.64 (s, 2H), 5.01 (s, 2H), 6.32 (d, 1H, J=7.3 Hz), 6.71 (d, 1H, J=8.7 Hz), 6.79 (d, 2H, J=8.7 Hz), 6.86 (d, 2H, J=8.7 Hz), 7.14-7.18 (dd, 4H, J=5.2, 5.2 Hz), 7.72 (t, 1H, J=7.6, 8.4 Hz), 7.71-7.75 (bs, 2H), 8.33 (s, 1H).

Example 11

1,3-Bis-(4-methoxy-benzyl)-6-[(6-propylamino-pyridin-2-ylmethyl)-amino]-1H-[1,3,5]triazine-2,4-dione, (Cpd 147)

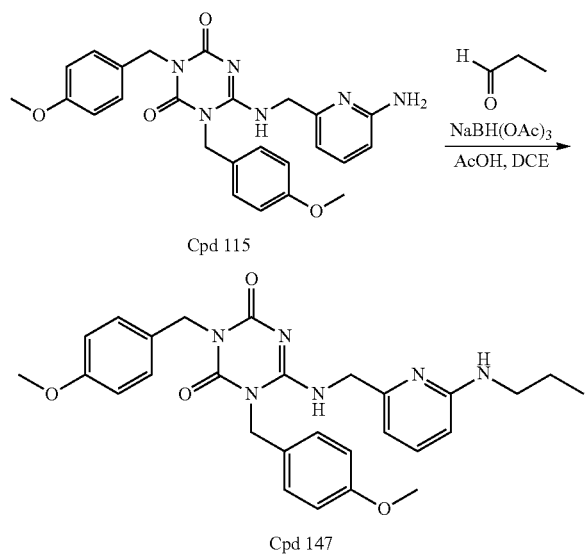

A. 1,3-Bis-(4-methoxy-benzyl)-6-[(6-propylamino-pyridin-2-ylmethyl)-amino]-1H-[1,3,5]triazine-2,4-dione (Cpd 147). A mixture of Compound 115 (30 mg, 0.13 mmol), propionaldehyde (5.8 μL, 0.086 mmol), sodium triacetoxyborohydride (18 mg, 0.086 mmol) and acetic acid (12 μL, 0.215 mmol) in dichloroethane (5 mL) was allowed to stir at room temperature. After four days, an additional 10 μL of propionaldehyde was added. After stirring an additional day, another 10 μL of propionaldehyde as added. The reaction was washed with saturated sodium bicarbonate and brine. The organic layer was dried over magnesium sulfate, filtered, and the filtrate was concentrated. The concentrate was purified by reverse phase chromatography to obtain compound 147 as its TFA salt. MS m/z (ES)=516.9 (M+H).

Example 12

6-[(6-Amino-pyridin-2-ylmethyl)-amino]-1,3-bis-(4-methoxy-benzyl)-1H-pyrimidine-2,4-dione (Cpd 148)

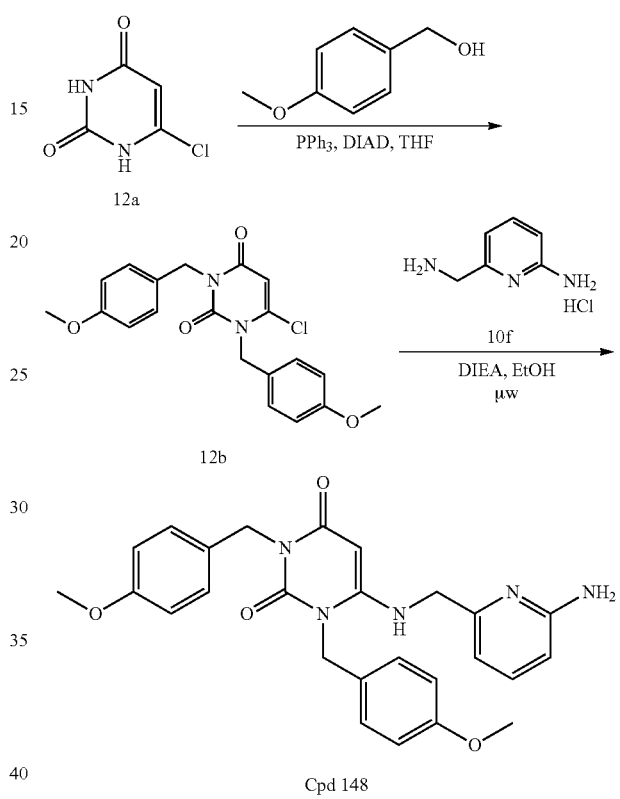

A. 6-Chloro-1,3-bis-(4-methoxy-benzyl)-1H-pyrimidine-2,4-dione (Cpd 10b). A solution of 6-chlorouracil 12a, (500 mg, 3.4 mmol), 4-methoxybenzyl alcohol (990 mg, 7.2 mmol), triphenylphosphine (2.9 g, 11.2 mmol), diisopropylazodicarboxylate (1.6 mL, 8.2 mmol) in THF (100 mL) was allowed to stir at room temperature overnight. The solution was concentrated. The concentrate was taken up in ethyl acetate and washed with saturated sodium bicarbonate and brine. The organic layer was dried over magnesium sulfate, filtered, and the filtrate was concentrated. The concentrate was purified by reverse phase chromatography to afford compound 12b. MS m/z (ES)=386.9 (M+H). $^1$H NMR (MeOD, d$_4$). δ 3.75 (s, 3H), 3.76 (s, 3H), 5.01 (s, 2H), 5.21 (s, 2H), 5.99 (s, 1H), 6.82-6.88 (dd, 4H, J=8.9, 8.9 Hz), 7.22 (d, 2H, 8.5 Hz), 7.32 (d, 2H, J=8.9 Hz).

B. 6-[(6-Amino-pyridin-2-ylmethyl)-amino]-1,3-bis-(4-methoxy-benzyl)-1H-pyrimidine-2,4-dione (Cpd 12c). A suspension of compound 10f, (50 mg, 0.13 mmol), compound 12b (25 mg, 0.13 mmol), diisopropylethylamine (57 μL, 0.52 mmol) in ethanol (3 mL) was irradiated at 140° C. for 20 minutes in a microwave instrument. The mixture was concentrated and the residue purified by reverse phase chromatography to obtain compound 148 as its TFA salt. MS m/z (ES)=473.9 (M+H). $^1$H NMR (DMSO, d$_6$). δ 3.72 (s, 6H), 4.23 (bs, 2H), 4.77 (s, 2H), 5.12 (s, 2H), 6.78 (d, 1H, J=9.4

Hz), 6.88 (m, 1H), 6.81 (d, 2H, J=8.4 Hz), 6.91 (d, 2H, J=9.0 Hz), 7.22 (dd, 4H, J=8.9, 8.9 Hz), 7.40 (t, 1H, J=5.4, 5.4 Hz), 7.72 (t, 1H, J=8.4, 7.9 Hz).

Other compounds of the present invention may be prepared by those skilled in the art by varying the starting materials, reagent(s) and conditions used. Using the general procedure of Example 12, the following compounds were prepared:

| Cpd | MS obs | MS calc |
|-----|--------|---------|
| 26  | 474.3  | 474.5   |
| 61  | 487.2  | 487.6   |

Example 13

3-(4-Fluoro-benzyl)-1-(4-methoxy-benzyl)-6-[(5,6,7,8-tetrahydro-1,8]naphthyridin-2-ylmethyl)-amino]-1H-[1,3,5]triazine-2,4-dione (Cpd 21)

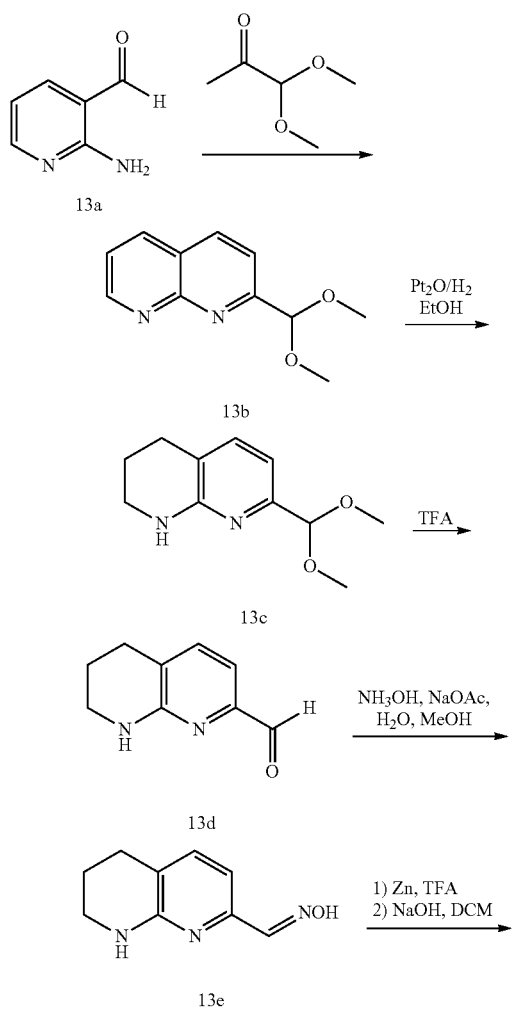

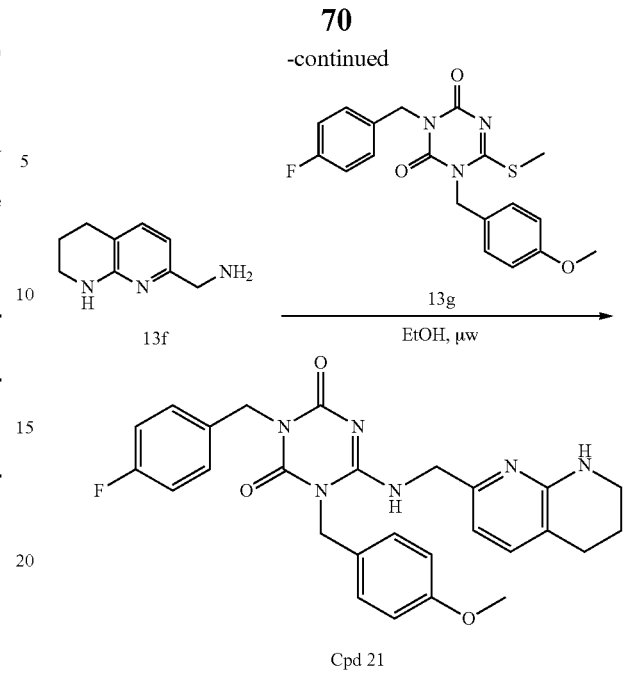

Cpd 21

A. 2-Dimethoxymethyl-[1,8]naphthyridine (Cpd 13b). A solution of 2-amino-3-pyridine carboxaldehyde (13a, 50 mg, 4.1 mmol), pyruvic aldehyde dimethyl acetal (641 µL, 5.3 mmol), 3N sodium hydroxide (1.8 mL, 5.3 mmol), ethanol (50 mL) and water (5 mL) was allowed to stir at room temperature overnight. The mixture was concentrated and the residue partitioned between ethyl acetate and brine. The organic layer was dried over magnesium sulfate, filtered, and the filtrate was concentrated to obtain 13b.

B. 7-Dimethoxymethyl-1,2,3,4-tetrahydro-[1,8]naphthyridine (Cpd 13c). A mixture of 13b (0.8 g, 3.9 mmol) and platinum oxide (27 mg, 0.12 mmol) in ethanol (100 mL) was placed under a hydrogen atmosphere at atmospheric pressure for 22 hours. The mixture was filtered through a pad of diatomaceous earth and the filtrate was concentrated to obtain product 13c (0.73 g) as a white solid.

C. 5,6,7,8-Tetrahydro-[1,8]naphthyridine-2-carbaldehyde (Cpd 13d). Compound 13c (0.73 g) was dissolved in trifluoroacetic acid (5 mL). The resulting mixture was allowed to stir at room temperature under argon for 1.5 hours. The mixture was concentrated. The residue was dissolved in methylene chloride and washed 2× with saturated sodium bicarbonate solution. The organic layer was dried over magnesium sulfate, filtered, and the filtrate was concentrated to obtain compound 13d.

D. 5,6,7,8-Tetrahydro-[1,8]naphthyridine-2-carbaldehyde oxime (Cpd 13e). A solution of hydroxylamine hydrochloride (0.46 g, 6.6 mmol), and sodium acetate trihydrate (0.90 g, 6.6 mmol) in water (50 mL) was heated to 60° C. To this mixture was added dropwise, a solution of 13d (0.54 g, 3.3 mmol) in methanol (50 mL). After stirring for 2 hours, the mixture was concentrated to approximately 50 mL. The residue was diluted with saturated sodium sulfate and extracted 2× with ethyl ether. The combined organic extracts were washed with saturated sodium bicarbonate solution, dried over sodium sulfate and concentrated to obtain compound 13e.

E. C-(5,6,7,8-Tetrahydro-[1,8]naphthyridin-2-yl)-methylamine (Cpd 13f). To a solution of 13e (0.46 g, 2.6 mmol) in trifluoroacetic acid (10 mL) was added zinc dust (0.95 g, 15 mmol). The mixture was stirred vigorously for 20 minutes. The resulting solution was poured into a mixture of 3N sodium hydroxide (43 mL, 130 mmol), and methylene chloride (50 mL) that was cooled in an ice bath. After warming to room temperature, the mixture was filtered through a pad of diatomaceous earth and rinsed with additional dichloromethane and water. The phases of the filtrate were separated. The organic layer was dried over sodium sulfate, filtered, and concentrated obtain the compound 13f. MS m/z (ES)=164.1 (M+H). $^1$H NMR (CDCl$_3$). δ 1.56-1.82 (bs, 2H), 1.91 (q, 2H, J=6.6, 5.9, 5.5, 6.6 Hz), 2.70 (t, 2H, J=6.2, 6.2 Hz), 3.40 (m, 2H), 3.71 (s, 2H), 4.84 (bs, 1H), 6.44 (d, 1H, J=7.2 Hz), 7.10 (d, 1H, J=7.2 Hz).

F. 3-(4-Fluoro-benzyl)-1-(4-methoxy-benzyl)-6-methylsulfanyl-1H-[1,3,5]triazine-2,4-dione (Cpd 13g). Compound 13g was obtained using the procedure described in Example 8, Step C, substituting 4-fluorobenzyl alcohol for 2,3-dihydro-1-benzofuran-5-ylmethanol.

G. 3-(4-Fluoro-benzyl)-1-(4-methoxy-benzyl)-6-[(5,6,7,8-tetrahydro-[1,8]naphthyridin-2-ylmethyl)-amino]-1H-[1,3,5]triazine-2,4-dione (Cpd 21). A mixture of 13g (50 mg, 0.13 mmol) and compound 13f (42 mg, 0.26 mmol) in ethanol (2 mL) was irradiated at 140° C. in a microwave instrument for two 20 minute cycles. The resulting mixture was concentrated and purified by reverse phase chromatography to obtain the desired compound 21. MS m/z (ES)=503.3 (M+H). $^1$H NMR (DMSO-d$_6$). δ 1.81 (bs, 2H), 2.72 (bs, 2H), 3.40 (bs, 2H), 4.49 (bs, 2H), 4.88 (s, 2H), 5.08 (s, 2H), 6.31-6.34 (d, 2H, J=7.3 Hz), 6.94 (d, 2H, J=8.7 Hz), 7.10-7.23 (m, 4H), 7.31-7.36 (m, 2H), 7.52 (d, 1H, J=7.3 Hz), 7.99 (bs, 1H), 8.40 (bs, 1H).

Example 14

1,3-Bis-(4-methoxy-benzyl)-6-(pyridin-3-yl-methoxy)-1H-pyrimidine-2,4-dione (Cpd 121)

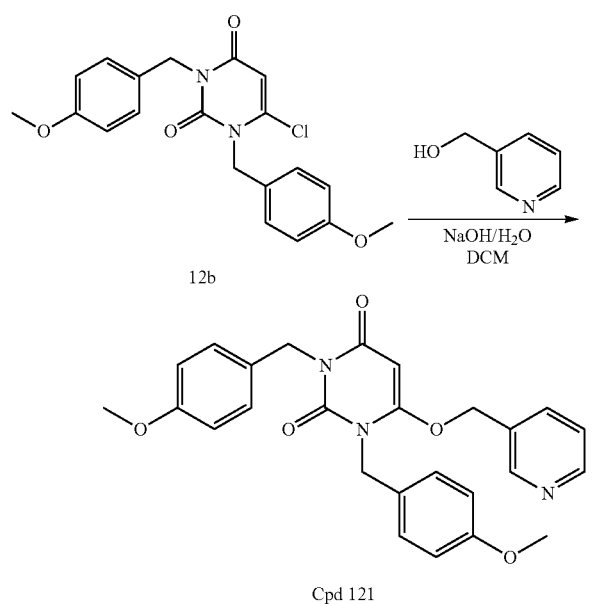

A solution of 12b (50 mg, 0.13 mmol) in dichloromethane (3 mL) was added to a mixture of pyridine 3-methanol (25 μL, 0.26 mmol), benzyltriethylammonium chloride (3 mg, 0.13 mmol) in 1N sodium hydroxide solution (2.6 mL). After stirring at room temperature for 24 hours, an additional 100 μL of pyridine 3-methanol was added. After stirring an additional 24 hours, the reaction mixture was separated, the organic layer dried over magnesium sulfate, filtered, and the filtrate was concentrated. The concentrate was purified by reverse phase chromatography to obtain Compound 121. MS m/z (ES)=459.9 (M+H). $^1$H NMR (DMSO-d$_6$). δ 3.71 (s, 6H), 4.92 (d, 4H, J=7.8 Hz), 5.29 (s, 2H), 5.45 (s, 1H), 6.84 (t, 4H, J=8.73, 8.91), 7.09 (d, 2H, J=8.74 Hz), 7.23 (d, 2H, J=8.61 Hz), 7.55 (q, 1H, J=5.04, 2.77, 5.07 Hz), 7.86 (d, 1H, J=7.99 Hz), 8.63 (s, 2H).

Other compounds of the present invention may be prepared by those skilled in the art by varying the starting materials, reagent(s) and conditions used. Using the general procedure of Example 14, the following compounds were prepared:

| Cpd | MS obs | MS calc |
|---|---|---|
| 190 | 474.9 | 475.5 |
| 202 | 503.3 | 503.6 |
| 225 | 488.9 | 489.5 |
| 232 | 476.2 | 475.5 |

Example 15

(3-Aminomethyl-pyridin-2-yl)-(2-methoxy-ethyl)-amine (Cpd 15c)

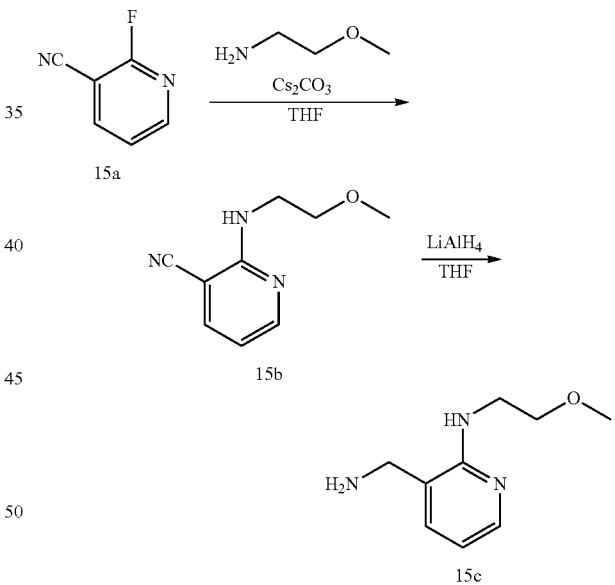

A. 2-(2-Methoxy-ethylamino)-nicotinonitrile (Cpd 15b) To a solution of 3-cyano-2-fluoropyridine (15a) (100 mg, 0.82 mmol) in tetrahydrofuran (1.6 mL) was added cesium carbonate (267 mg, 0.82 mmol) and 2-methoxyethylamine (68 mg, 0.9 mmol). The mixture was stirred at room temperature for 18 h, and then concentrated. The residue was taken up in dichloromethane/water, absorbed onto diatomaceous earth, and eluted with dichloromethane. The eluate was concentrated to provide compound 15b.

B. (3-Aminomethyl-pyridin-2-yl)-(2-methoxy-ethyl)-amine (Cpd 15c) To a cooled (0° C.) solution of lithium aluminum hydride (0.82 mL, 1M solution in tetrahydrofuran, 0.82 mmol) was added compound 15b in tetrahydrofuran (1 mL). The reaction mixture was stirred at 0° C. for 15 min, then stirred at room temperature for 1 h. After successively quenching with water (0.15 mL), sodium hydroxide (0.15 mL, 2N solution in water), and water (0.15 mL) the mixture was filtered and concentrated to furnish compound 15c.

Example 16

3-(4-Fluoro-benzyl)-1-(4-methoxy-benzyl)-6-{[2-(2-methoxy-ethylamino)-pyridin-3-ylmethyl]-amino}-1H-[1,3,5]triazine-2,4-dione (Cpd 28)

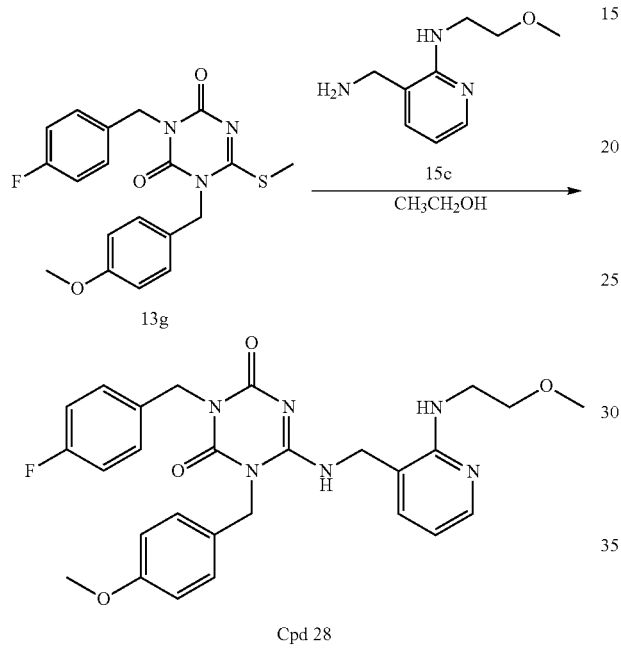

To a reaction vessel containing compound 13g (40 mg, 0.1 mmol) in ethanol (0.75 mL) was added compound 15c (36 mg, 0.2 mmol). The mixture was irradiated at 180° C. in a microwave instrument for two 30 min intervals, then concentrated. The residue was dissolved in methyl sulfoxide and purified by reverse phase chromatography to furnish the title compound 28 as its trifluoroacetate salt. $^1$H NMR (methanol-$d_4$): δ 7.78 (d, 1H, J=4.9 Hz), 7.68 (d, 1H, J=5.8 Hz), 7.46 (m, 2H), 7.12 (d, 2H, J=8.7 Hz), 7.02 (t, 2H, J=8.8 Hz), 6.85-6.80 (m, 3H), 5.10 (s, 2H), 5.03 (s, 2H), 4.57 (s, 2H), 3.75 (s, 3H), 3.59 (m, 4H), 3.19 (s, 3H); HRMS m/z (M+H)$^+$ calcd for $C_{27}H_{30}FN_6O_4$ 521.2313, found 521.2302.

Other compounds of the present invention may be prepared by those skilled in the art by varying the starting materials, reagent(s) and conditions used. Using the general procedure of Example 16, the following compounds were prepared:

| Cpd | MS obs | MS calc |
|---|---|---|
| 11 | 517.1 | 517.6 |
| 15 | 505.2 | 505.6 |
| 17 | 533.2 | 533.6 |
| 18 | 549.2 | 549.6 |
| 19 | 491.2 | 491.5 |
| 27 | 534.2 | 534.6 |
| 29 | 507.2 | 507.5 |
| 30 | 506.1 | 506.6 |
| 31 | 545.1 | 545.6 |
| 34 | 517.3 | 517.6 |
| 50 | 533.2 | 533.6 |
| 51 | 546.2 | 546.6 |
| 66 | 549.2 | 549.7 |
| 67 | 545.3 | 545.7 |
| 68 | 559.1 | 559.6 |
| 69 | 555.1 | 555.6 |
| 70 | 586.2 | 586.7 |
| 71 | 517.2 | 517.6 |
| 72 | 533.0 | 533.6 |
| 73 | 561.2 | 561.6 |
| 74 | 562.2 | 562.6 |

Example 17

6-[(2-Amino-pyridin-3-ylmethyl)-amino]-3-[2-(4-fluoro-phenoxy)-ethyl]-1-(4-methoxy-benzyl)-1H-[1,3,5]triazine-2,4-dione (Cpd 141)

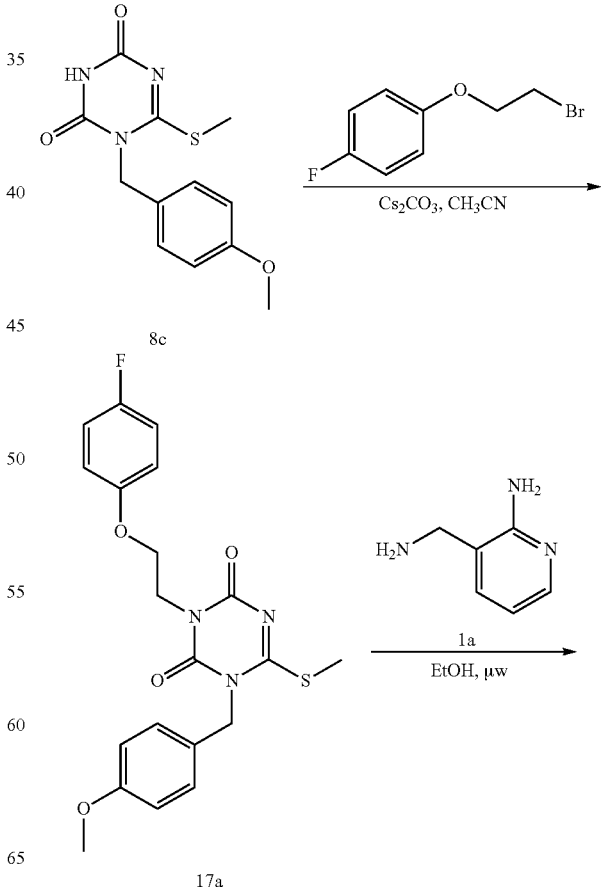

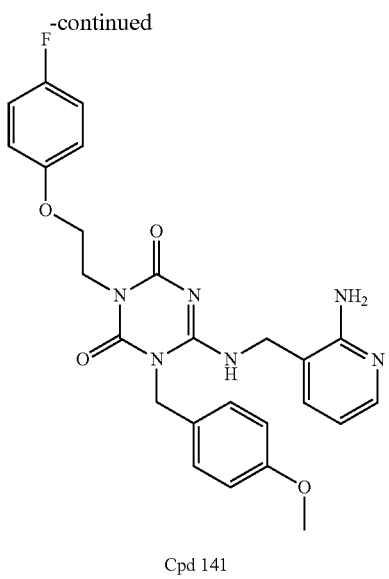

Cpd 141

A. 3-[2-(4-Fluoro-phenoxy)-ethyl]-1-(4-methoxy-benzyl)-6-methylsulfanyl-1H-[1,3,5]triazine-2,4-dione (Cpd 17a). To a reaction vessel containing compound 8c (28 mg, 0.1 mmol) in acetonitrile (0.5 mL) was added cesium carbonate (32 mg, 0.1 mmol) and 1-(2-bromo-ethoxy)-4-fluorobenzene (17.1 mg, 0.1 mmol). The mixture was stirred at room temperature for 16 h, then concentrated. The residue was taken up in dichloromethane/water, absorbed onto diatomaceous earth, and eluted with dichloromethane. The eluate was concentrated to provide compound 17a.

B. 6-[(2-Amino-pyridin-3-ylmethyl)-amino]-3-[2-(4-fluoro-phenoxy)-ethyl]-1-(4-methoxy-benzyl)-1H-[1,3,5]triazine-2,4-dione (Cpd 141). To Compound 17a in ethanol (0.5 mL) was added Compound 1a (18 mg, 0.15 mmol). The mixture was irradiated at 180° C. in a microwave instrument for two 30 min intervals, then concentrated. The residue was dissolved in methyl sulfoxide and purified by reverse phase chromatography to furnish the title compound 141 as its trifluoroacetate salt. $^1$H NMR (methanol-$d_4$): δ 7.80 (d, 1H, J=4.8 Hz), 7.61 (d, 1H, J=5.8 Hz), 7.17 (s, 1H), 7.14 (s, 1H), 6.98-6.79 (m, 8H), 5.12 (s, 2H), 4.50 (s, 2H), 4.28 (m, 2H), 4.22 (m, 2H), 3.77 (s, 3H); HRMS m/z (M+H)$^+$ calcd for $C_{25}H_{26}FN_6O_4$ 493.2000, found 493.1999.

Other compounds of the present invention may be prepared by those skilled in the art by varying the starting materials, reagent(s) and conditions used. Using the general procedure of Example 17, the following compounds were prepared:

| Cpd | MS obs | MS calc |
|---|---|---|
| 23 | 485.1 | 485.5 |
| 24 | 491.1 | 491.6 |
| 42 | 475.2 | 475.5 |
| 43 | 445.2 | 445.5 |
| 44 | 470.1 | 470.5 |
| 60 | 476.2 | 476.5 |
| 83 | 524.0 | 524.5 |
| 84 | 510.9 | 511.5 |
| 89 | 571.1 | 571.4 |
| 90 | 511.1 | 511.6 |
| 119 | 498.2 | 498.6 |
| 120 | 503.0 | 503.5 |
| 156 | 499.2 | 499.5 |
| 197 | 468.2 | 468.6 |
| 207 | 502.2 | 502.5 |
| 209 | 516.3 | 516.6 |
| 216 | 513.2 | 513.6 |
| 217 | 516.1 | 516.6 |
| 218 | 506.2 | 506.6 |
| 220 | 517.1 | 517.6 |
| 222 | 528.2 | 528.6 |
| 229 | 497.2 | 497.6 |
| 230 | 484.2 | 484.5 |

Additional $^1$H NMR Data for Compounds of Example 17

6-[(2-Amino-4,6-dimethyl-pyridin-3-ylmethyl)-amino]-1-(4-methoxy-benzyl)-3-(1-methyl-1H-benzotriazol-5-ylmethyl)-1H-[1,3,5]triazine-2,4-dione (Cpd 222). $^1$H NMR (methanol-$d_4$): δ 7.97 (s, 1H), 7.70 (m, 2H), 7.32 (d, 1H, J=8.7 Hz), 7.08 (d, 1H, J=8.7 Hz), 6.84 (m, 2H), 6.61 (s, 1H), 5.23 (s, 2H), 5.14 (s, 2H), 4.51 (s, 2H), 4.32 (s, 3H), 3.75 (s, 3H), 2.40 (s, 3H), 2.26 (s, 3H); HRMS m/z (M+H)$^+$ calcd for $C_{27}H_{30}N_9O_3$ 528.2472, found 517.2468.

Example 18

1-(4-Difluoromethoxy-benzyl)-6-[(4,6-dimethyl-pyridin-3-ylmethyl)-amino]-3-(4-fluoro-benzyl)-1H-[1,3,5]triazine-2,4-dione (Cpd 160)

-continued

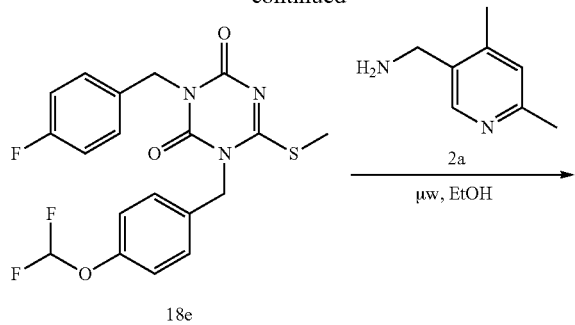

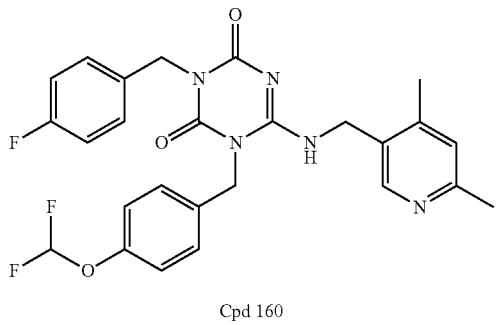

Cpd 160

A. (4-Difluoromethoxy-benzyl)-thiourea (18b). To a solution of compound 18a (2.0 g, 11.6 mmol) in dichloromethane (12 mL) at −78° C. was added ethereal hydrogen chloride (24 mL, 1.0 M solution in ethyl ether, 24 mmol). The mixture was allowed to warm to room temperature, then concentrated. To the resulting residue in 1,4-dioxane (32 mL) was added potassium isothiocyanate (1.7 g, 17.3 mmol). The mixture was stirred at reflux for 16 h, then concentrated. The residue was taken up in tetrahydrofuran (25 mL), poured into water (50 mL), and the layers separated. The aqueous layer was extracted with ethyl acetate (3×) and the combined organic layer was washed with 1N HCl and brine. The organic layer was dried over magnesium sulfate, filtered, and the filtrate was concentrated to provide compound 18b.

B. (4-Difluoromethoxy-benzyl)-thiourea hydroiodide (Cpd 18c). A mixture of Compound 18b (2.44 g, 10.5 mmol), iodomethane (1.8 g, 12.6 mmol), and methanol (13 mL) was stirred at room temperature for 18 h, then concentrated to a residue to provide Compound 18c, which was used without further purification in subsequent reactions.

C. 1-(4-Difluoromethoxy-benzyl)-6-methylsulfanyl-1H-[1,3,5]triazine-2,4-dione (Cpd 18d). To compound 18c in tetrahydrofuran (35 mL) was added cesium carbonate (17.1 g, 52.5 mmol). After cooling the mixture to 0° C., N-chlorocarbonyl isocyanate (4.4 g, 42 mmol) was added and the reaction mixture was stirred vigorously for 18 h, then concentrated. The resulting residue was taken up in dichloromethane and water and the layer was separated. The aqueous layer was extracted with dichloromethane and the combined organic layers were concentrated. The resultant residue was purified by flash chromatography (0-30% methanol/dichloromethane) to provide Compound 18d.

D. 1-(4-Difluoromethoxy-benzyl)-3-(4-fluoro-benzyl)-6-methylsulfanyl-1H-[1,3,5]triazine-2,4-dione (Cpd 18e). To a reaction vessel containing compound 18d (31 mg, 0.1 mmol) in acetonitrile (0.5 mL) was added cesium carbonate (32 mg, 0.1 mmol) and 4-fluorobenzyl bromide (18.9 mg, 0.1 mmol). The mixture was stirred at room temperature for 18 h, then concentrated. The residue was taken up in dichloromethane/water, absorbed onto diatomaceous earth, and eluted with dichloromethane. The eluate was concentrated to provide Compound 18e.

E. 1-(4-Difluoromethoxy-benzyl)-6-[(4,6-dimethyl-pyridin-3-ylmethyl)-amino]-3-(4-fluoro-benzyl)-1H-[1,3,5]triazine-2,4-dione (Cpd 160) To compound 18e in ethanol (0.5 mL) was added compound 2a (16 mg, 0.12 mmol). The mixture was irradiated at 180° C. in a microwave instrument for two 30 min intervals, then concentrated. The residue was dissolved in methyl sulfoxide and purified by reversed-phase chromatography to furnish the title compound 160 as its trifluoroacetate salt. $^1$H NMR (methanol-$d_4$): δ 8.49 (s, 1H), 7.64 (s, 1H), 7.41 (m, 2H), 7.23 (d, 2H, J=8.7 Hz), 7.12 (d, 2H, J=8.6 Hz), 7.00 (t, 2H, J=8.8 Hz), 6.82 (t, 1H, $^2J_{HF}$=73.8 Hz), 5.19 (s, 2H), 4.99 (s, 2H), 4.61 (s, 2H), 2.67 (s, 3H), 2.38 (s, 3H); HRMS m/z (M+H)$^+$ calcd for $C_{26}H_{25}F_3N_5O_3$ 512.1909, found 512.1911.

Other compounds of the present invention may be prepared by those skilled in the art by varying the starting materials, reagent(s) and conditions used. Using the general procedure of Example 18, the following compounds were prepared:

| Cpd | MS obs | MS calc |
| --- | --- | --- |
| 85 | 545.8 | 546.5 |
| 158 | 560.3 | 560.6 |
| 159 | 620.2 | 620.4 |
| 161 | 508.2 | 508.5 |
| 162 | 562.1 | 562.5 |
| 163 | 560.1 | 560.5 |
| 164 | 519.2 | 519.5 |
| 165 | 552.2 | 552.6 |
| 166 | 524.5 | 524.5 |
| 167 | 542.5 | 542.5 |
| 168 | 578.2 | 578.6 |
| 173 | 555.2 | 555.6 |
| 174 | 565.2 | 565.6 |
| 175 | 549.2 | 549.6 |
| 176 | 551.2 | 551.6 |
| 177 | 540.2 | 540.6 |
| 178 | 534.2 | 534.5 |
| 179 | 536.3 | 536.6 |
| 180 | 519.2 | 519.5 |
| 182 | 552.2 | 552.6 |
| 185 | 527.2 | 527.6 |
| 186 | 525.1 | 525.6 |
| 191 | 524.2 | 524.5 |
| 192 | 549.2 | 549.6 |
| 193 | 524.3 | 524.5 |
| 194 | 537.4 | 537.5 |
| 195 | 560.3 | 560.5 |
| 196 | 552.2 | 552.6 |
| 198 | 504.4 | 504.6 |
| 208 | 538.1 | 538.5 |
| 210 | 552.2 | 552.6 |
| 219 | 553.1 | 553.5 |
| 221 | 564.2 | 564.6 |
| 227 | 533.2 | 533.6 |
| 228 | 520.0 | 520.5 |
| 242 | 515.1 | 514.57 |
| 243 | 528.13 | 527.61 |
| 244 | 512.36 | 511.55 |
| 245 | 525.23 | 524.58 |
| 268 | 512.22 | 511.49 |

Additional $^1$H NMR Data for Compounds of Example 18

6-[(2-Amino-pyridin-3-ylmethyl)-amino]-1-(4-difluoromethoxy-benzyl)-3-(4-methoxy-benzyl)-1H-[1,3,5]triazine-2,4-dione (Cpd 35). $^1$H NMR (DMSO, $d_6$) δ 3.65 (s, 3H), 4.27 (d, 2H, J=5.03 Hz), 4.76 (s, 2H), 5.04 (s, 2H), 6.80 (m, 4H), 7.16 (m, 4H), 7.27 (d, 2H, J=8.72 Hz), 7.83 (d, 1H, J=6.07 Hz), 8.18 (m, 1H).

6-[(2-Amino-4,6-dimethyl-pyridin-3-ylmethyl)-amino]-1,3-bis-(2,3-dihydro-benzofuran-5-ylmethyl)-1H-[1,3,5]triazine-2,4-dione (Cpd 185). $^1$H NMR (DMSO, $d_6$) δ 2.36 (s, 3H), 2.37 (s, 3H), 3.10 (td, 4H, J=5.72, 3.59 Hz), 4.36 (m, 2H), 4.49 (td, 4H, J=5.05, 3.55 Hz), 4.81 (s, 2H), 5.00 (s, 2H), 6.65 (s, 1H), 6.68 (d, 2H, J=8.19 Hz), 7.01 (m, 4H), 7.50 (s, 1H), 8.01 (s, 1H).

Example 19

C-Imidazo[1,2-a]pyridin-8-yl-methylamine (Cpd 17c)

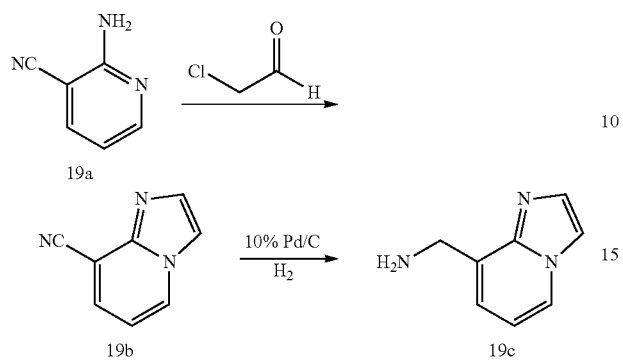

A. Imidazo[1,2-a]pyridine-8-carbonitrile (Cpd 19b). To a solution of 2-amino-3-cyanopyridine (Cpd 19a) (1.0 g, 8.4 mmol) in ethanol (20 mL) was added chloroacetaldehyde (1.57 g, 50 wt. % solution in water, 10.0 mmol). The mixture was irradiated at 120° C. in a microwave instrument for 30 min. After quenching with saturated aqueous sodium carbonate, the mixture was concentrated. The residue was taken up in dichloromethane/water and the layers were separated. The aqueous layer was extracted with dichloromethane (2×) and the combined organic layer was washed with brine, dried over MgSO$_4$, filtered, and the filtrate was concentrated to provide compound 19b.

B. C-Imidazo[1,2-a]pyridin-8-yl-methylamine (Cpd 19c). A mixture of compound 19b (413 mg, 2.88 mmol), palladium (100 mg, 10 wt. % support activated carbon), and ammonia (40 mL, 2M solution in methanol) was hydrogenated at 55 psi pressure for 18 h at room temperature. The reaction mixture was filtered through a pad of diatomaceous earth and washed with methanol. The filtrate was concentrated to provide compound 19c, which was used in subsequent reactions without further purification.

Example 20

6-[(Imidazo[1,2-a]pyridin-8-ylmethyl)-amino]-1,3-bis-(4-methoxy-benzyl)-1H-[1,3,5]triazine-2,4-dione (Cpd 188)

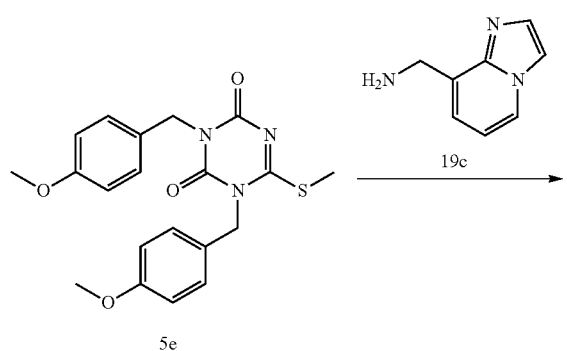

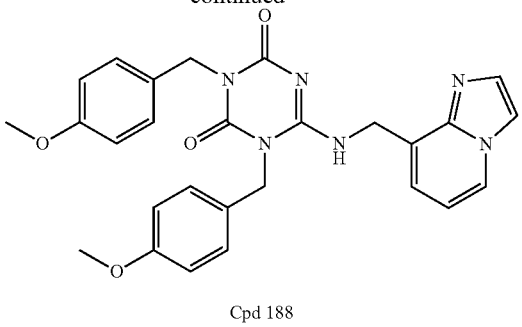

Cpd 188

A solution of compound 5e (60 mg, 0.15 mmol) and compound 19c (26 mg, 0.18 mmol) in ethanol (0.5 mL) was irradiated at 180° C. in a microwave instrument for two 30 min intervals, then concentrated. The residue was dissolved in methyl sulfoxide and purified by reversed-phase chromatography to furnish the title compound 188 as its trifluoroacetate salt. $^1$H NMR (methanol-d$_4$): δ 8.66 (d, 1H, J=6.8 Hz), 8.20 (d, 1H, J=2.2 Hz), 8.01 (d, 1H, J=2.2 Hz), 7.46 (d, 1H, J=7.4 Hz), 7.33 (d, 2H, J=8.6 Hz), 7.28 (t, 1H, J=7.0 Hz), 7.15 (d, 2H, J=8.6 Hz), 6.88 (d, 2H, J=8.8 Hz), 6.83 (d, 2H, J=8.8 Hz), 5.15 (s, 2H), 4.96 (s, 2H), 4.88 (s, 2H), 3.78 (s, 3H), 3.75 (s, 3H); HRMS m/z (M+Hr calcd for C$_{27}$H$_{27}$N$_6$O$_4$ 499.2094, found 499.2052.

Example 21

3-Ethynyl-2-nitro-pyridine (Cpd 21c)

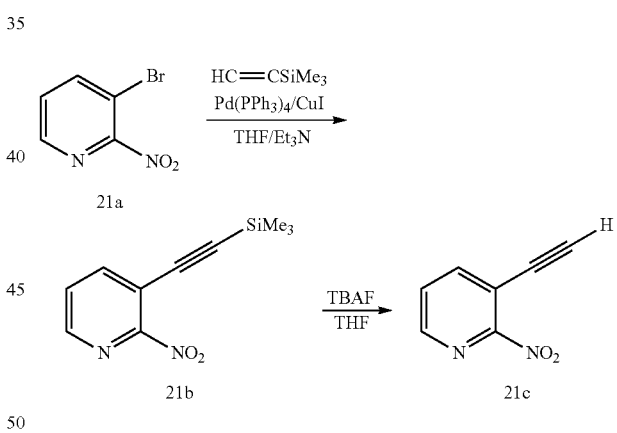

A. 2-Nitro-3-trimethylsilanylethynyl-pyridine (Cpd 21b). Compound 21a (500 mg, 2.5 mmol) and TMS-acetylene (500 µL) were dissolved in a mixture of dry THF/triethylamine (10 mL/2 mL) under a nitrogen atmosphere. Pd(PPh$_3$)$_4$ (70 mg) was added as one portion, followed by of copper (I) iodide (50 mg). The stirred solution was kept overnight at RT and evaporated. The residue was subjected to normal phase column chromatography (silica gel, heptane/EtOAc 2:1), providing compound 21b. $^1$H NMR (CDCl$_3$) δ 0.27 (s, 9H), 7.57 (dd, 1H, J=7.83 and 4.69 Hz), 8.06 (dd, 1H, J=7.86 and 1.70 Hz), 8.48 (dd, 1H, J=4.66 and 1.69 Hz).

B. 3-Ethynyl-2-nitro pyridine (Cpd 21c) Compound 21b was dissolved in dry THF (10 mL) at RT and 1 M TBAF in THF (1 mL) was added dropwise over 10 min. The reaction mixture was kept at RT for 1 h, evaporated, dissolved in EtOAc/heptane (1/1 mixture) and filtered through a silica gel plug. After evaporation, compound 21c was obtained and used in the next step without further purification.

Example 22

6-[2-(2-Amino-pyridin-3-yl)-ethyl]-1,3-bis-(4-methoxy-benzyl)-1H-pyrimidine-2,4-dione (Cpd 199)

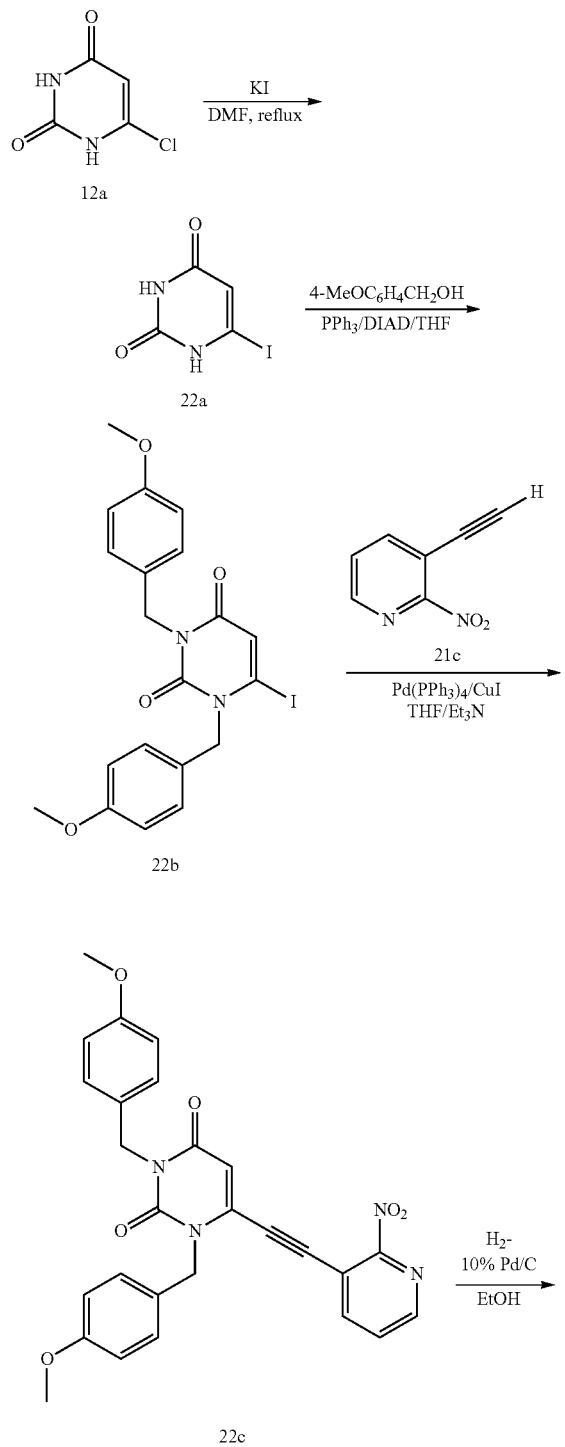

A. 6-Iodo-1H-pyrimidine-2,4-dione (Cpd 22a) Compound 12a (5 g, 34 mmol) and sodium iodide (20 g) were dissolved in anhydrous DMF (50 mL) and heated to reflux for 1.5 h (Ar atmosphere). The DMF was evaporated, and the solid residue dissolved in $H_2O$ (200 mL). The solution was stirred at RT for 4 h, a solid material was collected by vacuum filtration, and the solid was washed with $H_2O$ and dried. The solid was crystallized from EtOAc, providing compound 22a. $^1$H NMR (DMSO-$d_6$) δ 6.03 (s, 1H), 11.2 (s, 1H), 11.6 (s, 1H).

B. 6-Iodo-1,3-bis-(4-methoxy-benzyl)-1H-pyrimidine-2,4-dione (Cpd 22b). Compound 22a (1.00 g, 4.2 mmol), 4-methoxybenzyl alcohol (1.7 g, 3 eq), $PPh_3$ (4.00 g) were dissolved in dry THF (25 mL) under an atmosphere of $N_2$. DIAD was added dropwise at approximately 1 mL/min until the yellow color remained (about 4 eq total). The reaction mixture was stirred for 4 h at RT and evaporated. The residue was subjected to normal phase column chromatography (silica gel, gradient mixture heptane-ethyl acetate), providing compound 22b. $^1$H NMR (CDCl$_3$) δ 3.78 (s, 3H), 3.79 (s, 3H), 5.04 (s, 2H), 5.27 (s, 2H), 6.54 (s, 1H), 6.82 (d, J=7.3 Hz, 2H), 6.86 (d, J=8.7 Hz, 2H), 7.22 (d, J=7.3 Hz, 2H), 7.42 (d, J=8.7 Hz, 2H). MS m/z (ES) 479.1 (M+H).

C. 1,3-Bis-(4-methoxy-benzyl)-6-(2-nitro-pyridin-3-yl-ethynyl)-1H-pyrimidine-2,4-dione (Cpd 22c) Compound 22b (240 mg, 0.5 mmol) and compound 21c (150 mg, 1 mmol) were dissolved in a mixture of dry THF (10 mL) and Et$_3$N (2 mL). Pd(PPh$_3$)$_4$ (40 mg) and copper (I) iodide (20 mg) were added simultaneously in one portion. The reaction mixture was stirred overnight at RT under a $N_2$ atmosphere and evaporated. The residue was subjected to normal phase column chromatography (silica gel column, EtOAc), providing compound 22c. $^1$H NMR (CDCl$_3$) δ 3.76 (s, 3H), 3.78 (s, 3H), 5.06 (s, 2H), 5.23 (s, 2H), 6.17 (s, 1H), 6.82 (d, J=8.6 Hz), 7.27 (d, J=6.4 Hz, 2H), 7.44 (dd, J=6.7 and 2.02 Hz, 2H), 7.68 (dd, J=7.8 and 4.6 Hz, 1H), 8.06 (dd, J=7.8 and 1.7 Hz, 1H), 8.63 (dd, J=4.7 and 1.7 Hz, 1H).

D. 6-[2-(2-Amino-pyridin-3-yl)-ethyl]-1,3-bis-(4-methoxy-benzyl)-1H-pyrimidine-2,4-dione (Cpd 199). Compound 22c (100 mg, 0.2 mmol) was dissolved in EtOH (10 mL) and suspended with 10% Pd on carbon (40 mg). The reaction mixture was hydrogenated for 24 h at RT under atmospheric pressure, filtered through a Celite plug, and evaporated. The residual material was purified by reverse phase HPLC chromatography (water/acetonitrile gradient), and then lyophilized, to provide compound 199. $^1$H NMR (DMSO-d$_6$) δ 2.8 (m, 4H), 3.43 (s, 6H), 4.96 (s, 2H), 5.11 (s, 2H), 5.82 (s, 1H), 6.88 (m, 4H), 7.15 (m, 2H), 7.24 (m, 2H), 7.77 (m, 1H), 7.86 (m, 1H), 7.92 (m, 1H). MS m/z (ES) 473.2 (M+H).

Using an adaptation of the methods described in Example 22, compound 169 was prepared from compound 22i, substituting 3-ethynyl pyridine for compound 21c of Example 22, Step C.

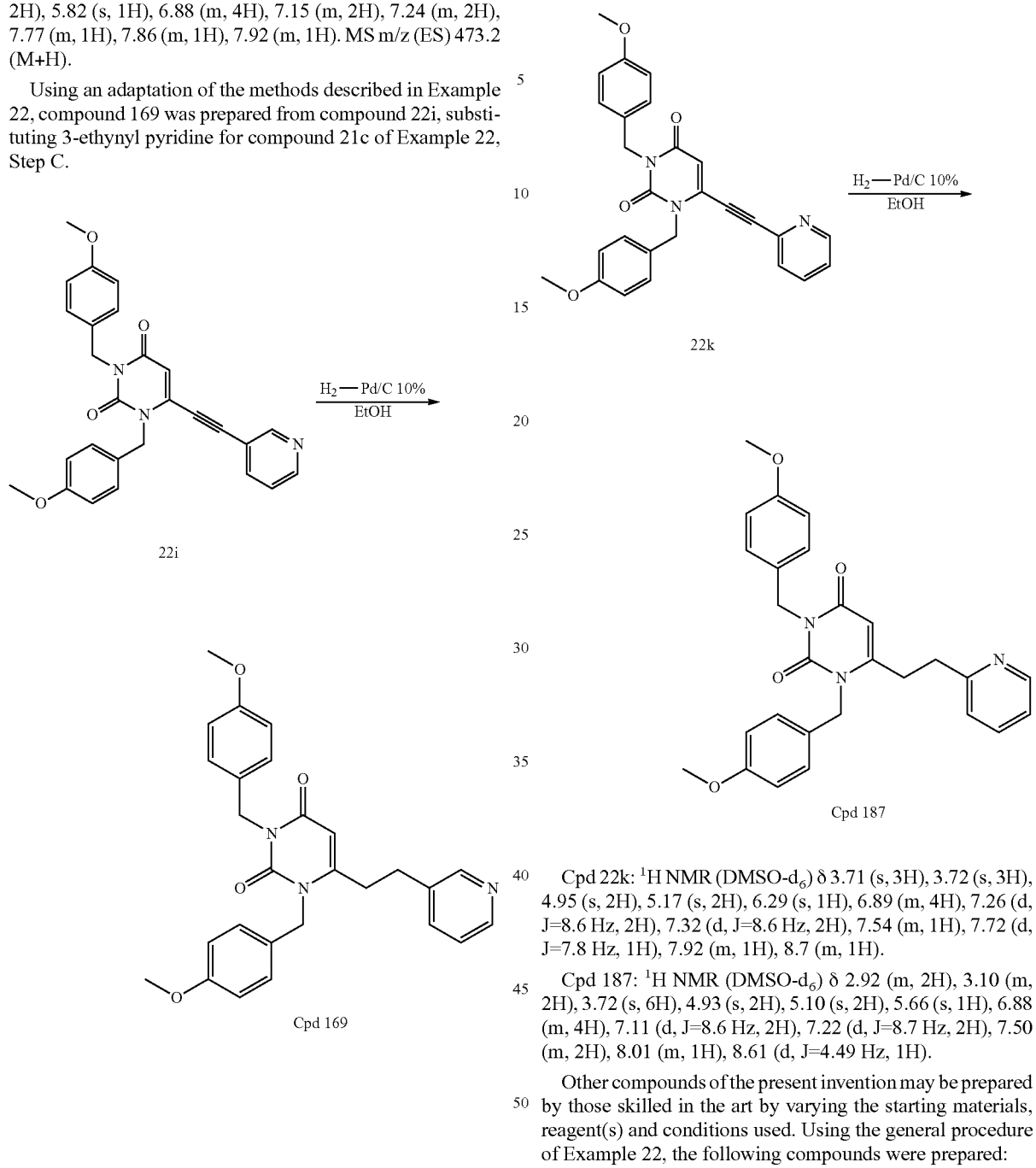

Cpd 22i: $^1$H NMR (DMSO-d$_6$) δ 3.71 (s, 3H), 3.72 (s, 3H), 4.95 (s, 2H), 5.19 (s, 2H), 6.27 (s, 1H), 6.87 (d, J=8.3 Hz, 2H), 6.89 (d, J=7.7 Hz, 2H), 7.28 (m, 4H), 7.52 (m, 1H), 8.1 (m, 1H), 8.8 (m, 2H).

Cpd 169: $^1$H NMR (DMSO-d$_6$) δ 2.88 (m, 2H), 2.95 (m, 2H), 3.72 (s, 6H), 4.94 (s, 2H), 5.11 (s, 2H), 5.72 (s, 1H), 6.87 (d, J=8.6 Hz, 2H), 6.89 (d, J=7.6 Hz, 2H), 7.11 (d, J=8.6 Hz, 2H), 7.22 (d, J=7.8 Hz, 2H), 7.79 (m, 1H), 8.20 (m, 1H), 8.71 (m, 2H).

Using an adaptation of the methods described in Example 22, compound 187 was prepared from compound 22k, substituting 2-ethynyl pyridine for compound 21c of Example 22, Step C.

Cpd 22k: $^1$H NMR (DMSO-d$_6$) δ 3.71 (s, 3H), 3.72 (s, 3H), 4.95 (s, 2H), 5.17 (s, 2H), 6.29 (s, 1H), 6.89 (m, 4H), 7.26 (d, J=8.6 Hz, 2H), 7.32 (d, J=8.6 Hz, 2H), 7.54 (m, 1H), 7.72 (d, J=7.8 Hz, 1H), 7.92 (m, 1H), 8.7 (m, 1H).

Cpd 187: $^1$H NMR (DMSO-d$_6$) δ 2.92 (m, 2H), 3.10 (m, 2H), 3.72 (s, 6H), 4.93 (s, 2H), 5.10 (s, 2H), 5.66 (s, 1H), 6.88 (m, 4H), 7.11 (d, J=8.6 Hz, 2H), 7.22 (d, J=8.7 Hz, 2H), 7.50 (m, 2H), 8.01 (m, 1H), 8.61 (d, J=4.49 Hz, 1H).

Other compounds of the present invention may be prepared by those skilled in the art by varying the starting materials, reagent(s) and conditions used. Using the general procedure of Example 22, the following compounds were prepared:

| Cpd | MS obs | MS calc |
| --- | --- | --- |
| 169 | 458.0 | 458.5 |
| 183 | 457.9 | 458.5 |
| 187 | 458.1 | 458.5 |
| 189 | 500.9 | 501.6 |
| 199 | 473.2 | 473.5 |
| 214 | 472.8 | 473.5 |

Example 23

6-[(2-Amino-4,6-dimethyl-1-oxy-pyridin-3-ylmethyl)-amino]-1-(4-difluoromethoxy-benzyl)-3-(2,3-dihydro-benzofuran-5-ylmethyl)-1H-[1,3,5]triazine-2,4-dione (Cpd 233)

Example 24

6-[(2-Amino-4,6-dimethyl-1-oxy-pyridin-3-ylmethyl)-amino]-1,3-bis-(2,3-dihydro-benzofuran-5-ylmethyl)-1H-[1,3,5]triazine-2,4-dione (Cpd 226)

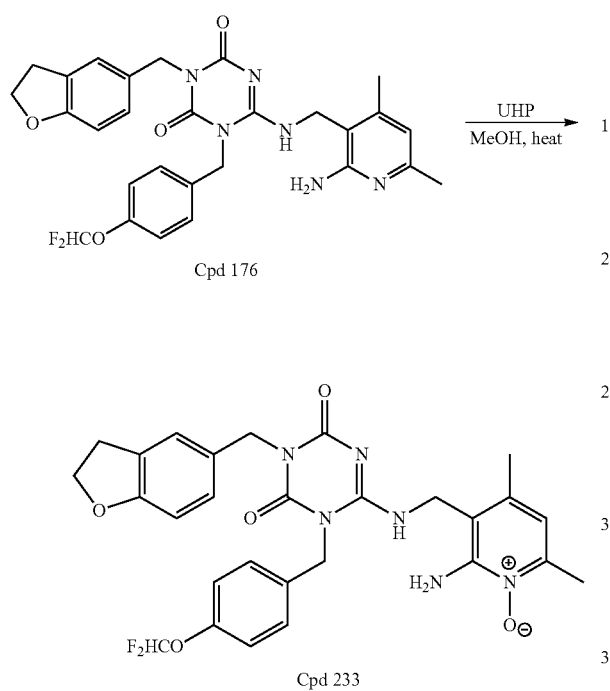

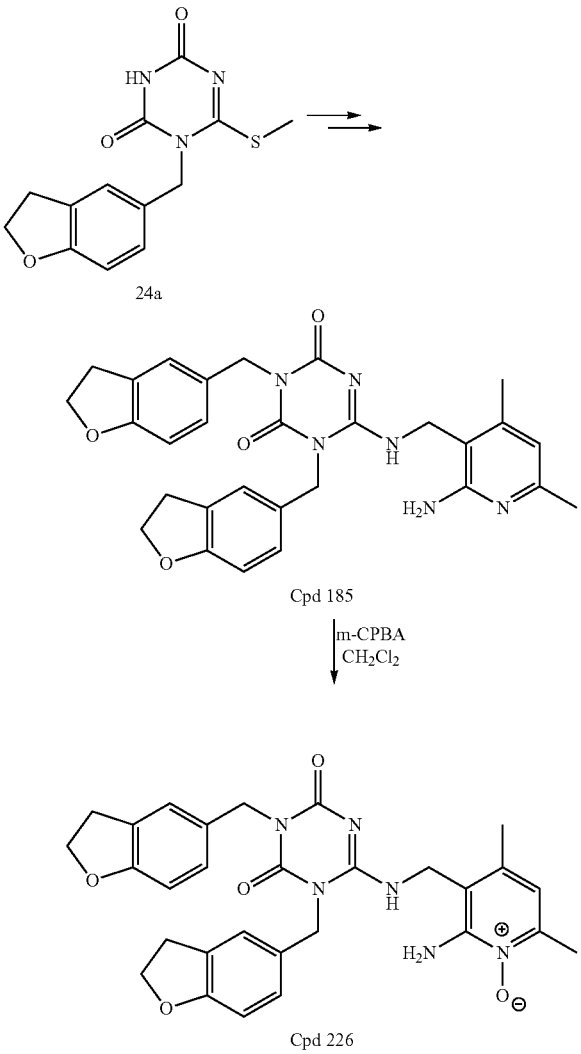

A. Compound 176 (50 mg, 0.09 mmol) was prepared from compound 18d using the method described in Example 5, substituting 2,3-dihydrobenzofuran-5-yl methanol for 4-methoxybenzyl alcohol in Step E; and substituting 2-amino-3-aminomethyl-4,6-dimethylpyridine for Compound 2a in Step F.

B. 6-[(2-Amino-4,6-dimethyl-1-oxy-pyridin-3-ylmethyl)-amino]-1-(4-difluoromethoxy-benzyl)-3-(2,3-dihydro-benzofuran-5-ylmethyl)-1H-[1,3,5]triazine-2,4-dione (Cpd 233). Compound 176 and urea-hydrogen peroxide addition complex (200 mg) were combined and the mixture was heated to 85° C. After 4 hours, the mixture was dissolved in methanol (3 mL) and the temperature was reduced to 70° C. After stirring overnight, the mixture was allowed to cool and was poured over H$_2$O (15 mL). The reaction was diluted with water, extracted with ethyl acetate (3×10 mL) and the combined extracts were dried over Na$_2$SO$_4$, filtered and reduced. Purification by reverse-phase prep HPLC afforded Cpd 233. MS m/z (ES)=566.8 (M+H); $^1$H NMR (DMSO, d$_6$) δ 2.29 (s, 3H), 2.38 (s, 3H), 3.11 (t, 2H, J=8.49 Hz), 4.40 (m, 2H), 4.48 (t, 2H, J=8.72 Hz), 4.80 (s, 2H), 5.04 (s, 2H), 6.68 (d, 2H, J=4.64 Hz), 7.15 (m, 4H), 7.20 (s, 1H), 7.25 (d, 2H, J=8.57 Hz).

A. Compound 24a was prepared by the methods described in Example 18, Steps A through C, substituting 2,3-dihydrobenzofuran-5-yl methyl amine for 4-difluoromethoxybenzyl amine in Step A.

B. Compound 185 (40 mg, 0.08 mmol) was prepared from compound 24a using the method described in Example 5, substituting 2,3-dihydrobenzofuran-5-yl methanol for 4-methoxybenzyl alcohol in Step E; and substituting 2-amino-3-aminomethyl-4,6-dimethylpyridine for Compound 2a in Step F.

C. 6-[(2-Amino-4,6-dimethyl-1-oxy-pyridin-3-ylmethyl)-amino]-1,3-bis-(2,3-dihydro-benzofuran-5-ylmethyl)-1H-[1,3,5]triazine-2,4-dione (Cpd 226). A solution of compound 185 in dichloromethane (4 mL) was treated with m-CPBA (72%, 30 mg, 0.15 mmol) and the mixture was stirred overnight at room temperature. The reaction was then poured over 10% Na$_2$S$_2$O$_4$ and the organic phase was extracted with CH$_2$Cl$_2$ (3×10 mL). The combined organic layers were then washed with saturated NaHCO$_3$ (3×10 mL) and were again extracted with dichloromethane (3×5 mL). The organic extracts were then combined and dried over Na$_2$SO$_4$, filtered, and reduced. Purification via reverse phase HPLC afforded Cpd 226 as its TFA salt. The resulting TFA salt was taken up in dichloromethane (5 mL) and was washed with saturated NaHCO$_3$ (3×5 mL). Combined organic extracts were dried over Na$_2$SO$_4$, filtered and reduced to afford Compound 226 as its free-base. M$^+$ (ES$^+$)=543.34.

Other compounds of the present invention may be prepared by those skilled in the art by varying the starting materials, reagent(s) and conditions used. Using the general procedure of Example 24, the following compounds were prepared:

| Cpd | MS obs | MS calc |
|-----|--------|---------|
| 32  | 491.2  | 491.5   |
| 53  | 476.2  | 476.5   |
| 118 | 504.2  | 504.6   |
| 269 | 488.19 | 487.52  |

Example 25

6-[2-(6-Amino-pyridin-2-yl)-ethyl]-1,3-bis-(4-methoxy-benzyl)-1H-pyrimidine-2,4-dione (Cpd 223)

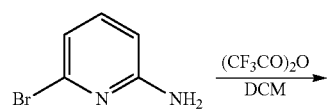

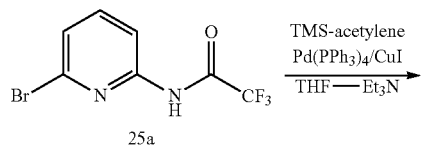
25a

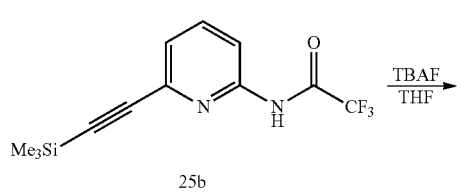
25b

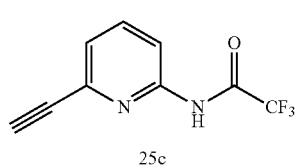
25c

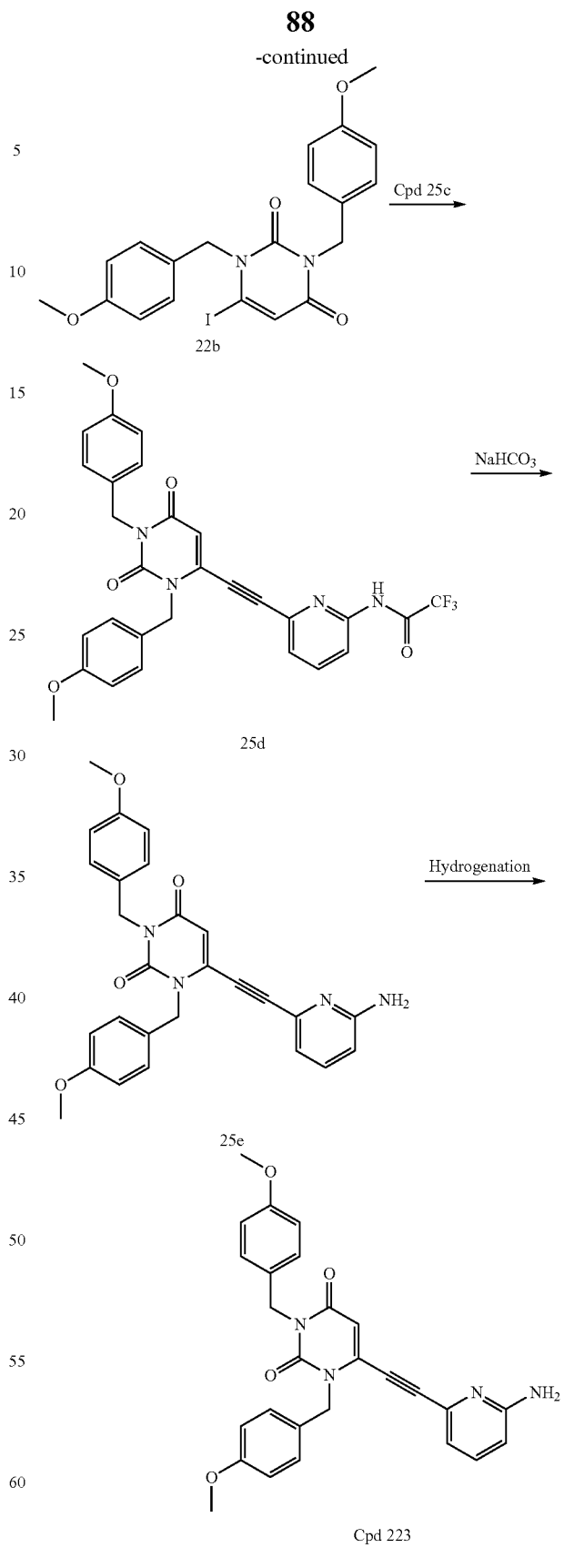

A. 6-Bromo-2-trifluoroacetamido-pyridine (Cpd 25a). 2-Amino-6-bromopyridine (800 mg) was dissolved in a mixture of DCM (30 mL) and TEA (2 mL), and the solution was cooled in an ice bath. Trifluoroacetic anhydride (2 mL) was added by 100 μL portions. The reaction mixture was allowed to warm up to room temperature, and then was washed sequentially with water and 10% sodium bicarbonate solution. The mixture was dried, filtered, and the filtrate was evaporated. The residue was subjected to normal phase column chromatography (silica gel, heptane/ethyl acetate 1:1), providing compound 25a. $^1$H NMR (CDCl$_3$) δ 8.65 (broad s, 1H), 8.15 (d. J=8.2 Hz, 1H), 7.67 (t, J=7.9 Hz, 1H), 7.37 (d, J=8.1 Hz, 1H).

B. 2,2,2-Trifluoro-N-(6-trimethylsilanylethynyl-pyridin-2-yl)-acetamide (Cpd 25b) Compound 25b was prepared using the methods described in Example 21, Step A. $^1$H NMR (CDCl$_3$) δ 8.57 (broad s, 1H), 7.96 (d, J=8.3 Hz, 1H), 7.57 (t, J=8.0 Hz, 1H), 7.15 (d, J=8.3 Hz, 1H), 0.09 (s, 9H).

C. N-(6-Ethynyl-pyridin-2-yl)-2,2,2-trifluoro-acetamide (Cpd 25c). Compound 25c was prepared using the methods described in Example 21, Step B, substituting compound 25b for compound 21b. Purification was achieved by normal phase column chromatography (silica gel, heptane/ethyl acetate 2:1). $^1$H NMR (CDCl$_3$) δ 8.62 (broad s, 1H), 8.20 (d, J=8.3 Hz, 1H), 7.80 (t, J=8.0 Hz, 1H), 7.38 (d, J=8.3 Hz, 1H), 3.21 (s, 1H).

D. N-{6-[1,3-Bis-(4-methoxy-benzyl)-2,6-dioxo-1,2,3,6-tetrahydro-pyrimidin-4-ylethynyl]-pyridin-2-yl}-2,2,2-trifluoro-acetamide (Cpd 25d). Compound 25d was prepared using the methods described in Example 22, Step C, substituting compound 25c for compound 21c. Purification was achieved by reverse phase HPLC. MS m/z 565.2 (M+H).

E. 6-(6-Amino-pyridin-2-ylethynyl)-1,3-bis-(4-methoxy-benzyl)-1H-pyrimidine-2,4-dione (Cpd 25e). Compound 25d (550 mg) was dissolved in EtOH (5 mL), and a saturated solution of NaHCO$_3$ (5 mL) was added. After stirring for 1 h at room temperature, the reaction mixture was concentrated under reduced pressure, and the resultant residue was subjected to reverse phase HPLC and subsequent lyophilization to afford compound 25e.

F. 6-[2-(6-Amino-pyridin-2-yl)-ethyl]-1,3-bis-(4-methoxy-benzyl)-1H-pyrimidine-2,4-dione (Cpd 223). Compound 223 was prepared using the methods described in Example 22, Step D, substituting compound 25e for compound 22c. Purification was achieved by reverse phase HPLC followed by lyophilization. MS m/z (ES) 470.9 (M+H).

Example 26

1,3-Bis-(4-methoxy-benzyl)-6-(2-pyridin-4-yl-vinyl)-1H-pyrimidine-2,4-dione (Cpd 184)

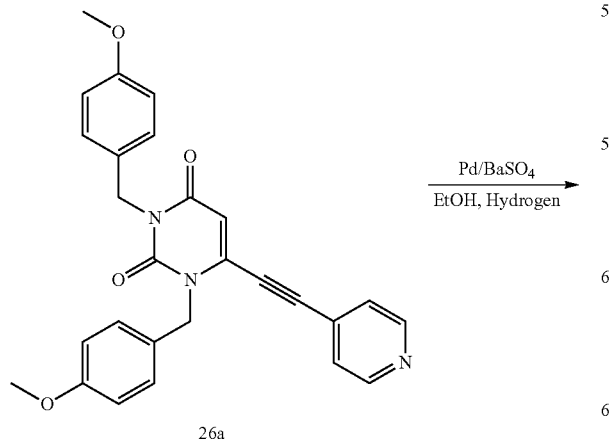

26a

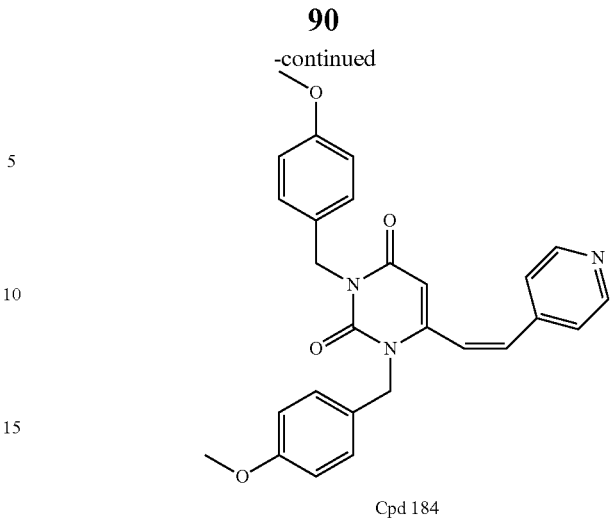

Cpd 184

Compound 26a was prepared using the methods described in Example 22, Step C, substituting 4-ethynylpyridine for compound 21c. Compound 26a (100 mg, TFA salt) was suspended with Pd on BaSO$_4$ (5%, 40 mg) in EtOH (20 mL). The reaction mixture was hydrogenated for 3 h at RT and atmospheric pressure, filtered through a pad of diatomaceous earth and concentrated under reduced pressure. The residual material was purified by HPLC, followed by lyophilization to give compound 184. MS m/z (ES) 455.9 (M+H).

Example 27

6-[(2-Amino-pyridin-3-ylmethyl)-amino]-1-(4-hydroxy-benzyl)-3-(4-methoxy-benzyl)-1H-[1,3,5]triazine-2,4-dione (Cpd 33)

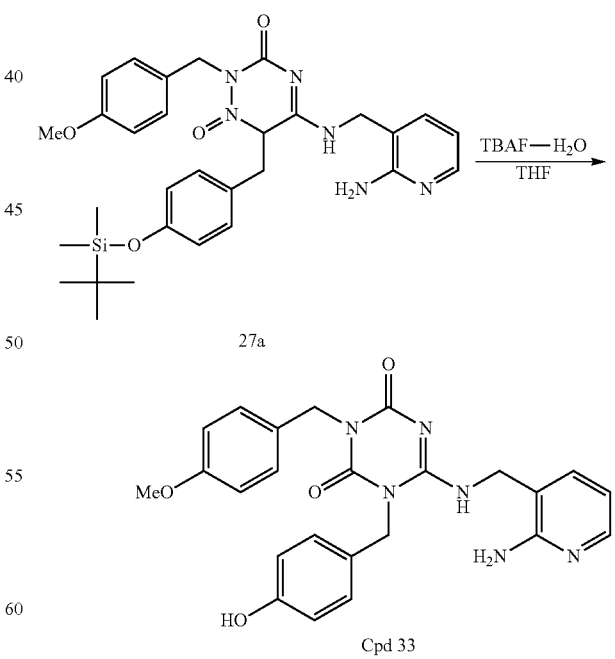

A. Compound 27a (80 mg, 0.14 mmol) was prepared according to the methods described in Example 2, and substituting [4-(tert-butyl-dimethyl-silanyloxy)-phenyl]-methanol for 4-methoxybenzyl alcohol in Step D.

B. 6-[(2-Amino-pyridin-3-ylmethyl)-amino]-1-(4-hydroxy-benzyl)-3-(4-methoxy-benzyl)-1H-[1,3,5]triazine-2,4-dione (Cpd 33). Compound 27a was suspended in THF (3 mL) and the reaction mixture was treated with tetrabutylammonium fluoride monohydrate (36 mg, 0.14 mmol). The solution was stirred at room temperature overnight. The mixture was then concentrated under nitrogen and the residue was purified by reverse phase HPLC to give the title compound 33. MS m/z (ES)=461.2 (M+H); $^1$H NMR (DMSO, $d_6$) δ 3.72 (s, 3H), 4.33 (m, 2H), 4.83 (s, 2H), 5.01 (s, 2H), 6.75 (m, 3H), 6.84 (d, 2H, J=8.71 Hz), 7.08 (d, 2H, J=8.56 Hz), 7.24 (d, 2H, J=8.63 Hz), 7.46 (d, 1H, J=8.06 Hz), 7.89 (d, 1H, J=4.88 Hz).

Example 28

6-{[(2-Amino-pyridin-3-ylmethyl)-amino]-methyl}-1,3-bis-(4-methoxy-benzyl)-1H-pyrimidine-2,4-dione (Cpd 7)

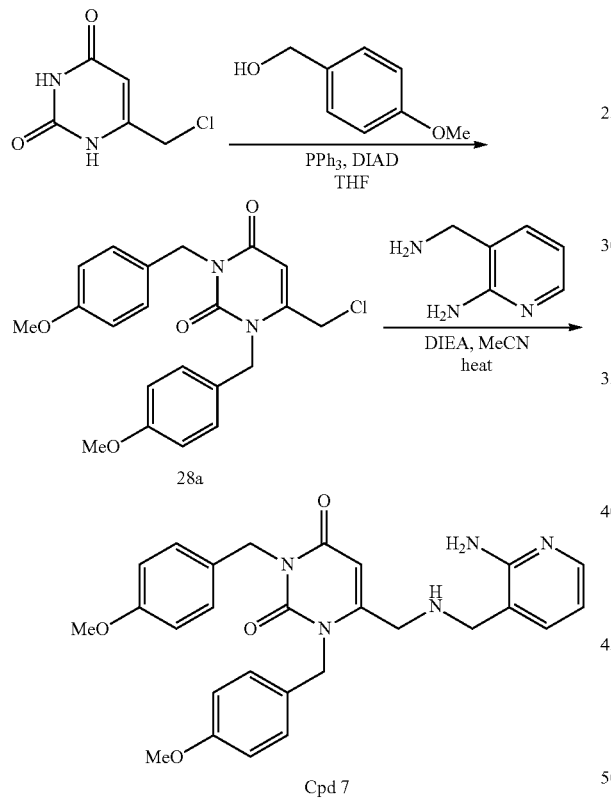

A. 6-Chloromethyl-1,3-bis-(4-methoxy-benzyl)-1H-pyrimidine-2,4-dione (Cpd 28a). 6-Chloromethyl uracil (500 mg, 3.1 mmol) was dissolved in THF (50 mL) and the solution was treated with 4-methoxybenzyl alcohol (860 mg, 6.2 mmol), triphenylphosphine (2.45 g, 9.3 mmol) and diisopropylazodicarboxylate (1.26 g, 6.2 mmol). The reaction was allowed to stir overnight at room temperature. The mixture was then poured over water (75 mL) and was extracted with ethyl acetate (3×50 mL). The combined organic extracts were dried over $Na_2SO_4$, filtered and reduced. Compound 28a was isolated and purified by normal phase column chromatography (silica gel, 20% EtOAc/heptane-100% EtOAc/heptane). $M^+$ ($ES^+$)=401.1.

B. 6-{[(2-Amino-pyridin-3-ylmethyl)-amino]-methyl}-1,3-bis-(4-methoxy-benzyl)-1H-pyrimidine-2,4-dione (Cpd 7). Cpd 28a (100 mg, 0.25 mmol) was dissolved in acetonitrile (5 mL) and the reaction mixture was treated with diisopropylethylamine (0.087 mL, 0.50 mmol), and 2-amino-3-methylaminopyridine (Cpd 1a) (31 mg, 0.25 mmol). The solution was heated to 80° C. and was allowed to stir for 4 hours. The mixture was then cooled to room temperature and was poured over saturated $NH_4Cl$ (15 mL). The desired product was extracted with ethyl acetate (3×10 mL) and the combined organic extracts were dried over $Na_2SO_4$, filtered and reduced. Purification and isolation by reverse phase HPLC gave compound 7. MS m/z (ES)=488.1 (M+H); $^1$H NMR (DMSO, $d_6$) δ2.83 (s, 2H), 3.02 (s, 2H), 4.07 (s, 6H), 4.26 (s, 2H), 4.34 (s, 2H), 5.24 (s, 1H), 6.05 (m, 5H), 6.20 (d, 2H, J=6.99 Hz), 6.54 (d, 2H, J=7.05 Hz), 6.92 (t, 2H, J=7.71 Hz).

Example 29

6-[(2-Amino-pyridin-3-ylmethyl)-amino]-1,3-bis-(4-methoxy-benzyl)-1H-[1,3,5]triazine-2,4-dione (Cpd 3)

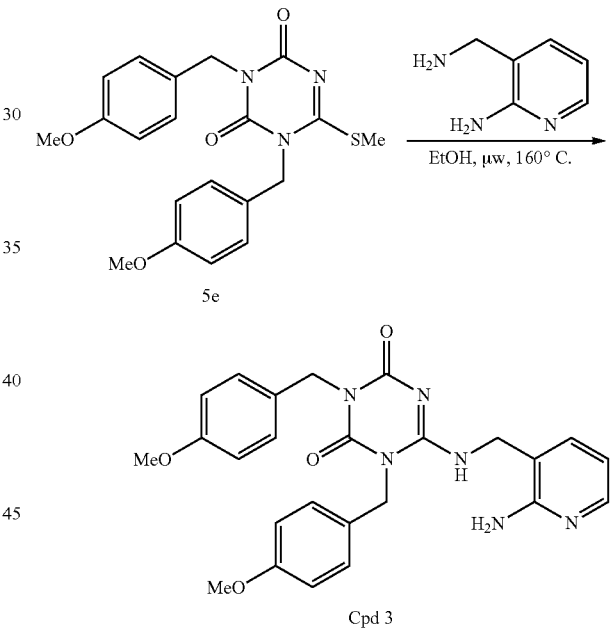

Cpd 5e (850 mg, 2.1 mmol) and Cpd 1a (524 mg, 4.3 mmol) were suspended in ethanol (10 mL) and the reaction mixture was irradiated at 160° C. for 100 minutes in a microwave instrument. The solution was reduced in vacuo and purified by reverse phase HPLC to afford the title compound 3. MS m/z (ES)=475.2 (M+H), $^1$H NMR (DMSO, $d_6$) δ 3.71 (s, 3H), 3.74 (s, 3H), 4.36 (d, 2H, J=4.59 Hz), 4.83 (s, 2H), 5.09 (s, 2H), 6.90 (m, 4H), 7.24 (d, 4H, J=8.64 Hz), 7.57 (d, 1H, J=7.08 Hz), 7.91 (d, 1H, J=6.39 Hz), 8.08 (s, 2H), 8.45 (m, 1H).

Example 30

Pyridin-3-yl-methanthiol (Cpd 30a)

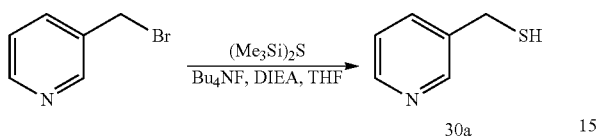

Pyridin-3-yl-methanthiol (Cpd 30a). To a mixture of 3-(bromomethyl)pyridine hydrobromide (500 mg, 2.0 mmol) and diisopropylethylamine (0.220 mL, 2.0 mmol) in THF (20 mL), cooled in a sodium chloride/ice bath (−5° C.), was added hexamethyldisilathiane (0.500 mL, 2.4 mmol) and tetrabutylammonium fluoride (575 mg, 2.2 mmol). The resulting mixture was allowed to warm to room temperature and stirred overnight. The mixture was then concentrated and the residue partitioned between ethyl acetate and saturated aqueous ammonium chloride. The organic layer was separated, dried over MgSO$_4$ and concentrated. The concentrate was purified by normal phase chromatography, eluting with ethyl acetate to obtain compound 30a. $^1$H NMR (MeOD, d$_4$) δ 3.77 (s, 2H), 7.38-7.41 (m, 1H), 7.84-7.86 (d, 1H, J=7.96), 8.38-8.40 (m, 1H), 8.50 (s, 1H).

Example 31

1,3-Bis-(4-methoxy-benzyl)-6-(pyridin-3-ylmethyl-sulfanyl)-1H-pyrimidine-2,4-dione (Cpd 211)

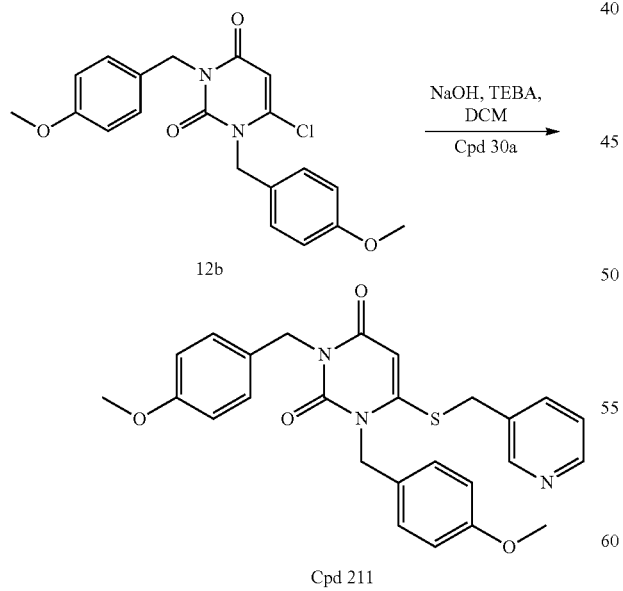

A solution of Compound 12b (97 mg, 0.25 mmol), Compound 30a (61 mg, 0.49 mmol), NaOH (3M, 1.67 mL, 5 mmol), and TEBA (6 mg, 0.025 mmol) in 2 mL of dichloromethane, was stirred vigorously overnight at room temperature. After 24 hours, an additional amount of Compound 12b was added (50 mg) and the mixture allowed to stir for a second night. The mixture was then separated, the organic layer was dried over MgSO$_4$, filtered, and the filtrate was concentrated. The concentrate was purified by reverse phase chromatography to obtain compound 211. MS m/z (ES)=475.8 (M+H). $^1$H NMR (DMSO, d$_6$). δ 3.72-3.73 (d, 6H, J=3.8 Hz), 4.47 (s, 2H), 4.91 (s, 2H), 5.07 (s, 2H), 5.85 (s, 1H), 6.84-6.89 (m, 4H), 7.12-7.15 (d, 2H, J=9.4 Hz), 7.21-7.23 (d, 2H, J=8.7 Hz), 7.57-7.61 (m, 1H), 8.03-8.06 (m, 1H), 8.61-8.63 (d, 1H, J=4.3 Hz), 8.73 (s, 1H).

Example 32

6-[(2-Amino-4-benzyloxymethyl-6-methyl-pyridin-3-ylmethyl)-amino]-1-(4-difluoromethoxy-benzyl)-3-(2,3-dihydro-benzofuran-5-ylmethyl)-1H-[1,3,5]triazine-2,4-dione (Cpd 270)

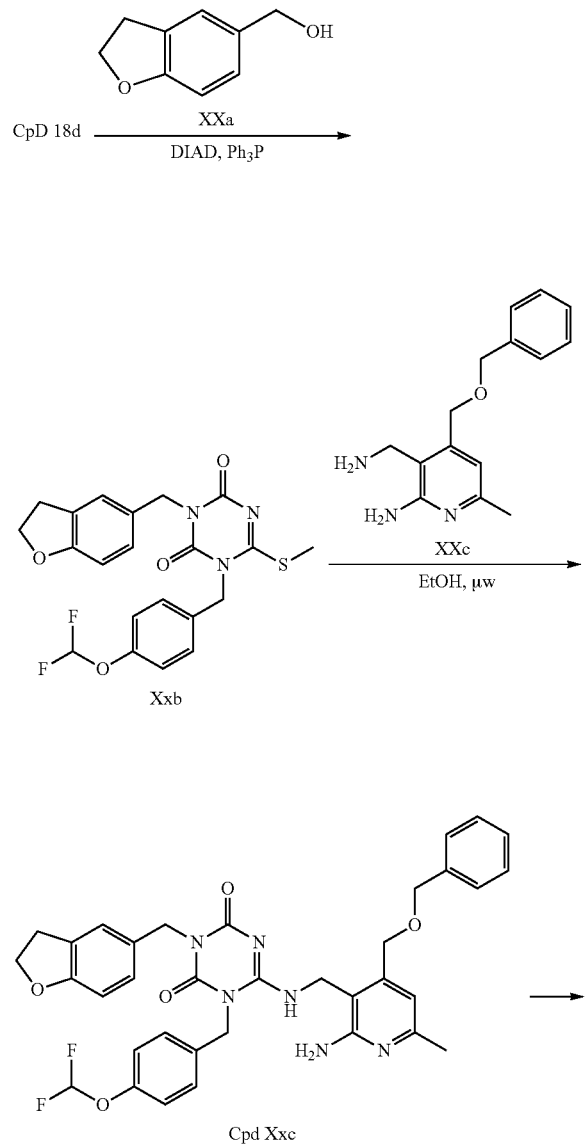

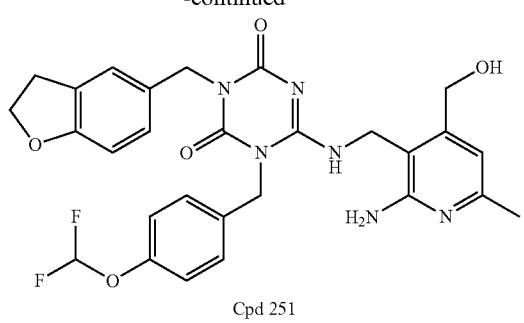

Cpd 251

To compound 18d (2.8 g, 8.9 mmol) in 100 mL of THF was added DIAD (2.1 mL, 10.7 mmol), triphenyl phosphine (17.8 mmol), and compound Xxa. The mixture was allowed to stir at rt under an atmosphere of Argon. The mixture was concentrated, diluted with EtOAc, and washed with water. The organic phase was partitioned, dried over MgSO$_4$, filtered, and the filtrate was concentrated to a yellow oil. The oil was purified by reverse-phase chromatography to furnish compound XXb.

Compound 270 was prepared by an adaptation of the method described in Example 5, Step F, substituting Compound XXI) for Compound 5e, and substituting Compound XXc for Compound 2a.

Other compounds of the present invention may be prepared by those skilled in the art by varying the starting materials, reagent(s) and conditions used. Using the general procedure of Example 32, the following compounds were prepared:

| Cpd | MS obs | MS calc |
|-----|--------|---------|
| 261 | 523.2  | 522.51  |
| 262 | 631.2  | 630.63  |

Example 33

6-[(2-Amino-4,6-dimethyl-pyridin-3-ylmethyl)-amino]-1-(4-methoxy-benzyl)-3-(5-methoxy-pentyl)-1H-[1,3,5]triazine-2,4-dione (Cpd 252)

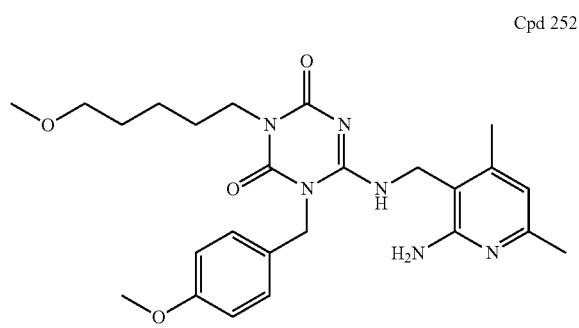

Cpd 252

Compound 252 was prepared from Compound 8c using an adaptation of the methods described in Example 8, substituting 5-methoxy-pentan-1-ol for 2,3-dihydro-1-benzofuran-5-ylmethanol in Step C.

Example 34

6-[(2-Amino-pyridin-3-ylmethyl)-amino]-1-(4-methoxy-benzyl)-3-(4-[1,2,3]thiadiazol-5-yl-benzyl)-1H-[1,3,5]triazine-2,4-dione (Cpd 240)

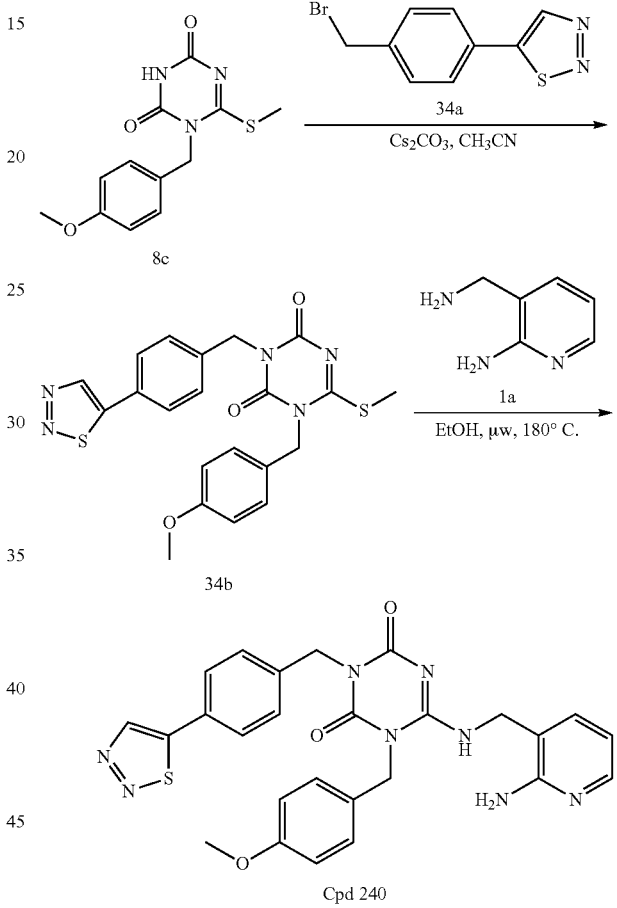

Cpd 240

A. To Compound 8c (0.028 g, 0.1 mmol) in 0.5 mL CH$_3$CN was added cesium carbonate (0.032 g, 0.1 mmol) followed by the addition of Compound 34a (0.0255 g, 0.1 mmol) and the mixture was stirred at 25° C. for 16 h. At that time the mixture was concentrated. The resulting residue was partitioned between methylene chloride and water, and the organic phase was dried and concentrated to give Compound 34b.

B. Compound 34b was dissolved in ethanol (0.5 mL) and Compound 1a (0.018 mg, 0.15 mmol) was added. The mixture was irradiated at 180° C. for two 30 min cycles in a microwave instrument. The reaction was concentrated, the resultant residue was dissolved in DMSO, and the product was purified and isolated by reverse phase HPLC to afford Compound 240. MS m/z (ES)=529.17 (M+H), 528.59 calc'd.

Using the methods described in the schemes and specific examples, and adaptations thereof, compounds 1 to 272 of Table 1 were prepared.

TABLE 1

| Cpd No. | A₁ | L₁ | D | W | Q |
|---|---|---|---|---|---|
| 1 | 3,4-dichloro-phenyl | CH₂ | 4-methoxy-phenylmethyl | N | 2-(pyridin-2-yl) ethyl-amino |
| 2 | 3,4-dichloro-phenyl | CH₂ | 4-methoxy-phenylmethyl | N | pyridin-3-yl-methyl-amino |
| 3 | 4-methoxy-phenyl | CH₂ | 4-methoxy-phenylmethyl | N | 2-amino-pyridin-3-yl-methyl-amino |
| 4 | 4-chloro-phenyl | CH₂ | 4-methoxy-phenylmethyl | N | 5-amino-pyridin-2-yl-methyl-amino |
| 5 | 4-chloro-phenyl | CH₂ | 4-methoxy-phenylmethyl | N | 6-amino-pyridin-3-yl-methyl-amino |
| 6 | 4-methoxy-phenyl | CH₂ | 4-methoxy-phenylmethyl | N | 4-amino-pyrimidin-5-yl-methyl-amino |
| 7 | 4-methoxy-phenyl | CH₂ | 4-methoxy-phenylmethyl | CH | 2-amino-pyridin-3-ylmethyl-aminomethyl |
| 8 | 4-fluoro-phenyl | CH₂ | 4-methoxy-phenylmethyl | N | 2-amino-pyridin-3-yl-methyl-amino |
| 9 | 4-methoxy-phenyl | CH₂ | 4-methoxy-phenylmethyl | N | 2-amino-quinolin-3-ylmethyl-amino |
| 10 | 4-fluoro-phenyl | CH₂ | 4-methoxy-phenylmethyl | N | 2-(2-amino-pyridin-3-yl)-ethylamino |
| 11 | 4-fluoro-phenyl | CH₂ | 4-methoxy-phenylmethyl | N | 2-N-pyrrolidinyl-pyridin-3-yl-methyl-amino |
| 12 | 4-methoxy-phenyl | CH₂ | 4-methoxy-phenylmethyl | N | 2-N-piperazinyl-pyridin-3-yl-methyl-amino |
| 13 | 4-methoxy-phenyl | CH₂ | 4-methoxy-phenylmethyl | N | 2-N-piperidinyl-pyridin-3-yl-methyl-amino |
| 14 | 4-fluoro-phenyl | CH₂ | 4-methoxy-phenylmethyl | N | 2-methylamino-pyridin-3-yl-methyl-amino |
| 15 | 4-fluoro-phenyl | CH₂ | 4-methoxy-phenylmethyl | N | 2-n-propylamino-pyridin-3-yl-methyl-amino |
| 16 | 4-fluoro-phenyl | CH₂ | 4-methoxy-phenylmethyl | N | 2-n-butylamino-pyridin-3-yl-methyl-amino |
| 17 | 4-fluoro-phenyl | CH₂ | 4-methoxy-phenylmethyl | N | 2-N-morpholino-pyridin-3-yl-methyl-amino |
| 18 | 4-fluoro-phenyl | CH₂ | 4-methoxy-phenylmethyl | N | 2-N-thiomorpholino-pyridin-3-yl-methyl-amino |
| 19 | 4-fluoro-phenyl | CH₂ | 4-methoxy-phenylmethyl | N | 2-ethylamino-pyridin-3-yl-methyl-amino |
| 20 | 4-methoxy-phenyl | CH₂ | 4-methoxy-phenylmethyl | N | 2-N-morpholino-pyridin-3-yl-methyl-amino |
| 21 | 4-fluoro-phenyl | CH₂ | 4-methoxy-phenylmethyl | N | 1,2,3,4-tetrahydro-[1,8]naphthyridin-7-yl-methyl-amino |
| 22 | 4-methoxy-phenyl | CH₂ | 4-methoxy-phenylmethyl | N | 4,6-dimethyl-pyridin-3-ylmethyl-amino |
| 23 | benzofuran-2-yl | CH₂ | 4-methoxy-phenylmethyl | N | 2-amino-pyridin-3-yl-methyl-amino |
| 24 | 4-methylthio-phenyl | CH₂ | 4-methoxy-phenylmethyl | N | 2-amino-pyridin-3-yl-methyl-amino |
| 25 | 4-methoxy-phenyl | CH₂ | 4-methoxy-phenylmethyl | N | 6-(4-fluoro-phenyl)-pyridin-3-yl-methyl-amino |
| 26 | 4-methoxy-phenyl | CH₂ | 4-methoxy-phenylmethyl | CH | 2-amino-pyridin-3-yl-methyl-amino |
| 27 | 4-fluoro-phenyl | CH₂ | 4-methoxy-phenylmethyl | N | 2-(2-dimethylamino-ethylamino)-pyridin-3-yl-methyl-amino |

TABLE 1-continued

| Cpd No. | A₁ | L₁ | D | W | Q |
|---|---|---|---|---|---|
| 28 | 4-fluoro-phenyl | CH₂ | 4-methoxy-phenylmethyl | N | 2-(2-methoxy-ethylamino)-pyridin-3-yl-methyl-amino |
| 29 | 4-fluoro-phenyl | CH₂ | 4-methoxy-phenylmethyl | N | 2-(2-hydroxy-ethylamino)-pyridin-3-yl-methyl-amino |
| 30 | 4-fluoro-phenyl | CH₂ | 4-methoxy-phenylmethyl | N | 2-(2-amino-ethylamino)-pyridin-3-yl-methyl-amino |
| 31 | 4-fluoro-phenyl | CH₂ | 4-methoxy-phenylmethyl | N | 2-cyclohexylamino-pyridin-3-yl-methyl-amino |
| 32 | 4-methoxy-phenyl | CH₂ | 4-methoxy-phenylmethyl | N | N-oxo-2-amino-pyridin-3-yl-methyl-amino |
| 33 | 4-methoxy-phenyl | CH₂ | 4-hydroxy-phenylmethyl | N | 2-amino-pyridin-3-yl-methyl-amino |
| 34 | 4-methoxy-phenyl | CH₂ | 4-methoxy-phenylmethyl | N | 2-n-propylamino-pyridin-3-yl-methyl-amino |
| 35 | 4-methoxy-phenyl | CH₂ | 4-difluoromethoxy-phenylmethyl | N | 2-amino-pyridin-3-yl-methyl-amino |
| 36 | 4-methoxy-phenyl | CH₂ | 4-methoxycarbonyl-phenylmethyl | N | 2-amino-pyridin-3-yl-methyl-amino |
| 37 | 4-methoxy-phenyl | CH₂ | 4-methylcarbonylamino-phenylmethyl | N | 2-amino-pyridin-3-yl-methyl-amino |
| 38 | 4-methoxy-phenyl | CH₂ | 4-trifluoromethoxy-phenylmethyl | N | 2-amino-pyridin-3-yl-methyl-amino |
| 39 | 4-methoxy-phenyl | CH₂ | 4-methoxy-phenylmethyl | N | pyridin-2-yl-methyl-amino |
| 40 | 4-methoxy-phenyl | CH₂ | 4-methoxy-phenylmethyl | N | pyridin-3-yl-methyl-amino |
| 41 | 4-methoxy-phenyl | CH₂ | 4-methoxy-phenylmethyl | N | pyridin-4-yl-methyl-amino |
| 42 | 3-methoxy-phenyl | CH₂ | 4-methoxy-phenylmethyl | N | 2-amino-pyridin-3-yl-methyl-amino |
| 43 | phenyl | CH₂ | 4-methoxy-phenylmethyl | N | 2-amino-pyridin-3-yl-methyl-amino |
| 44 | 4-cyano-phenyl | CH₂ | 4-methoxy-phenylmethyl | N | 2-amino-pyridin-3-yl-methyl-amino |
| 45 | 4-trifluoro-methoxy-phenyl | CH₂ | 4-methoxy-phenylmethyl | N | 2-amino-pyridin-3-yl-methyl-amino |
| 46 | 4-ethoxy-phenyl | CH₂ | 4-methoxy-phenylmethyl | N | 2-amino-pyridin-3-yl-methyl-amino |
| 47 | 4-nitro-phenyl | CH₂ | 4-methoxy-phenylmethyl | N | 2-amino-pyridin-3-yl-methyl-amino |
| 48 | 4-methoxy-phenyl | CH(allyl) | 4-methoxy-phenylmethyl | N | 2-amino-pyridin-3-yl-methyl-amino |
| 49 | 4-trifluoromethyl-phenyl | CH₂ | 4-methoxy-phenylmethyl | N | 2-amino-pyridin-3-yl-methyl-amino |
| 50 | 4-methoxy-phenyl | CH₂ | 4-methoxy-phenylmethyl | N | 2-(2-methoxy-ethylamino)-pyridin-3-yl-methyl-amino |
| 51 | 4-methoxy-phenyl | CH₂ | 4-methoxy-phenylmethyl | N | 2-(2-dimethylamino-ethylamino)-pyridin-3-yl-methyl-amino |
| 52 | 4-methoxy-phenyl | CH₂ | 4-aminocarbonyl-phenylmethyl | N | 2-amino-pyridin-3-yl-methyl-amino |

TABLE 1-continued

| Cpd No. | A₁ | L₁ | D | W | Q |
|---|---|---|---|---|---|
| 53 | 4-methoxy-phenyl | CH₂ | 4-methoxy-phenylmethyl | N | N-oxo-pyridin-3-yl-methyl-amino |
| 54 | 4-hydroxy-phenyl | CH₂ | 4-methoxy-phenylmethyl | N | 2-amino-pyridin-3-yl-methyl-amino |
| 55 | 3-fluoro-phenyl | CH₂ | 4-methoxy-phenylmethyl | N | 2-amino-pyridin-3-yl-methyl-amino |
| 56 | 4-methoxycarbon-yl-phenyl | CH₂ | 4-methoxy-phenylmethyl | N | 2-amino-pyridin-3-yl-methyl-amino |
| 57 | 4-methoxy-phenyl | CH₂ | 4-methoxy-phenylmethyl | N | 2-amino-5-phenyl-pyridin-3-yl-methyl-amino |
| 58 | 4-methoxy-phenyl | CH₂ | 4-methoxy-phenylmethyl | N | 2-amino-4-methoxy-pyridin-3-yl-methyl-amino |
| 59 | 4-methoxy-phenyl | CH₂ | 4-methoxy-phenylmethyl | N | 6-methyl-pyridin-3-yl-methyl-amino |
| 60 | 4-fluoro-phenyl | CH₂ | 4-methoxy-phenylmethyl | N | 4,6-dimethyl-pyridin-3-yl-methyl-amino |
| 61 | 4-methoxy-phenyl | CH₂ | 4-methoxy-phenylmethyl | CH | 4,6-dimethyl-pyridin-3-yl-methyl-amino |
| 62 | 4-methoxy-phenyl | CH₂ | 4-methoxy-phenylmethyl | N | 4-methyl-pyridin-2-yl-methyl-amino |
| 63 | 4-methoxy-phenyl | CH₂ | 4-ethyl-phenylmethyl | N | 2-amino-pyridin-3-yl-methyl-amino |
| 64 | 4-methoxy-phenyl | CH₂ | 4-methoxy-phenylmethyl | N | 6-trifluoromethyl-pyridin-2-yl-methyl-amino |
| 65 | 4-methoxy-phenyl | CH₂ | 4-methoxy-phenylmethyl | N | 3-methyl-pyridin-2-yl-methyl-amino |
| 66 | 4-methoxy-phenyl | CH₂ | 4-methoxy-phenylmethyl | N | 2-(2-methylthio-ethylamino)-pyridin-3-yl-methyl-amino |
| 67 | 4-methoxy-phenyl | CH₂ | 4-methoxy-phenylmethyl | N | 2-(3-methyl-butylamino)-pyridin-3-yl-methyl-amino |
| 68 | 4-methoxy-phenyl | CH₂ | 4-methoxy-phenylmethyl | N | 2-(tetrahydro-furan-2-yl-methyl-amino)-pyridin-3-yl-methyl-amino |
| 69 | 4-methoxy-phenyl | CH₂ | 4-methoxy-phenylmethyl | N | 2-(furan-2-ylmethyl-amino)-pyridin-3-yl-methyl-amino |
| 70 | 4-methoxy-phenyl | CH₂ | 4-methoxy-phenylmethyl | N | 2-(N-ethyl-pyrrolidin-2-ylmethyl-amino)-pyridin-3-yl-methyl-amino |
| 71 | phenyl | CH₂CH₂ | 4-methoxy-phenylmethyl | N | 2-(2-methoxy-ethylamino)-pyridin-3-yl-methyl-amino |
| 72 | phenoxy | CH₂CH₂ | 4-methoxy-phenylmethyl | N | 2-(2-methoxy-ethylamino)-pyridin-3-yl-methyl-amino |
| 73 | 2,3-dihydro-benzo[1,4]dioxin-2-yl | CH₂ | 4-methoxy-phenylmethyl | N | 2-(2-methoxy-ethylamino)-pyridin-3-yl-methyl-amino |
| 74 | 4-nitro-phenyl | CH₂CH₂ | 4-methoxy-phenylmethyl | N | 2-(2-methoxy-ethylamino)-pyridin-3-yl-methyl-amino |
| 75 | 4-methoxy-phenyl | CH₂ | 4-methythio-phenylmethyl | N | 2-amino-pyridin-3-yl-methyl-amino |

TABLE 1-continued

| Cpd No. | A₁ | L₁ | D | W | Q |
|---|---|---|---|---|---|
| 76 | 4-methoxy-phenyl | CH₂ | pyridin-4-ylmethyl | N | 2-amino-pyridin-3-yl-methyl-amino |
| 77 | 4-methoxy-phenyl | CH₂ | benzofuran-2-yl methyl | N | 2-amino-pyridin-3-yl-methyl-amino |
| 78 | 4-methoxy-phenyl | CH₂ | 5-methoxy-n-pentyl | N | 2-amino-pyridin-3-yl-methyl-amino |
| 79 | 4-methoxy-phenyl | CH₂ | n-hexyl | N | 2-amino-pyridin-3-yl-methyl-amino |
| 80 | 4-methoxy-phenyl | CH₂ | 3-methoxy-phenylmethyl | N | 2-amino-pyridin-3-yl-methyl-amino |
| 81 | 4-methoxy-phenyl | CH₂ | 3-cyano-phenylmethyl | N | 2-amino-pyridin-3-yl-methyl-amino |
| 82 | 4-methoxy-phenyl | CH₂ | 3-nitro-phenylmethyl | N | 2-amino-pyridin-3-yl-methyl-amino |
| 83 | 4-difluoromethoxy-phenyl | CH₂ | 4-methoxy-phenylmethyl | N | 4,6-dimethyl-pyridin-3-yl-methyl-amino |
| 84 | 4-difluoromethoxy-phenyl | CH₂ | 4-methoxy-phenylmethyl | N | 2-amino-pyridin-3-yl-methyl-amino |
| 85 | 4-difluoromethoxy-phenyl | CH₂ | 4-difluoromethoxy-phenylmethyl | N | 2-amino-pyridin-3-yl-methyl-amino |
| 86 | 4-methoxy-phenyl | CH₂ | 2-ethyl-phenylmethyl | N | 2-amino-pyridin-3-yl-methyl-amino |
| 87 | 4-methoxy-phenyl | CH₂ | 2-trifluoromethoxy-phenylmethyl | N | 2-amino-pyridin-3-yl-methyl-amino |
| 88 | 4-methoxy-phenyl | CH₂ | 2-cyano-phenylmethyl | N | 2-amino-pyridin-3-yl-methyl-amino |
| 89 | 4-iodo-phenyl | CH₂ | 4-methoxy-phenylmethyl | N | 2-amino-pyridin-3-yl-methyl-amino |
| 90 | 4-pyrazol-1-yl-phenyl | CH₂ | 4-methoxy-phenylmethyl | N | 2-amino-pyridin-3-yl-methyl-amino |
| 91 | 4-fluoro-phenyl | CH₂ | 4-trifluoromethoxy-phenylmethyl | N | 2-amino-pyridin-3-yl-methyl-amino |
| 92 | 4-methoxy-phenyl | CH₂ | 2-methoxy-phenylmethyl | N | 2-amino-pyridin-3-yl-methyl-amino |
| 93 | 4-methoxy-phenyl | CH₂ | 3-methoxycarbonyl-phenylmethyl | N | 2-amino-pyridin-3-yl-methyl-amino |
| 94 | 4-methoxy-phenyl | CH₂ | 2-(4-methoxy-phenyl)-ethyl | N | 2-amino-pyridin-3-yl-methyl-amino |
| 95 | 4-methoxy-phenyl | CH₂ | 6-methoxy-pyridin-3-ylmethyl | N | 2-amino-pyridin-3-yl-methyl-amino |
| 96 | 4-methoxy-phenyl | CH₂ | 4-difluoromethoxy-phenylmethyl | N | 4,6-dimethyl-pyridin-3-ylmethyl-amino |
| 97 | 4-methoxy-phenyl | CH₂ | 4-methoxy-phenylmethyl | N | 2-amino-4,6-dimethyl-pyridin-3-yl-methyl-amino |
| 98 | 4-methoxy-phenyl | CH₂ | 3-trifluoromethoxy-phenylmethyl | N | 2-amino-pyridin-3-yl-methyl-amino |
| 99 | 4-methoxy-phenyl | CH₂ | 3-trifluoromethoxy-phenylmethyl | N | 4,6-dimethyl-pyridin-3-yl-methyl-amino |
| 100 | 4-methoxy-phenyl | CH₂ | 4-methylthio-phenylmethyl | N | 4,6-dimethyl-pyridin-3-yl-methyl-amino |
| 101 | 4-methoxy-phenyl | CH₂ | pyridin-4-ylmethyl | N | 4,6-dimethyl-pyridin-3-yl-methyl-amino |

TABLE 1-continued

| Cpd No. | A$_1$ | L$_1$ | D | W | Q |
|---|---|---|---|---|---|
| 102 | 4-methoxy-phenyl | CH$_2$ | benzofuran-2-ylmethyl | N | 4,6-dimethyl-pyridin-3-ylmethyl-amino |
| 103 | 4-methoxy-phenyl | CH$_2$ | n-hexyl | N | 4,6-dimethyl-pyridin-3-yl-methyl-amino |
| 104 | 4-methoxy-phenyl | CH$_2$ | 6-methoxy-pyridin-3-ylmethyl | N | 4,6-dimethyl-pyridin-3-yl-methyl-amino |
| 105 | 4-methoxy-phenyl | CH$_2$ | 2-trifluoromethoxy-phenylmethyl | N | 4,6-dimethyl-pyridin-3-yl-methyl-amino |
| 106 | 4-methoxy-phenyl | CH$_2$ | 2-methoxy-phenylmethyl | N | 4,6-dimethyl-pyridin-3-yl-methyl-amino |
| 107 | 4-ethoxy-phenyl | CH$_2$ | 4-methoxy-phenylmethyl | N | 4,6-dimethyl-pyridin-3-yl-methyl-amino |
| 108 | 4-nitro-phenyl | CH$_2$ | 4-methoxy-phenylmethyl | N | 4,6-dimethyl-pyridin-3-yl-methyl-amino |
| 109 | 4-methoxy-phenyl | CH(allyl) | 4-methoxy-phenylmethyl | N | 4,6-dimethyl-pyridin-3-yl-methyl-amino |
| 110 | 4-trifluoromethyl-phenyl | CH$_2$ | 4-methoxy-phenylmethyl | N | 4,6-dimethyl-pyridin-3-yl-methyl-amino |
| 111 | 3-methoxy-phenyl | CH$_2$ | 4-methoxy-phenylmethyl | N | 4,6-dimethyl-pyridin-3-yl-methyl-amino |
| 112 | 3-fluoro-phenyl | CH$_2$ | 4-methoxy-phenylmethyl | N | 4,6-dimethyl-pyridin-3-yl-methyl-amino |
| 113 | pyridin-4-ylmethyl | CH$_2$ | 4-methoxy-phenylmethyl | N | 4,6-dimethyl-pyridin-3-yl-methyl-amino |
| 114 | 4-methoxycarbonyl-phenyl | CH$_2$ | 4-methoxy-phenylmethyl | N | 4,6-dimethyl-pyridin-3-yl-methyl-amino |
| 115 | 4-methoxy-phenyl | CH$_2$ | 4-methoxy-phenylmethyl | N | 6-amino-pyridin-2-yl-methyl-amino |
| 116 | 4-methoxy-phenyl | CH$_2$ | 4-fluoro-phenylmethyl | N | 4,6-dimethyl-pyridin-3-yl-methyl-amino |
| 117 | 4-methoxy-phenyl | CH$_2$ | 4-chloro-phenylmethyl | N | 4,6-dimethyl-pyridin-3-yl-methyl-amino |
| 118 | 4-methoxy-phenyl | CH$_2$ | 4-methoxy-phenylmethyl | N | N-oxo-4,6-dimethyl-pyridin-3-yl-methyl-amino |
| 119 | indol-3-yl | CH$_2$CH$_2$ | 4-methoxy-phenylmethyl | N | 2-amino-pyridin-3-yl-methyl-amino |
| 120 | 2,3-dihydro-benzo[1,4]dioxin-2-yl | CH$_2$ | 4-methoxy-phenylmethyl | N | 2-amino-pyridin-3-yl-methyl-amino |
| 121 | 4-methoxy-phenyl | CH$_2$ | 4-methoxy-phenylmethyl | CH | pyridin-3-yl-methoxy |
| 122 | 4-methoxy-phenyl | CH$_2$ | 4-methoxy-phenylmethyl | N | 6-trifluoromethyl-pyridin-3-yl-methyl-amino |
| 123 | 2,3-dihydro-benzofuran-5-yl | CH$_2$ | 4-methoxy-phenylmethyl | N | 4,6-dimethyl-pyridin-3-ylmethyl-amino |
| 124 | 3-nitro-4-methoxy-phenyl | CH$_2$ | 4-methoxy-phenylmethyl | N | 2-amino-pyridin-3-ylmethyl-amino |
| 125 | 4-methoxy-phenyl | CH$_2$ | 2,3-dihydro-benzofuran-5-yl methyl | N | 2-amino-pyridin-3-yl-methyl-amino |
| 126 | 4-methoxy-phenyl | CH$_2$ | benzofuran-5-yl methyl | N | 2-amino-pyridin-3-yl-methyl-amino |
| 127 | 4-methoxy-phenyl | CH$_2$ | indol-5-ylmethyl | N | 2-amino-pyridin-3-yl-methyl-amino |

TABLE 1-continued

| Cpd No. | A₁ | L₁ | D | W | Q |
|---|---|---|---|---|---|
| 128 | 4-methoxy-phenyl | CH₂ | 2,3-dihydro-benzofuran-5-yl methyl | N | 4,6-dimethyl-pyridin-3-yl-methyl-amino |
| 129 | 4-methoxy-phenyl | CH₂ | benzofuran-5-yl methyl | N | 4,6-dimethyl-pyridin-3-yl-methyl-amino |
| 130 | 4-methoxy-phenyl | CH₂ | indol-5-ylmethyl | N | 4,6-dimethyl-pyridin-3-yl-methyl-amino |
| 131 | 4-methoxy-phenyl | CH₂ | 4-methanesulfonyl-phenylmethyl | N | 2-amino-pyridin-3-yl-methyl-amino |
| 132 | 4-methoxy-phenyl | CH₂ | 4-methanesulfonyl-phenylmethyl | N | 4,6-dimethyl-pyridin-3-yl-methyl-amino |
| 133 | benzofuran-5-yl | CH₂ | 4-methoxy-phenylmethyl | N | 4,6-dimethyl-pyridin-3-ylmethyl-amino |
| 134 | benzofuran-5-yl | CH₂ | 4-methoxy-phenylmethyl | N | 2-amino-pyridin-3-ylmethyl-amino |
| 135 | 4-methoxy-phenyl | CH₂ | 4-t-butoxy-phenylmethyl | N | 2-amino-pyridin-3-yl-methyl-amino |
| 136 | 4-methoxy-phenyl | CH₂ | 3-nitro-4-methoxy-phenylmethyl | N | 4,6-dimethyl-pyridin-3-yl-methyl-amino |
| 137 | 4-methoxy-phenyl | CH₂ | 3-nitro-4-methoxy-phenylmethyl | N | 2-amino-pyridin-3-yl-methyl-amino |
| 138 | 4-methoxy-phenyl | CH₂ | indol-4-ylmethyl | N | 2-amino-pyridin-3-yl-methyl-amino |
| 139 | 4-methoxy-phenyl | CH₂ | indol-4-ylmethyl | N | 4,6-dimethyl-pyridin-3-yl-methyl-amino |
| 140 | 4-methoxy-phenyl | CH₂ | benzothiophen-5-ylmethyl | N | 2-amino-pyridin-3-yl-methyl-amino |
| 141 | 4-fluoro-phenoxy | CH₂CH₂ | 4-methoxy-phenylmethyl | N | 2-amino-pyridin-3-yl-methyl-amino |
| 142 | 4-methoxy-phenyl | CH₂ | benzothiophen-5-ylmethyl | N | 4,6-dimethyl-pyridin-3-yl-methyl-amino |
| 143 | 2-methoxy-phenyl | CH₂ | 4-methoxy-phenylmethyl | N | 2-amino-pyridin-3-yl-methyl-amino |
| 144 | 2-methoxy-phenyl | CH₂ | 4-methoxy-phenylmethyl | N | 4,6-dimethyl-pyridin-3-yl-methyl-amino |
| 145 | benzothio-phen-5-yl | CH₂ | 4-methoxy-phenylmethyl | N | 2-amino-pyridin-3-yl-methyl-amino |
| 146 | benzothio-phen-5-yl | CH₂ | 4-methoxy-phenylmethyl | N | 4,6-dimethyl-pyridin-3-ylmethyl-amino |
| 147 | 4-methoxy-phenyl | CH₂ | 4-methoxy-phenylmethyl | N | 6-n-propylamino-pyridin-2-yl-methyl-amino |
| 148 | 4-methoxy-phenyl | CH₂ | 4-methoxy-phenylmethyl | CH | 6-amino-pyridin-2-yl methyl-amino |
| 149 | 4-methoxy-phenyl | CH₂ | 4-methoxy-cyclohexylmethyl | N | 2-amino-pyridin-3-yl-methyl-amino |
| 150 | 4-methoxy-phenyl | CH₂ | 4-methoxy-cyclohexylmethyl | N | 4,6-dimethyl-pyridin-3-yl-methyl-amino |
| 151 | 4-methoxy-phenyl | CH₂ | 3,4-dichloro-phenylmethyl | N | 2-amino-pyridin-3-yl-methyl-amino |
| 152 | 4-methoxy-phenyl | CH₂ | 4-(isoindol-1,3-dione-2-yl)-phenylmethyl | N | 4,6-dimethyl-pyridin-3-yl-methyl-amino |
| 153 | 4-methoxy-phenyl | CH₂ | 3-methoxy carbonyl-n-propyl | N | 4,6-dimethyl-pyridin-3-yl-methyl-amino |
| 154 | 4-methoxy-phenyl | CH₂ | 4-methoxy-phenylmethyl | N | 2-(pyridin-2-yl)-ethylamino |

TABLE 1-continued

| Cpd No. | A₁ | L₁ | D | W | Q |
|---|---|---|---|---|---|
| 155 | 4-methoxy-phenyl | CH₂ | indol-4-ylmethyl | N | 2-amino-4,6-dimethyl-pyridin-3-yl-methyl-amino |
| 156 | 4-fluoro-phenyl | CH₂ | 4-difluoromethoxy-phenylmethyl | N | 6-amino-pyridin-2-yl-methyl-amino |
| 157 | 4-methoxy-phenyl | CH₂ | 2,3-dihydro-benzofuran-5-yl methyl | N | 2-amino-4,6-dimethyl-pyridin-3-yl-methyl-amino |
| 158 | 4-pyrazol-1-yl-phenyl | CH₂ | 4-difluoromethoxy-phenylmethyl | N | 4,6-dimethyl-pyridin-3-yl-methyl-amino |
| 159 | 4-iodo-phenyl | CH₂ | 4-difluoromethoxy-phenylmethyl | N | 4,6-dimethyl-pyridin-3-yl-methyl-amino |
| 160 | 4-fluoro-phenyl | CH₂ | 4-difluoromethoxy-phenylmethyl | N | 4,6-dimethyl-pyridin-3-yl-methyl-amino |
| 161 | 4-methyl-phenyl | CH₂ | 4-difluoromethoxy-phenylmethyl | N | 4,6-dimethyl-pyridin-3-yl-methyl-amino |
| 162 | 4-trifluoromethyl-phenyl | CH₂ | 4-difluoromethoxy-phenylmethyl | N | 4,6-dimethyl-pyridin-3-yl-methyl-amino |
| 163 | 4-difluorometh-oxy-phenyl | CH₂ | 4-difluoromethoxy-phenylmethyl | N | 4,6-dimethyl-pyridin-3-yl-methyl-amino |
| 164 | 4-cyano-phenyl | CH₂ | 4-difluoromethoxy-phenylmethyl | N | 4,6-dimethyl-pyridin-3-yl-methyl-amino |
| 165 | 4-methoxycarbon-yl-phenyl | CH₂ | 4-difluoromethoxy-phenylmethyl | N | 4,6-dimethyl-pyridin-3-yl-methyl-amino |
| 166 | phenoxy | CH₂CH₂ | 4-difluoromethoxy-phenylmethyl | N | 4,6-dimethyl-pyridin-3-yl-methyl-amino |
| 167 | 4-fluoro-phenoxy | CH₂CH₂ | 4-difluoromethoxy-phenylmethyl | N | 4,6-dimethyl-pyridin-3-yl-methyl-amino |
| 168 | 4-[1,2,3]thiadiazol-4-yl-phenyl | CH₂ | 4-difluoromethoxy-phenylmethyl | N | 4,6-dimethyl-pyridin-3-ylmethyl-amino |
| 169 | 4-methoxy-phenyl | CH₂ | 4-methoxy-phenylmethyl | CH | 2-(pyridin-3-yl)-ethyl |
| 170 | 4-methoxy-phenyl | CH₂ | indol-6-ylmethyl | N | 2-amino-pyridin-3-yl-methyl-amino |
| 171 | 4-methoxy-phenyl | CH₂ | indol-7-ylmethyl | N | 2-amino-pyridin-3-yl-methyl-amino |
| 172 | 4-methoxy-phenyl | CH₂ | indol-7-ylmethyl | N | 4,6-dimethyl-pyridin-3-yl-methyl-amino |
| 173 | 4-methylthio-phenyl | CH₂ | 4-difluoromethoxy-phenylmethyl | N | 2-amino-4,6-dimethyl-pyridin-3-yl-methyl-amino |
| 174 | benzothio-phen-5-yl | CH₂ | 4-difluoromethoxy-phenylmethyl | N | 2-amino-4,6-dimethyl-pyridin-3-yl-methyl-amino |
| 175 | benzofuran-5-yl | CH₂ | 4-difluoromethoxy-phenylmethyl | N | 2-amino-4,6-dimethyl-pyridin-3-yl-methyl-amino |
| 176 | 2,3-dihydro-benzofuran-5-yl | CH₂ | 4-difluoromethoxy-phenylmethyl | N | 2-amino-4,6-dimethyl-pyridin-3-yl-methyl-amino |
| 177 | 4-methylthio-phenyl | CH₂ | 4-difluoromethoxy-phenylmethyl | N | 4,6-dimethyl-pyridin-3-yl-methyl-amino |
| 178 | benzofuran-5-yl | CH₂ | 4-difluoromethoxy-phenylmethyl | N | 4,6-dimethyl-pyridin-3-yl-methyl-amino |
| 179 | 2,3-dihydro-benzofuran-5-yl | CH₂ | 4-difluoromethoxy-phenylmethyl | N | 4,6-dimethyl-pyridin-3-yl-methyl-amino |
| 180 | 2-cyano-phenyl | CH₂ | 4-difluoromethoxy-phenylmethyl | N | 4,6-dimethyl-pyridin-3-yl-methyl-amino |

TABLE 1-continued

| Cpd No. | A₁ | L₁ | D | W | Q |
|---|---|---|---|---|---|
| 181 | 4-hydroxy-phenyl | CH₂ | 4-difluoromethoxy-phenylmethyl | N | 4,6-dimethyl-pyridin-3-yl-methyl-amino |
| 182 | 4-methylcarbonyloxy-phenyl | CH₂ | 4-difluoromethoxy-phenylmethyl | N | 4,6-dimethyl-pyridin-3-ylmethyl-amino |
| 183 | 4-methoxy-phenyl | CH₂ | 4-methoxy-phenylmethyl | CH | 2-(pyridin-4-yl)-ethyl |
| 184 | 4-methoxy-phenyl | CH₂ | 4-methoxy-phenylmethyl | CH | cis-2-pyridin-4-yl-vinyl |
| 185 | 2,3-dihydro-benzofuran-5-yl | CH₂ | 2,3-dihydro-benzofuran-5-ylmethyl | N | 2-amino-4,6-dimethyl-pyridin-3-yl-methyl-amino |
| 186 | benzofuran-5-yl | CH₂ | 2,3-dihydro-benzofuran-5-yl methyl | N | 2-amino-4,6-dimethyl-pyridin-3-yl-methyl-amino |
| 187 | 4-methoxy-phenyl | CH₂ | 4-methoxy-phenylmethyl | CH | 2-pyridin-2-yl-ethyl |
| 188 | 4-methoxy-phenyl | CH₂ | 4-methoxy-phenylmethyl | N | imidazo[1,2-a]pyridin-8-yl-methyl-amino |
| 189 | 4-methoxy-phenyl | CH₂ | 4-methoxy-phenylmethyl | CH | 2-(2-aminocarbonyl-pyridin-3-yl)-ethyl |
| 190 | 4-methoxy-phenyl | CH₂ | 4-methoxy-phenylmethyl | CH | 2-amino-pyridin-3-yl-methoxy |
| 191 | 4-hydroxymethyl-phenyl | CH₂ | 4-difluoromethoxy-phenylmethyl | N | 4,6-dimethyl-pyridin-3-yl-methyl-amino |
| 192 | 1-methyl-1H-benzotriazol-5-yl | CH₂ | 4-difluoromethoxy-phenylmethyl | N | 4,6-dimethyl-pyridin-3-yl-methyl-amino |
| 193 | 2-methoxy-phenyl | CH₂ | 4-difluoromethoxy-phenylmethyl | N | 4,6-dimethyl-pyridin-3-yl-methyl-amino |
| 194 | 4-aminocarbonyl-phenyl | CH₂ | 4-difluoromethoxy-phenylmethyl | N | 4,6-dimethyl-pyridin-3-yl-methyl-amino |
| 195 | 2,6-difluoro-4-methoxy-phenyl | CH₂ | 4-difluoromethoxy-phenylmethyl | N | 4,6-dimethyl-pyridin-3-yl-methyl-amino |
| 196 | benzo[1,2,3]thiadiazol-5-yl | CH₂ | 4-difluoromethoxy-phenylmethyl | N | 4,6-dimethyl-pyridin-3-yl-methyl-amino |
| 197 | methoxy | (CH₂)₅ | 4-methoxy-phenylmethyl | N | 4,6-dimethyl-pyridin-3-yl-methyl-amino |
| 198 | methoxy | (CH₂)₅ | 4-difluoromethoxy-phenylmethyl | N | 4,6-dimethyl-pyridin-3-yl-methyl-amino |
| 199 | 4-methoxy-phenyl | CH₂ | 4-methoxy-phenylmethyl | CH | 2-(2-amino-pyridin-3-yl)-ethyl |
| 200 | 4-methoxy-phenyl | CH₂ | 2,4-dimethoxy-phenylmethyl | N | 2-amino-pyridin-3-yl-methyl-amino |
| 201 | 4-methoxy-phenyl | CH₂ | 4-methoxy-phenylmethyl | N | 4-methyl-pyridin-3-yl-methyl-amino |
| 202 | 4-methoxy-phenyl | CH₂ | 4-methoxy-phenylmethyl | CH | 2-amino-4,6-dimethyl-pyridin-3-yl-methoxy |
| 203 | 4-methoxy-phenyl | CH₂ | 3-fluoro-4-methoxy-phenylmethyl | N | 2-amino-pyridin-3-yl-methyl-amino |
| 204 | 4-methoxy-phenyl | CH₂ | 3-fluoro-4-methoxy-phenylmethyl | N | 4,6-dimethyl-pyridin-3-yl-methyl-amino |
| 205 | 4-methoxy-phenyl | CH₂ | 2-fluoro-4-methoxy-phenylmethyl | N | 2-amino-pyridin-3-yl-methyl-amino |
| 206 | 4-methoxy-phenyl | CH₂ | 2-fluoro-4-methoxy-phenylmethyl | N | 4,6-dimethyl-pyridin-3-yl-methyl-amino |
| 207 | benzo(1,3)dioxal-5-yl | CH₂ | 4-methoxy-phenylmethyl | N | 4,6-dimethyl-pyridin-3-yl-methyl-amino |
| 208 | benzo(1,3)dioxal-5-yl | CH₂ | 4-difluoromethoxy-phenylmethyl | N | 4,6-dimethyl-pyridin-3-yl-methyl-amino |

TABLE 1-continued

| Cpd No. | A₁ | L₁ | D | W | Q |
|---|---|---|---|---|---|
| 209 | 2,3-dihydro-benzo[1,4]dioxin-6-yl | CH₂ | 4-methoxy-phenylmethyl | N | 4,6-dimethyl-pyridin-3-yl-methyl-amino |
| 210 | 2,3-dihydro-benzo[1,4]dioxin-6-yl | CH₂ | 4-difluoromethoxy-phenylmethyl | N | 4,6-dimethyl-pyridin-3-yl-methyl-amino |
| 211 | 4-methoxy-phenyl | CH₂ | 4-methoxy-phenylmethyl | CH | pyridin-3-yl-methylthio |
| 212 | 4-methoxy-phenyl | CH₂ | 2-methyl-2,3-dihydro-benzofuran-5-yl methyl | N | 2-amino-4,6-dimethyl-pyridin-3-yl-methyl-amino |
| 213 | 4-methoxy-phenyl | CH₂ | 4-methoxy-phenylmethyl | N | 2-(N-piperidinyl)-4,6-dimethyl-pyridin-3-yl-methyl-amino |
| 214 | 4-methoxy-phenyl | CH₂ | 4-methoxy-phenylmethyl | CH | 2-(4-amino-pyridin-3-yl)-ethyl |
| 215 | 4-methoxy-phenyl | CH₂ | 4-methoxy-phenylmethyl | N | 2-(pyridin-4-yl)-ethylamino |
| 216 | 1-methyl-1H-benzo-triazol-5-yl | CH₂ | 4-methoxy-phenylmethyl | N | 4,6-dimethyl-pyridin-3-yl-methyl-amino |
| 217 | benzo[1,2,3]thiadiazol-5-yl | CH₂ | 4-methoxy-phenylmethyl | N | 4,6-dimethyl-pyridin-3-yl-methyl-amino |
| 218 | 3-fluoro-4-methoxy-phenyl | CH₂ | 4-methoxy-phenylmethyl | N | 4,6-dimethyl-pyridin-3-yl-methyl-amino |
| 219 | benzo(1,3)dioxal-5-yl | CH₂ | 4-difluoromethoxy-phenylmethyl | N | 2-amino-4,6-dimethyl-pyridin-3-yl-methyl-amino |
| 220 | benzo(1,3)dioxal-5-yl | CH₂ | 4-methoxy-phenylmethyl | N | 2-amino-4,6-dimethyl-pyridin-3-yl-methyl-amino |
| 221 | 1-methyl-1H-benzotriazol-5-yl | CH₂ | 4-difluoromethoxy-phenylmethyl | N | 2-amino-4,6-dimethyl-pyridin-3-yl-methyl-amino |
| 222 | 1-methyl-1H-benzotriazol-5-yl | CH₂ | 4-methoxy-phenylmethyl | N | 2-amino-4,6-dimethyl-pyridin-3-yl-methyl-amino |
| 223 | 4-methoxy-phenyl | CH₂ | 4-methoxy-phenylmethyl | CH | 2-(6-amino-pyridin-2-yl)ethyl |
| 224 | 4-methoxy-phenyl | CH₂ | 5-methoxy-n-pentyl | N | 2-amino-4,6-dimethyl-pyridin-3-yl-methyl-amino |
| 225 | 4-methoxy-phenyl | CH₂ | 4-methoxy-phenylmethyl | CH | 1-(2-amino-pyridin-4-yl)-ethoxy |
| 226 | 2,3-dihydro-benzofuran-5-yl | CH₂ | 2,3-dihydro-benzofuran-5-yl methyl | N | N-oxo-2-amino-4,6-dimethyl-pyridin-3-yl-methyl-amino |
| 227 | indol-5-yl | CH₂ | 4-difluoromethoxy-phenylmethyl | N | 4,6-dimethyl-pyridin-3-yl-methyl-amino |
| 228 | indol-5-yl | CH₂ | 4-difluoromethoxy-phenylmethyl | N | 2-amino-pyridin-3-yl-methyl-amino |
| 229 | indol-5-yl | CH₂ | 4-methoxy-phenylmethyl | N | 4,6-dimethyl-pyridin-3-yl-methyl-amino |
| 230 | indol-5-yl | CH₂ | 4-methoxy-phenylmethyl | N | 2-amino-pyridin-3-yl-methyl-amino |
| 231 | 4-chloro-phenyl | CH₂ | 4-methoxy-phenylmethyl | N | 2-amino-pyridin-3-yl-methyl-amino |
| 232 | 4-methoxy-phenyl | CH₂ | 4-methoxy-phenylmethyl | CH | 2-amino-pyrimidin-4-ylmethoxy |
| 233 | 2,3-dihydro-benzofuran-5-yl | CH₂ | 4-difluoromethoxy-phenylmethyl | N | N-oxo-2-amino-4,6-dimethyl-pyridin-3-yl-methyl-amino |
| 234 | 4-methoxy-phenyl | CH₂ | 4-methoxy-phenylmethyl | N | ![structure: -N(H)-CH(CH₃)-(pyridin-2-yl)] |

TABLE 1-continued
| Cpd No. | A₁ | L₁ | D | W | Q |
|---|---|---|---|---|---|
| 235 | 4-methoxyphenyl | CH₂ | 4-methoxyphenylmethyl | N | 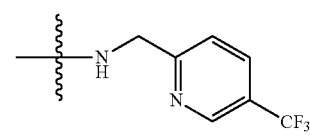 [SMILES: *NCc1ccc(C(F)(F)F)cn1] |
| 236 | 4-methoxyphenyl | CH₂ | 4-methoxyphenylmethyl | N | 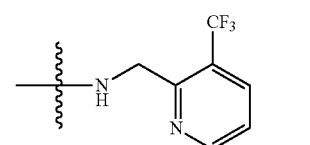 |
| 237 | 4-methoxyphenyl | CH₂ | 4-methoxyphenylmethyl | N | 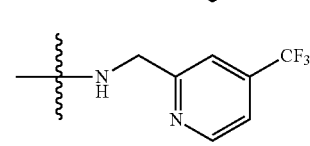 |
| 238 | 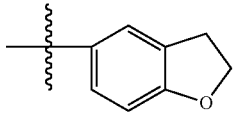 [SMILES: *c1ccc2c(c1)CCO2] | CH₂ | —(CH₂)₅OCH₃ | N | 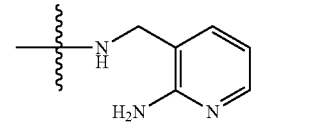 |
| 239 | 4-methoxyphenyl | (CH₂)₂ | —(CH₂)₅OCH₃ | N | 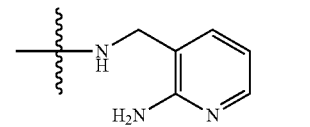 |
| 240 | 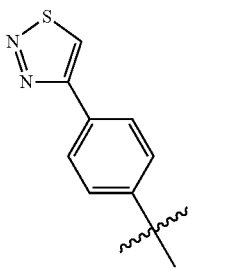 [SMILES: *c1ccc(-c2csnn2)cc1] | CH₂ | 4-methoxyphenylmethyl | N | 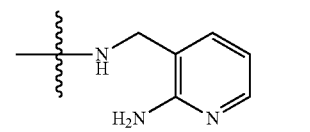 [SMILES: *NCc1cccnc1N] |
| 241 | 4-methoxyphenyl | CH₂ | 4-methoxyphenylmethyl | N | 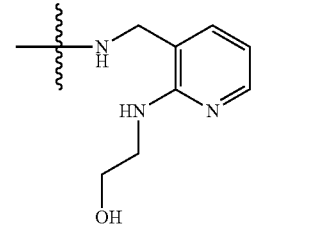 [SMILES: *NCc1cccnc1NCCO] |
| 242 | 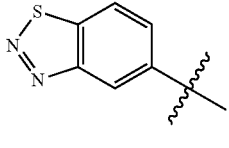 [SMILES: *c1ccc2snnc2c1] | CH₂ | 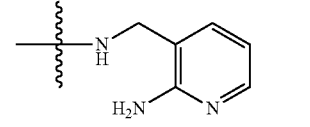 [SMILES: *NCc1cccnc1N] | N | 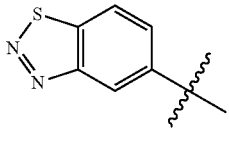 |
| 243 | 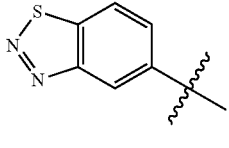 [SMILES: *c1ccc2snnc2c1] | CH₂ | 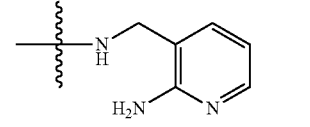 [SMILES: *NCc1cccnc1N] | N | 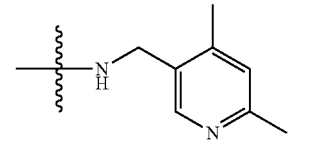 [SMILES: *NCc1cnc(C)cc1C] |

US 8,372,973 B2
TABLE 1-continued
| Cpd No. | A₁ | L₁ | D | W | Q |
|---|---|---|---|---|---|
| 244 | 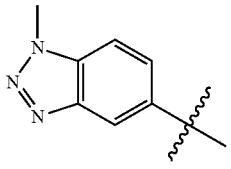 [SMILES: *c1ccc2c(c1)nnn2C] | CH₂ | 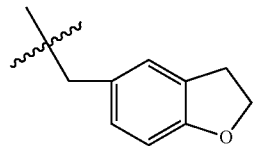 [SMILES: *Cc1ccc2c(c1)CCO2] | N | 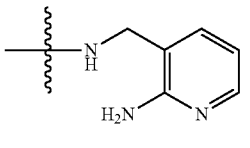 |
| 245 | 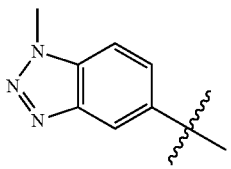 [SMILES: *c1ccc2c(c1)nnn2C] | CH₂ | 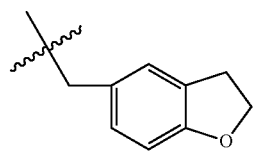 | N | 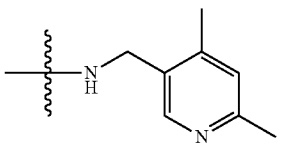 [SMILES: *NCc1cnc(C)cc1C] |
| 246 | 4-methoxy-phenyl | CH₂ | 4-methoxy-phenylmethyl | N | 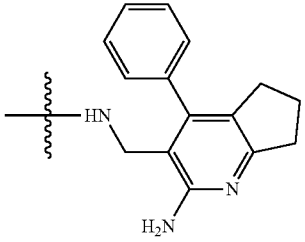 [SMILES: *NCc1c(N)nc2c(c1-c1ccccc1)CCC2] |
| 247 | 4-methoxy-phenyl | CH₂ | 4-methoxy-phenylmethyl | N | 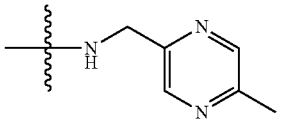 |
| 248 | 4-methoxy-phenyl | CH₂ | 4-methoxy-phenylmethyl | N | 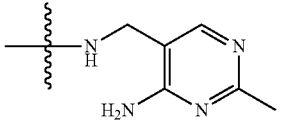 [SMILES: *NCc1cnc(C)nc1N] |
| 249 | 4-methoxy-phenyl | CH₂ | 4-methoxy-phenylmethyl | CH | 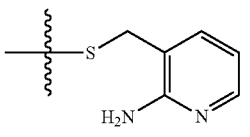 |
| 250 | 4-methoxy-phenyl | CH₂ | 4-methoxy-phenylmethyl | N | 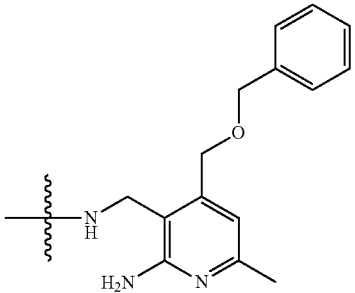 [SMILES: *NCc1c(COCc2ccccc2)cc(C)nc1N] |
| 251 | 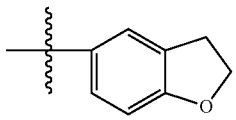 [SMILES: *c1ccc2c(c1)CCO2] | CH₂ | 4-difluoromethoxy-phenylmethyl | N | 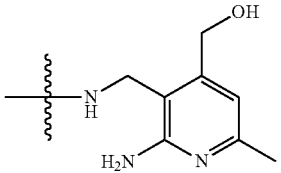 [SMILES: *NCc1c(CO)cc(C)nc1N] |

TABLE 1-continued
| Cpd No. | A₁ | L₁ | D | W | Q |
|---|---|---|---|---|---|
| 252 | methoxy | (CH₂)₅ | 4-methoxy-phenylmethyl | N | 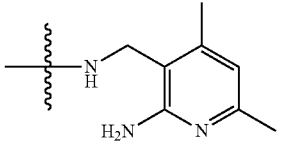 [SMILES: *NCc1c(C)cc(C)nc1N] |
| 253 | 4-chloro-phenyl | CH₂ | —(CH₂)₅OCH₃ | N | 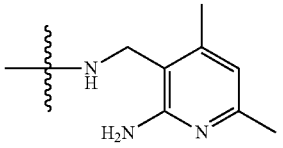 [SMILES: *NCc1c(C)cc(C)nc1N] |
| 254 | phenyl | CH₂ | —(CH₂)₅OCH₃ | N | 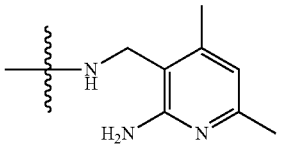 [SMILES: *NCc1c(C)cc(C)nc1N] |
| 255 | 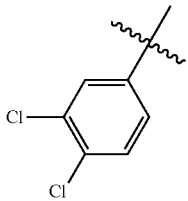 [SMILES: *c1ccc(Cl)c(Cl)c1] | CH₂ | —(CH₂)₅OCH₃ | N | 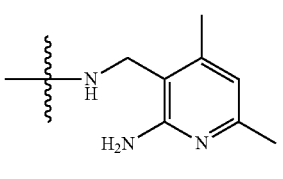 [SMILES: *NCc1c(C)cc(C)nc1N] |
| 256 | 4-chloro-phenyl | CH₂ | —(CH₂)₅OCH₃ | N | 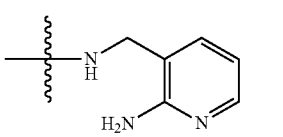 |
| 257 | 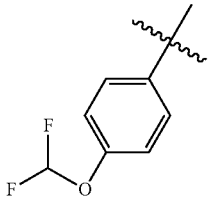 [SMILES: *c1ccc(OC(F)F)cc1] | CH₂ | —(CH₂)₅OCH₃ | N | 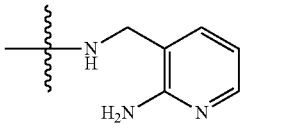 [SMILES: *NCc1cccnc1N] |
| 258 | 4-methoxy-phenyl | CH₂ | —(CH₂)₅OCH₃ | N | 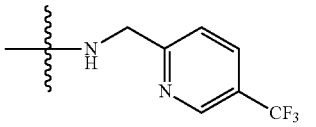 |
| 259 | 4-methoxy-phenyl | CH₂ | 4-methoxy-phenylmethyl | N | 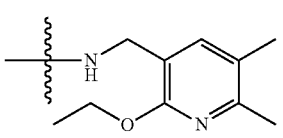 [SMILES: *NCc1cc(C)c(C)nc1OCC] |
| 260 | 4-methoxy-phenyl | CH₂ | 4-methoxy-phenylmethyl | N | 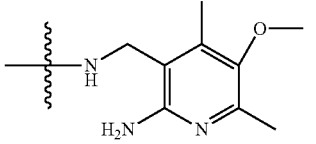 [SMILES: *NCc1c(N)nc(C)c(OC)c1C] |

TABLE 1-continued

| Cpd No. | A₁ | L₁ | D | W | Q |
|---|---|---|---|---|---|
| 261 | 2,3-dihydrobenzofuran-5-yl | CH₂ | 4-difluoromethoxy-phenylmethyl | N | -NH-CH₂-(5-methylpyrazin-2-yl) |
| 262 | 2,3-dihydrobenzofuran-5-yl | CH₂ | 4-difluoromethoxy-phenylmethyl | N | -NH-CH₂-[2-amino-4-methyl-6-(4-fluorophenyl)pyridin-3-yl] |
| 263 | 4-methoxy-phenyl | CH₂ | 4-methoxy-phenylmethyl | N | -NH-CH₂-(2-amino-4,5,6-trimethylpyridin-3-yl) |
| 264 | 4-methoxy-phenyl | CH₂ | 4-methoxy-phenylmethyl | N | -HN-CH₂-(2-amino-4-methyl-6,7-dihydro-5H-cyclopenta[b]pyridin-3-yl) |
| 265 | 4-methoxy-phenyl | CH₂ | 4-methoxy-phenylmethyl | N | -NH-CH₂-(2-amino-4-propyl-6-propylpyridin-3-yl) |
| 266 | CF₃ | (CH₂)₂ | 4-methoxy-phenylmethyl | N | -NH-CH₂-(2-amino-4,6-dimethylpyridin-3-yl) |
| 267 | 4-methoxy-phenyl | CH₂ | 4-methoxy-phenylmethyl | N | -NH-CH₂-(6-methylpyridin-2-yl) |
| 268 | 2-amino-4-hydroxyphenyl | CH₂ | 4-difluoromethoxy-phenylmethyl | N | -NH-CH₂-(2-aminopyridin-3-yl) |

TABLE 1-continued

| Cpd No. | A₁ | L₁ | D | W | Q |
|---|---|---|---|---|---|
| 269 | 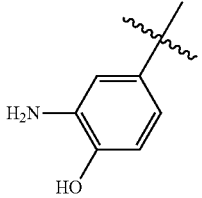 [SMILES: *c1ccc(O)c(N)c1] | CH₂ | 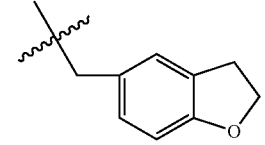 [SMILES: *Cc1ccc2c(c1)CCO2] | N | 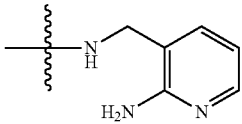 |
| 270 | 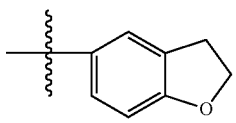 [SMILES: *c1ccc2c(c1)CCO2] | CH₂ | 4-difluoromethoxy-phenylmethyl | N | 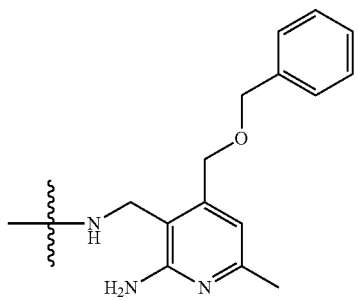 [SMILES: *NCc1c(COCc2ccccc2)cc(C)nc1N] |
| 271 | 4-methoxyphenyl | CH₂ | 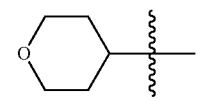 | N | 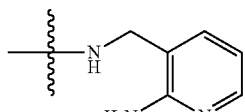 |
| 272 | 4-methoxyphenyl | CH₂ | 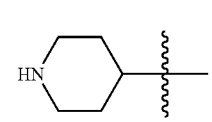 | N | 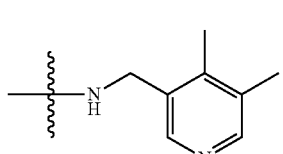 |

BIOLOGICAL EXAMPLES

Biological Example 1

Expression, Isolation, and Purification of Prokineticin-1

Recombinant N-terminal FLAG-tagged human prokineticin-1 (sequence-MRGATRVSIMLLLVTVSDCDYKD-DDDKAVITGACERDVQCGAGTCCAISLWLR GLRM-CTPLGREGEECHPGSHKVPFFRKRKHHTCPCLPNLL-CSRFPDGRYRCS MDLKNINF) was expressed in stably transfected HEK 293 cells.

HEK 293 cells were grown to 100% confluence in DMEM selective high-glucose media (Invitrogen, Carlsbad, Calif.) containing 10% FBS, 20 mM HEPES, sodium pyruvate, penicillin and streptomycin (50 μg/ml each), and G418 (400 mg/L). The DMEM media used to culture the HEK 293 cells was replenished every other day with fresh media over a two-week period of time. Culture media containing the PK-1 peptide was collected, and filtered in 500 mL 0.2 μm pore size filters (Corning Incorporated, Corning, N.Y.). The filtrate was stored in a filtrate bottle at 4° C. The PK-1 peptide containing media was purified by gravity flow passage of media over M2 agarose columns (Sigma Chemical, St. Louis, Mo.) at 4° C. Following media passage, the agarose columns were washed with sterile 1×PBS (pH 7.4) until protein could no longer be detected by OD 280 nm. Columns were then eluted with a 0.1 M glycine-HCl solution at pH 2.8. The eluted material was immediately neutralized, by collecting into tubes containing 1M Tris pH8. Peak fractions were identified by OD 280 and pooled. The pooled fractions were subjected to Enterokinase cleavage of Flag epitope 4 units/mL overnight at room temperature. Enterokinase was removed, and sample aliquot was stored at −80° C.

Results of Mass Spectral Analysis of Prokineticin 1 Ligand from Above Purification The samples were analyzed using Maldi TOF-MS and LC— Electrospray-Mass Spectral Analysis.
Desired Protein Sequence:

AVITGACERDVQCGAGTCCAISLWLRGLRMCTPLGREGEECHPGSHKVP
FFRKRKHHTCPCLPNLLCSRFPDGRYRCSMDLKNINF

Calculated Avg. Molecular Mass=9667.4.
MALDI-TOF Analysis
Sample Preparation

The protein sample solution (10 μL) was desalted using a C4 Zip Tip according to the User Guide for Reversed-Phase ZipTip, 2002 Millipore Corporation.
Mass Spectrometry A Micromass TOF Spec E mass spectrometer was used to determine molecular mass. MassLynx software 3.4 was used for the system control and data acquisition. MALDI positive ion mass spectra were acquired over a mass range of 0-80,000 Da. The raw MS data were baseline subtracted and smoothed using Masslynx software and compared to the masses obtained from a reference standard.

Masses of eluting components were calculated using the Agilent deconvolution software.

Results

The mass spectral data shows the presence of the desired protein (molecular mass=9667) and an additional related component with a measured molecular mass of 9172 in about the same abundance based on mass spectral response. This mass agrees, within measurement error, with a possible truncation product missing the last four C-terminal residues indicated below.

Proposed Additional Protein Component Sequence

AVITGACERDVQCGAGTCCAISLWLRGLRMCTPLGREGEECHPGSHKVP

FFRKRKHHTCPCLPNLLCSRFPDGRYRCSMDLK.

Calculated Avg. Molecular Mass=9178.8. No other related protenaceous components were detected. The mass accuracy for all measurements is approximately 0.1%.

Biological Example 2

Functional Assay

Screening Procedure for PK1 Antagonists on the Fluorometric Imaging Plate Reader (FLIPR)

At a time of 24 h prior to running the assay, in cell culture media (DMEM containing high Glucose and L-glutamine, 10% FBS, 1% Pen/Streptomycin, 1% Sodium Pyruvate, 20 mM HEPES, Zeocin 200 mg/L), 100 4 of $1.3*10^6$/ml HEK 293 GPR73 (prokineticin 1 receptor) expressing cells were plated in a 96 well poly-d-lysine coated plate (Costar), and incubated at 37° C. and 5% $CO_2$. On the day in which the assay was run, the media was removed and 200 4 of 5x Calcium Plus Dye (Molecular Devices) which was previously resuspended with 200 mL of assay buffer [HBSS w/$Ca^{2+}$ and $Mg^{2+}$ w/o phenol red, 20 mM HEPES, 0.1% BSA, 10 mL probenecid (710 mg probenecid in 5 mL of 1N NaOH, to which was then added 5 mL HBSS containing 20 mM HEPES)] was added to each well of the 96-well plate. The plate was incubated at 37° C. and 5% $CO_2$ for 30 min in dark. The plate was removed and allowed to reach RT for 15 min in the dark. The assay was then run on the FLIPR. In Brief: base line read for 1 min, compound added (25 µL) and incubated for 4 min, 15 seconds, PK1 ligand preparation added (25 µL) for a final concentration of a previously determined $EC_{50}$ and fluorescence was counted for 1 min, 45 seconds. Baseline is described as the amount of relative fluorescence read when buffer alone is added to cells. Baseline was subtracted from all wells. Percent of control was calculated as follows: (Baseline subtracted well value is divided by baseline subtracted max value)*100. Percent inhibition is 100 minus the percent of control value.

The $IC_{50}$ is defined as the amount of a given compound required to inhibit 50% of the maximum signal that is generated by the concentration of PK1 preparation used in our assay. $IC_{50}$ values were calculated using GraphPad Prism.

Table 2 includes data generated from the PK1 functional assay described in Example 2.

TABLE 2

| Cpd | $Ca^{2+}$ Mobilization $IC_{50}$ (µM) | $Ca^{2+}$ Mobilization % Inh @10 µM |
|---|---|---|
| 1 | >10 | 37 |
| 2 | >10 | 47 |
| 3 | 0.034, 0.061. | 83, 94, 100* |

TABLE 2-continued

| Cpd | $Ca^{2+}$ Mobilization $IC_{50}$ (µM) | $Ca^{2+}$ Mobilization % Inh @10 µM |
|---|---|---|
|  | 0.082* |  |
| 4 | 0.357 | 94 |
| 5 | 1.12 | 81 |
| 6 | 0.176 | 90 |
| 7 | 6.2 | 60 |
| 8 | 0.535, 0.669 | 89, 86 |
| 9 | 0.295 | 95 |
| 10 | 1.25 | 82 |
| 11 | 6.79 | 54 |
| 12 | 1.29 | 74 |
| 13 | 0.544 | 72 |
| 14 | 0.793 | 90 |
| 15 | 0.327 | 95 |
| 16 | 0.348 | 89 |
| 17 | 2.43 | 73 |
| 18 | 5.48 | 58 |
| 19 | 0.885 | 83 |
| 20 | 0.177 | 95 |
| 21 | 0.656 | 85 |
| 22 | 0.009, 0.070, 0.105* | 88, 96, 97* |
| 23 | 0.231 | 97 |
| 24 | 0.115 | 60 |
| 25 | 2.74 | 89 |
| 26 | 0.045 | 84 |
| 27 | 0.088 | 102 |
| 28 | 0.046, 0.339, 0.847* | 85, 90, 91* |
| 29 | 0.11 | 111 |
| 30 | 1.24 | 68 |
| 31 | 0.939 | 91 |
| 32 | 1.22 | 78 |
| 33 | 0.049, 0.077 | 95, 102 |
| 34 | 0.081 | 98 |
| 35 | 0.034 | 85 |
| 36 | 0.27 | 84 |
| 37 | 0.25 | 86 |
| 38 | 0.391 | 91 |
| 39 | 0.063, 0.082 | 92, 95 |
| 40 | 0.557 | 83 |
| 41 | 1.06 | 72 |
| 42 | >10 | 49 |
| 43 | 0.801 | 78 |
| 44 | 2.02 | 66 |
| 45 | >10 | 40 |
| 46 | 0.522 | 80 |
| 47 | 0.826 | 80 |
| 48 | 0.956 | 75 |
| 49 | 3.17 | 64 |
| 50 | 0.024, 0.072 | 91, 100 |
| 51 | 0.207 | 93 |
| 52 | 0.973 | 94 |
| 53 | >10 | 45 |
| 54 | 3.47, >10 | 42, 64 |
| 55 | >10 | 44 |
| 56 | >10 | 47 |
| 57 | 4.77 | 59 |
| 58 | 0.089 | 95 |
| 59 | 0.178 | 94 |
| 60 | 0.35 | 88 |
| 61 | 0.036, 0.697 | 87, 101 |
| 62 | 2.03 | 52 |
| 63 | 0.271 | 83 |
| 64 | 5.26, 8.51 | 50, 51 |
| 65 | >10 | 8, 32 |
| 66 | 0.401 | 92 |
| 67 | 4.82 | 55 |
| 68 | 0.217 | 95 |
| 69 | 0.337 | 93 |
| 70 | 0.560 | 94 |
| 71 | >10 | 38 |
| 72 | 1.17 | 81 |
| 73 | 5.93 | 58 |
| 74 | 7.46 | 54 |
| 75 | 0.131 | 99 |
| 76 | 1.46 | 67 |
| 77 | 0.449 | 91 |

TABLE 2-continued

| Cpd | Ca$^{2+}$ Mobilization IC$_{50}$ (μM) | Ca$^{2+}$ Mobilization % Inh @10 μM |
|---|---|---|
| 78 | 0.036, 0.113 | 94, 95 |
| 79 | 0.679 | 85 |
| 80 | 2.03 | 70 |
| 81 | >10 | 36 |
| 82 | >10 | 38 |
| 83 | 0.668 | 82 |
| 84 | 1.22 | 70 |
| 85 | 4.5 | 62 |
| 86 | >10 | 31 |
| 87 | >10 | 53 |
| 88 | >10 | 41 |
| 89 | 0.817 | 82 |
| 90 | 2.33 | 71 |
| 91 | 3.98 | 59 |
| 92 | 5.16 | 58 |
| 93 | 0.116 | 96 |
| 94 | 0.373 | 91 |
| 95 | 0.084 | 92 |
| 96 | 0.273 | 92 |
| 97 | 0.006, 0.007, 0.019* | 90, 96, 98* |
| 98 | 0.736 | 77 |
| 99 | 0.1 | 91 |
| 100 | 0.533 | 62 |
| 101 | 3.3 | 60 |
| 102 | 0.11 | 99 |
| 103 | >10 | 41 |
| 104 | 0.193 | 96 |
| 105 | 0.437 | 85 |
| 106 | 0.025, 0.074 | 99, 101 |
| 107 | 0.868 | 89 |
| 108 | >10 | 42 |
| 109 | 0.681 | 89 |
| 110 | 9.07 | 48 |
| 111 | 7.88 | 57 |
| 112 | 2.55 | 74 |
| 113 | >10 | 42 |
| 114 | 6.31 | 48 |
| 115 | 0.244 | 98 |
| 116 | 0.391 | 95 |
| 117 | 0.218 | 97 |
| 118 | 1.37 | 80 |
| 119 | >10 | 40 |
| 120 | >10 | 40 |
| 121 | 6.33 | 58 |
| 122 | 0.194 | 76 |
| 123 | 0.684 | 83 |
| 124 | 0.815 | 61 |
| 125 | 0.054, 0.014 | 97, 99 |
| 126 | 0.232 | 89 |
| 127 | 0.607 | 81 |
| 128 | 0.126, 0.214 | 93, 98 |
| 129 | 0.120 | 88 |
| 130 | 0.245 | 92 |
| 131 | 0.122 | 100 |
| 132 | 0.247 | 79 |
| 133 | 0.582 | 88 |
| 134 | 0.225 | 86 |
| 135 | 0.186 | 94 |
| 136 | 0.015, 0.034 | 92, 102 |
| 137 | 1.04 | 68 |
| 138 | 1.512, 2.7 | 61, 73 |
| 139 | 0.011, 0.021, 0.260* | 92, 97, 100* |
| 140 | 0.192 | 91 |
| 141 | 1.13 | 82 |
| 142 | 0.387 | 76 |
| 143 | >10 | 31 |
| 144 | >10 | 36 |
| 145 | 0.317 | 90 |
| 146 | 2.14 | 80 |
| 147 | 0.110 | 99 |
| 148 | 0.503 | 86 |
| 149 | 0.788 | 86 |
| 150 | 0.595 | 78 |
| 151 | 2.40 | 60 |
| 152 | 0.240 | 91 |
| 153 | 0.703 | 81 |
| 154 | 0.657, 0.952 | 79, 80 |
| 155 | 0.002, 0.007 | 98, 100 |
| 156 | 3.22 | 70 |
| 157 | 0.004, 0.011 | 92, 96 |
| 158 | 3.84 | 62 |
| 159 | >10 | 31 |
| 160 | 0.628 | 71 |
| 161 | 4.78 | 53 |
| 162 | >10 | 31 |
| 163 | >10 | 38 |
| 164 | 2.01 | 64 |
| 165 | 6.15 | 52 |
| 166 | 1.70 | 73 |
| 167 | 2.62 | 65 |
| 168 | 1.52 | 68 |
| 169 | 0.226, 0.973 | 78, 86 |
| 170 | 0.032 | 96 |
| 171 | >10 | 46 |
| 172 | 0.515 | 88 |
| 173 | 0.207 | 97 |
| 174 | 0.290 | 87 |
| 175 | 0.057, 0.093 | 96, 99 |
| 176 | 0.023, 0.048, 0.130* | 96, 98 |
| 177 | 0.640 | 79 |
| 178 | 8.65 | 46 |
| 179 | 4.53 | 61 |
| 180 | >10 | 37 |
| 181 | 3.73 | 61 |
| 182 | 8.51 | 55 |
| 183 | 2.46 | 68 |
| 184 | 2.69 | 65 |
| 185 | 0.015, 0.080, 0.118* | 92, 94, 98* |
| 186 | 0.074, 0.097 | 99, 100 |
| 187 | >10 | 41 |
| 188 | 0.579 | 66 |
| 189 | >10 | 38 |
| 190 | 0.502 | 79 |
| 191 | 8.37 | 50 |
| 192 | 0.146, 1.06 | 80, 82 |
| 193 | >10 | 39 |
| 194 | 6.22 | 49 |
| 195 | 0.374, >10 | 23, 89 |
| 196 | 0.451 | 84 |
| 197 | 2.84 | 54 |
| 198 | 1.04 | 64 |
| 199 | 0.169, 0.691 | 92, 95 |
| 200 | 0.304 | 87 |
| 201 | 0.327 | 95 |
| 202 | 0.830 | 70 |
| 203 | 0.060 | 103 |
| 204 | 0.068 | 102 |
| 205 | 0.106 | 102 |
| 206 | 0.046 | 102 |
| 207 | 0.461, 0.471 | 92, 93 |
| 208 | 1.27 | 73 |
| 209 | 7.73 | 51 |
| 210 | >10 | 39 |
| 211 | 4.58 | 52 |
| 212 | 0.021, 0.050 | 103, 99 |
| 213 | >10 | 45 |
| 214 | 7.16 | 53 |
| 215 | 0.5, 2.78 | 104, 68 |
| 216 | 1.065 | 80 |
| 217 | 1.01 | 81 |
| 218 | 0.104 | 94 |
| 219 | 0.136, 0.158 | 94, 97 |
| 220 | 0.043 | 98 |
| 221 | 0.045, 0.072 | 98, 96 |
| 222 | 0.06 | 98 |
| 223 | 5.68 | 53 |
| 224 | 0.007, 0.011 | 97 |
| 225 | 3.78 | 68 |
| 226 | 0.922 | 85 |
| 227 | >10 | 44 |
| 228 | 3.40 | 63 |

TABLE 2-continued

| Cpd | $Ca^{2+}$ Mobilization $IC_{50}$ (μM) | $Ca^{2+}$ Mobilization % Inh @10 μM |
|---|---|---|
| 229 | >10 | 41 |
| 230 | 2.75 | 66 |
| 231 | 0.245 | 89 |
| 232 | >10 | 33 |
| 233 | 0.069, 0.130 | 96, 97 |
| 234 | 2.59 | 66 |
| 235 | 0.085 | 98 |
| 236 | 1.27 | 64 |
| 237 | 1.68 | 69 |
| 242 | 0.251 | 95 |
| 243 | 0.914 | 75 |
| 244 | 0.121 | 94 |
| 245 | >10 | 45 |
| 246 | 8.32 | 48 |
| 247 | 0.027, 0.030 | 100, 97 |
| 248 | 0.034 | 103 |
| 249 | 0.194 | 90 |
| 250 | 8.63 | 48 |
| 251 | 0.225 | 93 |
| 252 | 1.35 | 71 |
| 253 | 0.009 | 97 |
| 254 | 0.098 | 96 |
| 255 | 0.078 | 99 |
| 256 | 0.118 | 99 |
| 257 | 1.52 | 76 |
| 261 | 0.772 | 87 |
| 262 | >10 | 0.89 |
| 263 | 0.094 | 99 |
| 264 | 0.074 | 95 |
| 265 | 0.441 | 95 |
| 266 | >10 | 36 |
| 267 | >10 | 10 |
| 268 | >10 | 24 |
| 269 | >10 | 22 |
| 270 | >10 | 12 |
| 271 | 0.357 | 89 |
| 272 | >10 | 45 |

*Where multiple values are displayed for a single compound. These values representative of values determined upon multiple testing.

Biological Example 3

Effect of PK1 on Secretion and Gut Mucosal Ion Transport in Mammals

Methodology. Segments of ileum starting at a point 2 cm proximal to the ileocecal junction and extending 10 cm proximally were freshly excised, placed into Krebs-Ringer bicarbonate (KRB) solution, and emptied of their contents as a plastic rod was gently inserted into the intact segment. Ileal segments were scored with the back-edge of scalpel blade along the entire mesenteric border, and the intact muscular layers including the myenteric plexus were carefully removed with flat-head forceps. Three rectangular tissue sheets approximately 1.5 cm in length were prepared from the remaining muscle-stripped, mucosa-submucosa tissues and cut with care taken to avoid Peyer's patches. Each tissue sheet containing intact submucosal ganglia was pinned over a rectangular portal (total cross-sectional area of exposed mucosa=0.50 $cm^2$) between halves of an acrylic mounting cassette that was inserted between the tissue-bathing reservoirs of a modified Ussing-type flux chamber (Physiologic Instruments, Inc., San Diego, Calif.).

The apical (i.e., mucosal) and basolateral (i.e., serosal) surface of each tissue was bathed with 6 ml of an oxygenated KRB solution maintained at 36° C. Once mounted, tissues were allowed to equilibrate for 0.5-1 h before electrical field stimulation and addition of secretagogues or drugs. The KRB solution contained (in mM) 120 NaCl, 6 KCl, 1.2 $MgCl_2$, 1.2 $NaH_2PO_4$, 14.4 $NaHCO_3$, 2.5 $CaCl_2$, and 11.5 glucose or 11.5 mannitol. The KRB solution was continuously aerated with 95% $O_2$: 5% $CO_2$ and maintained at pH 7.3. Each chamber was equipped with a pair of saturated KCl-agar bridges for measurement of transmural electrical potential difference (PD) across the tissue, and a pair of Ag—AgCl agar electrodes connected to an automated voltage-clamp device (model VCC MC6, or model VCC MC8, Physiologic Instruments, Inc., San Diego, Calif.) that compensated for solution resistance between the PD-sensing bridges and for deviations detected from a transmural potential difference (PD) across the tissues that were clamped at 0 mV. Tissue conductance (G) was calculated (in mS) by determining the current necessary to change PD by 1 mV using bipolar pulses from a pulse generator. Short-circuit current (Isc in μA), an index of net active ion transport, was measured continuously. Tissue conductance (Gt in mS), an index of the barrier function to passive flow of ions, was calculated from changes in Isc and the transepithelial potential difference for each tissue.

Baseline recordings of short-circuit current (Isc) and G for each tissue were acquired and recorded for an additional 15 min period prior to the start of an experimental protocol. Stimulated changes in Isc were measured and recorded continuously with a computerized data acquisition system (PowerLab 8SP, ADInstruments, Inc., Colorado Springs, Colo.). Neurally-evoked changes in Isc were obtained by application of electrical field stimulation (80V, 0.5 ms, 10 Hz, 5 s) from the outputs of an electronic stimulator (S-48, Grass-Telefactor, Astro-Med, Inc., West Warwick, R.I.) attached via aluminum foil electrodes placed in direct contact with the mucosal surface at opposite poles of each tissue. Pharmacological agents and secretagogues were routinely added to the basolateral-side reservoir. Agonist or secretagogue effects on Isc were continuously recorded following basolateral addition. Concentration-response curves were constructed from the cumulative, step-wise addition of pre-determined increasing amounts of agonist or secretagogue that were added at or near the peak Isc response to the preceding lower concentration. Effects of antagonists or inhibitors of secretion were evaluated after a 10-20 minute exposure period that was followed by challenge with a specific agonist or secretagogue.

Statistical Analysis. All values are reported as means±SE. Electrophysiological data obtained with Ussing flux-type chambers were normalized to tissue surface area and expressed per $cm^2$. Stimulated changes in ion transport were determined as the absolute difference between a baseline value prior to stimulation and the maximal response (ΔIsc) evoked by a given stimulus or secretagogue. An estimated $EC_{50}$ for the stimulatory action of PK1 on epithelial secretion was determined from a 7-point cumulative concentration-response test using a computer calculated curve-fitting function in PRISM (GraphPad Software, Inc.). An unpaired, two-tailed Student's t-test was used to determine statistical significance between any two groups, e.g., control and experimental tissues. An ANOVA in conjunction with a post hoc Neuman-Keuls multiple comparisons test was used to determine significant differences among multiple groups. P<0.05 was considered statistically significant.

Summary of results. The basal Isc was 35.2±2.4 μA/$cm^2$ and tissue conductance (G) was 33.7±0.9 mS/$cm^2$ (n=79 tissues from 34 rats). Following a single-dose addition of PK1 to the Krebs solution bathing the basolateral tissue surface, Isc gradually increased to a peak value within 2-4 min and then declined back toward baseline within 10-15 min. The PK1-evoked increases in Isc were concentration dependent with an $EC_{50}$ of approximately 8.2 nM determined from cumulative concentration-response studies (see FIG. 2). The maximal response for the PK1-evoked response occurred at 100 nM; 100 nM PK1 evoked an increase in Isc of 28.7±2.9 µA/cm² from baseline (n=42 tissues from 29 rats) and 10 nM PK1 evoked an increase of 13.5±2. µA/cm² (n=33 tissues from 22 rats). The concentrations of 10 nM and 100 nM were used in all subsequent studies. PK1 had no significant effect on G in any of our studies. The pro-secretory effect of PK1 was not blocked in the presence of the nerve conduction toxin, Tetrodotoxin (TTX), or blockade of muscarinic receptors present on mucosal enterocytes by the anti-cholinergic drug, Atropine, indicating that the its action is not dependent on intrinsic neural activity in the tissues. The PK1 evoked increase in Isc requires the presence of endogenous PK1 receptors since exogenous PK1 peptide added to ileum mucosal tissues from PK1 receptor knock-out mice failed to elicit a significant change in Isc compared to wild-type littermates.

Biological Example 4

Small Molecule PK1 Receptor Antagonists are Effective at Suppressing Both PK1 and Cholera Toxin Stimulated Gut Secretion in Rat Ileum Methodology. The basic methodology for Ussing-type ion flux chambers used in these studies was the same as that described in detail above with the following modifications to the experimental protocol. Following a 30-45 minute equilibration period, baseline-stable tissues were subjected to a train of electrical field stimulation (EFS; 80 V, 0.5 ms, 10 Hz, 5 s) applied from contacts connecting the foil electrodes on opposite poles of the tissue to the polarized, isolated outputs from an electronic square-pulse stimulator. The responses to two sequential EFS were used to gauge tissue viability and comparability of the responses of individual tissues from each rat and between rats. Tissue conductance was measured at periodic intervals as changes in the amplitudes of brief short-circuit current responses evoked by application of 1 mV amplitude bi-polar pulses from a pulse generator using Ohm's Law. Three to four tissues from each rat were studied. The tissues from a given animal were grouped and assigned accordingly: one control tissue which received only vehicle followed by two consecutive doses of PK-1 ligand added in a cumulative fashion to the basolateral surface of the tissue; the remaining two to three tissues from the same animal were assigned to be exposed to a given PK-1 receptor antagonist (e.g., 3-4 tissues from 1 rat: Control, Antagonist$_1$, Antagonist$_2$, and/or Antagonist$_3$). Test compound was added to the basolateral tissue side reservoir at a final concentration of 1 µM and allowed a 15 minute incubation period prior to challenge with the PK1 peptide. At the end of this 15 min exposure period, PK1 ligand at 10 and 100 nM was added in a cumulative fashion to each tissue to characterize the inhibitory effect of the test compound. At the conclusion of the experiment, EFS was re-applied to gauge tissue viability and stability of responsiveness.

For the Cholera toxin studies, paired mucosal tissues were obtained from each rat and mounted in Ussing-type chambers. Following tissue equilibration, baseline-stable and conductance-stable tissues were exposed to 1 µg/ml Cholera toxin (i.e., one tissue from each pair) added to the mucosa together with simultaneous addition of DMSO vehicle or Compound 3 of the present invention (i.e., one tissue from each pair) to the serosa at a final concentration of 10 µM to start the experiment. From this point on, baseline Isc and periodic assessment of tissue conductance were monitored and recorded for up to 4 hours.

Summary of results. Pre-treatment of tissues with PK1 antagonists alone had no measurable effect on baseline Isc and tissue conductance (G). The results indicate that suppression of the PK1 evoked increase in Isc in isolated rat ileum mucosa was successfully achieved in the presence of Compound 3 of the present invention, which was identified using a functional cell based screening assay (i.e., mobilization of intracellular $Ca^{2+}$) as a putative antagonist at the PK1 receptor. In trials with this compound, the observed suppression of the Isc response evoked by two ascending cumulative concentrations of PK1 showed characteristics of a significant surmountable antagonism (see FIG. 3). These data strongly suggest that good efficacy can be achieved in the selective functional blockade of the PK1 receptor by this small molecule inhibitor to modulate the pro-secretory effect of PK1 on the intestinal epithelium. The selectivity of the functional blockade of the PK1 receptor by Compound 3 was confirmed by testing this compound against an unrelated cholinergic secretagogue, carbachol. Compound 3 failed to suppress the pro-secretory effect of carbachol tested at two different concentrations added in an ascending cumulative fashion to the serosal side of each tissue in the Ussing-type flux chambers (see FIG. 4).

To investigate the potential anti-secretory efficacy of selective small molecule PK1 receptor antagonists, we established a model of secretory diarrhea ex vivo in the Ussing-type flux chambers with mucosal exposure to Cholera toxin. Mucosal application of Cholera toxin mimics the route of exposure for this disease-causing agent in animals and man. Pre-treatment of isolated rat ileum mucosa with Compound 3 (10 µM added to the serosa), did significantly suppress the sustained increase in baseline Isc over time evoked by 1 µg/ml Cholera toxin added to the mucosa by approximately 50-60% (see FIG. 5). These data suggest the potential for the efficacious use of PK1 receptor antagonists from this chemical class in gut disease states that have a significant secretory diarrhea component.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I):

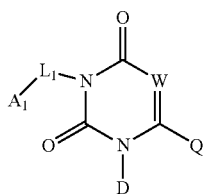

Formula (I)

wherein:

$A_1$ is $CF_3$, $C_{1-4}$-alkoxy, aryl, aryloxy, benzofused heterocyclyl, or heteroaryl; wherein aryl, aryloxy, and heteroaryl are optionally substituted with pyrazol-1-yl or [1,2,3]thiadiazol-4-yl; or aryl, aryloxy, the benzo portion of benzofused heterocyclyl, and heteroaryl are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl; provided that $A_1$ is other than 3,5-di-t-butyl-phenyl;

$L_1$ is —$(CH_2)_r$—, —$CH_2C_{2-4}$alkenyl-, or —$CH_2CH_2X(CH_2)_s$—, wherein $L_1$ is optionally substituted with one to two substituents independently selected from the group consisting of $C_{1-6}$alkyl, $C_{2-6}$alkenyl, $C_{2-6}$alkynyl, and halogen; and, r is an integer of 1 to 5; such that r is greater than or equal to 4 when $A_1$ is $C_{1-4}$-alkoxy;

s is an integer of 1 to 3;

X is O or S;

D is -P-$A_2$;

wherein P is —$(CH_2)_{1-2}$— or —$CH_2CH=CH$— when $A_2$ is phenyl, benzofused heterocyclyl, heteroaryl, or $C_{3-8}$cycloalkyl; alternatively, P is —$(CH_2)_{3-6}$— when $A_2$ is hydrogen, $C_{1-4}$-alkoxy, or $C_{1-4}$alkoxycarbonyl; and wherein P is optionally substituted with one to two substituents independently selected from the group consisting of $C_{1-6}$alkyl, $C_{2-6}$alkenyl, $C_{2-6}$alkynyl, and halogen;

$A_2$ is hydrogen, $C_{1-4}$-alkoxy, $C_{1-4}$-alkoxycarbonyl, phenyl, benzofused heterocyclyl, heteroaryl, tetrahydro-pyranyl, piperidinyl, or $C_{3-8}$cycloalkyl; wherein phenyl, heteroaryl, the benzo portion of benzofused heterocyclyl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, N-isoindole-1,3-dione, $C_{1-6}$alkylthio, $C_{1-6}$alkylsulfonyl, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; such that no more than two substituents on $A_2$ are aryl($C_{1-6}$)alkoxy, phenyl, N-isoindole-1,3-dione, or a non fused $C_{3-6}$cycloalkyloxy;

provided that $A_2$ is other than 3,5-di-t-butyl-phenyl;

W is $C(R_W)$; wherein $R_W$ is H or $C_{1-2}$alkyl;

Q is selected from the group consisting of (a) to (g), wherein (a) is —$NH(CH_2)_2$—$Ar_1$ wherein $Ar_1$ is pyridinyl optionally substituted one to three $C_{1-4}$-alkyl substituents or a substituent selected from the group consisting of $C_{1-4}$-alkoxy and amino;

provided that when $Ar_1$ is unsubstituted pyridin-3-yl or unsubstituted pyridin-4-yl, and $A_2$ is 4-methoxy-phenyl, $A_1$ is other than unsubstituted phenyl or 3,4-dichlorophenyl;

(b) is —$NHCH(R_z)$—$Ar_2$ wherein $R_z$ is H or $C_{1-3}$alkyl; $Ar_2$ is pyridinyl, pyrimidinyl, pyrazinyl,

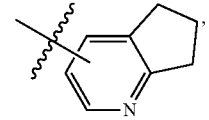

1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein $Ar_2$ is optionally substituted with one to three substituents independently selected from the group consisting of $C_{1-4}$-alkyl, trifluoromethyl, hydroxyl-$C_{1-4}$-alkyl, amino($C_{1-4}$)alkyl, ($C_{1-4}$-alkyl)amino-($C_{1-4}$)alkyl, di($C_{1-4}$-alkyl)amino-($C_{1-4}$)alkyl, $C_{1-4}$-alkoxy, $C_{3-8}$ cycloalkylamino, amino, ($C_{1-6}$alkyl)amino, and di($C_{1-6}$alkyl)amino; or $Ar_2$ is optionally substituted with one amino group and three substituents independently selected from the group consisting of $C_{1-4}$-alkyl and $C_{1-4}$alkoxy;

wherein the $C_{1-6}$alkyl group of ($C_{1-6}$alkyl)amino and di($C_{1-6}$alkyl)amino is optionally substituted with amino, ($C_{1-4}$-alkyl)amino, di($C_{1-4}$-alkyl)amino, $C_{3-8}$cycloalkylamino, $C_{1-4}$alkoxy, $C_{1-4}$-alkylthio, hydroxy, a 5 to 6 membered heteroaryl, or a 5 to 6 membered heterocyclyl; wherein a nitrogen atom of the 5 to 6 membered heterocyclyl is optionally substituted with a $C_{1-4}$-alkyl substituent;

and wherein pyridin-2-yl and pyridin-3-yl are optionally further substituted with N-pyrrolidinyl, N-piperazinyl, N-piperidinyl, N-morpholinyl, N-thiomorpholinyl, —$CH_2$-O-$CH_2$—PH, and phenyl; wherein the phenyl substituent of pyridin-2-yl and pyridin-3-Y1 is optionally substituted with one to three substituents independently selected from the group consisting of $C_{1-4}$-alkyl, $C_{1-4}$-alkoxy, and halogen;

provided that when Q is —NHCH$_2$(2-amino-pyridin-3-yl), and A$_1$ is pyridin-4-yl, 4-$C_{1-6}$alkyl-phenyl, 3,4-dichloro-phenyl, or 4-methanesulfonyl-phenyl, A$_2$ is other than 4-methoxy-phenyl;

provided that when Q is —NHCH$_2$(2-amino-pyridin-3-yl), L$_1$ is —(CH$_2$)$_2$— or —(CH$_2$)$_5$—, and A$_1$ is methoxy, A$_2$ is other than 4-difluoromethoxy-phenyl or 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(c) is —CH$_2$NHCH$_2$—Ar$_3$, wherein W is CH, and Ar$_3$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and that the point of attachment to quinolinyl is at the 2, 3, or 4-position;

wherein Ar$_3$ is optionally substituted with one to three substituents independently selected from the group consisting of $C_{1-4}$-alkyl, amino($C_{1-4}$)alkyl, ($C_{1-4}$-alkyl)amino-($C_{1-4}$)alkyl, di($C_{1-4}$-alkyl)amino-($C_{1-4}$)alkyl, $C_{1-4}$-alkoxy, amino, ($C_{1-6}$alkyl)amino, and di($C_{1-6}$alkyl)amino;

and wherein the $C_{1-6}$alkyl group of ($C_{1-6}$alkyl)amino and di($C_{1-6}$alkyl)amino is optionally substituted with amino, ($C_{1-4}$-alkyl)amino, di($C_{1-4}$-alkyl)amino, $C_{3-8}$cycloalkylamino, $C_{1-4}$alkoxy, or hydroxy;

(d) is —(CH$_2$)$_2$—Ar$_4$, wherein Ar$_4$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; wherein Ar$_4$ is optionally substituted with one to three substituents independently selected from the group consisting of $C_{1-4}$-alkyl, amino($C_{1-4}$)alkyl, ($C_{1-4}$alkyl)amino-($C_{1-4}$)alkyl, di($C_{1-4}$-alkyl)amino-($C_{1-4}$)alkyl, $C_{1-4}$-alkoxy, amino, ($C_{1-6}$alkyl)amino, di($C_{1-6}$alkyl)amino, halogen, and aminocarbonyl;

and wherein the $C_{1-6}$alkyl group of ($C_{1-6}$alkyl)amino and di($C_{1-6}$alkyl)amino is optionally substituted with amino, ($C_{1-4}$-alkyl)amino, di($C_{1-4}$-alkyl)amino, $C_{3-8}$cycloalkylamino, $C_{1-4}$alkoxy, or hydroxy;

(e) is —CH=CH—Ar$_5$; wherein Ar$_5$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; wherein Ar$_5$ is optionally substituted with one to three substituents independently selected from the group consisting of $C_{1-4}$-alkyl, amino($C_{1-4}$)alkyl, ($C_{1-4}$alkyl)amino-($C_{1-4}$)alkyl, di($C_{1-4}$-alkyl)amino-($C_{1-4}$)alkyl, $C_{1-4}$-alkoxy, amino, ($C_{1-6}$alkyl)amino, di($C_{1-6}$alkyl)amino, halogen, and aminocarbonyl;

and wherein the $C_{1-6}$alkyl group of ($C_{1-6}$alkyl)amino and di($C_{1-6}$alkyl)amino is optionally substituted with amino, ($C_{1-4}$-alkyl)amino, di($C_{1-4}$-alkyl)amino, $C_{3-8}$cycloalkylamino, $C_{1-4}$alkoxy, or hydroxy;

(f) is —O—CH(R$_1$)—Ar$_6$ when W is CH; or (f) is —S—CH(R$_1$)—Ar$_6$ and W is CH; wherein R$_1$ is hydrogen or $C_{1-4}$-alkyl, and Ar$_6$ is pyridinyl, pyrimidinyl, 1,2,3,4-tetrahydro-[1,8]naphthyridinyl, imidazo[1,2-a]pyridinyl, or quinolinyl such that the point of attachment to 1,2,3,4-tetrahydro-[1,8]naphthyridinyl is at the 6 or 7 position, and the point of attachment to quinolinyl is at the 2, 3, or 4-position;

wherein Ar$_6$ is optionally substituted with one to three substituents independently selected from the group consisting of $C_{1-4}$-alkyl, amino($C_{1-4}$)alkyl, ($C_{1-4}$alkyl)amino-($C_{1-4}$)alkyl, di($C_{1-4}$alkyl)amino-($C_{1-4}$)alkyl, $C_{1-4}$-alkoxy, amino, ($C_{1-6}$alkyl)amino, di($C_{1-6}$alkyl)amino, halogen, and aminocarbonyl;

and wherein the $C_{1-6}$alkyl group of ($C_{1-6}$alkyl)amino and di($C_{1-6}$alkyl)amino is optionally substituted with amino, ($C_{1-4}$alkyl)amino, di($C_{1-4}$alkyl)amino, $C_{3-8}$cycloalkylamino, $C_{1-4}$alkoxy, or hydroxy;

provided that when Q is —O—CH(R$_1$)—Ar$_6$, A$_1$ and A$_2$ are 4-methoxy-phenyl, and R$_1$ is hydrogen, Ar$_6$ is other than unsubstituted pyridin-2-yl or 2-amino-pyridin-4-yl;

and (g) is —X$_1$-(CH(R$_x$))$_2$—Ar$_7$ when W is CH; wherein X$_1$ is O or S, R$_x$ is H or $C_{1-4}$-alkyl, and Ar$_7$ is pyridinyl, pyrimidinyl, 1,2,3,4-tetrahydro-[1,8]naphthyridinyl, imidazo[1,2-a]pyridinyl, or quinolinyl such that the point of attachment to 1,2,3,4-tetrahydro-[1,8]naphthyridinyl is at the 6 or 7 position, and the point of attachment to quinolinyl is at the 2, 3, or 4-position;

wherein $Ar_7$ is optionally substituted with one to three substituents independently selected from the group consisting of $C_{1-4}$-alkyl, amino($C_{1-4}$)alkyl, ($C_{1-4}$alkyl)amino-($C_{1-4}$)alkyl, di($C_{1-4}$alkyl)amino-($C_{1-4}$)alkyl, $C_{1-4}$-alkoxy, amino, ($C_{1-6}$alkyl)amino, di($C_{1-6}$alkyl)amino, halogen, and aminocarbonyl;

and wherein the $C_{1-6}$alkyl group of ($C_{1-6}$alkyl)amino and di($C_{1-6}$alkyl)amino is optionally substituted with amino, ($C_{1-4}$alkyl)amino, di($C_{1-4}$alkyl)amino, $C_{3-8}$cycloalkylamino, $C_{1-4}$alkoxy, or hydroxy;

provided that when Q is –O($CH_2$)$_2$—$Ar_7$ and $A_1$ and $A_2$ are 4-methoxy-phenyl, $Ar_7$ is other than unsubstituted pyridin-2-yl or unsubstituted pyridin-3-yl;

wherein a nitrogen atom of $Ar_1$, $Ar_2$, $Ar_3$, $Ar_4$, $Ar_5$, $Ar_6$, and $Ar_7$ is optionally substituted with oxo;

and an enantiomer, a diastereomer, a tautomer, or a pharmaceutically acceptable salt thereof.

2. The compound of claim 1 wherein $A_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of $C_{1-4}$alkyl, $C_{1-4}$alkoxy, nitro, fluoro, chloro, iodo, halogenated $C_{1-4}$alkyl, halogenated $C_{1-4}$alkoxy, and $C_{1-4}$alkylthio; provided that $A_1$ is other than 3,5-di-t-butyl-phenyl.

3. The compound of claim 1 wherein $A_1$ is substituted phenyl, benzotriazolyl, benzofuranyl, benzo[1,3]dioxalyl, or 2,3-dihydro-benzofuranyl; wherein phenyl is substituted with, and benzotriazolyl and benzofuranyl are optionally substituted with, one to three substituents independently selected from the group consisting of $C_{1-4}$-alkyl, $C_{1-4}$alkoxy, nitro, fluoro, chloro, iodo, halogenated $C_{1-4}$alkyl, halogenated $C_{1-4}$alkoxy, and $C_{1-4}$alkylthio; provided that $A_1$ is other than 3,5-di-t-butyl-phenyl.

4. The compound of claim 2 wherein $A_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of $C_{1-3}$alkyl, methoxy, fluoro, chloro, trifluoromethyl, trifluoromethoxy, and methylthio.

5. The compound of claim 4 wherein $A_1$ is substituted phenyl, heteroaryl, or a benzofused heterocyclyl selected from the group consisting of benzo[1,3]dioxalyl and 2,3-dihydro-benzofuranyl; wherein substituted phenyl and heteroaryl are optionally substituted with one to three substituents independently selected from the group consisting of $C_{1-3}$alkyl, methoxy, fluoro and methylthio.

6. The compound of claim 5 wherein $A_1$ is substituted phenyl, benzotriazolyl, benzofuranyl, benzo[1,3]dioxalyl, or 2,3-dihydro-benzofuranyl; wherein phenyl is substituted at the 4-position with methoxy, fluoro, or methylthio; and wherein $A_1$ other than substituted phenyl is optionally substituted with one to two substituents independently selected from the group consisting of methyl, methoxy, fluoro and methylthio.

7. The compound of claim 1 wherein $L_1$ is —($CH_2$)$_r$—, wherein $L_1$ is optionally substituted with one to two substituents independently selected from the group consisting of $C_{1-4}$-alkyl and $C_{2-4}$alkenyl and r is 1 or 2.

8. The compound of claim 7 wherein $L_1$ is —$CH_2$—.

9. The compound of claim 1 wherein P is —($CH_2$)$_{1-2}$— when $A_2$ is phenyl, benzofused heterocyclyl, heteroaryl, or $C_{3-8}$cycloalkyl; alternatively, P is —($CH_2$)$_{4-6}$—when $A_2$ is hydrogen, $C_{1-4}$-alkoxy, or $C_{1-4}$-alkoxycarbonyl.

10. The compound of claim 9 wherein P is —$CH_2$— when $A_2$ is phenyl, benzofused heterocyclyl, heteroaryl, or $C_{3-8}$cycloalkyl; alternatively, P is —($CH_2$)$_{4-6}$— when $A_2$ is hydrogen, $C_{1-4}$-alkoxy, or $C_{1-4}$-alkoxycarbonyl.

11. The compound of claim 1 wherein $A_2$ is hydrogen, $C_{1-4}$-alkoxy, $C_{1-4}$alkoxycarbonyl, phenyl, benzofused heterocyclyl, heteroaryl other than pyridin-4-yl, or $C_{3-8}$cycloalkyl; wherein phenyl, heteroaryl, and $C_{3-8}$cycloalkyl are optionally substituted with one to two substituents independently selected from the group consisting of $C_{1-6}$alkyl, $C_{1-6}$alkoxy, fluoro, chloro, halogenated $C_{1-6}$alkoxy, phenyl, N-isoindole-1,3-dione, $C_{1-6}$alkylthio, $C_{1-6}$alkylsulfonyl, $C_{1-6}$alkoxycarbonyl, nitro, hydroxy, and $C_{1-6}$alkylcarbonylamino; provided that no more than one substituent of $A_2$ is phenyl or N-isoindole-1,3-dione; and provided that $A_2$ is other than 3,5-di-t-butyl-phenyl.

12. The compound of claim 11 wherein $A_2$ is $C_{1-4}$-alkoxy, phenyl, benzofused heterocyclyl, or a heteroaryl other than pyridin-4-yl; wherein phenyl and heteroaryl are optionally substituted with one to two substituents independently selected from the group consisting of $C_{1-4}$-alkyl, $C_{1-4}$alkoxy, fluoro, chloro, halogenated $C_{1-4}$-alkoxy, N-isoindole-1,3-dione, $C_{1-4}$-alkylthio, $C_{1-4}$-alkylsulfonyl, $C_{1-4}$-alkoxycarbonyl, nitro, hydroxy, and $C_{1-4}$alkylcarbonylamino; provided that no more than one substituent of $A_2$ is N-isoindole-1,3-dione; and provided that $A_2$ is other than 3,5-di-t-butyl-phenyl.

13. The compound of claim 12 wherein $A_2$ is $C_{1-4}$-alkoxy, phenyl, benzofused heterocyclyl, or a heteroaryl other than pyridin-4-yl; wherein phenyl and heteroaryl are optionally substituted with one to two substituents independently selected from the group consisting of $C_{1-4}$-alkoxy, fluoro, halogenated $C_{1-4}$alkoxy, $C_{1-4}$-alkylthio, $C_{1-4}$alkylsulfonyl, $C_{1-4}$alkoxycarbonyl, nitro, and hydroxy.

14. The compound of claim 13 wherein $A_2$ is $C_{1-4}$-alkoxy, phenyl, 2,3-dihydro-benzofuranyl, indolyl, benzofuranyl, pyridin-3-yl, or benzothiophenyl; wherein $A_2$ other than $C_{1-4}$-alkoxy is optionally substituted with one to two substituents independently selected from the group consisting of $C_{1-4}$-alkoxy, fluoro, fluorinated $C_{1-4}$-alkoxy, $C_{1-4}$alkylthio, $C_{1-4}$-alkylsulfonyl, $C_{1-4}$-alkoxycarbonyl, nitro, and hydroxy.

15. The compound of claim 1 wherein Q is selected from the group consisting of (a)-(g) wherein:

(a) is —NH($CH_2$)$_2$—$Ar_1$ wherein $Ar_1$ is pyridinyl substituted with one to three $C_{1-4}$-alkyl substituents or a substituent selected from the group consisting of $C_{1-4}$-alkoxy and amino;

(b) is —NH$CH_2$—$Ar_2$ wherein $Ar_2$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein $Ar_2$ is optionally substituted with one to three substituents independently selected from the group consisting of $C_{1-4}$alkyl, trifluoromethyl, $C_{1-4}$-alkoxy, amino, ($C_{1-6}$alkyl)amino, and di($C_{1-6}$alkyl)amino;

wherein the $C_{1-6}$alkyl group of ($C_{1-6}$alkyl)amino and di($C_{1-6}$alkyl)amino is optionally substituted with ($C_{1-4}$-alkyl)amino, di($C_{1-4}$-alkyl)amino, $C_{1-4}$-alkoxy, $C_{1-4}$-alkylthio, hydroxy, a 5 to 6 membered heteroaryl, or a 5 to 6 membered heterocyclyl; wherein a nitrogen atom of the 5 to 6 membered heterocyclyl is optionally substituted with a $C_{1-4}$alkyl substituent;

and wherein pyridin-2-yl and pyridin-3-yl are optionally further substituted with N-pyrrolidinyl, N-piperazinyl, N-piperidinyl, N-morpholinyl, N-thiomorpholinyl, and phenyl; wherein the phenyl substituent of pyridin-2-yl and pyridin-3-Y1 is optionally substituted with one to three substituents independently selected from the group consisting of $C_{1-4}$-alkyl, $C_{1-4}$-alkoxy, and halogen;

provided that when Q is —NHCH$_2$(2-amino-pyridin-3-yl), and $A_1$ is pyridin-4-yl, 4-$C_{1-6}$alkyl-phenyl, 3,4-dichloro-phenyl, or 4-methanesulfonyl-phenyl, $A_2$ is other than 4-methoxy-phenyl;

provided that when Q is —NHCH$_2$(2-amino-pyridin-3-yl), $L_1$ is —(CH$_2$)$_2$— or —(CH$_2$)$_5$—, and $A_1$ is methoxy, $A_2$ is other than 4-difluoromethoxy-phenyl or 4-methoxy-phenyl;

provided that when Q is —NHCH$_2$(2-amino-pyridin-3-yl), and $A_1$ is benzotriazol-1-yl, $A_2$ is other than 4-difluoromethoxy-phenyl;

provided that when Q is —NHCH$_2$(2-amino-pyridin-3-yl), $L_1$ is —(CH$_2$)$_3$—, and $A_1$ is pyrrol-1-yl, $A_2$ is other than 4-methoxy-phenyl;

provided that when Q is —NHCH$_2$(2-amino-pyridin-3-yl), $L_1$ is —(CH$_2$)$_2$—, and $A_1$ is 4-nitro-phenyl or ethoxy, $A_2$ is other than 4-methoxy-phenyl;

provided that when Q is —NHCH$_2$(2-amino-pyridin-3-yl), and $A_1$ is 4-fluoro-phenyl, $A_2$ is other than 4-fluoro-phenyl;

provided that when Q is —NHCH$_2$(6-amino-pyridin-2-yl), and $A_1$ is 4-fluoro-phenyl, $A_2$ is other than 4-trifluoromethoxy-phenyl;

provided that when Q is —NHCH$_2$(6-methyl-pyridin-2-yl), and $A_1$ is 4-methoxy-phenyl, $A_2$ is other than 4-methoxy-phenyl;

provided that when Q is —NHCH$_2$(imidazo[1,2-a]pyridinyl), and $A_1$ is 4-fluoro-phenyl, $A_2$ is other than 4-methoxy-phenyl;

provided that when Q is —NHCH$_2$(pyridin-4-yl), and $A_1$ is unsubstituted phenyl or 3,4-dichloro-phenyl, $A_2$ is other than 4-methoxy-phenyl;

provided that when Q is —NHCH$_2$(4,6-dimethyl-pyridin-3-yl), and $A_1$ is 4-methoxy-phenyl, —P-$A_2$ is other than —(CH$_2$)-5-methoxy;

provided that when Q is —NHCH$_2$(4,6-dimethyl-pyridin-3-yl), $L_1$ is —(CH$_2$)$_2$—, and $A_1$ is pyrazol-1-yl, $A_2$ is other than 4-difluoromethoxy-phenyl;

provided that when Q is —NHCH$_2$(4,6-dimethyl-pyridin-3-yl) and $A_1$ is 4-methoxy-phenyl, $A_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and $A_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, $A_2$ is other than 4-difluoromethoxy-phenyl;

and, provided that when Q is —NHCH$_2$(4,6-dimethyl-pyridin-3-yl) and $A_1$ is 3-nitro-4-methoxy-phenyl, 2,6-difluoro-4-methoxy-phenyl, or 3,4-dichloro-phenyl, $A_2$ is other than 4-methoxy-phenyl;

(c) is —CH$_2$NHCH$_2$—Ar$_3$, wherein Ar$_a$ is pyridinyl optionally substituted with amino;

(d) is —(CH$_2$)$_2$—Ar$_4$, wherein Ar$_4$ is pyridinyl, or pyrimidinyl; wherein Ar$_4$ is optionally substituted with one to two substituents independently selected from the group consisting of $C_{1-4}$-alkyl, $C_{1-4}$-alkoxy, amino, ($C_{1-6}$alkyl)amino, and di($C_{1-6}$alkyl)amino;

(e) is —CH═CH-pyridinyl; and (f) is —O—CH(R$_1$)—Ar$_6$ when W is CH; or, (f) is —S—CH(R$_1$)—Ar$_6$ and W is CH; wherein R$_1$ is hydrogen or $C_{1-4}$-alkyl, and Ar$_6$ is pyridinyl or pyrimidinyl; wherein Ar$_6$ is optionally substituted with one to three substituents independently selected from the group consisting of $C_{1-4}$-alkyl, $C_{1-4}$-alkoxy, amino, ($C_{1-6}$alkyl)amino, di($C_{1-6}$alkyl)amino, halogen, and aminocarbonyl;

and wherein the $C_{1-6}$alkyl group of ($C_{1-6}$alkyl)amino and di($C_{1-6}$alkyl)amino is optionally substituted with amino, ($C_{1-4}$-alkyl)amino, di($C_{1-4}$-alkyl)amino, $C_{3-8}$cycloalkylamino, $C_{1-4}$alkoxy, or hydroxy;

provided that when Q is —O—CH(R$_1$)—Ar$_6$, $A_1$ and $A_2$ are 4-methoxy-phenyl, and R$_1$ is hydrogen, Ar$_6$ is other than unsubstituted pyridin-2-yl or 2-amino-pyridin-4-yl;

and (g) is —X$_1$-(CH(R$_x$))$_2$—Ar$_7$ and W is CH; wherein X$_1$ is O, R$_x$ is H, and Ar$_7$ is pyridinyl or pyrimidinyl; wherein Ar$_7$ is optionally substituted with one to two substituents independently selected from the group consisting of $C_{1-4}$-alkyl, $C_{1-4}$-alkoxy, amino, ($C_{1-6}$alkyl)amino, and di($C_{1-6}$alkyl)amino;

provided that when Q is —O(CH$_2$)$_2$—Ar$_7$ and $A_1$ and $A_2$ are 4-methoxy-phenyl, Ar$_7$ is other than unsubstituted pyridin-2-yl or unsubstituted pyridin-3-yl;

wherein a nitrogen atom of Ar$_1$, Ar$_2$, Ar$_3$, Ar$_4$, Ar$_6$, and Ar$_7$ is optionally substituted with oxo.

16. The compound of claim 15 wherein Q is selected from the group consisting of (b) and (d) wherein:

(b) is —NHCH$_2$—Ar$_2$ wherein Ar$_2$ is pyridinyl, pyrimidinyl, or quinolinyl; such that the point of attachment to quinolinyl is at the 2, 3, or 4-position; and wherein Ar$_2$ is optionally substituted with one to three substituents independently selected from the group consisting of $C_{1-4}$alkyl, trifluoromethyl, $C_{1-4}$alkoxy, amino, ($C_{1-4}$alkyl)amino, and di($C_{1-4}$alkyl)amino;

wherein the $C_{1-4}$-alkyl group of ($C_{1-4}$-alkyl)amino and di($C_{1-4}$-alkyl)amino is optionally substituted with ($C_{1-4}$-alkyl)amino, di($C_{1-4}$-alkyl)amino, $C_{1-4}$-alkoxy, $C_{1-4}$-alkylthio, hydroxy, a 5 to 6 membered heteroaryl, or a 5 to 6 membered heterocyclyl;

and wherein pyridin-2-yl and pyridin-3-yl are optionally further substituted with N-morpholinyl;

provided that when Q is —NHCH$_2$(2-amino-pyridin-3-yl), and $A_1$ is pyridin-4-yl or phenyl substituted with a substituent selected from the group consisting of 4-$C_{1-6}$alkyl, 3,4-dichloro, and 4-methanesulfonyl, $A_2$ is other than 4-methoxy-phenyl;

provided that when Q is —NHCH$_2$(2-amino-pyridin-3-yl), $L_1$ is —(CH$_2$)$_2$— or —(CH$_2$)$_5$—, and $A_1$ is methoxy, $A_2$ is other than phenyl substituted with 4-difluoromethoxy or 4-methoxy;

provided that when Q is —NHCH$_2$(2-amino-pyridin-3-yl), and $A_1$ is benzotriazol-1-yl, $A_2$ is other than 4-difluoromethoxy-phenyl;

provided that when Q is —NHCH$_2$(2-amino-pyridin-3-yl), $L_1$ is —(CH$_2$)$_3$—, and $A_1$ is pyrrol-1-yl, $A_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl; and provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl (d) is —(CH$_2$)$_2$—Ar$_4$ and W is CH; wherein Ar$_4$ is pyridinyl is optionally substituted with one to two substituents independently selected from the group consisting of C$_{1-4}$-alkyl, C$_{1-4}$-alkoxy, amino, (C$_{1-6}$alkyl)amino, and di(C$_{1-6}$alkyl)amino;

wherein a nitrogen atom of Ar$_2$ and Ar$_4$ is optionally substituted with oxo.

17. The compound of claim 16 wherein Q is selected from the group consisting of (b) and (d) wherein:

(b) is —NHCH$_2$—Ar$_2$ wherein Ar$_2$ is pyridin-2-yl, pyridin-3-yl, or pyrimidinyl; wherein Ar$_2$ is optionally substituted with one to three substituents independently selected from the group consisting of C$_{1-4}$-alkyl, trifluoromethyl, C$_{1-4}$-alkoxy, amino, and (C$_{1-4}$alkyl)amino;

wherein the C$_{1-4}$-alkyl group of (C$_{1-4}$-alkyl)amino is optionally substituted with di(C$_{1-4}$alkyl)amino, C$_{1-4}$-alkoxy, or hydroxy;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-6}$alkyl-phenyl, 3,4-dichloro-phenyl, or 4-methanesulfonyl-phenyl, A$_2$ is other than 4-methoxy-phenyl;

provided that when Q is —NHCH$_2$(2-amino-pyridin-3-yl), L$_1$ is —(CH$_2$)$_2$— or —(CH$_2$)$_5$—, and A$_1$ is methoxy, A$_2$ is other than 4-difluoromethoxy-phenyl or 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(d) is —(CH$_2$)$_2$—Ar$_4$ and W is CH; wherein Ar$_4$ is pyridinyl is optionally substituted with amino wherein a nitrogen atom of Ar$_2$ and Ar$_4$ is optionally substituted with oxo.

18. The compound of claim 17 wherein Q is —NHCH$_2$—Ar$_2$ wherein Ar$_2$ is unsubstituted pyridin-2-yl, 4,6-dimethyl-pyridin-3-yl, 2-amino-pyridin-3-yl, or 2-((C$_{1-4}$alkyl)amino)-pyridin-3-yl;

wherein the C$_{1-4}$alkyl group of (C$_{1-4}$-alkyl)amino is optionally substituted with di(C$_{1-4}$alkyl)amino, C$_{1-4}$-alkoxy, or hydroxy;

and wherein 2-amino-pyridin-3-Y1 is optionally further substituted with 4,6-dimethyl or 4-methoxy;

provided that when Q is —NHCH$_2$(2-amino-pyridin-3-yl), and A$_1$ is pyridin-4-yl, 4-t-butyl-phenyl, 3,4-dichloro-phenyl, or 4-methanesulfonyl-phenyl, A$_2$ is other than 4-methoxy-phenyl;

provided that when Q is —NHCH$_2$(2-amino-pyridin-3-yl), L$_1$ is —(CH$_2$)$_2$— or —(CH$_2$)$_5$—, and A$_1$ is methoxy, A$_2$ is other than 4-difluoromethoxy-phenyl or 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), L$_1$ is —(CH$_2$)$_3$—, and A$_1$ is pyrrol-1-yl, A$_2$ is other than 4-methoxy-phenyl;

provided that when Q is —NHCH$_2$(2-amino-pyridin-3-yl), L$_1$ is —(CH$_2$)$_2$—, and A$_1$ is 4-nitro-phenyl or ethoxy, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, 3-cyano-phenyl, 3-nitro-phenyl, and 3-trifluoromethyl-4-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

wherein a nitrogen atom of Ar$_2$ is optionally substituted with oxo.

19. A compound of Formula (I)

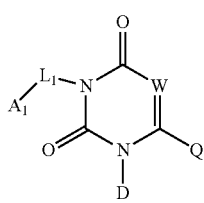

Formula (I)

wherein:

A$_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of C$_{1-4}$-alkyl, C$_{1-4}$-alkoxy, nitro, fluoro, chloro, iodo, halogenated C$_{1-4}$alkyl, halogenated C$_{1-4}$-alkoxy, and C$_{1-4}$-alkylthio; provided that A$_1$ is other than 3,5-di-t-butyl-phenyl;

L$_1$ is —(CH$_2$)$_r$—, wherein L$_1$ is optionally substituted with one to two substituents independently selected from the group consisting of C$_{1-4}$-alkyl and C$_{2-4}$alkenyl and r is 1 or 2;

D is -P-A$_2$;

wherein P is —(CH$_2$)$_{1-2}$— when A$_2$ is phenyl, benzofused heterocyclyl, heteroaryl, or C$_{3-8}$cycloalkyl; alternatively, P is —(CH$_2$)$_{4-6}$—, when A$_2$ is hydrogen, C$_{1-4}$-alkoxy, or C$_{1-4}$alkoxycarbonyl;

A$_2$ is hydrogen, C$_{1-4}$-alkoxy, C$_{1-4}$-alkoxycarbonyl, phenyl, benzofused heterocyclyl, heteroaryl other than pyridin-4-yl, or C$_{3-8}$cycloalkyl; wherein phenyl, heteroaryl and C$_{3-8}$cycloalkyl are optionally substituted with one to two substituents independently selected from the group consisting of C$_{1-6}$alkyl, C$_{1-6}$alkoxy, fluoro, chloro, halogenated C$_{1-6}$alkoxy, phenyl, N-isoindole-1,3-dione, C$_{1-6}$alkylthio, C$_{1-6}$alkylsulfonyl, C$_{1-6}$alkoxycarbonyl, nitro, hydroxy, and C$_{1-6}$alkylcarbonylamino; provided that no more than one substituent of A$_2$ is phenyl or N-isoindole-1,3-dione; and provided that A$_2$ is other than 3,5-di-t-butyl-phenyl;

W is CH;

Q is selected from the group consisting of (a)-(g) wherein:

(a) is —NH(CH$_2$)$_2$—Ar$_1$ wherein Ar$_1$ is pyridinyl substituted with one to three C$_{1-4}$-alkyl substituents or a substituent selected from the group consisting of C$_{1-4}$-alkoxy and amino;

(b) is —NHCH$_2$—Ar$_2$ wherein Ar$_2$ is pyridinyl, pyrimidinyl, 1,2,3,4-tetrahydro-[1,8]naphthyridinyl, imidazo[1,2-a]pyridinyl, or quinolinyl; such that the point of attachment to 1,2,3,4-tetrahydro-[1,8]naphthyridinyl is at the 6 or 7 position, and the point of attachment to quinolinyl is at the 2, 3, or 4-position; and wherein Ar$_2$ is optionally substituted with one to three substituents independently selected from the group consisting of C$_{1-4}$alkyl, trifluoromethyl, C$_{1-4}$alkoxy, amino, (C$_{1-6}$alkyl)amino, and di(C$_{1-6}$alkyl)amino;

wherein the C$_{1-6}$alkyl group of (C$_{1-6}$alkyl)amino and di(C$_{1-6}$alkyl)amino is optionally substituted with (C$_{1-4}$-alkyl)amino, di(C$_{1-4}$-alkyl)amino, C$_{1-4}$-alkoxy, C$_{1-4}$-alkylthio, hydroxy, a 5 to 6 membered heteroaryl, or a 5 to 6 membered heterocyclyl; wherein a nitrogen atom of the 5 to 6 membered heterocyclyl is optionally substituted with a C$_{1-4}$alkyl substituent;

and wherein pyridin-2-yl and pyridin-3-yl are optionally further substituted with N-pyrrolidinyl, N-piperazinyl, N-piperidinyl, N-morpholinyl, N-thiomorpholinyl, and phenyl; wherein the phenyl substituent of pyridin-2-yl and pyridin-3-Y1 is optionally substituted with one to three substituents independently selected from the group consisting of C$_{1-4}$-alkyl, C$_{1-4}$-alkoxy, and halogen;

provided that when Q is —NHCH$_2$(2-amino-pyridin-3-yl), and A$_1$ is pyridin-4-yl, 4-C$_{1-4}$alkyl-phenyl or 3,4-dichloro-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), L$_1$ is —(CH$_2$)$_2$—, and A$_1$ is 4-nitro-phenyl, A$_2$ is other than 4-methoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl), L$_1$ is —(CH$_2$)$_2$—, and A$_1$ is pyrazol-1-yl, A$_2$ is other than 4-difluoromethoxy-phenyl;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, and 3-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-nitro-phenyl, 2-trifluoromethyl-phenyl, 2-difluoromethoxy-phenyl, 3-difluoromethoxy-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(c) is —CH$_2$NHCH$_2$—Ar$_3$, wherein Ar$_3$ is pyridinyl optionally substituted with amino;

(d) is —(CH$_2$)$_2$—Ar$_4$, wherein Ar$_4$ is pyridinyl, or pyrimidinyl; wherein Ar$_4$ is optionally substituted with one to two substituents independently selected from the group consisting of C$_{1-4}$-alkyl, C$_{1-4}$-alkoxy, amino, (C$_{1-6}$alkyl)amino, and di(C$_{1-6}$alkyl)amino;

(e) is —CH═CH-pyridinyl; and (f) is —O—CH(R$_1$)—Ar$_6$ when W is CH; or (f) is —S—CH(R$_1$)—Ar$_6$ and W is CH; wherein R$_1$ is hydrogen or C$_{1-4}$-alkyl, and Ar$_6$ is pyridinyl or pyrimidinyl; wherein Ar$_6$ is optionally substituted with one to three substituents independently selected from the group consisting of C$_{1-4}$-alkyl, C$_{1-4}$-alkoxy, amino, (C$_{1-6}$alkyl)amino, di(C$_{1-6}$alkyl)amino, halogen, and aminocarbonyl;

and wherein the C$_{1-6}$alkyl group of (C$_{1-6}$alkyl)amino and di(C$_{1-6}$alkyl)amino is optionally substituted with amino, (C$_{1-4}$alkyl)amino, di(C$_{1-4}$alkyl)amino, C$_{3-8}$cycloalkylamino, C$_{1-4}$alkoxy, or hydroxy;

provided that when Q is —O—CH(R$_1$)—Ar$_6$, A$_1$ and A$_2$ are 4-methoxy-phenyl, and R$_1$ is hydrogen, Ar$_6$ is other than unsubstituted pyridin-2-yl or 2-amino-pyridin-4-yl;

(g) is —X$_1$—(CH(R$_x$))$_2$—Ar$_7$ and W is CH; wherein X$_1$ is O, R$_x$ is H, and Ar$_7$ is pyridinyl or pyrimidinyl; wherein Ar$_7$ is optionally substituted with one to two substituents independently selected from the group consisting of C$_{1-4}$-alkyl, C$_{1-4}$-alkoxy, amino, (C$_{1-6}$alkyl)amino, and di(C$_{1-6}$alkyl)amino;

provided that when Q is —O(CH$_2$)$_2$—Ar$_7$ and A$_1$ and A$_2$ are 4-methoxy-phenyl, Ar$_7$ is other than unsubstituted pyridin-2-yl or unsubstituted pyridin-3-yl wherein a nitrogen atom of Ar$_1$, Ar$_2$, Ar$_3$, Ar$_4$, Ar$_6$, and Ar$_7$ is optionally substituted with oxo;

and an enantiomer, a diastereomer, a tautomer, or a pharmaceutically acceptable salt thereof.

20. The compound of claim 19 wherein:

A$_1$ is aryl, heteroaryl, or a benzofused heterocyclyl selected from the group consisting of benzo[1,3]dioxalyl and 2,3-dihydro-benzofuranyl; wherein aryl and heteroaryl are optionally substituted with one to three substituents independently selected from the group consisting of C$_{1-3}$alkyl, methoxy, fluoro, chloro, trifluoromethyl, trifluoromethoxy, and methylthio;

L$_1$ is —CH$_2$—;

D is -P-A$_2$;

wherein P is —CH$_2$— when A$_2$ is phenyl, benzofused heterocyclyl, or heteroaryl; alternatively, P is —(CH$_2$)$_{4-6}$—, when A$_2$ is C$_{1-4}$-alkoxy;

A$_2$ is C$_{1-4}$-alkoxy, phenyl, benzofused heterocyclyl, or a heteroaryl other than pyridin-4-yl; wherein phenyl and heteroaryl are optionally substituted with one to two substituents independently selected from the group consisting of C$_{1-4}$-alkyl, C$_{1-4}$-alkoxy, fluoro, chloro, halogenated C$_{1-4}$-alkoxy, N-isoindole-1,3-dione, C$_{1-4}$-alkylthio, C$_{1-4}$alkylsulfonyl, C$_{1-4}$-alkoxycarbonyl, nitro, hydroxy, and C$_{1-4}$-alkylcarbonylamino; provided that no more than one substituent of A$_2$ is N-isoindole-1,3-dione; and provided that A$_2$ is other than 3,5-di-t-butyl-phenyl;

W is CH

Q is selected from the group consisting of (b) and (d) wherein:

(b) is —NHCH$_2$—Ar$_2$ wherein Ar$_2$ is pyridinyl, pyrimidinyl, or quinolinyl; such that the point of attachment to quinolinyl is at the 2, 3, or 4-position; and wherein Ar$_2$ is optionally substituted with one to three substituents independently selected from the group consisting of C$_{1-4}$-alkyl, trifluoromethyl, C$_{1-4}$-alkoxy, amino, (C$_{1-4}$-alkyl)amino, and di(C$_{1-4}$-alkyl)amino;

wherein the C$_{1-4}$-alkyl group of (C$_{1-4}$-alkyl)amino and di(C$_{1-4}$-alkyl)amino is optionally substituted with (C$_{1-4}$-alkyl)amino, di(C$_{1-4}$-alkyl)amino, C$_{1-4}$-alkoxy, C$_{1-4}$-alkylthio, hydroxy, a 5 to 6 membered heteroaryl, or a 5 to 6 membered heterocyclyl;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-3}$alkyl-phenyl, or 3,4-dichloro-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is unsubstituted phenyl or 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl) and A$_1$ is 4-methoxy-phenyl, A$_2$ is other than 2-ethyl-phenyl, 4-ethyl-phenyl, 3-methoxy-phenyl, or 3-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2-trifluoromethyl-phenyl, 2-trifluoromethoxy-phenyl, 2,4-difluoro-phenyl, 2,6-difluoro-phenyl, 2,6-dichloro-phenyl, 2-chloro-4-fluoro-phenyl, 2,6-difluoro-4-methoxy-phenyl, or 4-trifluoromethoxy-phenyl, A$_2$ is other than 4-difluoromethoxy-phenyl;

and, provided that when Q is —NHCH$_2$(4,6-dimethyl-pyridin-3-yl) and A$_1$ is 3-nitro-4-methoxy-phenyl, 2,6-difluoro-4-methoxy-phenyl, or 3,4-dichloro-phenyl, A$_2$ is other than 4-methoxy-phenyl;

(d) is —(CH$_2$)$_2$—Ar$_4$ and W is CH; wherein Ar$_4$ is pyridinyl is optionally substituted with one to two substituents independently selected from the group consisting of C$_{1-4}$-alkyl, C$_{1-4}$alkoxy, amino, (C$_{1-6}$alkyl)amino, and di(C$_{1-6}$alkyl)amino;

wherein a nitrogen atom of Ar$_2$ and Ar$_4$ is optionally substituted with oxo;

and an enantiomer, a diastereomer, a tautomer, or a pharmaceutically acceptable salt thereof.

21. The compound of claim 20 wherein:

A$_1$ is substituted phenyl, heteroaryl, or a benzofused heterocyclyl selected from the group consisting of benzo[1,3]dioxalyl and 2,3-dihydro-benzofuranyl; wherein substituted phenyl is substituted with, and heteroaryl is optionally substituted with, one to three substituents independently selected from the group consisting of C$_{1-3}$alkyl, methoxy, fluoro and methylthio;

L$_1$ is —CH$_2$—;

D is -P-A$_2$; wherein P is —CH$_2$— when A$_2$ is phenyl, benzofused heterocyclyl, or heteroaryl; alternatively, P is —(CH$_2$)$_{4-6}$—, when A$_2$ is C$_{1-4}$-alkoxy;

A$_2$ is C$_{1-4}$-alkoxy, phenyl, benzofused heterocyclyl, or a heteroaryl other than pyridin-4-yl; wherein phenyl and heteroaryl are optionally substituted with one to two substituents independently selected from the group consisting of C$_{1-4}$-alkoxy, fluoro, halogenated C$_{1-4}$-alkoxy, C$_{1-4}$-alkylthio, C$_{1-4}$alkylsulfonyl, C$_{1-4}$-alkoxycarbonyl, nitro, and hydroxy;

W is CH;

Q is selected from the group consisting of (b) and (d) wherein:

(b) is —NHCH$_2$—Ar$_2$ wherein Ar$_2$ is pyridin-2-yl, pyridin-3-yl, or pyrimidinyl; wherein Ar$_2$ is optionally substituted with one to three substituents independently selected from the group consisting of C$_{1-4}$alkyl, trifluoromethyl, C$_{1-4}$-alkoxy, amino, and (C$_{1-4}$alkyl)amino;

wherein the C$_{1-4}$alkyl group of (C$_{1-4}$-alkyl)amino is optionally substituted with di(C$_{1-4}$alkyl)amino, C$_{1-4}$-alkoxy, or hydroxy;

and wherein pyridin-2-yl and pyridin-3-yl are optionally further substituted with N-morpholinyl;

provided that when Q is —NHCH$_2$(2-amino-pyridin-3-yl), and A$_1$ is pyridin-4-yl, 4-C$_{1-3}$alkyl-phenyl, or 3,4-dichloro-phenyl, A$_2$ is other than 4-methoxy-phenyl;

provided that when Q is —NHCH$_2$(2-amino-pyridin-3-yl), and A$_1$ is benzotriazol-1-yl, A$_2$ is other than 4-difluoromethoxy-phenyl;

provided that when Q is —NHCH$_2$(2-amino-pyridin-3-yl), and A$_1$ is 4-fluoro-phenyl, A$_2$ is other than 4-fluoro-phenyl;

provided that when Q is —NHCH$_2$(6-amino-pyridin-2-yl), and A$_1$ is 4-fluoro-phenyl, A$_2$ is other than 4-trifluoromethoxy-phenyl;

provided that when Q is —NHCH$_2$(6-methyl-pyridin-2-yl), and A$_1$ is 4-methoxy-phenyl, A$_2$ is other than 4-methoxy-phenyl;

provided that when Q is —NHCH$_2$(imidazo[1,2-a]pyridinyl), and A$_1$ is 4-fluoro-phenyl, A$_2$ is other than 4-methoxy-phenyl;

provided that when Q is —NHCH$_2$(pyridin-4-yl), and A$_1$ is 3,4-dichloro-phenyl, A$_2$ is other than 4-methoxy-phenyl;

provided that when Q is —NHCH$_2$(4,6-dimethyl-pyridin-3-yl), and A$_1$ is 4-methoxy-phenyl, —P-A$_2$ is other than —(CH$_2$)-5-methoxy;

provided that when Q is —NHCH$_2$(4,6-dimethyl-pyridin-3-yl) and A$_1$ is 4-methoxy-phenyl, A$_2$ is other than 3-methoxy-phenyl or 3-nitro-phenyl;

provided that when Q is —NHCH$_2$(4,6-dimethyl-pyridin-3-yl) and A$_1$ is quinolin-8-yl, benzotriazol-1-yl, 3,5-dimethyl-pyrazolyl, 2-fluoro-phenyl, 2-chloro-phenyl, 2,4-difluoro-phenyl, 2,6-difluoro-phenyl, 2,6-dichloro-phenyl, 2-chloro-4-fluoro-phenyl, or 2,6-difluoro-4-methoxy-phenyl, A$_2$ is other than 4-difluoromethoxy-phenyl;

and, provided that when Q is —NHCH$_2$(4,6-dimethyl-pyridin-3-yl) and A$_1$ is 2,6-difluoro-4-methoxy-phenyl or 3,4-dichloro-phenyl, A$_2$ is other than 4-methoxy-phenyl;

(d) is —(CH$_2$)$_2$—Ar$_4$ and W is CH; wherein Ar$_4$ is pyridinyl is optionally substituted with amino;

wherein a nitrogen atom of Ar$_2$ and Ar$_4$ is optionally substituted with oxo;

and an enantiomer, a diastereomer, a tautomer, or a pharmaceutically acceptable salt thereof.

22. The compound of claim 21 wherein:

A$_1$ is substituted phenyl, benzotriazolyl, benzofuranyl, benzo[1,3]dioxalyl or 2,3-dihydro-benzofuranyl; wherein phenyl is substituted at the 4-position with methoxy, fluoro, or methylthio; and wherein A$_1$ other than substituted phenyl is optionally substituted with one to two substituents independently selected from the group consisting of methyl, methoxy, fluoro and methylthio;

L$_1$ is —CH$_2$—;

D is -P-A$_2$;

wherein P is —CH$_2$— when A$_2$ is phenyl, 2,3-dihydro-benzofuranyl, indolyl, benzofuranyl, pyridin-3-yl, or benzothiophenyl; alternatively, P is —(CH$_2$)$_{4-6}$—, when A$_2$ is C$_{1-4}$alkoxy;

A$_2$ is C$_{1-4}$-alkoxy, phenyl, 2,3-dihydro-benzofuranyl, indolyl, benzofuranyl, pyridin-3-yl, or benzothiophenyl; wherein A$_2$ other than C$_{1-4}$-alkoxy is optionally substituted with one to two substituents independently selected from the group consisting of C$_{1-4}$alkoxy, fluoro, fluorinated C$_{1-4}$alkoxy, C$_{1-4}$alkylthio, C$_{1-4}$alkylsulfonyl, C$_{1-4}$alkoxycarbonyl, nitro, and hydroxy;

W is CH;

Q is —NHCH$_2$—Ar$_2$ wherein Ar$_2$ is unsubstituted pyridin-2-yl, 4,6-dimethyl-pyridin-3-yl, 2-amino-pyridin-3-yl, or 2-((C$_{1-4}$alkyl)amino)-pyridin-3-yl;

wherein the $C_{1-4}$-alkyl group of ($C_{1-4}$-alkyl)amino is optionally substituted with di($C_{1-4}$alkyl)amino, $C_{1-4}$-alkoxy, or hydroxy;

and wherein 2-amino-pyridin-3-Y1 is optionally further substituted with 4,6-dimethyl or 4-methoxy;

provided that when Q is —NHCH$_2$(2-amino-pyridin-3-yl), and $A_1$ is pyridin-4-yl or 4-methyl-phenyl, $A_2$ is other than 4-methoxy-phenyl;

provided that when Q is —NHCH$_2$(2-amino-pyridin-3-yl), and $A_1$ is benzotriazol-1-yl, $A_2$ is other than 4-difluoromethoxy-phenyl;

provided that when Q is —NHCH$_2$(2-amino-pyridin-3-yl), and $A_1$ is 4-fluoro-phenyl, $A_2$ is other than 4-fluoro-phenyl;

provided that when Q is —NHCH$_2$(6-amino-pyridin-2-yl), and $A_1$ is 4-fluoro-phenyl, $A_2$ is other than 4-trifluoromethoxy-phenyl;

provided that when Q is —NHCH$_2$(6-methyl-pyridin-2-yl), and $A_1$ is 4-methoxy-phenyl, $A_2$ is other than 4-methoxy-phenyl;

provided that when Q is —NHCH$_2$(imidazo[1,2-a]pyridinyl), and $A_1$ is 4-fluoro-phenyl, $A_2$ is other than 4-methoxy-phenyl;

provided that when Q is —NHCH$_2$(4,6-dimethyl-pyridin-3-yl), and $A_1$ is 4-methoxy-phenyl, —P-$A_2$ is other than —(CH$_2$)-5-methoxy;

provided that when Q is —NHCH$_2$(4,6-dimethyl-pyridin-3-yl) and $A_1$ is 4-methoxy-phenyl, $A_2$ is other than 3-methoxy-phenyl or 3-nitro-phenyl; and provided that when Q is —NHCH$_2$(4,6-dimethyl-pyridin-3-yl) and $A_1$ is benzotriazol-1-yl, $A_2$ is other than 4-difluoromethoxy-phenyl;

wherein a nitrogen atom of $Ar_2$ and $Ar_4$ is optionally substituted with oxo;

and an enantiomer, a diastereomer, a tautomer, or a pharmaceutically acceptable salt thereof.

23. A pharmaceutical composition comprising a compound of Formula (I)

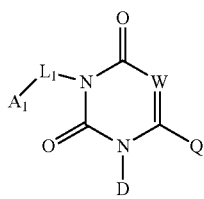

Formula (I)

the compound selected from the group consisting of wherein $A_1$ is 4-methoxy-phenyl, $L_1$ is CH$_2$, D is 4-methoxy-phenylmethyl, W is CH, and Q is 2-amino-pyridin-3-ylmethyl-aminomethyl;

wherein $A_1$ is 4-methoxy-phenyl, $L_1$ is CH$_2$, D is 4-methoxy-phenylmethyl, W is CH, and Q is 2-amino-pyridin-3-ylmethyl-amino;

wherein $A_1$ is 4-methoxy-phenyl, $L_1$ is CH$_2$, D is 4-methoxy-phenylmethyl, W is CH, and Q is 4,6-dimethyl-pyridin-3-ylmethyl-amino;

wherein $A_1$ is 4-methoxy-phenyl, $L_1$ is CH$_2$, D is 4-methoxy-phenylmethyl, W is CH, and Q is pyridin-3-ylmethoxy;

wherein $A_1$ is 4-methoxy-phenyl, $L_1$ is CH$_2$, D is 4-methoxy-phenylmethyl, W is CH, and Q is 6-amino-pyridin-2-ylmethyl-amino;

wherein $A_1$ is 4-methoxy-phenyl, $L_1$ is CH$_2$, D is 4-methoxy-phenylmethyl, W is CH, and Q is 2-pyridin-3-yl-ethyl;

wherein $A_1$ is 4-methoxy-phenyl, $L_1$ is CH$_2$, D is 4-methoxy-phenyl, W is CH, and Q is 2-pyridin-4-yl-ethyl;

wherein $A_1$ is 4-methoxy-phenyl, $L_1$ is CH$_2$, D is 4-methoxy-phenyl, W is CH, and Q is cis-2-pyridin-4-yl-vinyl;

wherein $A_1$ is 4-methoxy-phenyl, $L_1$ is CH$_2$, D is 4-methoxy-phenylmethyl, W is CH, and Q is 2-pyridin-2-yl-ethyl;

wherein $A_1$ is 4-methoxy-phenyl, $L_1$ is CH$_2$, D is 4-methoxy-phenylmethyl, W is CH, and Q is 2-(2-aminocarbonyl-pyridin-3-yl)-ethyl;

wherein $A_1$ is 4-methoxy-phenyl, $L_1$ is CH$_2$, D is 4-methoxy-phenylmethyl, W is CH, and Q is 2-amino-pyridin-3-ylmethoxy;

wherein $A_1$ is 4-methoxy-phenyl, $L_1$ is CH$_2$, D is 4-methoxy-phenylmethyl, W is CH, and Q is 2-amino-4,6-dimethyl-pyridin-3-ylmethoxy;

wherein $A_1$ is 4-methoxy-phenyl, $L_1$ is CH$_2$, D is 4-methoxy-phenylmethyl, W is CH, and Q is pyridin-3-ylmethylthio;

wherein $A_1$ is 4-methoxy-phenyl, $L_1$ is CH$_2$, D is 4-methoxy-phenylmethyl, W is CH, and Q is 2-(4-amino-pyridin-3-yl)-ethyl;

wherein $A_1$ is 4-methoxy-phenyl, $L_1$ is CH$_2$, D is 4-methoxy-phenylmethyl, W is CH, and Q is 2-(6-amino-pyridin-2-yl)ethyl;

wherein $A_1$ is 4-methoxy-phenyl, $L_1$ is CH$_2$, D is 4-methoxy-phenylmethyl, W is CH, and Q is 1-(2-amino-pyridin-4-yl)-ethoxy; and wherein $A_1$ is 4-methoxy-phenyl, $L_1$ is CH$_2$, D is 4-methoxy-phenylmethyl, W is CH, and Q is 2-amino-pyrimidin-4-ylmethoxy.

24. A pharmaceutical composition comprising a compound, or salt according to claim 1 admixed with a pharmaceutically acceptable carrier, excipient or diluent.

25. A veterinary composition comprising a compound, or salt according to claim 1 admixed with a veterinarily acceptable carrier, excipient or diluent.

26. A method of treating a disease in a mammal in which the disease is irritable bowel syndrome or inflammatory bowel disease which method comprises administering to a mammal in need thereof a therapeutically effective amount of a compound or salt of claim 1.

27. The method of claim 26 wherein the irritable bowel syndrome is diarrhea—predominant or alternating diarrhea/constipation forms, and the inflammatory bowel disease is ulcerative colitis and Crohn's disease.

28. The method of claim 27 wherein said therapeutically effective amount comprises a dose range of from about 0.1 mg to about 1,000 mg.

29. The method of claim 28 wherein said therapeutically effective amount comprises a dose range of from about 50 mg to about 1000 mg.

30. The method of claim 29 wherein said therapeutically effective amount comprises a dose range of from about 100 mg to about 1000 mg.

* * * * *

SEQUENCE LISTING

<160> NUMBER OF SEQ ID NOS: 3

<210> SEQ ID NO 1
<211> LENGTH: 113
<212> TYPE: PRT
<213> ORGANISM: Artificial Sequence
<220> FEATURE:
<223> OTHER INFORMATION: Recombinant N-terminal FLAG-tagged human -continued prokineticin-1

<400> SEQUENCE: 1

Met Arg Gly Ala Thr Arg Val Ser Ile Met Leu Leu Val Thr Val
1               5                   10                  15

Ser Asp Cys Asp Tyr Lys Asp Asp Asp Lys Ala Val Ile Thr Gly
            20                  25                  30

Ala Cys Glu Arg Asp Val Gln Cys Gly Ala Gly Thr Cys Cys Ala Ile
        35                  40                      45

Ser Leu Trp Leu Arg Gly Leu Arg Met Cys Thr Pro Leu Gly Arg Glu
    50                  55                  60

Gly Glu Glu Cys His Pro Gly Ser His Lys Val Pro Phe Phe Arg Lys
65              70                  75                  80

Arg Lys His His Thr Cys Pro Cys Leu Pro Asn Leu Leu Cys Ser Arg
                85                  90                  95

Phe Pro Asp Gly Arg Tyr Arg Cys Ser Met Asp Leu Lys Asn Ile Asn
            100                 105                 110

Phe

<210> SEQ ID NO 2
<211> LENGTH: 86
<212> TYPE: PRT
<213> ORGANISM: Artificial Sequence
<220> FEATURE:
<223> OTHER INFORMATION: Recombinant N-terminal FLAG-tagged human
      prokineticin-1 after enterokinase cleavage of Flag-tag

<400> SEQUENCE: 2

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65              70                  75                  80

Leu Lys Asn Ile Asn Phe
                85

<210> SEQ ID NO 3
<211> LENGTH: 82
<212> TYPE: PRT
<213> ORGANISM: Artificial Sequence
<220> FEATURE:
<223> OTHER INFORMATION: Truncation product missing last four C-terminal
      residues of recombinant N-terminal FLAG-tagged human
      prokineticin-1 after enterokinase cleavage of Flag-tag

<400> SEQUENCE: 3

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

```
Pro Phe Phe Arg Lys Arg Lys His His Thr Cys Pro Cys Leu Pro Asn
    50              55                  60
Leu Leu Cys Ser Arg Phe Pro Asp Gly Arg Tyr Arg Cys Ser Met Asp
65                  70                  75              80
Leu Lys
```